US009540432B2

(12) United States Patent
Barghorn et al.

(10) Patent No.: US 9,540,432 B2
(45) Date of Patent: *Jan. 10, 2017

(54) ANTI-Aβ GLOBULOMER 7C6 ANTIBODIES

(71) Applicants: ABBVIE INC., North Chicago, IL (US); ABBVIE DEUTSCHLAND GMBH & CO. KG, Wiesbaden (DE)

(72) Inventors: Stefan Barghorn, Mannheim (DE); Heinz Hillen, Hassloch (DE); Boris Labkovsky, Wales, MA (US); Andreas R. Striebinger, Speyer (DE); Patrick Keller, Darmstadt (DE); Ulrich Ebert, Mannheim (DE)

(73) Assignees: ABBVIE DEUTSCHLAND GMBH & CO. KG, Wiesbaden (DE); ABBVIE INC., North Chicago, IL (US)

( * ) Notice: Subject to any disclaimer, the term of this patent is extended or adjusted under 35 U.S.C. 154(b) by 142 days.

This patent is subject to a terminal disclaimer.

(21) Appl. No.: 13/893,780

(22) Filed: May 14, 2013

(65) Prior Publication Data

US 2014/0127191 A1    May 8, 2014

Related U.S. Application Data

(63) Continuation of application No. 11/574,876, filed as application No. PCT/EP2006/011530 on Nov. 30, 2006, now Pat. No. 8,691,224.

(60) Provisional application No. 60/740,866, filed on Nov. 30, 2005, provisional application No. 60/779,171, filed on Mar. 3, 2006, provisional application No. 60/787,361, filed on Mar. 30, 2006, provisional application No. 60/842,400, filed on Sep. 5, 2006.

(51) Int. Cl.
| C07K 16/00 | (2006.01) |
| C07K 16/18 | (2006.01) |
| C07K 14/47 | (2006.01) |
| A61K 38/00 | (2006.01) |

(52) U.S. Cl.
CPC .......... C07K 16/18 (2013.01); C07K 14/4711 (2013.01); *A61K 38/00* (2013.01)

(58) Field of Classification Search
None
See application file for complete search history.

(56) References Cited

U.S. PATENT DOCUMENTS

| 4,399,216 A | 8/1983 | Axel et al. |
| 4,510,245 A | 4/1985 | Cousens et al. |
| 4,526,039 A | 7/1985 | Ceccon et al. |
| 4,582,788 A | 4/1986 | Erlich |
| 4,634,665 A | 1/1987 | Axel et al. |
| 4,666,829 A | 5/1987 | Glenner et al. |
| 4,683,194 A | 7/1987 | Saiki et al. |
| 4,683,202 A | 7/1987 | Mullis |
| 4,816,397 A | 3/1989 | Boss et al. |
| 4,816,567 A | 3/1989 | Cabilly et al. |
| 4,880,078 A | 11/1989 | Inoue et al. |
| 4,946,778 A | 8/1990 | Ladner et al. |
| 4,968,615 A | 11/1990 | Koszinowski et al. |
| 4,980,286 A | 12/1990 | Morgan et al. |
| 5,107,065 A | 4/1992 | Shewmaker et al. |
| 5,128,326 A | 7/1992 | Balazs et al. |
| 5,134,062 A | 7/1992 | Blass |
| 5,168,062 A | 12/1992 | Stinski |
| 5,179,017 A | 1/1993 | Axel et al. |
| 5,218,100 A | 6/1993 | Muller-Hill et al. |
| 5,223,409 A | 6/1993 | Ladner et al. |
| 5,225,539 A | 7/1993 | Winter |
| 5,231,000 A | 7/1993 | Majocha et al. |
| 5,231,020 A | 7/1993 | Jorgensen et al. |
| 5,231,170 A | 7/1993 | Averback |
| 5,234,814 A | 8/1993 | Card et al. |
| 5,258,498 A | 11/1993 | Huston et al. |
| 5,262,332 A | 11/1993 | Selkoe |

(Continued)

FOREIGN PATENT DOCUMENTS

| AU | 2007200047 | 1/2007 |
| CA | 2541522 | 9/2007 |

(Continued)

OTHER PUBLICATIONS

United States Patent Office Action for U.S. Appl. No. 11/885,362 dated Sep. 26, 2013 (11 pages).

(Continued)

*Primary Examiner* — Daniel E Kolker
*Assistant Examiner* — Aditi Dutt
(74) *Attorney, Agent, or Firm* — Neal, Gerber & Eisenberg LLP

(57) ABSTRACT

Anti-Aβ globulomer antibodies, antigen-binding moieties thereof, corresponding hybridomas, nucleic acids, vectors, host cells, methods of producing said antibodies, compositions comprising said antibodies, uses of said antibodies and methods of using said antibodies.

The present invention relates to anti-Aβ globulomer antibodies having a binding affinity to Aβ(20-42) globulomer that is greater than the binding affinity of the antibody to Aβ(1-42) globulomer, antigen-binding moieties thereof, hybridomas producing said antibodies, nucleic acids encoding said antibodies, vectors comprising said nucleic acids, host cells comprising said vectors, methods of producing said antibodies, compositions comprising said antibodies, therapeutic and diagnostic uses of said antibodies and corresponding methods relating to Alzheimer's disease and other amyloidoses.

14 Claims, 28 Drawing Sheets

(56) References Cited

U.S. PATENT DOCUMENTS

| | | |
|---|---|---|
| 5,290,540 A | 3/1994 | Prince et al. |
| 5,403,484 A | 4/1995 | Ladner et al. |
| 5,427,908 A | 6/1995 | Dower et al. |
| 5,441,870 A | 8/1995 | Seubert et al. |
| 5,455,169 A | 10/1995 | Mullan |
| 5,516,637 A | 5/1996 | Huang et al. |
| 5,530,101 A | 6/1996 | Queen et al. |
| 5,538,845 A | 7/1996 | Knops et al. |
| 5,545,806 A | 8/1996 | Lonberg et al. |
| 5,565,332 A | 10/1996 | Hoogenboom et al. |
| 5,565,352 A | 10/1996 | Hochstrasser et al. |
| 5,567,720 A | 10/1996 | Averback |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,593,846 A | 1/1997 | Schenk et al. |
| 5,605,811 A | 2/1997 | Seubert et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,648,260 A | 7/1997 | Winter et al. |
| 5,658,727 A | 8/1997 | Barbas et al. |
| 5,661,016 A | 8/1997 | Lonberg et al. |
| 5,665,355 A | 9/1997 | Primi |
| 5,679,377 A | 10/1997 | Bernstein et al. |
| 5,679,531 A | 10/1997 | Koenig |
| 5,693,753 A | 12/1997 | Koenig |
| 5,693,762 A | 12/1997 | Queen et al. |
| 5,698,426 A | 12/1997 | Huse |
| 5,705,330 A | 1/1998 | Shah et al. |
| 5,705,401 A | 1/1998 | Masters et al. |
| 5,714,350 A | 2/1998 | Co et al. |
| 5,714,352 A | 2/1998 | Jakobovits |
| 5,721,130 A | 2/1998 | Seubert et al. |
| 5,723,323 A | 3/1998 | Kauffman et al. |
| 5,733,743 A | 3/1998 | Johnson et al. |
| 5,750,349 A | 5/1998 | Suzuki et al. |
| 5,750,753 A | 5/1998 | Kimae et al. |
| 5,763,192 A | 6/1998 | Kauffman et al. |
| 5,766,846 A | 6/1998 | Schlossmacher et al. |
| 5,766,886 A | 6/1998 | Studnicka et al. |
| 5,770,429 A | 6/1998 | Lonberg et al. |
| 5,780,225 A | 7/1998 | Wigler et al. |
| 5,786,180 A | 7/1998 | Konig |
| 5,807,715 A | 9/1998 | Morrison et al. |
| 5,814,318 A | 9/1998 | Lonberg et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,837,500 A | 11/1998 | Ladner et al. |
| 5,855,913 A | 1/1999 | Hanes et al. |
| 5,874,064 A | 2/1999 | Edwards et al. |
| 5,877,397 A | 3/1999 | Lonberg et al. |
| 5,879,909 A | 3/1999 | Perl |
| 5,882,644 A | 3/1999 | Chang et al. |
| 5,885,793 A | 3/1999 | Griffiths et al. |
| 5,912,015 A | 6/1999 | Bernstein et al. |
| 5,912,120 A | 6/1999 | Goldstein et al. |
| 5,916,597 A | 6/1999 | Lee et al. |
| 5,916,771 A | 6/1999 | Hort et al. |
| 5,934,272 A | 8/1999 | Lloyd et al. |
| 5,939,598 A | 8/1999 | Kucherlapati et al. |
| 5,955,285 A | 9/1999 | Averback |
| 5,955,317 A | 9/1999 | Suzuki et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jokobovits et al. |
| 6,010,913 A | 1/2000 | Vandermeeren et al. |
| 6,018,024 A | 1/2000 | Seubert et al. |
| 6,019,968 A | 2/2000 | Platz et al. |
| 6,075,181 A | 6/2000 | Kucherlapati et al. |
| 6,091,001 A | 7/2000 | Jakobovits et al. |
| 6,114,133 A | 9/2000 | Seubert et al. |
| 6,114,598 A | 9/2000 | Kucherlapati et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,218,506 B1 | 4/2001 | Krafft et al. |
| 6,284,221 B1 | 9/2001 | Schenk et al. |
| 6,287,793 B1 | 9/2001 | Schenk et al. |
| 6,294,171 B2 | 9/2001 | Mcmichael |
| 6,309,892 B1 | 10/2001 | Averback |
| 6,323,218 B1 | 11/2001 | Bush et al. |
| 6,333,034 B1 | 12/2001 | Gupta-Bansal et al. |
| 6,350,861 B1 | 2/2002 | Co et al. |
| 6,387,674 B1 | 5/2002 | Trasciatti et al. |
| 6,582,945 B1 | 6/2003 | Raso |
| 6,610,493 B1 | 8/2003 | Citron et al. |
| 6,660,843 B1 | 12/2003 | Feige et al. |
| 6,664,442 B2 | 12/2003 | McConlogue et al. |
| 6,699,658 B1 | 3/2004 | Wittrup et al. |
| 6,710,226 B1 | 3/2004 | Schenk |
| 6,713,450 B2 | 3/2004 | Frangione et al. |
| 6,743,427 B1 | 6/2004 | Schenk |
| 6,750,324 B1 | 6/2004 | Schenk |
| 6,761,888 B1 | 7/2004 | Schenk |
| 6,785,434 B2 | 8/2004 | Castoldi et al. |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,815,175 B2 | 11/2004 | Weksler |
| 6,849,416 B2 | 2/2005 | Wiltfang et al. |
| 6,866,849 B2 | 3/2005 | Schenk |
| 6,866,850 B2 | 3/2005 | Schenk |
| 6,872,554 B2 | 3/2005 | Raso |
| 6,875,434 B1 | 4/2005 | Schenk |
| 6,905,686 B1 | 6/2005 | Schenk |
| 6,913,745 B1 | 7/2005 | Schenk |
| 6,919,075 B1 | 7/2005 | Solomon et al. |
| 6,972,127 B2 | 12/2005 | Schenk |
| 6,982,084 B2 | 1/2006 | Schenk |
| 7,014,855 B2 | 3/2006 | Schenk |
| 7,022,500 B1 | 4/2006 | Queen et al. |
| 7,045,531 B1 | 5/2006 | Bush et al. |
| 7,060,270 B2 | 6/2006 | Nicolau et al. |
| 7,067,133 B2 | 6/2006 | Nicolau |
| 7,094,884 B2 | 8/2006 | Scholz et al. |
| 7,122,374 B1 | 10/2006 | Saido et al. |
| 7,135,181 B2 | 11/2006 | Jensen et al. |
| 7,169,389 B2 | 1/2007 | Di Padova et al. |
| 7,179,463 B2 | 2/2007 | Lannfelt et al. |
| 7,179,606 B2 | 2/2007 | Jackowski et al. |
| 7,179,892 B2 | 2/2007 | Basi et al. |
| 7,186,881 B2 | 3/2007 | Games et al. |
| 7,189,703 B2 | 3/2007 | Balin et al. |
| 7,189,819 B2 | 3/2007 | Basi et al. |
| 7,195,761 B2 | 3/2007 | Holtzman et al. |
| 7,195,881 B2 | 3/2007 | Geffard |
| 7,196,163 B2 | 3/2007 | Hazuda et al. |
| 7,226,730 B1 | 6/2007 | De La et al. |
| 7,238,488 B2 | 7/2007 | Maresh et al. |
| 7,238,788 B2 | 7/2007 | Lee |
| 7,247,301 B2 | 7/2007 | Van De et al. |
| 7,256,273 B2 | 8/2007 | Basi et al. |
| 7,270,818 B2 | 9/2007 | Averback |
| 7,279,165 B2 | 10/2007 | Bachmann et al. |
| 7,318,923 B2 | 1/2008 | Tsurushita et al. |
| 7,320,790 B2 | 1/2008 | Hinton et al. |
| 7,320,793 B2 | 1/2008 | Renner et al. |
| 7,335,491 B2 | 2/2008 | Drapeau et al. |
| 7,339,035 B2 | 3/2008 | Yanagisawa et al. |
| 7,342,091 B2 | 3/2008 | Kapurniotu et al. |
| 7,371,365 B2 | 5/2008 | Poduslo et al. |

(56) References Cited

U.S. PATENT DOCUMENTS

| | | | |
|---|---|---|---|
| 7,375,190 B2 | 5/2008 | Cheng et al. | |
| 7,413,884 B2 | 8/2008 | Raso | |
| 7,427,342 B2 | 9/2008 | Barber | |
| 7,625,560 B2 | 12/2009 | Basi et al. | |
| 7,772,375 B2 | 8/2010 | Greferath et al. | |
| 7,892,544 B2 | 2/2011 | Pfeifer et al. | |
| 7,902,328 B2 | 3/2011 | Hillen et al. | |
| 8,691,224 B2* | 4/2014 | Barghorn et al. | 424/133.1 |
| 2001/0029293 A1 | 10/2001 | Gallatin et al. | |
| 2002/0009445 A1 | 1/2002 | Du et al. | |
| 2002/0015941 A1 | 2/2002 | Kim et al. | |
| 2002/0086014 A1 | 7/2002 | Korman et al. | |
| 2002/0086847 A1 | 7/2002 | Chain | |
| 2002/0094335 A1 | 7/2002 | Chalifour et al. | |
| 2002/0132758 A1 | 9/2002 | Shell | |
| 2002/0137134 A1 | 9/2002 | Gerngross | |
| 2002/0162129 A1 | 10/2002 | Lannfelt et al. | |
| 2002/0182644 A1 | 12/2002 | Diamandis | |
| 2002/0182660 A1 | 12/2002 | Fong | |
| 2002/0188106 A1 | 12/2002 | Mandelkow et al. | |
| 2002/0197258 A1 | 12/2002 | Ghanbari et al. | |
| 2003/0065141 A1 | 4/2003 | Carter et al. | |
| 2003/0068316 A1 | 4/2003 | Klein et al. | |
| 2003/0073655 A1 | 4/2003 | Chain | |
| 2003/0077278 A1 | 4/2003 | Gallatin et al. | |
| 2003/0077757 A1 | 4/2003 | Andrews | |
| 2003/0086938 A1 | 5/2003 | Jensen et al. | |
| 2003/0100011 A1 | 5/2003 | Jackowski et al. | |
| 2003/0100058 A1 | 5/2003 | Roschke et al. | |
| 2003/0108551 A1 | 6/2003 | Nicolau et al. | |
| 2003/0114510 A1 | 6/2003 | Ingram et al. | |
| 2003/0147882 A1 | 8/2003 | Solomon et al. | |
| 2003/0148356 A1 | 8/2003 | Cruts et al. | |
| 2003/0157117 A1 | 8/2003 | Rasmussen et al. | |
| 2003/0180722 A1 | 9/2003 | Godbole et al. | |
| 2003/0185826 A1 | 10/2003 | Tobinick | |
| 2003/0185827 A1 | 10/2003 | Rodriguez et al. | |
| 2003/0186333 A1 | 10/2003 | Loring et al. | |
| 2003/0186374 A1 | 10/2003 | Hufton et al. | |
| 2003/0190689 A1 | 10/2003 | Crosby et al. | |
| 2003/0194403 A1 | 10/2003 | Van De et al. | |
| 2003/0195347 A1 | 10/2003 | Baker et al. | |
| 2003/0228307 A1 | 12/2003 | Ramakrishnan et al. | |
| 2003/0229907 A1 | 12/2003 | Hsiao et al. | |
| 2003/0232758 A1 | 12/2003 | St. George-Hyslop et al. | |
| 2004/0013647 A1 | 1/2004 | Solomon et al. | |
| 2004/0013680 A1 | 1/2004 | Bush et al. | |
| 2004/0018590 A1 | 1/2004 | Gerngross et al. | |
| 2004/0043418 A1 | 3/2004 | Holtzman et al. | |
| 2004/0053371 A1 | 3/2004 | Maresh et al. | |
| 2004/0058414 A1 | 3/2004 | Queen et al. | |
| 2004/0081657 A1 | 4/2004 | Schenk | |
| 2004/0116337 A1 | 6/2004 | Kapurniotu et al. | |
| 2004/0127471 A1 | 7/2004 | Reisberg | |
| 2004/0138296 A1 | 7/2004 | Robertson et al. | |
| 2004/0142872 A1 | 7/2004 | Poduslo et al. | |
| 2004/0146512 A1 | 7/2004 | Rosenthal et al. | |
| 2004/0157267 A1 | 8/2004 | Huang | |
| 2004/0157779 A1 | 8/2004 | Schenk | |
| 2004/0166119 A1 | 8/2004 | Schenk | |
| 2004/0170641 A1 | 9/2004 | Schenk | |
| 2004/0175394 A1 | 9/2004 | Schenk | |
| 2004/0185039 A1 | 9/2004 | Kohler et al. | |
| 2004/0191264 A1 | 9/2004 | Nielsen et al. | |
| 2004/0192898 A1 | 9/2004 | Jia et al. | |
| 2004/0213800 A1 | 10/2004 | Seubert et al. | |
| 2004/0223912 A1 | 11/2004 | Montalto et al. | |
| 2004/0223970 A1 | 11/2004 | Afar et al. | |
| 2004/0228865 A1 | 11/2004 | Schenk | |
| 2004/0241164 A1 | 12/2004 | Bales et al. | |
| 2004/0242845 A1 | 12/2004 | Nicolau et al. | |
| 2004/0248197 A1 | 12/2004 | Holtzman et al. | |
| 2004/0265308 A1 | 12/2004 | Schenk | |
| 2004/0265919 A1 | 12/2004 | Vanderstichele et al. | |
| 2005/0009110 A1 | 1/2005 | Chang | |
| 2005/0014821 A1 | 1/2005 | Tsai et al. | |
| 2005/0019330 A1 | 1/2005 | Schenk | |
| 2005/0019343 A1 | 1/2005 | Schenk | |
| 2005/0031651 A1 | 2/2005 | Gervais et al. | |
| 2005/0037026 A1 | 2/2005 | Schenk | |
| 2005/0042664 A1 | 2/2005 | Wu et al. | |
| 2005/0048584 A1 | 3/2005 | Lamping et al. | |
| 2005/0053614 A1 | 3/2005 | Schenk | |
| 2005/0057813 A1 | 3/2005 | Hasei et al. | |
| 2005/0059591 A1 | 3/2005 | Schenk et al. | |
| 2005/0059802 A1 | 3/2005 | Schenk et al. | |
| 2005/0090439 A1 | 4/2005 | Chalifour et al. | |
| 2005/0112543 A1 | 5/2005 | Bush et al. | |
| 2005/0118651 A1 | 6/2005 | Basi et al. | |
| 2005/0123544 A1 | 6/2005 | Schenk et al. | |
| 2005/0124016 A1 | 6/2005 | LaDu et al. | |
| 2005/0129691 A1 | 6/2005 | Gerlai | |
| 2005/0129695 A1 | 6/2005 | Mercken et al. | |
| 2005/0142131 A1 | 6/2005 | Hinton et al. | |
| 2005/0142132 A1 | 6/2005 | Schenk et al. | |
| 2005/0147613 A1 | 7/2005 | Raso | |
| 2005/0153381 A1 | 7/2005 | Marusich et al. | |
| 2005/0163744 A1 | 7/2005 | Rasmussen et al. | |
| 2005/0163788 A1 | 7/2005 | Schenk | |
| 2005/0169925 A1 | 8/2005 | Bardroff et al. | |
| 2005/0175626 A1 | 8/2005 | Delacourte et al. | |
| 2005/0249725 A1 | 11/2005 | Schenk et al. | |
| 2005/0249727 A1 | 11/2005 | Schenk | |
| 2005/0255122 A1 | 11/2005 | Schenk | |
| 2005/0272025 A1 | 12/2005 | Suo et al. | |
| 2006/0008458 A1 | 1/2006 | Solomon | |
| 2006/0029603 A1 | 2/2006 | Ellis et al. | |
| 2006/0029611 A1 | 2/2006 | Schenk | |
| 2006/0034858 A1 | 2/2006 | Schenk | |
| 2006/0039906 A1 | 2/2006 | Holtzman et al. | |
| 2006/0057646 A1 | 3/2006 | Wiltfang et al. | |
| 2006/0057701 A1 | 3/2006 | Rosenthal et al. | |
| 2006/0057702 A1 | 3/2006 | Rosenthal et al. | |
| 2006/0062786 A1 | 3/2006 | Salcedo et al. | |
| 2006/0073149 A1 | 4/2006 | Bales et al. | |
| 2006/0099211 A1 | 5/2006 | Monthe et al. | |
| 2006/0104968 A1 | 5/2006 | Bookbinder et al. | |
| 2006/0105394 A1 | 5/2006 | Pomara | |
| 2006/0110388 A1 | 5/2006 | Davies et al. | |
| 2006/0111301 A1 | 5/2006 | Mattner | |
| 2006/0127954 A1 | 6/2006 | Mercken et al. | |
| 2006/0141541 A1 | 6/2006 | McIntyre | |
| 2006/0160161 A1 | 7/2006 | Pavliakova et al. | |
| 2006/0165682 A1 | 7/2006 | Basi et al. | |
| 2006/0166275 A1 | 7/2006 | Krafft et al. | |
| 2006/0166311 A1 | 7/2006 | Okochi et al. | |
| 2006/0188505 A1 | 8/2006 | Skurkovich et al. | |
| 2006/0193850 A1 | 8/2006 | Warne et al. | |
| 2006/0198851 A1 | 9/2006 | Basi et al. | |
| 2006/0228349 A1 | 10/2006 | Acton et al. | |
| 2006/0234947 A1 | 10/2006 | Gazit | |
| 2006/0240007 A1 | 10/2006 | Sanders | |
| 2006/0241038 A1 | 10/2006 | Watanabe et al. | |
| 2006/0246075 A1 | 11/2006 | Mercken et al. | |
| 2006/0257420 A1 | 11/2006 | Zimmerman | |
| 2006/0257882 A1 | 11/2006 | Shimkets | |
| 2006/0280733 A1 | 12/2006 | Kayed et al. | |
| 2006/0292152 A1 | 12/2006 | Rosenthal et al. | |
| 2007/0009931 A1 | 1/2007 | Kirsch | |
| 2007/0010435 A1 | 1/2007 | Frangione et al. | |
| 2007/0010657 A1 | 1/2007 | Klocke et al. | |
| 2007/0015217 A1 | 1/2007 | Durham et al. | |
| 2007/0015218 A1 | 1/2007 | Cao et al. | |
| 2007/0021345 A1 | 1/2007 | Gazit | |
| 2007/0031416 A1 | 2/2007 | Shoji et al. | |
| 2007/0036789 A1 | 2/2007 | Chung | |
| 2007/0036794 A1 | 2/2007 | Devaux | |
| 2007/0042424 A1 | 2/2007 | Ebinuma et al. | |
| 2007/0048312 A1 | 3/2007 | Klein et al. | |
| 2007/0071675 A1 | 3/2007 | Wu et al. | |
| 2007/0072307 A1 | 3/2007 | Godavarti et al. | |
| 2007/0081998 A1 | 4/2007 | Kinney et al. | |
| 2007/0082350 A1 | 4/2007 | Landfield et al. | |
| 2007/0086994 A1 | 4/2007 | Wallach et al. | |

(56) References Cited

U.S. PATENT DOCUMENTS

| | | |
|---|---|---|
| 2007/0098721 A1 | 5/2007 | Hillen et al. |
| 2007/0105092 A1 | 5/2007 | Paul et al. |
| 2007/0110750 A1 | 5/2007 | Glabe et al. |
| 2007/0111252 A1 | 5/2007 | Suzuki et al. |
| 2007/0122405 A1 | 5/2007 | Roschke et al. |
| 2007/0128191 A1 | 6/2007 | Barrio |
| 2007/0134247 A9 | 6/2007 | Solomon |
| 2007/0135337 A2 | 6/2007 | Chalifour et al. |
| 2007/0140966 A1 | 6/2007 | Chang et al. |
| 2007/0148167 A1 | 6/2007 | Strohl |
| 2007/0160616 A1 | 7/2007 | Rosenthal et al. |
| 2007/0167522 A1 | 7/2007 | Imawaka et al. |
| 2007/0190046 A1 | 8/2007 | DeMaattos et al. |
| 2007/0196367 A1 | 8/2007 | Dinu |
| 2007/0213512 A1 | 9/2007 | Krafft et al. |
| 2007/0218069 A1 | 9/2007 | Gordon et al. |
| 2007/0218499 A1 | 9/2007 | Lambert et al. |
| 2007/0231331 A1 | 10/2007 | Dewji et al. |
| 2007/0248606 A1 | 10/2007 | Lannfelt et al. |
| 2007/0264276 A1 | 11/2007 | Chalifour et al. |
| 2007/0280953 A1 | 12/2007 | Rosenberg et al. |
| 2007/0292410 A1 | 12/2007 | Cashman et al. |
| 2007/0292895 A1 | 12/2007 | Shi et al. |
| 2008/0009467 A1 | 1/2008 | Henderson |
| 2008/0014194 A1 | 1/2008 | Schenk et al. |
| 2008/0014596 A1 | 1/2008 | Jerecic et al. |
| 2008/0025988 A1 | 1/2008 | Yamaguchi et al. |
| 2008/0029911 A1 | 2/2008 | Jeon et al. |
| 2008/0044356 A1 | 2/2008 | Lesne et al. |
| 2008/0044406 A1 | 2/2008 | Johnson-Wood et al. |
| 2008/0051690 A1 | 2/2008 | Mattner et al. |
| 2008/0057053 A1 | 3/2008 | Stolen |
| 2008/0057593 A1 | 3/2008 | Vanderstichele et al. |
| 2008/0058276 A1 | 3/2008 | Lu et al. |
| 2008/0058330 A1 | 3/2008 | Paris et al. |
| 2008/0089885 A1 | 4/2008 | Smith et al. |
| 2008/0096818 A1 | 4/2008 | Schenk et al. |
| 2008/0107601 A1 | 5/2008 | Lauwereys et al. |
| 2008/0107649 A1 | 5/2008 | Zurbriggen |
| 2008/0113444 A1 | 5/2008 | Pray |
| 2008/0131422 A1 | 6/2008 | Sugimura et al. |
| 2008/0199879 A1 | 8/2008 | Takayama et al. |
| 2008/0220449 A1 | 9/2008 | Vasan et al. |
| 2008/0292639 A1 | 11/2008 | Shen et al. |
| 2008/0299111 A1 | 12/2008 | Delacourte et al. |
| 2009/0018084 A1 | 1/2009 | Krafft et al. |
| 2009/0023159 A1 | 1/2009 | Mendez |
| 2009/0035295 A1 | 2/2009 | Hillen et al. |
| 2009/0035307 A1 | 2/2009 | Barghorn et al. |
| 2009/0074775 A1 | 3/2009 | Holtzman et al. |
| 2009/0155246 A1 | 6/2009 | Gellerfors et al. |
| 2009/0156471 A1 | 6/2009 | Gazit et al. |
| 2009/0162362 A1 | 6/2009 | Sarasa |
| 2009/0162878 A1 | 6/2009 | Kim et al. |
| 2009/0175847 A1 | 7/2009 | Hillen |
| 2009/0191190 A1 | 7/2009 | Barghorn |
| 2009/0214515 A1 | 8/2009 | Holzman |
| 2009/0232801 A1 | 9/2009 | Hillen |
| 2009/0238831 A1 | 9/2009 | Hillen |
| 2010/0028333 A1 | 2/2010 | Getty et al. |
| 2010/0173828 A1 | 7/2010 | Hillen |
| 2010/0209346 A1 | 8/2010 | Hillen et al. |
| 2011/0092445 A1 | 4/2011 | Barghorn |
| 2011/0212109 A1 | 9/2011 | Barghorn |
| 2011/0256138 A1 | 10/2011 | Barghorn |
| 2011/0287005 A1 | 11/2011 | Hillen |
| 2012/0034166 A1 | 2/2012 | Hillen |

FOREIGN PATENT DOCUMENTS

| | | |
|---|---|---|
| CN | 1396183 | 2/2003 |
| CN | 1446581 | 10/2003 |
| CN | 1673369 | 9/2005 |
| CN | 1721437 | 1/2006 |
| CN | 1803842 | 7/2006 |
| CN | 101058608 | 10/2007 |
| CN | 101084909 | 12/2007 |
| CN | 101152576 | 4/2008 |
| DE | 19902550 | 7/2000 |
| DE | 10055703 | 5/2002 |
| DE | 10303974 | 8/2004 |
| DE | 102004039326 | 2/2006 |
| EP | 0045665 | 2/1982 |
| EP | 0050424 | 9/1985 |
| EP | 0285159 | 10/1988 |
| EP | 0341491 | 11/1989 |
| EP | 0084796 | 5/1990 |
| EP | 0391714 | 10/1990 |
| EP | 0411974 | 2/1991 |
| EP | 0415801 | 3/1991 |
| EP | 0237362 | 3/1992 |
| EP | 0201184 | 12/1992 |
| EP | 0229246 | 8/1993 |
| EP | 0368684 | 3/1994 |
| EP | 0239400 | 8/1994 |
| EP | 0613007 | 8/1994 |
| EP | 0623675 | 11/1994 |
| EP | 0557270 | 5/1995 |
| EP | 0519598 | 6/1995 |
| EP | 0440619 | 1/1996 |
| EP | 0304013 | 6/1996 |
| EP | 0589877 | 11/1996 |
| EP | 0436597 | 4/1997 |
| EP | 0258017 | 6/1997 |
| EP | 0783104 | 7/1997 |
| EP | 0444856 | 9/1997 |
| EP | 0816492 | 1/1998 |
| EP | 0592127 | 4/1998 |
| EP | 0274826 | 8/1998 |
| EP | 0527839 | 12/1998 |
| EP | 1038958 | 9/2000 |
| EP | 1094080 | 4/2001 |
| EP | 1130032 | 11/2001 |
| EP | 1172378 | 1/2002 |
| EP | 1176195 | 1/2002 |
| EP | 0877939 | 6/2002 |
| EP | 0683234 | 5/2003 |
| EP | 1308461 | 5/2003 |
| EP | 1408333 | 4/2004 |
| EP | 1420032 | 5/2004 |
| EP | 1270592 | 9/2004 |
| EP | 1467212 | 10/2004 |
| EP | 0592106 | 11/2004 |
| EP | 1200470 | 11/2004 |
| EP | 0519596 | 2/2005 |
| EP | 1538163 | 6/2005 |
| EP | 1632242 | 3/2006 |
| EP | 1092767 | 10/2006 |
| EP | 1717250 | 11/2006 |
| EP | 0998495 | 12/2006 |
| EP | 1731913 | 12/2006 |
| EP | 1049712 | 1/2007 |
| EP | 1741783 | 1/2007 |
| EP | 1346041 | 2/2007 |
| EP | 1752472 | 2/2007 |
| EP | 1592476 | 4/2007 |
| EP | 0970203 | 5/2007 |
| EP | 1787998 | 5/2007 |
| EP | 0948536 | 6/2007 |
| EP | 1160256 | 6/2007 |
| EP | 1379546 | 6/2007 |
| EP | 1792991 | 6/2007 |
| EP | 1842859 | 10/2007 |
| EP | 1861422 | 12/2007 |
| EP | 1878751 | 1/2008 |
| EP | 1434053 | 3/2008 |
| EP | 1521831 | 4/2008 |
| EP | 1778837 | 4/2008 |
| EP | 1911765 | 4/2008 |
| EP | 1781644 | 5/2008 |
| EP | 0911398 | 6/2008 |
| EP | 1976877 | 10/2008 |
| EP | 2009445 | 12/2008 |
| EP | 1623719 | 1/2009 |

(56) References Cited

FOREIGN PATENT DOCUMENTS

| | | |
|---|---|---|
| EP | 1681566 | 8/2009 |
| EP | 1766396 | 8/2010 |
| EP | 1720909 | 11/2011 |
| FR | 2740454 | 4/1997 |
| FR | 2741881 | 6/1997 |
| GB | 1495159 | 12/1977 |
| GB | 2371303 | 7/2002 |
| GR | 1005016 | 10/2005 |
| JP | 63240797 | 10/1988 |
| JP | 4252195 | 9/1992 |
| JP | 4320694 | 11/1992 |
| JP | 7209295 | 8/1995 |
| JP | 7209296 | 8/1995 |
| JP | 07238096 | 9/1995 |
| JP | 7309900 | 11/1995 |
| JP | 8245700 | 9/1996 |
| JP | 9067397 | 3/1997 |
| JP | 10075781 | 3/1998 |
| JP | 10210982 | 8/1998 |
| JP | 2000050885 | 2/2000 |
| JP | 2000354487 | 12/2000 |
| JP | 2001231578 | 8/2001 |
| JP | 2002040023 | 2/2002 |
| JP | 2002253252 | 9/2002 |
| JP | 2004107260 | 4/2004 |
| JP | 2005185281 | 7/2005 |
| JP | 2006166879 | 6/2006 |
| JP | 2006213621 | 8/2006 |
| JP | 2006265189 | 10/2006 |
| JP | 2007077103 | 3/2007 |
| JP | 2007300856 | 11/2007 |
| JP | 2007319127 | 12/2007 |
| JP | 2008096311 | 4/2008 |
| KR | 100806914 | 2/2008 |
| WO | WO 88/03951 | 6/1988 |
| WO | WO 89/06689 | 7/1989 |
| WO | WO 89/07657 | 8/1989 |
| WO | WO 90/02809 | 3/1990 |
| WO | WO 90/05144 | 5/1990 |
| WO | WO 90/12870 | 11/1990 |
| WO | WO 90/14424 | 11/1990 |
| WO | WO 90/14430 | 11/1990 |
| WO | WO 90/14443 | 11/1990 |
| WO | WO 91/05548 | 5/1991 |
| WO | WO 91/09967 | 7/1991 |
| WO | WO 91/17271 | 11/1991 |
| WO | WO 92/01047 | 1/1992 |
| WO | WO 92/02551 | 2/1992 |
| WO | WO 92/00969 | 6/1992 |
| WO | WO 92/09690 | 6/1992 |
| WO | WO 92/11018 | 7/1992 |
| WO | WO 92/15679 | 9/1992 |
| WO | WO 92/18619 | 10/1992 |
| WO | WO 92/19244 | 11/1992 |
| WO | WO 92/20791 | 11/1992 |
| WO | WO 92/22324 | 12/1992 |
| WO | WO 93/01288 | 1/1993 |
| WO | WO 93/08302 | 4/1993 |
| WO | WO 93/11236 | 10/1993 |
| WO | WO 94/02602 | 3/1994 |
| WO | WO 94/17197 | 8/1994 |
| WO | WO 95/07707 | 3/1995 |
| WO | WO 95/11311 | 4/1995 |
| WO | WO 95/11994 | 5/1995 |
| WO | WO 95/15982 | 6/1995 |
| WO | WO 95/16787 | 6/1995 |
| WO | WO 95/20401 | 8/1995 |
| WO | WO 96/20218 | 7/1996 |
| WO | WO 96/20698 | 7/1996 |
| WO | WO 96/28187 | 9/1996 |
| WO | WO 96/33735 | 10/1996 |
| WO | WO 96/34096 | 10/1996 |
| WO | WO 96/39512 | 12/1996 |
| WO | WO 96/40731 | 12/1996 |
| WO | WO 97/08320 | 3/1997 |
| WO | WO 97/10505 | 3/1997 |
| WO | WO 97/18476 | 5/1997 |
| WO | WO 97/29131 | 8/1997 |
| WO | WO 97/32572 | 9/1997 |
| WO | WO 97/44013 | 11/1997 |
| WO | WO 97/46678 | 12/1997 |
| WO | WO 98/05350 | 2/1998 |
| WO | WO 98/07850 | 2/1998 |
| WO | WO 98/13490 | 4/1998 |
| WO | WO 98/16654 | 4/1998 |
| WO | WO 98/22120 | 5/1998 |
| WO | WO 98/24893 | 6/1998 |
| WO | WO 98/28445 | 7/1998 |
| WO | WO 98/31346 | 7/1998 |
| WO | WO 98/31700 | 7/1998 |
| WO | WO 98/33815 | 8/1998 |
| WO | WO 98/41201 | 9/1998 |
| WO | WO 98/47343 | 10/1998 |
| WO | WO 98/49286 | 11/1998 |
| WO | WO 98/50433 | 11/1998 |
| WO | WO 98/51793 | 11/1998 |
| WO | WO 99/05175 | 2/1999 |
| WO | WO 99/09150 | 2/1999 |
| WO | WO 99/12870 | 3/1999 |
| WO | WO 99/13908 | 3/1999 |
| WO | WO 99/15154 | 4/1999 |
| WO | WO 99/20253 | 4/1999 |
| WO | WO 99/22024 | 5/1999 |
| WO | WO 99/25044 | 5/1999 |
| WO | WO 99/27944 | 6/1999 |
| WO | WO 99/27949 | 6/1999 |
| WO | WO 91/10737 | 7/1999 |
| WO | WO 91/10741 | 7/1999 |
| WO | WO 99/33815 | 7/1999 |
| WO | WO 99/36569 | 7/1999 |
| WO | WO 99/40909 | 8/1999 |
| WO | WO 99/45031 | 9/1999 |
| WO | WO 99/45962 | 9/1999 |
| WO | WO 99/53049 | 10/1999 |
| WO | 99/55842 | 11/1999 |
| WO | WO 99/58157 | 11/1999 |
| WO | WO 99/58564 | 11/1999 |
| WO | WO 99/59571 | 11/1999 |
| WO | WO 99/62505 | 12/1999 |
| WO | WO 99/66903 | 12/1999 |
| WO | WO 00/09560 | 2/2000 |
| WO | WO 00/17345 | 3/2000 |
| WO | WO 00/18805 | 4/2000 |
| WO | WO 00/29446 | 5/2000 |
| WO | WO 00/32805 | 6/2000 |
| WO | WO 00/35939 | 6/2000 |
| WO | WO 00/37504 | 6/2000 |
| WO | WO 00/56772 | 9/2000 |
| WO | WO 00/58344 | 10/2000 |
| WO | WO 00/72870 | 12/2000 |
| WO | WO 00/72876 | 12/2000 |
| WO | WO 00/72880 | 12/2000 |
| WO | WO 00/75328 | 12/2000 |
| WO | WO 00/77178 | 12/2000 |
| WO | WO 00/78807 | 12/2000 |
| WO | WO 01/10900 | 2/2001 |
| WO | WO 01/16364 | 3/2001 |
| WO | WO 01/18169 | 3/2001 |
| WO | WO 01/32712 | 5/2001 |
| WO | WO 01/39796 | 6/2001 |
| WO | WO 01/42306 | 6/2001 |
| WO | WO 01/62284 | 8/2001 |
| WO | WO 01/62801 | 8/2001 |
| WO | WO 01/68860 | 9/2001 |
| WO | WO 01/83519 | 11/2001 |
| WO | WO 01/83525 | 11/2001 |
| WO | WO 01/85093 | 11/2001 |
| WO | WO 01/90182 | 11/2001 |
| WO | WO 01/98361 | 12/2001 |
| WO | WO 02/00245 | 1/2002 |
| WO | WO 02/03911 | 1/2002 |
| WO | WO 02/21141 | 3/2002 |
| WO | WO 02/30980 | 4/2002 |
| WO | WO 02/34777 | 5/2002 |

(56) References Cited

FOREIGN PATENT DOCUMENTS

| | | |
|---|---|---|
| WO | WO 02/36614 | 5/2002 |
| WO | 02/46237 | 6/2002 |
| WO | WO 02/055552 | 7/2002 |
| WO | WO 02/059155 | 8/2002 |
| WO | WO 02/062851 | 8/2002 |
| WO | WO 02/074240 | 9/2002 |
| WO | WO 02/081505 | 10/2002 |
| WO | WO 02/085922 | 10/2002 |
| WO | WO 02/088306 | 11/2002 |
| WO | WO 02/088307 | 11/2002 |
| WO | WO 02/094870 | 11/2002 |
| WO | WO 02/094985 | 11/2002 |
| WO | WO 02/096350 | 12/2002 |
| WO | WO 02/096937 | 12/2002 |
| WO | WO 03/000714 | 1/2003 |
| WO | WO 03/008626 | 1/2003 |
| WO | WO 03/014162 | 2/2003 |
| WO | WO 03/014329 | 2/2003 |
| WO | WO 03/015617 | 2/2003 |
| WO | WO 03/015691 | 2/2003 |
| WO | WO 03/015812 | 2/2003 |
| WO | WO 03/016466 | 2/2003 |
| WO | WO 03/016467 | 2/2003 |
| WO | WO 03/020212 | 3/2003 |
| WO | WO 03/028668 | 4/2003 |
| WO | WO 03/031475 | 4/2003 |
| WO | WO 03/035835 | 5/2003 |
| WO | WO 03/039467 | 5/2003 |
| WO | WO 03/045128 | 6/2003 |
| WO | WO 03/046012 | 6/2003 |
| WO | WO 03/047499 | 6/2003 |
| WO | WO 03/051374 | 6/2003 |
| WO | WO 03/070760 | 8/2003 |
| WO | WO 03/074081 | 8/2003 |
| WO | 03/074715 | 9/2003 |
| WO | WO 03/074004 | 9/2003 |
| WO | WO 03/074569 | 9/2003 |
| WO | WO 03/076455 | 9/2003 |
| WO | WO 03/077858 | 9/2003 |
| WO | 03/080672 | 10/2003 |
| WO | WO 03/089460 | 10/2003 |
| WO | WO 03/090772 | 11/2003 |
| WO | WO 03/091734 | 11/2003 |
| WO | WO 03/095429 | 11/2003 |
| WO | WO 03/100419 | 12/2003 |
| WO | WO 03/104437 | 12/2003 |
| WO | WO 03/105658 | 12/2003 |
| WO | WO 2004/001422 | 12/2003 |
| WO | WO 2004/003019 | 1/2004 |
| WO | WO 2004/003563 | 1/2004 |
| WO | WO 2004/006861 | 1/2004 |
| WO | WO 2004/009776 | 1/2004 |
| WO | WO 2004/011674 | 2/2004 |
| WO | WO 2004/011943 | 2/2004 |
| WO | WO 2004/013172 | 2/2004 |
| WO | WO 2004/014296 | 2/2004 |
| WO | WO 2004/014367 | 2/2004 |
| WO | WO 2004/016282 | 2/2004 |
| WO | WO 2004/016655 | 3/2004 |
| WO | WO 2004/018997 | 3/2004 |
| WO | WO 2004/019045 | 3/2004 |
| WO | WO 2004/024090 | 3/2004 |
| WO | WO 2004/029093 | 4/2004 |
| WO | WO 2004/029630 | 4/2004 |
| WO | WO 2004/031241 | 4/2004 |
| WO | WO 2004/031400 | 4/2004 |
| WO | WO 2004/032868 | 4/2004 |
| WO | WO 2004/033397 | 4/2004 |
| WO | WO 2004/038411 | 5/2004 |
| WO | WO 2004/041067 | 5/2004 |
| WO | WO 2004/043989 | 5/2004 |
| WO | WO 2004/044204 | 5/2004 |
| WO | WO 2004/045525 | 6/2004 |
| WO | WO 2004/050707 | 6/2004 |
| WO | WO 2004/050850 | 6/2004 |
| WO | WO 2004/050876 | 6/2004 |
| WO | WO 2004/056318 | 7/2004 |
| WO | WO 2004/058239 | 7/2004 |
| WO | WO 2004/058258 | 7/2004 |
| WO | WO 2004/058820 | 7/2004 |
| WO | WO 2004/062556 | 7/2004 |
| WO | 2004/068931 | 8/2004 |
| WO | WO 2004/065419 | 8/2004 |
| WO | WO 2004/065569 | 8/2004 |
| WO | WO 2004/067561 | 8/2004 |
| WO | WO 2004/069182 | 8/2004 |
| WO | WO 2004/071408 | 8/2004 |
| WO | WO 2004/072286 | 8/2004 |
| WO | WO 2004/074837 | 9/2004 |
| WO | WO 2004/078140 | 9/2004 |
| WO | WO 2004/085712 | 10/2004 |
| WO | WO 2004/087733 | 10/2004 |
| WO | WO 2004/087735 | 10/2004 |
| WO | WO 2004/090544 | 10/2004 |
| WO | WO 2004/095031 | 11/2004 |
| WO | WO 2004/098631 | 11/2004 |
| WO | WO 2004/104597 | 12/2004 |
| WO | WO 2004/108895 | 12/2004 |
| WO | WO 2004/111250 | 12/2004 |
| WO | WO 2005/000897 | 1/2005 |
| WO | WO 2005/005638 | 1/2005 |
| WO | WO 2005/011599 | 2/2005 |
| WO | WO 2005/012330 | 2/2005 |
| WO | WO 2005/014618 | 2/2005 |
| WO | WO 2005/016236 | 2/2005 |
| WO | WO 2005/018424 | 3/2005 |
| WO | WO 2005/018536 | 3/2005 |
| WO | WO 2005/025516 | 3/2005 |
| WO | WO 2005/025592 | 3/2005 |
| WO | WO 2005/025616 | 3/2005 |
| WO | WO 2005/026360 | 3/2005 |
| WO | WO 2005/027965 | 3/2005 |
| WO | WO 2005/028511 | 3/2005 |
| WO | WO 2005/033142 | 4/2005 |
| WO | WO 2005/033145 | 4/2005 |
| WO | WO 2005/037209 | 4/2005 |
| WO | WO 2005/040212 | 5/2005 |
| WO | WO 2005/041650 | 5/2005 |
| WO | WO 2005/044306 | 5/2005 |
| WO | WO 2005/046605 | 5/2005 |
| WO | WO 2005/047484 | 5/2005 |
| WO | WO 2005/047860 | 5/2005 |
| WO | WO 2005/051998 | 6/2005 |
| WO | WO 2005/052002 | 6/2005 |
| WO | WO 2005/053604 | 6/2005 |
| WO | WO 2005/058815 | 6/2005 |
| WO | WO 2005/058940 | 6/2005 |
| WO | WO 2005/120571 | 7/2005 |
| WO | WO 2005/070965 | 8/2005 |
| WO | WO 2005/072777 | 8/2005 |
| WO | WO 2005/080986 | 9/2005 |
| WO | WO 2005/081872 | 9/2005 |
| WO | WO 2005/090971 | 9/2005 |
| WO | WO 2005/095457 | 10/2005 |
| WO | WO 2005/096730 | 10/2005 |
| WO | WO 2005/100584 | 10/2005 |
| WO | WO 2005/105841 | 11/2005 |
| WO | WO 2005/105847 | 11/2005 |
| WO | WO 2005/105998 | 11/2005 |
| WO | WO 2005/108378 | 11/2005 |
| WO | WO 2005/110056 | 11/2005 |
| WO | WO 2005/123775 | 12/2005 |
| WO | WO 2005/123776 | 12/2005 |
| WO | WO 2006/005588 | 1/2006 |
| WO | WO 2006/005707 | 1/2006 |
| WO | WO 2006/014478 | 2/2006 |
| WO | WO 2006/014638 | 2/2006 |
| WO | WO 2006/015976 | 2/2006 |
| WO | WO 2006/016644 | 2/2006 |
| WO | WO 2006/033688 | 3/2006 |
| WO | WO 2006/036291 | 4/2006 |
| WO | WO 2006/037604 | 4/2006 |
| WO | WO 2006/038729 | 4/2006 |
| WO | WO 2006/039327 | 4/2006 |

(56) References Cited

FOREIGN PATENT DOCUMENTS

| | | |
|---|---|---|
| WO | WO 2006/039470 | 4/2006 |
| WO | WO 2006/040153 | 4/2006 |
| WO | WO 2006/041934 | 4/2006 |
| WO | WO 2006/047254 | 5/2006 |
| WO | WO 2006/047670 | 5/2006 |
| WO | WO 2006/050041 | 5/2006 |
| WO | WO 2006/050667 | 5/2006 |
| WO | WO 2006/052924 | 5/2006 |
| WO | WO 2006/053428 | 5/2006 |
| WO | WO 2006/055178 | 5/2006 |
| WO | WO 2006/066049 | 6/2006 |
| WO | WO 2006/066089 | 6/2006 |
| WO | WO 2006/066118 | 6/2006 |
| WO | WO 2006/066171 | 6/2006 |
| WO | WO 2006/066233 | 6/2006 |
| WO | WO 2006/067792 | 6/2006 |
| WO | WO 2006/069081 | 6/2006 |
| WO | WO 2006/069202 | 6/2006 |
| WO | WO 2006/081171 | 8/2006 |
| WO | WO 2006/083533 | 8/2006 |
| WO | WO 2006/083689 | 8/2006 |
| WO | WO 2006/087550 | 8/2006 |
| WO | WO 2006/094192 | 9/2006 |
| WO | WO 2006/094724 | 9/2006 |
| WO | WO 2006/095041 | 9/2006 |
| WO | WO 2006/096529 | 9/2006 |
| WO | WO 2006/096653 | 9/2006 |
| WO | WO 2006/099543 | 9/2006 |
| WO | WO 2006/100679 | 9/2006 |
| WO | WO 2006/103116 | 10/2006 |
| WO | WO 2006/110748 | 10/2006 |
| WO | WO 2006/116369 | 11/2006 |
| WO | WO 2006/118959 | 11/2006 |
| WO | WO 2006/119449 | 11/2006 |
| WO | WO 2006/121656 | 11/2006 |
| WO | WO 2006/125830 | 11/2006 |
| WO | WO 2006/128163 | 11/2006 |
| WO | WO 2006/133164 | 12/2006 |
| WO | WO 2006/137354 | 12/2006 |
| WO | WO 2007/005358 | 1/2007 |
| WO | WO 2007/005359 | 1/2007 |
| WO | WO 2007/008547 | 1/2007 |
| WO | WO 2007/011639 | 1/2007 |
| WO | WO 2007/011834 | 1/2007 |
| WO | WO 2007/017686 | 2/2007 |
| WO | WO 2007/019620 | 2/2007 |
| WO | WO 2007/021886 | 2/2007 |
| WO | WO 2007/022416 | 2/2007 |
| WO | WO 2007/040437 | 4/2007 |
| WO | WO 2007/042261 | 4/2007 |
| WO | WO 2007/047967 | 4/2007 |
| WO | WO 2007/047995 | 4/2007 |
| WO | WO 2007/050359 | 5/2007 |
| WO | WO 2007/053661 | 5/2007 |
| WO | WO 2007/059135 | 5/2007 |
| WO | WO 2007/059203 | 5/2007 |
| WO | WO 2007/062088 | 5/2007 |
| WO | WO 2007/062852 | 6/2007 |
| WO | WO 2007/064917 | 6/2007 |
| WO | WO 2007/064919 | 6/2007 |
| WO | WO 2007/064972 | 6/2007 |
| WO | WO 2007/067512 | 6/2007 |
| WO | WO 2007/068411 | 6/2007 |
| WO | WO 2007/068429 | 6/2007 |
| WO | WO 2007/082750 | 7/2007 |
| WO | WO 2007/068412 | 8/2007 |
| WO | WO 2007/088399 | 8/2007 |
| WO | WO 2007/088712 | 8/2007 |
| WO | WO 2007/090872 | 8/2007 |
| WO | WO 2007/092861 | 8/2007 |
| WO | WO 2007/096076 | 8/2007 |
| WO | WO 2007/097251 | 8/2007 |
| WO | WO 2007/098417 | 8/2007 |
| WO | WO 2007/103788 | 9/2007 |
| WO | WO 2007/106617 | 9/2007 |
| WO | WO 2007/108756 | 9/2007 |
| WO | WO 2007/109107 | 9/2007 |
| WO | WO 2007/109749 | 9/2007 |
| WO | WO 2007/112288 | 10/2007 |
| WO | WO 2007/113172 | 10/2007 |
| WO | WO 2007/118984 | 10/2007 |
| WO | WO 2007/119685 | 10/2007 |
| WO | WO 2007/123345 | 11/2007 |
| WO | WO 2007/125351 | 11/2007 |
| WO | WO 2007/127393 | 11/2007 |
| WO | WO 2007/127448 | 11/2007 |
| WO | WO 2007/129457 | 11/2007 |
| WO | WO 2007/144198 | 12/2007 |
| WO | WO 2007/149032 | 12/2007 |
| WO | WO 2008/002893 | 1/2008 |
| WO | WO 2008/008939 | 1/2008 |
| WO | WO 2008/011348 | 1/2008 |
| WO | WO 2008/012101 | 1/2008 |
| WO | WO 2008/015384 | 2/2008 |
| WO | WO 2008/021296 | 2/2008 |
| WO | WO 2008/022349 | 2/2008 |
| WO | WO 2008/027526 | 3/2008 |
| WO | WO 2008/028939 | 3/2008 |
| WO | WO 2008/030251 | 3/2008 |
| WO | WO 2008/030973 | 3/2008 |
| WO | WO 2008/031911 | 3/2008 |
| WO | WO 2008/045962 | 4/2008 |
| WO | WO 2008/047111 | 4/2008 |
| WO | WO 2008/051017 | 5/2008 |
| WO | WO 2008/051326 | 5/2008 |
| WO | WO 2008/057240 | 5/2008 |
| WO | WO 2008/060364 | 5/2008 |
| WO | WO 2008/061795 | 5/2008 |
| WO | WO 2008/064244 | 5/2008 |
| WO | WO 2008/067464 | 6/2008 |
| WO | WO 2008/070229 | 6/2008 |
| WO | WO 2008/071394 | 6/2008 |
| WO | WO 2008/084402 | 7/2008 |
| WO | WO 2008/104385 | 9/2008 |
| WO | WO 2008/104386 | 9/2008 |
| WO | WO 2008/107677 | 9/2008 |
| WO | WO 2008/110885 | 9/2008 |
| WO | WO 2008/122441 | 10/2008 |
| WO | WO 2008/124940 | 10/2008 |
| WO | WO 2008/129023 | 10/2008 |
| WO | WO 2008/130449 | 10/2008 |
| WO | WO 2008/131298 | 10/2008 |
| WO | WO 2008/134034 | 11/2008 |
| WO | WO 2008/143708 | 11/2008 |
| WO | 20081150949 | 12/2008 |
| WO | WO 2008/150467 | 12/2008 |
| WO | WO 2008/150946 | 12/2008 |
| WO | WO 2008/156621 | 12/2008 |
| WO | WO 2008/156622 | 12/2008 |
| WO | WO 2009/008890 | 1/2009 |
| WO | WO 2009/008891 | 1/2009 |
| WO | WO 2009/009768 | 1/2009 |
| WO | WO 2009/044160 | 4/2009 |
| WO | WO 2009/048537 | 4/2009 |
| WO | WO 2009/048538 | 4/2009 |
| WO | WO 2009/048539 | 4/2009 |
| WO | 2009/134711 | 11/2009 |
| WO | 2010/011947 | 1/2010 |
| WO | WO 2010/097012 | 9/2010 |
| WO | 2012/024187 | 2/2012 |

OTHER PUBLICATIONS

United States Patent Office Notice of Allowance for U.S. Appl. No. 11/574,876 dated Sep. 30, 2013 (11 pages).
Ma, B. et al., "Polymorphic C-terminal-sheet interactions determine the formation of fibril or amyloid-derived diffusible ligand-like globulomer for the Alzheimer A42 dodecamer," J. Biol. Chem. (2010) 285(47):37102-37110.
European Patent Office Action for Application No. 10179297 dated Jul. 21, 2014 (9 pages).
European Patent Office Action for Application No. 10179281 dated Jul. 21, 2014 (11 pages).

(56) References Cited

OTHER PUBLICATIONS

European Patent Office Action for Application No. 10179255 dated Jul. 21, 2014 (11 pages).
European Patent Office Action for Application No. 11715837 dated Oct. 10, 2014 (4 pages).
United States Patent Office Action for U.S. Appl. No. 13/085,891 dated Nov. 26, 2013 (10 pages).
Aisen, P.S. et al., "The development of anti-amyloid etherapy for Alzheimer's disease: from secretase modulators to polymerisation inhibitors," CNS Drugs (2005) 19(12):989-996.
Albert, S.E. et al., "Time-dependent induction of protective anti-influenza immune responses in human peripheral blood lymphocyte/SCID mice," J. Immunol. (1997) 153(3):1393-1403.
Almquist, R.G. et al., "Synthesis and biological activity of a ketomethylene analogue of a tripeptide inhibitor of angiotensin converting enzyme," J. Med. Chem. (1980) 23:1392-1398.
Altschul, S.F. et la., "Gapped BLAST and PSI_BLAST: a new generation of protein database search programs," Nucl. Acids Res. (1997) 25(17):3389-3402.
Ames, R.S. et al., "Conversion of murine Fabs isolated from a combinatorial phage display library to full length immunoglobulins," J. Immunol. Meth. (1995) 184:177-186.
Arai, K. et al., "an ELISA to determine the biodistribution of human monoclonal antibody in tumor-xenografted SCID mice," J. Immunol. Meth. (1998) 217:79-85.
Ardaillou, R., "An Ang II antagonist improves the Alzheimer's disease of the mouse," Medecine/Sciences (2008) 24(1):41.
Arispe, N. et al., "Alzheimer disease amyloid beta protein forms calcium channels in bilayer membranes: blockage by tromethamine and aluminum," Proc. Natl. Acad. Sci. (1993) 90:567-571.
Armstrong, J. et al., "Familial Alzheimer disease associated with A713T mutation in APP," Neurosci. Letters (2004) 370;241-243.
Asakura, K. et al., "Alpha-eudesmol, a P/Q-type Ca2+ channel blocker, inhibits neurogenic vasodilatation and extravasation following electrical stimulation of trigeminal gangion," Brain Res. (2000) 873:94-101, abstract.
Asakura, K. et al., "P/Q-type Ca2+ channel blocker game-agatoxin IVA protects against brain injury after focal ischemia in rats," Brain Res. (1997) 776:140-145, abstract.
Askanas, V. et al., "Inclusion-body myositis: a myodegenerative conformational disorder associated with Abeta, protein misfolding, and proteasome inhibition," Neurology (2006) 66(2) Supp 1:S39-48.
Askanas, V. et al., "Molecular pathology and pathogenesis of inclusion-body myositis," Microscopy Res. Technique (2005) 67:114-120.
Askanas, V. et al., "Proposed pathogenetic cascade of inclusion-body myositis: importance of amyloid-beta, misfolded proteins, predisposing genes, and aging," Curr. Opin. Rheumatol. (2003) 15(6):737-744.
Atherton et al., "the fluorenylmethoxycarbonyl amino protecting group," The Peptides: Analysis, Synthesis, Biology (1987) 9:1-38, Academic Press.
Ausubel, et al., Current Protocols in Molecular Biology (1993) Table of Contents.
Ausubel, F. et al., Short Protocols in molecular biology, 3rd Edition (1995), Table of Contents.
Ausubel, F.M. et al., Current Protocols in Molecular Biology (1989).
Author Guidelines, Journal of Neurochemistry, Version 13, Jun. 2012, 14 pages.
Auvynet, C. et al., "Structural requirements for antimicrobial versus chemoattractant activities for dermaseptin S9," FEBS J. (2008) 2754134-4151.
Awasthi et al., "Amyloid-beta causes apoptosis of newronal cells via caspase cascade, which can be prevented by amyloid-beta-derived short peptides," Exp. Neurology (2005) 196(2):282-289.
Azzazy, H.M.E. et al., "Phage display technology: clinical applications and recent innovations," Clin. Biochem. (2002) 35:425-445.

Babcook, J.S. et al., "A novel strategy for generating monoclonal antibodies from single, isolated lymphocytes producing antibodies of defined specificities," Proc. Natl. Acad. Sci. (1996) 93:7843-7848.
Bagriantsev, S. et al., "Modulation of Abeta SUB 42 low-n oligomerization using a novel yeast reporter system," BMC Biol. (2006) 4:32, 12 pages.
Banker, G.A. et al., "Rat hippocampal neurons in dispersed cell culture," Brain Res. (1977) 126(3):397-425.
Barany, G. et al., "Solid-phase peptide synthesis," in The Peptides: Analysis, Synthesis, Biology, (1980), Academic Press, Gross editor, vol. 2, p. 1-284.
Barbas, III, C.F. et al., "Assembly of combinatorial antibody libraries on phage surfaces: the gene III site," proc. Natl. Acad. Sci. USA (1991) 88:7978-7982.
Barghorn, S. et al., "Globular amyloid beta-peptide 1-42 oligomer—a homogeneous and stable neuropathological protein in Alzheimer's disease," J. Neurochem. (2005) 95(1):834-847.
Barrow, C.J. et al., "Solution conformations and aggregational properties of synthetic amyloid beta-peptides of Alzheimer's disease. Analysis of circular dichroism spectra," J. Mol. Biol. (1992) 225(4):1075-1093.
Bartolini, M. et al., "Insight into the kinetic of amyloid beta (1-42) peptide self-aggregation: elucidation of inhibitors' mechanism of action," Chembiochem. (2007) 8(17):2152-61.
Bateman, D. et al., "Specific binding of Alzheimer amyloid peptides to the cell surface implicates the presence of a membrane receptor," Neurobiol. of Aging (2004) 9th International Conf. On Alzheimers Disease and Related Disorders, Philadelphia, PA, Jul. 17-22, 2004.
Bateman, R.J. et al., "Human amyloid-beta synthesis and clearance rates as measured in cerebrospinal fluid in vivo," Nature Med. (2006) 12(7):856-861.
Bates, K.A. et al., "Clearance mechanisms of Alzheimer's amyloid-Beta peptide: implications for therapeutic design and diagnostic tests," Mol. Psych. (2009) 14(5):469-486.
Bayer, T.A. et al., "Review on the APP/PS1K1 mouse model: intraneuronal A beta accumulation triggers axonopathy, neuron loss and working memory impairment," Genes Brain Behav. (2008) 7:6-11.
Bedzyk, W.D. et al., "Active site structure and antigen binding properties of idiotypically cross-reactive anti-fluorescein monoclonal antibodies," J. Biol. Chem. (1990) 265(1):133-138.
Bell, K.A. et al., MAPK recruitment by beta-amyloid in organotypid hippocampal slice cultures depends on physical state and exposure time, J. Neurochem. (2004) 91(2):349-361.
Belokon, Y.N. et al., "Improved procedures for the synthesis of (S)-2-[N-(N'-benzyl-prolyl)amino]benzophenoe (BPB) and Ni(II) complexes of Schiff's bases derived from BPB and amino acids," Tetrahedron: Asymmetry (1998) 9:4249-4252.
Bennett et al., "Immunization therapy for Alzheimer disease?" Neurology (2005) 64:10-12.
Berman, D.E. et al., "Oligomeric amyloid-beta peptide disrupts phosphatidylinositol-4,5-bisphosphate metabolism," Nat. Neurosci. (2008) 11(5):547-554.
Bernstein, S.L. et al., "Amyloid beta-protein: monomer structure and early aggregation states of Abeta42 and its pro SUP 19 alloform," J. Am. Chem. Soc. (2005) 127(7):2075-2084.
Bernstein, S.L. et al., "Amyloid-beta protein oligomerization and the importance of tetramers and dodecamers in the aetiology of Alzheimer's disease," Nature Chem. (2009) 1:326-331.
Better, M. et al., "*Escherichia coli* secretion of an active chimeric antibody fragment," Science (1988) 240:10411043.
Bezprozvanny, I. et al., "Neuronal calcium mishandling and the pathogenesis of Alzheimer's disease," Trends Neurosci. (2008) 31(9):454-463.
Bharadwaj, P. e al., "A new method to measure cellular toxicity of non-fibrillar and fibrillar Alzheimer's Abeta using yeast," J. Alzheimer's Disease (2008) 13(2):147-150.
Bhaskar, K. et al., "The P13K-Akt-mTOR pathway regulates a oligomer induced neuronal cell cycle events," Mol. Neurodegeneration (2009) 4:1.

(56) References Cited

OTHER PUBLICATIONS

Bieniarz, C. et al., "Extended length heterobifunctional coupling agents for protein conjugations," Bioconjug. Chem. (1996) 7(1):88-95.
Bird, R.E. et al., "Single-chain antigen-binding proteins," Science (1988) 242:423-426.
Birren, B. et al., Genome Analysis—A Laboratory Manual, vols. 1 & 2, Table of Contents (1998).
Bitan, G. et al., "A molecular switch in amyloid assembly: met35 and amyloid beta-protein oligomerization," J. Am. Chem. Soc. (2003) 125:15359-15365.
Bitan, G. et al., "Amyloid beta-protein (Abeta) assembly: Abeta40 and Abeta42 oligomerize through distinct pathways," Proc. Natl. Acad. Sci. USA (2003) 100(1):330-335.
Bitan, G. et al., "Primary-quaternary structure relationships controlling early A beta oligomerizationpeptide revolution: genomics, proteomics and therapeutics," 18th American Peptide Symposium, Boston, MA Jul. 19-23, 2003, 765-767.
Bitan, G. et al., "Towards inhibition of amyloid beta-protein oligomerization," Biopolymers (2005) 80573, 19th American Peptide Symposium, San Diego, CA Jun. 18-23, 2005.
Bobich, J.A. et al., "Incubation of nerve endings with a physiological concentration of Abeta SUB 1-42 activates CaV2.2(N-type)-voltage operated calcium channels and acutely increases glutamate and noradrenaline release," J. Alzheimer's Dis. (2004) 6(3):243-255.
Bocher, W.O. et al., "Antigen-specific B and T cells in human/ouse radiation chimera following immunization in vivo," Immunol (1999) 96:634-641.
Bombil, F. et al., "A promising model of primaray human immunization in human-scid mouse," Immuolbiol. (1996) 195:360-375.
Boridy, S. et al., "The binding of pullalan modified cholesteryl nanogels to Abeta oligomers and their suppression of cytotoxicity," Biomaterials (2009) 30(29):5583-5591.
Boss, M.A. et al., "Genetically engineered antibodies," Immunol. (1985) 6(1):12-13.
Boutaud, O. et al., "PGH SUB 2-derived levuglandin adducts increase the neurotoxicity of amyloid beta 1-42," J. Neurochem. (2006) 96(4):917-923.
Boutaud, O. et al., "Prostaglandin H2 (PGH2) accelerates formation of amyloid beta1-42 oligomers," J. Neurochem. (2002) 82:1003-1006.
Boyd-Kimball, D. et al., "Neurotoxicity and oxidative stress in D1M-substituted Alzheimer's Abeta(1-42): relevance to N-terminal methionine chemistry in small model peptides," Peptides (2005) 26:665-673.
Bravo, R. et al., "Sulfated polysaccharides promote the assembly of amyloid beta 1-42 peptide into stable fibrils of reduced cytotocity," J. Biol. Chem. (2008) 283:32471-32483.
Brettschneider, S. et al., "Decreased serum amyloid Beta1-42 autoantibody levels in Alzheimer's disease, determined by a newly developed immuno-precipitation assay with radiolabeled amyloid beta1-42 peptide," Biol. Psychiatry (2005) 57:813-816.
Brinkley, M.A., "A survey of methods for preparing protein conjugates with dyes, haptens and crosslinking reagents," Bioconjugate Chem. (1992) 3:2-13.
Brinkman, U. et al., "Phage display of disulfide-stabilized FV fragments," J. Immunol. Meth. (1995) 182:41-50.
Britschgi, M. et al., "Neuroprotective natural antibodies to assemblies of amyloidogenic peptides decrease with normal aging and advancing Alzheimer's disease," Proc. Natl. Acad. Sci. USA(2009) 106(29):12145-12150.
Brorson et al., "Mutational analysis of avidity and fine specificity of anti-levan antibodies," J. Immunol. (1999) 163:6694-6701.
Brown, J.P. et al., "Protein antigens of normal and malignant human cells identified by immunoprecipitation with monoclonal antibodies," J. Biol. Chem. (1980) 255(11):4980-4983.
Brown, J.P. et al., "Structural characterization of human melanoma-associated antigen p97 with monoclonal antibodies," J. Immunol. (1981) 127(2):539-546.

Brummell et al., "Probing the combining site of an anti-carbohydrate antibody by saturation-mutagenesis: role of the heavy-chain CDR3 residues," Biochem. (1993) 32:1180-1187.
Brunger et al., "Crystallography and NMR system: a new software suite for macromolecular structure determination," Acta Crystallogr. (1998) D54(Pt5):905-921.
Brutlag, D. "Computational Molecular Biology—Multiple Sequence Alignment," (2007).
Buchwald, H. et al., "Long-term continuous intravenous heparin administration by an implantable infusion pump in ambulatory patients with recurrent venous thrombosis," Surgery (1980) 88:507-516.
Buraei, Z. et al., "Roscovitine differentially affects CaV2 and Kv channels by binding to the open state," Neuropharmacology (2007) 52:883-894.
Burks et al., "In vitro scanning saturation mutagenesis of an antibody binding pocket," Proc. Natl. Acad. Sci. USA (1997) 94:412-417.
Burton, D.R. et al., "Human antibodies from combinatorial libraries," Adv. in Immunol. (1994) 57:191-208.
Butler, D. et al., "Cellular responses to protein accumulation involve autophagy and lysosomal enzyme activation," Rejuvenation Res. (2005) 8(4):227-237.
Carlsson, J. et al., "Protein thiolation and reversible protein-protein conjugation. N-succinimidyl 3-(2-pyridyldithio) propionate, a new heterobifunctional reagent," Biochem. J. (1978) 173(3):723-737.
Carter, D.A. et al., "More missense in amyloid gene," Nat. Genet. (1992) 2:255-256.
Carter, P. et al., "Humanization of an anti-p185HER2 antibody for human cancer therapy," Proc. Natl. Acad.Sci. (1992) 89:4285-4289.
Casset et al., "A peptide mimetic of an anti-CD4 monoclonal antibody by rational design," Biochem. Biophys. Res. Comm. (2003) 307:198-205.
Catterall, W.A. et al., "International Union of Pharmacology. XLVIII. Nomenclature and structure-function relationships of voltage-gated calcium channels," Pharm. Rev. (2005) 57(4):411-425.
Cecchini, C. et al., "Increased susceptibility to amyloid toxicity in familial Alzheimer's fibroblasts," Neurobiol. Aging (2007) 28(6):863-876.
Cecchini, M. et al., "A molecular dynamics approach to the structural characterization of amyloid aggregation," J. Mol. Biol. (2006) 357(4):1306-1321.
Chacon, M.A. et al., "Frizzled-1 is involved in he neuroprotective effect of Wnt3a against Abeta oligomers," J. Cell. Physiol. (2008) 217(1):215-227.
Chaiken, I.M., "Semisynthetic peptides and proteins," CRC Crit. Rev. Biochem. (1981) 11(3):255-301.
Chamat, S. et al., "Human monoclonal antibodies isolated from spontaneous Epstein-Barr virus-transformed tumors of Hu-SPL-SCID mice and specific for fusion protein display broad neutralizing activity toward respiratory syncytial virus," J. Infect. Dis. (1999) 180:268-277.
Chander, H. et al., "Binding of trypsin to fibrililar amyloid beta-protein," Brain Res. (2006) 1082(1):173-181.
Chang, L. et al., "Femtomole immunodetection of synthetic and endogenous amyloid-beta oligomers and its application to Alzheimer's disease drug candidate screening," J. Mol. Neurosci. (2003) 20(3):305-313.
Chanki, H. et al., "Ex situ atomic force microscopy analysis of beta-amyloid self-assembly and deposition on a synthetic template," Langmuir (2006) 16(22):6977-6985.
Chen et al., "Selection and analysis of an optimized anti-VEGF antibody: crystal structure of an affinity-matured Fab in complex with antigen," J. Mol. Biol. (1999) 293:865-881.
Chen, K. et al., "Cooperation between NOD2 and toll-like receptor 2 ligands in the up-regulation of mouse mFPR2, a G-protein-coupled Aalpha SUB 42 peptide receptor, in microglial cells," J. Leukocyte Biol. (2008) 83(6):1467-1475.
Chen, Y-R. et al., "Distinct early folding and aggregation properties of Alzheimer amyloid-beta peptides A beta 40 and A beta 42—stable trimer or tetramer formation by A beta 42," J. Biol. Chem. (2006) 281:24414-24422.

(56) References Cited

OTHER PUBLICATIONS

Chiang, H-C. et al., "Distinctive roles of different beta-amyloid 42 aggregates in modulation of synaptic functions," FASEB Journal (2009) 23(6):1969-1977.
Chiang, P.K. et al., "The many faces of amyloid beta in Alzheimer's disease," Curr. Mol. Med. (2008) 8(6):580-584.
Chiarini, A. et al., "Calcium-sensing receptor (CaSR) in human brain's pathophysiology: roles in late-onset Alzheimer's disease (LOAD)," Curr. Pharma. Biotech. (2009) 10(3):317-326.
Choo-Smith, LP et al., "The interaction between Alzheimer amyloid beta (1-40) peptide and ganglioside Gmi-containing membranes," FEBS Lett. (1997) 402:95-98.
Chothia, C. et al., "Canonical structures for the hypervariable regions of immunoglobulins," J. Mol. Biol. (1987) 196:901-917.
Chothia, C. et al., "Conformations of immunoglobulin hypervariable regions," Nature (1989) 342:877-883.
Chothia, C. et al., "Structural repertoire of the human VH segments," J. Mol. Biol. (1992) 227:799-817.
Chrisey, L. et al., "Covalent attachment of synthetic DNA to self-assembled monolayer films," Nucl. Acids. Res. (1996) 24(15):3031-3039.
Christensen, D.D., "Changing the course of Alzheimer's disease: anti-amyloid disease-modifying treatments on the horizon," Primary Care Companion J. Clin. Psych. (2007) 9(1):32-41.
Chromy et al., "Oligomer/conformation-dependent Abeta antibodies," Abstracts of the Annual Meeting of the Society for Neuroscience (2000) 26(1-2):4.
Chromy, B. et al., "Self-assembly of a beta 1-42 into globular neurotoxins," Biochem. (2003) 42(17):12749-12760.
Chromy, B.A. et al., "Stability of small oligomers of Abeta1-42(ADDLs)," Society for Neuroscience Abstracts (1999) Abstract No. 252129, 29th Annual Meeting of the Society for Neuroscience, Miami Beach, FL, Oct. 23-28, 1999.
Chung, H. et al., "Degradation of beta-amyloid peptide by microglia," Society for Neuroscience Abstracts (2000) 26 Abstract No. 858.10, 30th Annual Meeting of the Society of Neuroscience, New Orleans, LA, Nov. 4-9, 2000.
Ciccotosto, G.B. et al., "Methionine oxidation: implications for the mechanism of toxicity of the beta-amyloid peptide from Alzheimer's disease," Lett. Peptide Sci. (2003) 10(5-6):413-417.
Clackson, T. et al., "Making antibody fragments using phage display libraries," Nature (1991) 352:624-628.
Clark, M.S., Plant Molecular Biology—A Laboratory Manual, Table of Contents (1997).
Cleary, J.P. et al., "Cognitive effects of oligomeric and fibril Abeta in rats," Soc. For Neuroscience Abstract Viewer and Itinerary Planner (2002) Abstract No. 882.2, 32nd Annual meeting of the Society for Neuroscience, Orlando, FL, Nov. 2-7, 2002.
Cleek, R.L. et al., "Biodegradable polymeric carriers for a bFGF antibody for cardiovascular application," Proc. Intl. Symp. Control. Re. Bioact. Mater. (1997) 24:853-854.
Co, M.S. et al., "Genetically engineered deglycosylation of the variable domain increases the affinity of an anti-Cd33 monoclonal antibody," Molec. Immunol. (1993) 30(15):1361-1367.
Cole, G.M. et al., "Alzheimer's amyloid story finds its star," Trends Mol. Med. (2006) 12(9):395-396.
Cole, G.M. et al., "Cat and mouse," Neuron (2006) 51(6):671-672.
Cole, G.M. et al., "Docosahexaenoic acid protecs from amyloid and dendritic pathology in an Alzheimer's disease mouse model," Nutrition and Health (2006) 18(3):249-259.
Cole, M.S. et al., "Human IgG2 variants of chimmeric anti-CD3 are nonmitogenic to T cells," J. Immunol. (1997) 159(7):3613-3621.
Colman, P.M., "Effects of amino acid sequence changes on antibody-antigen interactions," Research in Immunol (1994) 145:33-36.
Colombo, R. et al., "CE can identify small molecules that selectively target soluble oligomers of amyloid beta protein and display antifibrillogenic activity," Electrophoresis (2009) 30(8):1418-1429.
Costantini, C. et al., "The expression of p75 neurotrophin receptor protects against the neurotoxicity of soluble oligomers of beta-amyloid," Exp. Cell Res. (2005) 311(1):126-134.

Craft, J.M. et al., "Enhanced susceptibility of S-100B transgenic mice to neuroinflammation and neuronal dysfunction induced by intracerebroventricular infusion of human beta-amyloid," Glia (2005) 51(3):209-216.
Crouch, P.J. et al., "Soluble oligomeric amyloid beta 1-42 specifically inhibits cytochrome c oxidase of human mitochondria," Mitochondrial Medicine (2004) 4:71-72.
Crouse, N.R. et al., "Oligomeric amyloid-beta(1-42) induces THP-1 human monocyte adhesion and maturation," Brain Res. (2009) 1254:109-119.
Dahlgren, K.N. et al., "Oligomeric and fibrillar species of amyloid-beta peptides differentially affect neuronal viability," J. Biol. Chem. (2002) 277(35):32046-32053.
Das, U. et al., "Interface peptide of Alzheimer's amyloid beta: application in purification," Biochem. Biophys. Res. Commun. (2007) 362(2):538-542.
Dasilva, K.A. et al., "Reduced oligomeric and vascular amyloid-beta following immunization of TgCRND8 mice with an Alzheimer's DNA vaccine," Vaccine (2009) 27136-1376.
De Felice, F.G. et al., "Alzheimer's disease-type neuronal tau hyperphosphorylation induced by Abeta oligomers," Neurobiol. Aging (2008) 29(9):1334-1347.
De Pascalis, R. et al., "Grafting of 'abbreviated' complementarity-determining regions containing specificity-determining residues essential for ligand contact to engineer a less immunogenic humanized monoclonal antibody," J. Immunol. (2002) 169:3076-3084.
Dealmeida, E.R.P. et al., "Transgenic expression of two marker genes under the control of an arabidopsis rbcS promoter: sequences encoding the Rubisco transit peptide increase expression levels," Mol Gen. Genet. (1989) 218:78-86.
deChaves, P.E. et al., "Lipid rafts in amyloid beta endocytosis and amyloid beta-induced apoptosis," J. Neurochem. (2009) 110(2):146, S20-23.
DeMattos et al., "P4-358 in vitro and in vivo characterization of beta-amyloid antibodies binding to cerebral amyloid angiopathy (CAA) and the selective exacerbation of CAA-associated microhemorrhage," Neurobiol. Aging (2004) 25(S2):S577.
DeMattos, R.B. et al., "Peripheral anti-Abeta antibody alters CNS and plasma Abeta clearance and decreases brain Abeta burden in a mouse model of Alzheimer's disease," Proc. Natl. Acad. Sci. USA (2001) 98(15):8850-8855.
Demeester, N. et al., "Comparison of the aggregation properties, secondary structure and apoptotic effects of wild-type, Flemish and Dutch N-terminally truncated amyloid beta peptides," Euro. J. Neurosci. (2001) 13(11):2015-2024.
Demuro, A. et al., "Calcium dysregulation and membrane disruption as a ubiquitous neurotoxic mechanism of soluble amyloid oligomers," J. Biol. Chem. (2005) 280(17):17294-17300.
Denkewalter et al., "Fortschritte der arzneimittelforschung progress in drug research progres des receherches pharmaceutiques," (1996) 10:224-285.
Dewachter, I. et al., "Neuronal deficiency of presenillin 1 inhibits amyloid plaque formation and corrects hippocampal long-term potentiation but not a cognitive defect of amyloid precursor protein [V7171] transgenic mice," J. Neurosci. (2002) 22(9):3445-3453.
Dickson, D.W. et al., "Correlations of synaptic and pathological markers with cognition of the elderly," Neurobiol. Aging (1995) 16(3):285-304.
Dillen, K. et al., "A two decade contribution of molecular cell biology to the centennial of Alzheimer's disease: are we progressing toward therapy?" Int. Rev. Cytol. (2006) 254:215-300.
Dingledine, R. et al., Brain slices, Plenum Press (1984) Table of Contents.
Donnet et al., "Plasma treatment effect on the surface energy of carbon and carbon fibers," Carbon (1986) 24(6):757-770.
Du, Y. et al., "Reduced levels of amyloid beta-peptide antibody in Alzheimer disease," Neurology (2001) 57:801-805.
Dufner, P. et al., "Harnessing phage and ribosome display for antibody optimisation," Trends Biotech. (2006) 24(11):523-529.
During, M.J. et al., "Controlled release of dopamine from a polymeric brain implant: in vivo characterization," Ann. Neurol. (1989) 25:351-356.

(56) References Cited

OTHER PUBLICATIONS

Durocher, Y. et al., "High-level and high-throughput recombinant protein prouction by transient transfection of suspension-growing human 293-EBNA1 cells," Nucl. Acid. Res. (2002) 30(2):e9-11.
Eckenhoff, R.G. et al., "Anesthetics and neurodegenerative disorders: a molecular basis for concern?" Anesthesiology Abstracts of Scientific Papers Annual Meeting, 2003, Abstract No. A-848, 2003 Annual Meeting of the American Society of Anesthesiologists, San Francisco, CA, Oct. 11-15, 2003.
Eckert, A. et al., "Oligomeric and fibrillar species of beta-amyloid (A beta 42) both impair mitochondrial function in P301L tau transgenic mice," J. Mol. Med. (2008) 86(11):1255-67.
Eisenberg et al., "Analysis of membrane and surface protein sequences with the hydrophobic moment plot," J. Mol. Biol. (1984) 179(1):125-142.
Englund, H. et al., Oligomerization partially explains the lowering of A beta 42 in Alzheimer's disease cerebrospinal fluid, Neurodegenerative Dis. (2009) 6:139-147.
Eren, R. et al., "Human monoclonal antibodies specific to hepatitis B virus generated in a human/mouse radiation chimera: the Trimera system," Immunol. (1998) 93:154-161.
Esteras-Chopo, A. et al., "New strategy for the generation of specific D-peptide amyloid inhibitors," J. Mol. Biol. (2008) 377:1372-1381.
Evans et al., "Design of a nonpeptidal ligands for a peptide receptor: cholecystokinin antagonists," J. Med. Chem. (1987) 30:1229.
Evans, C.G. et al., "Heat shock proteins 70 and 90 inhibit early stages of amyloid beta-(1-42) aggregation in vitro," J. Biol. Chem. (2006) 281:33182-33191.
Evans, N.A. et al., "Abeta SUB 1-42 reduces synapse number and inhibits neurite outgrowth in primary cortical and hippocampal neurons: a quantitative analysis," J. Neurosci. Methods (2008) 175(1):96-103.
Evin, G., "gamma-secretase modulators: hopes and setbacks for the future of Alzheimer's treatment," Expert Rev. Neurother. (2008) 8(11):1611-1613.
Fauchere, "Elements for the rational design of peptide drugs," Adv. Drug Res. (1986) 15:29-69.
Feld, M. et al., "Effect on memory of acute administration of naturally secreted fibrils and synthetic amyloid-beta peptides in an invertebrate model," Neurobiol. Learn. Mem. (2008) 89(4):407-418.
Ferrao-Gonzales, A et al., "Controlling beta-amyloid oligomerization by the use of naphthalene sulfonates: trapping low molecular weight oligomeric species," J. Biol. Chem. (2005) 280(41):34747-34754.
Fishwild, D.M. et al., "High-avidity human IgGx monoclonal antibodies from a novel strain of minilocus transgenic mice," Nature Biotech. (1996) 14:845-851.
Flink, M.T. et al., "Ca2+ channels as targets of neurolgoical disease: Lambert-Eaton Syndrome and other Ca2+ channelopathies," J. Bioeng. Biomembr. (2003) 35(6):697-718.
Foote, J. et al., "Antibody framework residues affecting the conformation of the hypervariable loops," J. Mol. Biol. (1992) 224:487-499.
Forsell, C. et al., "Amyloid precursor protein mutation at codon 713 (Ala→Val) does not cause schizophrenia: non-pathogenic variant found at codon 705 (silent)," Neurosci. Lett. (1995) 184:90-93.
Fradinger, E.A. et al., "C-terminal peptides coassemble into Abeta42 oligomers and protect neurons against Abeta42-induced neurotoxicity," Proc. Natl. Acad. Sci. USA 92008) 105(37):14175-14180.
Fuchs, P. et al., "Targeting recombinant antibodies to the surface of *Escherichia coli*: fusion to a peptidoglycan associated lipoprotein," BioTech. (1991) 9:1369-1372.
Funke, S.A. et al., "Detection of amyloid-beta aggregates in body fluids: a suitable method for early diagnosis of Alzheimer's disease?" Current Alzheimer's Research (2009) 6(3):285-289.
Galfre, G. et al., "Antibodies to major histocompatibility antigens produced by hybrid cell lines," Nature (1977) 266(5602):550-552.
Gallo, M.L. et al., "the human immunoglobulin loci introduced into mice: V(D) and J gene segment usage similar to that of adult humans," Eur. J. Immunol. (2000) 30:534-540.
Garrard, L.J. et al., "FAB assembly and enrichment in a monovalent phage display system," BioTech. (1991) 9:1373-1377.
Garzon, D.J. et al., "Oligomeric amyloid decreases basal levels of brain-derived neurotrophic factor (BDNF) mRNA via specific downregulation of BDNF transcripts IV and V in differentiated human neuroblastoma cells," J. Neurosci. (2007) 27(10):2628-2635.
Gavilondo, J.V. et al., "Antibody engineering at the millennium," BioTechniques (2002) 29:128-145.
Gefter, M.L. et al., "A simple method for polyethylene glycol-promoted hybridization of mouse myeloma cells," Somatic Cell Genetics (1997) 3(2):231-236.
Gellermann, G.P. et al., "Abeta-globulomers are formed independently of the fibril pathway," Neurobiol. of Dis. (2008) 30(2):212-220.
Gervais, F. et al., "Targeting soluble Abeta peptide with tramiprosate for the treatment of brain amyloidosis," Neurobiol. Aging (2007) 28(4):537-547.
Ghiso, J. et al., "Systemic catabolism of Alzheimer's Abeta40 and Abeta42," J. Biol. Chem. (2004) 279:45897-45908.
Ghosal, K. et al., "Alzheimer's disease-like pathological features in transgenic mice expressing the APP intracellular domain," Proc. Natl. Acad. Sci. (2009) 106(43):18367-18372.
Giacobini, E. et al., "One hundred years after the discovery of Alzheimer's disease. A turning point for therapy? The multifaceted aspects of Alzheimer's disease: from social to molecular problems," J. Alzheimer's Disease (2007) 12(1):37-52.
Gibbs, M.E. et al., "Rescue of Abeta SUB 1-42-induced memory impairment in day-old chick by facilitation of astrocytic oxidative metabolism: implications for Alzheimer's disease," J. Neurochem. (2009) 109 Suppl. 1:230-236.
Giege, R. et al., "An introduction to the crystallogenesis of biological macromolecules," Crystallization of Nucleic Acids & Proteins, a Practical Approach, 2nd Edition: 1-16 (1999).
Giliberto, L. et al., "Mutant presenilin 1 increases the expression and activity of BACE1," J. Biol. Chem. (2009) 284(14):9027-9038.
Gillies, S.D. et al., "High-level expression of chimeric antibodies using adapted cDNA variable region cassettes," J. Immunol. Meth. (1989) 125:191-202.
Giuffrida, M.L. et al., "A beta(25-35) and its C- and/or N-blocked derivatives: copper driven structural features and neurotoxicity," J. Neursci. Res. (2007) 85:623-633.
Giuffrida, M.L. et al., "Beta-amyloid monomers are neuroprotective," J. Neurosci. (2009) 29(34):10582-10587.
Goeddel, D., "Systems for heterologous gene expression," Meth. in Enzymol. (1990) 185:3-7.
Goldspiel, B.R. et al., "Human gene therapy," Clin. Pharm. (1993) 12:488-505.
Gong, Y. et al., "Abeta-derived diffusible ligands in Alzheimer's disease brain as therapeutic antibody targets," Abstracts of the Annual Meeting of the Society of Neuroscience (2002) 1 page.
Gong, Y., "Alzheimer's disease-affected brain: presence of oligomeric A ligands (ADDLs) suggests a molecular basis for reversible memory loss," Proc. Natl. Acad. Sci. (2003) 100(18):10417-10422.
Gonzalo-Ruiz, A. et al., "Oligomers of beta-amyloid (1-42) peptide induce co-localization of AB and TAU proteins associated with calpain activity," J. Neurochem. (2009) 110:57-58.
Goodson, J.M., "Dental applications" in Medical Applications of Controlled Release, (1984) vol. II, Chapter 6, 115-138.
Gowing, E. et al., "Chemical characterization of A beta 17-42 peptide, a component of diffuse amyloid deposits of Alzheimer disease," J. Biol. Chem. (1994) 269:10987-10988.
Grabarek, Z. et al., "Zero-length crosslinking procedure with the use of active esters," Anal. Biochem. (1990) 185(1):131-135.
Grabowski, T.J. et al., "Novel amyloid precursor protein mutation in an Iowa family with dementia and severe cerebral amyloid angiopathy," Ann. Neurol. (2001) 49(6):697-705.
Grace, S.Y. et al., "Abeta induces oxidative-degradative stress through NADPH oxidase and phopholipase A2," J. Neurochem.

(56) References Cited

OTHER PUBLICATIONS (2009) 110222, 22nd Biennial Meeting of the International Society of Neurochemistry, South Korea, Aug. 23-29, 2009.
Gram, H. et al., "In vitro selection and affinity maturation of antibodies from a naïve combinatorial immunoglobulin library," Proc. Natl. Acad. Sci. USA (1992) 89:3576-3580.
Grange, P.De La. et al., "FAST DB: a website resource for the study of the expression regulation of human gene products," Nucl. Acids Res. (2005) 33(13):4276-4284.
Green, L.L. et al., "Antigen-specific human monoclonal antibodies from mice engineered with human Ig heavy and light chain YACs," Nature Genetics (1994) 7(1):13-21.
Green, L.L. et al., "Regulation of B cell development by variable gene complexity in mice reconsituted with human immunoglobulin yeast artificial chromosomes," J. Exp. Med. (1998) 188(3):483-495.
Green, L.L., "Antibody engineering via genetic engineering of the mouse: XenoMouse strains are a vehicle for the facile generation of therapeutic human monoclonal antibodies," J. Immunol. Meth. (1999) 231:11-23.
Griffiths, A.D. et al., "Human anti-self antibodies with high specificity from phage display libraries," The EMBO Journal (1993) 12(2):725-734.
Guo, L. et al., "APOE down regulates pro-inflammatory responses induced by oligomeric Abeta in activated glia," Soc. for Neurosci. Abstract Viewer and Itinerary Planner (2002), Abstract No. 883.12, 32nd Annual meeting of the Society for Neuroscience, Orlando, FL, Nov. 2-7, 2002.
Ha, C. et al., "Ex situ atomic force microscopy analysis of beta-amyloid self-assembly and deposition on a synthetic template," Langmuir (2006) 22:6977-6985.
Ha, C. et al., "Metal ions differntially influence the aggregation and deposition of Alzheimer's beta-amyloid on a solid template," Biochem. (2007) 46(20):6118-6125.
Ha, H.J. et al., "Development of herbal medicine for Alzheimer's disease from RHEI rhizoma," J. Neurochem. (2009) 110114.
Haass, C. et al., "Soluble protein oligomers in neurodegeneration: lessons from the Alzheimer's amyloid beta-peptide," Nat. Rev. Mol. Cell Biol. (2007) 8(2):101-112.
Hachiya, N.S. et al., "Oligomeric Aip2p/Dld2p modifies the protein conformation of both properly folded and misfolded substrates in vitro," Biochem. Biophys. Res. Comm. (2004) 323(1):339-344.
Hagemeyer, C.E. et al., "Single-chain antibodies as diagnostic tools and therapeutic agents," Thromb. Haemost. (2009) 101:1012-1019.
Halladay, M.W. et al., "Synthesis of hydroxyethelene and ketomethylene dipeptide isosteres," Tetrahedron Lett. (1983) 24:4401-4404.
Hann, M.M., "On the double bond isostere of the peptide bond: preparation of an enkephalin analogue," J. Chem. Soc. Perkin Transactions (1982) 1:307-314.
Harding, F.A. et al., "Class switching in human immunoglobulin transgenic mice," Ann. N.Y. Acad. Sci. (1995) 764:536-546.
Hardy, J. et al., "The amyloid hypothesis of Alzheimer's disease: progress and problems on the road to therapeutics," Science (2002) 297:353-356.
Harris-White, M.E. et al., "Effects of low dose, low MW soluble amyloid oligomers on spatial memory performance," Society for Neurosci. Abstr. Viewer and Itin. Plann. (2003) Abstract No. 240.11, 33rd Annual Meeting of the Society of Neuroscience, Nov. 8-12, 2003, New Orleans.
Hartley, D.M. et al., "Transglutaminase induces protofibril-like amyloid beta-protein assemblies that are protease-resistant and inhibit long-term potentiation," J. Biol. Chem. (2008) 283(24):16790-16800.
Hashida, S. et al., "More useful maleimide compounds for the conjugation of Fab to horseradish peroxidase through thiol groups in the hinge," J. Appl. Biochem. (1984) 6:56-63.
Hashimoto, M. et al., "Role of protein aggregation in mitochondrial dysfunction and neurodegeneration in Alzheimer's and Parkinson's disease," Neuromol. Med. (2003) 4(1-2):21-36.

Hawkins, R.E., "Selection of phage antibodies by binding affinity—imicking affinity maturation," J. Mol. Biol. (1992) 226:889-896.
Hay, B.N. et al., "Bacteriophage cloning and Escherichia coli expression of a human IgM fab," Hum. Antibod. Hybridomas (1992) 3:81-85.
Hayes, G.M. et al., "Production of beta-amyloid by primary human foetal mixed brain cell cultures and its modulation by exogeneous soluble beta-amyloid," Neurosci. (2002) 113(3):641-646.
Head, E. et al., "A two-year study with fibrillar beta-amyloid (Abeta) immunization in aged canines: effects on cognitive function and brain Abeta," J. Neurosci. (2008) 28(14):3555-3566.
Head, E. et al., "The efffects of immunization with fibrillar or oligomeric Abeta in the brain and CSF of aged canines: a pilot study," Society for Neuroscience Abstract Viewer and Itinerary Planner (2003) Abstract No. 525.24, 33rd Annual Meeting of the Society of Neuroscience, New Orleans, LA, Nov. 8-12, 2003.
Heard, C. et al., "Two neutralizing human anti-RSV antibodies: cloning, expression, and characterization," Molec. Med. (1999) 5:35-45.
Heinitz, K. et al., "Toxicity mediated by soluble oligomers of beta-amyloid(1-42) on cholinergic SN56.B5.G4 cells," J. Neurochem. 92006) 98(6):1930-1945.
Helisalmi, S. et al., "Screening for amyloid beta precursor protein codon 665, 670/671 and 717 mutations in Finnish patients with Alzheimer's disease," Neurosci. Lett. (1996) 205:68-70.
Herz, U. et al., "The humanized (Hu-PBMC) SCID mouse as an in vivo model for human IgE production and allergic inflammation of the skin," Int. Arch Allergy Immunol. (1997) 113(1-3):150-152.
Hess et al., "cooperation of glycolytic enzymes," J. Adv. Enzyme Reg. (1968) 7:149-167.
Hieter, P.A. et al., "Evolution of human immunoglobulin kJ region genes," J. Biol. Chem. (1982) 257(3):1516-1522.
Higgins, D.G. et al., "Fast and sensitive multiple sequence alignments on a microcomputer," CABIOS Comm. (1989) 5(2):151-153.
Higuchi, R., "Using PCR to engineer DNA," PCR Technol: Princ. & Appl. for DNA Amplification (1989) 61-70.
Hilbich, C. et al., "Aggregation and secondary structure of synthetic amyloid betaA4 peptides of Alzheimer's disease," J. Mol. Biol. (1991) 218:149-163.
Hillen, H. et al., "Generation and therapeutic efficacy of highly oligomer-specific beta-amyloid antibodies," J. Neurosci. (2010) 30(31):10369-10379.
Hirko, A.C. et al., "Peripheral transgene expression of plasma gelsolin reduces amyloid in transgenic mouse models of Alzheimer's disease," Mol. Ther. (2007) 15(9):1623-9.
Hock, C. et al., "Clinical observations with AN-1792 using TAPIR analyses," Neurodegenerative Dis. (2006) 2(5):273-276.
Holliger, P. et al., "Diabodies small bivalent and bispecific antibody fragments," Proc. Natl. Acad. Sci. (1993) 90:6444-6448.
Holm et al., "Functional mapping and single chain construction of the anti-cytokeratin 8 monoclonal antibody TS1," Mol. Immunol. (2007) 44:1075-1084.
Hong, H-S. et al., "Combining the rapid MTT formazan exocytosis assay and the MC65 protection assay led to the discovery of carbozole analogs as small molecule inhibitors of Abeta oligomer-induced cytotoxicity," Brain Res. (2007) 1130(1):223-234.
Hong, H-S. et al , "Inhibition of Alzheimer's amyloid toxocity with a tricyclic pyrone molecule in vitro and in vivo," J. Neurochem. (2009) 108(4):1097-1108.
Hoogenboom, H.R. et al., "Multi-subunit proteins on the surface of silamentous phage: methodologies for displaying antibody (Fab) heavy and light chains," Nucl. Acids Res. (1991) 19(15):4133-4137.
Hoogenboom, H.R. et al., "Natural and designer binding sites made by phage display technology," Immunol. Today (2000) 21(8):371-378.
Hoogenboom, H.R., "Designing and optimizing library selection strategies for generating high-affinity antibodies," Tibtech (1997) 15:62-70.
Hoozemans, J.J.M. et al., "Always around, never the same: pathways of amyloid beta induced neurodegeneration throughout the pathogenic cascade of Alzheimer's disease," Curr. Med. Chem. (2006) 13(22):2599-2605.

(56) References Cited

OTHER PUBLICATIONS

Hossain, S. et al., "Mechanism of docosahexaenoic acid-induced inhibition of in vitro Abeta1-42 fibrillation and Abeta1-42-induced toxicity in SH-S5Y5 cells," J. Neurochem. (2009) 111(2):568-579.

Howard III, M.A. et al., "Intracerebral drug delivery in rats with lesion-induced memory deficits," J. Neurosurg. (1989) 71:105-112.

Howlett, D.R. et al., "The pathology of APP transgenic mice: a model of Alzheimer's disease or simply overexpression of APP?" Histol. Histopathol. (2009) 24(1):83-100.

Hoyer, W. et al., "Stabilization of a beta-hairpin in monomeric Alzheimer's amyloid-beta peptide inhibits amyloid formation," Natl. Acad. Sci. Proc. Natl. Acad. Sci. (2008) 105(13):5099-5104.

Hruby, V.J., "Conformational restrictions of biologically active peptides via amino acid side chain groups," Life Sci. (1982) 31:189-199.

Hsiao et al., "Correlative memory deficits, abeta elevation, and amyloid plaques in transgenic mice," Science (1996) 274(5284):99-102.

Huang, C. et al., "Isoproterenol potentiates synaptic transmission primarily by enhancing presynaptic calcium influx via P- and/or Q-type calcium channels in the rat amygdala," J. Neurosci. (1996) 16(3):1026-1033.

Huang, C.C. et al., "Selective enhancement of P-type calcium currents by isoproterenol in the rat amygdata," J. Neurosci. (1998) 18(6):2276-2282.

Huang, X. et al., "Metal—dependence of Abeta oligomerization," Soc. for Neurosci. Abstract Viewer and Itinerary Planner (2002), Abstract No. 19.1, 32nd Annual meeting of the Society for Neuroscience, Orlando, FL, Nov. 2-7, 2002.

Huse, W.D. et al., "Generation of a large combinatorial library of the immunoglobulin repertoire in phage lambda," Science (1989) 246:1275-1281.

Huston, J.S. et al., "Protein engineering of antibody binding sites: recovery of specific activity in all anti-digoxin single-chain Fv analogue produced in *Escherichia coli*," PNAS (1988) 85:5879-5883.

Huston, J.S. et al., "Protein engineering of single-chain Fv analogs and fusion proteins," Meth. in Enzymol. (1991) 203:46-88.

Hutchins, W.A. et al., "Human immune response to a peptide mimic of neisseria meningitis serogroup C in hu-PBMC-SCID mice," Hybridoma (1999) 18(2):121-129.

Hyman et al., "Autoantibodies to Amyloid-beta and Alzheimer's disease," Ann. Neurol. (2001) 49:808-810.

Iijima, K. et al., "A beta 42 mutants with different aggregation profiles induce distinct pathologies in *Drosophila*," PLoS One (2008) 3 Article No. E1703.

Ilan, E. et al., "The hepatitis B virus-trimera mouse: a model for human HBV infection and evaluation of anti-HBV therapeutic agents," Hepatology (1999) 29:553-562.

Ingelbrect, I.L.W. et al., "Different 3' end regions strongly influence the level of gene expression in plant cells," The Plant Cell (1989) 1:671-780.

Jang et al., "The structural basis for DNA binding by an anti-DNA autoantibody," Molec. Immunol. (1998) 35:1207-1217.

Janssen, J.C. et al., "Early onset familial Alzheimer's disease: mutation frequency in 31 families," Neurology (2003) 60(2):235-239.

Jefferis, R., "Glycosylation of recombinant antibody therapeutics," Biotechnol. Prog. (2005) 21:11-16.

Jennings-White, C. et al., "Synthesis of ketomethylene analogogs of dipeptides," Tetrahedr. Lett. (1982) 23(25):2533-2534.

Jensen, M.T. et al., "Lifelong immunization with human beta-amyloid (1-42) protects Alzheimer's transgenic mice against cognitive impairment throughout aging," Neurosci. (2005) 130:667-684.

Jiang, S. et al., "Recent progress of synthetic studies to peptide and peptidomimetic cyclization," Curr. Org. Chem. (2008) 12(17):1502-1542.

Joerchel, S. et al., "Oligomeric beta-amyloid(1-42) induces the expression of Alzheimer disease-relevant proteins in cholinergic SN56.B5.G4 cells as revealed by proteomic analysis," Int. J. Developm. Neurosci. (2008) 26(3-4):301-308.

Johansson, A.S. et al., "Attenuated amyloid-beta aggregation and neurotoxicity owing to methionine oxidation," NeuroReport (2007) 18(6):559-563.

Johansson, A.S. et al., "Dramatic changes in fibrillization rate and oligomer/protofibrillar formation of beta-amyloid peptide with oxidized methionine: implications for novel therapeutic approaches in Alzheimer's disease," Soc. for Neurosci. Abstract Viewer and Itinerary Planner (2002), Abstract No. 123.8, 32nd Annual meeting of the Society for Neuroscience, Orlando, FL, Nov. 2-7, 2002.

Johansson, A-S. et al., "Docosahexaenoic acid stabilizes soluble amyloid-beta protofibrils and sustains amyloid-beta-induced neurotoxicity in vitro," FEBS J. (2007) 274(14):990-1000.

Johansson, A-S. et al., "Physiochemical characterization of the Alzheimer's disease-related peptides Abeta1-42Arctic and Abeta1-42wt," FEBS Journal (2006) 273(12):2618-2630.

Johnsson, B. et al., "Comparison of methods for immobilozation to carboxymethyl dextran sensor surfaces by analysis of the specific activity of monoclonal antibodies," J. Mol. Rec. (1995) 8:125-131.

Johnsson, B. et al., "Immobilizataion of progeins to a carboxymethyldextran-modified gold surface for biospecific interaction analysis in surface plasmon resonance sensors," Anal. Biochem. (1991) 198:268-277.

Joliot, A. et al., "Antennapedia homeobox peptide regulates neural morphogenesis," Proc. Natl. Acad. Sci. USA (1991) 88:1864-1868.

Jones, C.T. et al., "Mutation in codon 713 of the beta-amyloid precursor protein gene presenting with schizophrenia," Nat. Genet. (1992) 1(4):306-309.

Jones, J.D.G. et al., "High level expression of introduced chimaeric genes in regenerated transformed plants," EMBO J. (1985) 4(10):2411-2418.

Jonsson, U. et al., "Introducing a biosensor based technology for real-time biospecific interaction analysis," Ann. Biol. Clin. (1993) 51:19-26.

Jonsson, U. et al., "Real-time biospecific interaction analysis using surface plasmon resonance and a sensor chip technology," BioTechniques (1991) 11(5):620-627.

Jungbauer, L.M. et al., "Preparation of fluorescently-labeled amyloid-beta peptide assemblies: the effect of luorophore conjugation on structure and function," J. Mol. Recogn. (2009) 22(5):403-413.

Kabat, E.A. et al., "Attempts to locate complementarity-determining residues in the variable positions of light and heavy chains," Ann. NY Acad. Sci. (1971) 190:382-391.

Kabat, E.A. et al., Sequences of Proteins of Immunological Interest, 5th Edition, NIH Publ. #91/3242 (1981), Table of Contents.

Kaiser et al., "Peptide and protein synthesis by segment synthesis-condensation," Science (1989) 243:187.

Kakio, A. et al., "Interactions of amyloid beta-protein with various gangliosides in raft-like membranes: importance of GM1 ganglioside-bound form as an endogenous seed fr Alzheimer amyloid," Biochem. (2002) 41:7385-7390.

Kamino, K. et al., "Linkage and mutational analysis of familial Alzheimer disease kindreds for the APP gene region," Am. J. Hum. Genet. (1992) 51(5):998-1014.

Kanemitsu, H. et al., "Human neprilysin is capable of degrading amyloid beta peptide not only in the monomeric form but also the pathologica oligomeric form," Neursci. Lett. (2003) 350:113-116.

Kaufman, R.J. et al., "Amplification and expression of sequences contrasfected with a modular dihydrofolate reductase complementary DNA gene," Mol. Biol. (1982) 159:601-621.

Kawarabayashi, T. et al., "Age-dependent changes in brain, CSF, and plasma amyloid beta protein in the Tg2576 transgenic mouse model of Alzheimer's disease," J. Neurosci. (2001) 21(3):372-381.

Kawarabayashi, T. et al., "Dimeric amyloid beta protein rapidly accumulates in lipid rafts followed by apolipoprotein E and phosphorylated Tau accumulation in the Tg2576 mouse model of Alzheimer's disease," J. Neurosci. (2004) 24(15):3801-3809.

Kayed, R. et al., "Common structure of soluble amyloid oligomers implies common mechanism of pathogenesis," Science (2003) 300(18):486-489.

(56) References Cited

OTHER PUBLICATIONS

Kellermann, S-A. et al., "Antibody discovery: the use of transgenic mice to generate human monoclonal antibodies for therapeutics," Curr. Opin. in Biotechnol. (2002) 13:593-597.

Kenneth, R.H. in Monoclonal Antibodies: A New Dimension in Biological Analyses, Plenum Publishing Corp. New York, New York (1980).

Kent, S.B.H., "Chemical synthesis of peptides and proteins," Ann. Rev. Biochem. (1988) 57:957-989.

Keowkase, R. et al., "Mechanism of CNS drugs and their combinations for Alzheimer's disease," Central Nervous System Agents in Medicinal Chemistry (2008) 8(4):241-248.

Kettleborough, C.A. et al., "Isolation of tumor cell-specific single-chain Fv from immunized mice using phage-antibody libraries and the re-construction of whole antibodies from these antibody fragments," Eur. J. Immunol. (1994) 24:952-958.

Kim, N.D. et al., "Putative therapeutic agents for the learning and memory deficits of people with Down syndrome," Bioorg. Med. Chem. Lett. (2006) 16(14):3772-3776.

Kim, Y.S. et al., "Biological tuning of synthetic tactics in solid-phase synthesis: application to Abeta(1-42)" J. Org. Chem. (2004) 69(22):7776-7778.

Kipriyanov, S.M. et al., "Recombinant single-chain Fv fragments carrying C-terminal cysteine residues: production of bivalent and biotinylated miniantibodies," Mol. Immun. (1994) 31(14):1047-1058.

Kipriyanov, S.M. et al., "Single-chain antibody streptavidin fusions: tetrameric bifunctional scFv-complexes with biotin binding activity and enhanced affinity to antigen," Hum. Antibod. Hybridomas (1995) 6(3):93-101.

Kirkitadze, M.d. et al., "Identification and characterization of key kinetic intermediates in amyloid B-protein fibrillogenesis," J. Mol. Biol. (2001) 312:1103-1119.

Kitamura, Y. et al., "Stress proteins and regulation of microglial amyloid-beta phagocytosis," Folia Pharmacologica Japonica (2004) 124(6):407-413.

Kitchin, K. et al., "Cloning, expression, and purification of an anti-desipramine single chain antibody in NS/0 myeloma cells," J. Pharm. Sci. (1995) 84(10):1184-1189.

Klafki, H-W. et al., "Electrophoretic separation of beta-A4 peptides (1-40) and 1-42)," Anal. Biochem. (1996) 237:24-29.

Klein, W., "A beta toxicity in Alzheimers disease; globular oligomers (ADDLs) as new vaccine and drug targets," Neurochem. Intl. (2002) 41(5):345-352.

Klyubin, I. et al., "Amyloid beta-protein (abeta) bearing the arctic mutation is a more potent inhibitor of LTP than wild type Abeta," Society for Neuroscience Abstract Viewer and Itinerary Planner (2003), 2003Abstract No. 904.13, 33rd Annual Meeting of the Society of Neuroscience, New Orleans, LA, Nov. 8-12, 2003.

Knappik, A. et al., "Fully synthetic human combinatorial antibody libraries (hUCAL) based on modular consensus frameworks and CDRs randomized with trinucleotides," J. Mol. Biol. (2000) 296:57-86.

Knowles, J.K. et al., "the p75 neurotrophin receptor promotes amyloid-beta(1-42)-induced neuritic dystrophy in vitro and in vivo," J. Neurosci. (2009) 29:10627-10637.

Kobayashi et al., "Tryptophan H33 plays an important role in Pyrimidine (6-4) pyrimidone photo product binding by a high-affinity antibody," Protein Eng. (1999) 12:879-884.

Koh, S-H. et al., "Amyloid-beta-induced neurotoxicity is reduced by inhibition of glycogen synthase kinase-3," Brain Res. (2008) 1188:254-262.

Kohler, "Continuous cultues of fused cells secreting antibody of predefined specificity," Nature (1975) 256:495-497.

Kokubo, H. et al., "Oligomeric proteins ultrastructurally localize to cell processes, especially to axon terminals with higher density, but not to lipid rafts in Tg2576 mouse brain," Brain Res. (2005) 1045(1-2):224-228.

Kontermann, Antibody Engineering, Springer-Verlag, Berlin, Table of Contents (2001).

Kooistra, J. et al., "A new function of human htra2 as an amyloid-beta oligomerization inhibitor," J. Alzheimer's Disease (2009) 17(2):281-294.

Kortekaas, P. et al., "Development of HVA and LVA calcium currents in pyramidal CA1 neurons in the hippocampus of the rat," Dev. Brain Res. (1997) 101(1-2):139-147.

Kranenburg, O. et al., "beta-Amyloid (Abeta) cuases detachment of N1E-115 neuroblastoma cells by acting as a scaffold for cell-associated plasminogen activity," Mol. Cell. Neurosci. (2005) 28(3):496-508.

Kriegler, M., Gene Transfer and Expression—A Laboratory Manual (1990) Table of Contents.

Kumar et al., "Molecular cloning and expression of the Fabs of human autoantibodies in *Escherichia coli*," J. Biol. Chem. (2000) 275:35129-35136.

Kumar, A. et al., "Neuropathology and therapeutic management of Alzheimer's disease—an update," Drugs of the Future (2008) 33(5):433-446.

Kumar-Singh, S. et al., "Dense-core senile plaques in the Flemish variant of Alzheimer's disease are vasocentric," Am. J. Pathol. (2002) 161(2):507-520.

Kuo, Y-M. et al., "Water-soluble Abeta (N-40, N-42) oligomers in normal and Alzheimer disease brains," J. Biol. Chem. (1996) 271(8):4077-4081.

Kwon, Y.E. et al., "Synthesis, in vitro assay, and molecular modeling of new piperidine derivatives having dual inhibitory potency against acetylcholinesterase and Abeta SUB 1-42 aggregation for Alzheimer's disease therapeutics," Bioorg. Med. Chem. (2007) 15(20):6596-6607.

Lacor et al., "Synaptic targeting by Alzheimer's-related amyloid beta oligomers," J. Neurosci. (2004) 24:10191-10200.

Laemmli, U.K. et al., "Cleavage of structural proteins during the assembly of the head of bacteriophage T4," Nature (1970) 227:680-685.

Lahiri, D.K. et al., "Lethal weapon: amyloid beta-peptide, role in the oxidative stress and neurodegeneration of Alzheimer's disease," Neurobiol Aging (2004) 25(5):581-587.

Lam, a.R. et al., "Effects of the Arctic (E22-G) mutation on amyloid beta-protein folding: discrete molecular dynamics study," J. Amer. Chem. Soc. (2008) 130(51):17413-22.

Lam, X.M. et al., "Microencapsulation of recombinant humanized monoclonal antibody for local delivery," Proceedings Intl. Symp. Control. Rel. Bioact. Mater. (1997) 24:759-760.

Lambert, M.P. et al., "Diffusible, nonfibrillar ligands derived from a Beta1-42 are potent central nervous system neurotoxins," Proc. Natl. Acad. Sci. (1998) 95:6448-6453.

Lambert, M.P. et al., "Monoclonal antibodies that target pathological assemblies of A beta," J. Neurochem. (2007) 100(1):23-35.

Lambert, M.P. et al., Vaccination with soluble AB oilgerm generates toxicity-neutralizing antibodies, J. Neurochem. (2001) 79(3):595-605.

Langer & Peppas, Editors, Journal of Macromolec. Sci. (1983) 23:61-127.

Langer, R., New methods of drug delivery, Science (1990) 249:1527-1533.

Lanni, C. et al., "Studies and screening of molecules interacting with beta amyloid and other amyloidogenic proteins," Society for Neuroscience Abstract Viewer and Itinerary Planner (2003) Abstract No. 841.1, 33rd Annual Meeting of the Society of Neuroscience, New Orleans, LA, Nov. 8-12, 2003.

Lashuel, H.A. et al., "Amyloid pores from pathogenic mutations," Nature (2002) 418(6895):291.

Lau, T-L. et al., "Cholesterol and clioquinol modulation of A beta(1-42) interaction with phospholipid bilayers and metals," Biochimica et biophysica acta 92007) 1768(12):3135-44.

Lauren, J. et al., "Cellular prion protein mediates impairment of synaptic plasticity by amyloid-beta oligomers," Nature (2009) 457(7233):1128-1132.

Lazo, N.D. et al., "On the nucleation of amyloid beta-protein monomer folding," Protein Sci. (2005) 14(6):1581-15196.

Leader, K.A. et al., "Antibody responses to the blood group antigen D in SCID mice reconstituted with human blood mononuclear cells," Immunology (1992) 76:229-234.

(56) References Cited

OTHER PUBLICATIONS

Lecanu, L. et al., "Caprospinol: moving from a neuroactive steroid to a neurotropic drug," Exp. Opin. Invest. Drugs (2009) 18(3):265-276.
Lee, C-C. et al., "Insulin rescues amyloid beta-induced impairment of hippocampal long-term potentiation," Neurobiol. Aging (2009) 30(3):377-387.
Lee, D.H.S., et al., "Differential physiologic responses of alpha7 nicotinic acetylcholine receptors to beta-amyloid SUB 1-40 and beta-amyloid SUB 10-42," J. Neurobiol. (2003) 55(1):25-30.
Lee, E.B. et al., "Secretion and intracellular generation of truncated Abeta in beta-site amyloid-beta precursor protein-cleaving enzyme expressing human neurons," J. Biol Chem. (2003) 278(7):4458-4466.
Lee, E.B. et al., "Targeting amyloid-beta peptide (Abeta) oligomers by passive immunization with a conformation-selective monoclonal antibody improves learning and memory in Abeta precursor protein (APP) transgenic mice," J. Biol. Chem. (2006) 281(7):4292-4299.
Lee, H-K. et al., "The insulin/Akt signaling pathway is targeted by intracellular beta-amyloid," Mol. Biol. Cell (2009) 20(5):1533-1544.
Lee, T.Y. et al., "Artificial proteases toward catalytic drugs for amyloid diseases," Pure and Applied Chem. (2009) 81:255-262.
Lemere, C.A. et al., "Amyloid-beta immunotherapy for the prevention and treatment of Alzheimer disease: lessons from mice, monkeys, and humans," Rejuvenation Res. (2006) 9(1):77-84.
Lemere, C.A. et al., "Developing novel immunogens for a safe and effective Alzheimer's disease vaccineNeurotherapy: Progress in Restorative Neuroscience and Neurology," Progress in Brain Research (2009) 175:83-93.
Lerner, E.A., "How to make a hybridoma," The Yale Journal of Biology and Medicine (1981) 54(5):387-402.
Leveille, F. et al., "Influence des formes oligomeriques du peptide amyloide beta 1-42 sur la viabilite neuronale," Revue Neurologique (2007) 163(11)-2:4S23.
LeVine, H. et al., "Alzheimer's .beta.-peptide oligomer formation at physiologic concentrations," Anal. Biochem. (2004) 335:81-90.
Levitt, M., "Molecular dynamics of native protein," J. Mol. Biol. (1983) 168:595-620.
Levy et al., "Inhibition of calcification of bioprosthetic heart valves by local controlled-release diphosphonate," Science (1985) 228:190-192.
Lewis, H. et al., "Quantification of Alzheimer pathology in ageing and dementia: age-related accumulation of amyloid-beta(42) peptide in vascular dementia," Neuropath. Appl. Neurobiol. (2006) 32(2):103-118.
Li, H. et al., "SAR and mechanistic studies of tetrapeptide inhibitors of A beta 42-induced neurotoxicity," Biopolymers (2009) 92(4):P077.
Liao, Y.J. et al., "Anti-Ca2+ channel antibody attenuates Ca2+ currents and mimics cerebellar ataxia in vio," Proc. Natl. Acad. Sci. USA (2008) 105(7):2705-2710.
Liirs, T. et al., "3D structure of Alzheimer's amyloid-beta (1-42) fibrils," Proc. Natl. Acad. Sci. (2005) 102(48):17342-17347.
Lindberg, C. et al., "beta-amyloid protein structure determines the nature of cytokine release from rat microglia," J. Mol. Neurosci. (2005) 271-12.
Little, M. et al., "Of mice and men: hybridoma and recombinant antibodies," Immun. Today (2000) 21(8):364-370.
Liu, M. et al., "Progress in soluble Abeta oligomers in Alzheimer's disease and drugs targeting Abeta oligomers," Chinese Pharmacological Bulletin (2008) 24(12):1554-1557.
Liu, Q. et al., "A novel nicotinic acetylcholine receptor subtype in basal forebrain cholinergic neurons with high sensitivity to amyloid peptides," J. Neurosci. (2009) 29(4):918-929.
Liu, R. et al., "Residues 17-20 and 35-35 of beta-amyloid play critical roles in aggregation," J. Neurosci Res. (2004) 75(2):162-171.
Liu, R. et al., "Trehalose differentially inhibits aggregation and neurotoxicity of beta-amyloid 40 and 42," Neurobiol. Dis. (2005) 20(1):74-81.
Lonberg, N. et al., "Antigen-specific human antibodies from mice comprising four distinct genetic modifications," Nature (1994) 368:856-859.
Lonberg, N. et al., "Human antibodies from transgenic mice," Intern. Rev. Immunol. (1995) 13:65-92.
Lue, L-F et al., "Soluble amyloid beta peptide concentration as a predictor of synaptic change in Alzheimer's disease," Am. J. Path. (1999) 155(3):853-862.
Lunn, M.P.T. et al., "High-affinity anti-ganglioside IgG antibodies raised in complex ganglioside knockout mice: reexamination of FDIa immunolocalization," J. Neurochem. (2000) 75:404-412.
Ma, Q.L. et al., "p21-activated kinase-aberrant activation and translocation in Alzheimer's disease pathogenesis," J. Biol. Chem. (2008) 283(20):14132-14143.
Macao, B. et al., "Recombinant amyloid beta-peptide production by coexpression with an affibody ligand," BMC Biotechnology (2008) 8:82.
MacCallum, R. M. et al., "Antibody-antigen interactions: contact analysis and binding site topography," J. Mol. Biol. (1996) 262:732-745.
Maccioni, R.B. et al., "What have we learned from the tau hypothesis? Current hypothesis and research milestones in Alzheimer's disease current hypotheses and research milestones in Alzheimer's disease," International Summitt Meeting on Current Hypotheses on Alzheimer Disease, Renaca, Chile, Nov. 22-25, 2007.
MacQuitty, J.M. et al., "GenPharm's knockout mice," Science (1992) 257:1188.
Mader, C. et al., "Interaction of the crystalline bacterial cell surface layer protein SbsB and the secondary cell wall polymer of geobacillus stearothermophilus PV72 assessed by real-time surface plasmon resonance biosensor technology," J. Bacteriol. (2004).
Madrigal, J.L.M. et al., "Neuroprotective actions of noradrenaline: effects of glutathione synthesis and activation of peroxisome proliferator activated receptor delta," J. Neurochem. (2007) 103(5):2092-101.
Maier, M. et al., "Short amyloid-beta immunogens reduce cerebral in an Alzheimer's disease mouse model in the absence of an Amyloid-beta-specific cellular immune response," J. Neurosci. (2006) 26(18):4717-4728.
Maliga, P. et al., Methods in Plant Molecular Biology—A Laboratory Manual, Table of Contents (1995).
Mandal, P.K. et al., "Alzheimer's disease: halothane induces Abeta peptide to oligomeric form—solution NMR studies," Neurochem. Res. (2006) 31(7):883-890.
Manelli, A.M. et al., "A beta 42 neurotoxicity in primary co-cultures: effect of apoE isoform and A beta conformation," Neurobiol. of Aging 92007) 281139-1147.
Manelli, A.M. et al., "ApoE and Abeta1-42 interactions," J. Mol. Neurosci. (2004) 23235-246.
Manelli, A.M. et al., "Glial activation by oligomeric versus fibrillar Abeta1-42," Soc. for Neurosci. Abstract Viewer and Itinerary Planner (2002), Abstract No. 193.9, 32nd Annual meeting of the Society for Neuroscience, Orlando, FL, Nov. 2-7, 2002.
Marachalonis, J.J. et al., "Evolutionary factors in the emergence of the combinatorial germline antibody repertoire," Adv. Exp. Med. Biol. (2001) 484:13-30.
Maria, T.J. et al., "Upregulation of p21(Cip1) in activated glial cells," Glia (2009) 57524-534.
Mariette, X., "Nucleotidic sequence analysis of the variable domains of four human monoclonal IgM with an antibody activity to myelin-associated glycoprotein," Eur. J. Immunol. (1993) 23:846-851.
Marlow, L. et al., "APH1, PEN2 and Nicastrin increase Abeta levels and gamma-secretase activity," Biochem. Biophys. Res. Comm. (2005) 305(3):502-509.
Masliah, E. et al., "Progress in the development of new treatments for combined Alzheimer's and Parkinson's diseases," Drug Development Res. (2002) 56282-292.

(56) References Cited

OTHER PUBLICATIONS

Masman, MF. Et al., "In silico study of full-length amyloid beta 1-42 tri- and penta-oligomers in solution," J. Phys. Chem. B. (2009) 113:11710-11719.
Masters, C.L. et al., "Amyloid plaque core portein in Alzheimer disease and Down syndrome," Proc. Natl. Acad. Sci. USA (1985) 82:4245-4249.
Mastrangelo, I.A. et al., "High-resolution atomic force microscopy of soluble A.beta.42 oligomers," J. Mol. Biol. (2006) 358:106-119.
Masuda, Y. et al., "Identification of physiological and toxic conformations in Abeta42 aggregates," Chem Bio Chem. (2009) 10(2):287-295.
Mathura, V.S. et al., "Model of Alzheimer's disease amyloid-beta peptide based on a RNA binding protien," Biochem. Biophys. Res. Comm. (2005) 332(2):585-592.
Mattson et al., "A practical approach to crosslinking," Mol. Biol. Reports (1993) 17:167-183.
Mattson, M.P., "Pathways towards and away from Alzheimer's disease," Nature (2004) 430:631-639.
Mattson, M.P., "Pathways towards and away from Alzheimer's disease," Nature (2004) 431(7004):107.
Maurer, M.H. et al., "the proteome of neural stem cells from adult rat hippocampus," Proteome Sci. (2003) 1(1):4.
May, K., "Buying a new immnoassay system?" BioTechnology-TIBTECH (1993) 11:272-273.
McCafferty, J. et al., "Phage antibodies: filamentous phage displaying antibody variable domains," Nature (1990) 348:552-554.
McLaurin, J. et al., "Inositol steroisomers stabilize an oligomeric aggregate of Alzheimer amyloid beta peptide and inhibit Abeta-induced toxicity," J. Biol. Chem. (2000) 27518495-18502.
McLaurin, J. et al., "Review modulating factors in amyloid-beta fibril formation," J. Structural Biol. (2000) 130(2-3):259-270.
McLean, C.A. et al., "Soluble pool of Abeta amyloid as a determinant of severity of neurodegeneration in Alzheimer's disease," Am. Neurol. Assoc. (1999) 46:860-866.
Meijer et al., "Biochemical and cellular effects of roscovitine, a potent and selective inhibitor of the cyclin-dependent kinases cdc2, cdk2 and cdk5," Eur. J. Biochem. (1997) 243(1-2):527-536.
Meli, G. et al., "Direct in vivo intracellular selection of conformation-sensitive antibody domains targeting Alzheimer's amyloid-beta oligomers," J. Mol. Biol. (2009) 287(3):584-606.
Mendez, M.J. et al., "Functional transplant of megabase human immunoglobulin loci recapitulates human antibody response in mice," Nat. Genet. (1997) 15(2):146-156.
Merrifield, B., "Solid phase synthesis," Science (1986) 232:342.
Merrifield, J., "The total synthesis of an enzyme with ribonuclease A activity," J. Am. Chem. Soc. (1969) 91:501-502.
Miller, Y. et al., "Polymorphism of Alzheimer's A beta(17-42) (p3) oligomers: the importance of the turn location and its conformation," Biophys. J. (2009) 971168-1177.
Minkeviciene, R. et al., "Amyloid beta-induced neuronal hyperexcitability triggers progressive epilepsy," J. Neurosci. (2009) 29(11):3453-3462.
Mizushima, S. et al., "pEF-BOX, a powerful mammalian expression vector," Nucl. Acids Res. (1990) 18(17):5322.
Moechars et al., "Early phenotypic changes in transgenic mice that overexpress different mutants of amyloid precursor protein in brain," J. Biol. Chem. (1999) 274(10):6483-6492.
Moir et al., "Autoantibodies to redox-modified oligomeric Abeta are attenuated in the plasma of Alzheimer's disease patients," J. Biol. Chem. (2005) 280:17458-17463.
Monien, B.H. et al., "A novel approach to Alzheimer's disease therapy: inhibition of A beta 42 oligomerization by C-terminal A beta 42 fragments," J. Peptide Sci. (2006) 12147.
Morgan, R.a. et al., "Human gene therapy," Ann. Rev. Biochem. (1993) 62:191-217.
Morgan, T.E. et al., "Abeta-derived diffusible ligands (ADDLs): Clusterin (apo J), congo red binding and toxicity," Society for Neuroscience Abstracts (1999) Abstract No. 252130, 29th Annual Meeting of the Society for Neuroscience, Miami Beach, FL, Oct. 23-28, 1999.
Morley, J.S., "Modulation of the action of regulatory peptides by structural modification," TIPS (1980) 463-468.
Morrison, S.L. et al., "Chimeric human antibody molecules: mouse antigen-binding domains with human constant region domains," Proc. Natl. Acad. Sci. (1984) 81:6851-6855.
Morrison, S.L., "Transfectomas provide novel chimeric antibodies," Science (1986) 229:1202-1207.
Mueller, W. et al., "Apolipoprotein E isoforms increase intracellular Ca2+ differentially through an omega-agatoxin IVA-sensitive Ca2+ channel," Brain Pathology (1998) 8(4):641-653.
Mullan et al., "A locus for familial early-onset Alzheimer's disease on the long arm of chromosome 14, proximal to the alphal-amtichymotrypain gene," Nature Genet. (1992) 2:340-342.
Mullan, M. et al., "A pathogenic mutation for probable Alzheimer's disease in the APP gene at the N-terminus of beta-amyloid," Nat. Genet. (1992) 1(5):345-347.
Muller, W. et al., "Impaired Ca-signling in astroycytes from the Ts16 mouse model of Down syndrome," Neurosci. Lett. (1997) 223(2):81-84.
Mulligan, R.C., "The basic science of gene therapy," Science (1993) 260:926-932.
Mullis, K. et al., "Specific enzymatic amplification of DNA in vitro: the polymerase chain reaction," Cold Spring Harbor Symp. Quant. Biol. (1986) 51:263-273.
Munter, L-M. et al., "GxxxG motifs within the amyloid precursor protein transmembrane sequence are critical for the etiology of Abeta42," EMBO J. (2007) 26(6):1702-1712.
Murphy, W.J. et al., "CD40 stimulation promotes human dsecondary immunoglobulin responses in HuPBL-SCID chimeras," Clin. Immunol. (1999) 90(1):22-27.
Murphy, W.J. et al., "The huPBL-SCID mouse as a means to examine human immune functionin vivo," Immunol. (1996) 8:233-241.
Murray, M.M. et al, "Amyloid beta protein: a beta 40 inhibits A beta 42 oligomerization," J. Am. Chem. Soc. (2009) 131:6316-6317.
Myagkova, M.A. et al., "Autoantibodies to beta-amyloid and neurotransmitters in patients with Alzheimer's disease and senile dementia of the Alzheimer type," Bulletin of Exp. Biol. Med. (2001) 2:127-129.
Nagele, R.G. et al., "Contribution of glial cells to the development of amyloid plaques in Alzheimer's disease," Neurobiol of Aging (2004) 25(5):663-674.
Naslund, J. et al., "Relative abundance of Alzheimer Abeta amyloid peptide variants in Alzheimer disease and normal aging," Proc. Natl. Acad. Sci. (1994) 91:8378-8382.
Nath et al., "Autoantibodies to amyloid B-peptide (AB) are increased in Alzheimer's disease patients and AB antibodies can enhance AB neurotoxicity," Neuromol. Med. (2003) 3:29-39.
Needleman, S.B. et al., "A general method applicable to the search for similarities in the amino acid sequence of two proteins," J. Mol. Biol. (1970) 48:443-453.
Nerelius, C. et al., "Alpha-Helix targeting reduces amyloid-beta peptide toxicity," Proc. Natl. Acad. Sci. USA (2009) 106(23):9191-9196.
Neuberger, M.S. et al., "Recombinant antibodies possessing novel effector functions," Nature (1984) 312:604-608.
Nguyen, H. et al., "Production of human monoclonal antibodies in SCID mouse," Microbiol. Immunol. (1997) 41(12):901-907.
Nicholas, M.R. et al., "Different amyloid-ent amyloid-beta aggregation states induced monocyte differentiation or activation," J. Neurochem. (2009) 10867, 40th Annual Meeting of the American Society for Neurochemistry, Charleston, South Carolina, Mar. 7-11, 2009.
Nielsen, H.M. et al., "Preferential uptake of amyloid beta 1-42 oligomers by primary human astrocytes in vitro: influence of SAP and C1q," Mol. Immunol. (2009) 262860, 12th European Meeting on Complement in Human Disease, Hungary, Sep. 5-8, 2009.

(56) References Cited

OTHER PUBLICATIONS

Nilges, M. et al., "Determination of three-dimensional structures of proteins from interproton distance data by hybrid distance geometry-dynamical simulated annealing calculations," FEBS Lett. (1989) 229(2):317-324.
Nimmrich, V. et al., "Amyloid beta oligomers (A beta(1-42) globulomer) suppress spontaneous synaptic activity by inhibition of P/Q-type calcium currents," J. Neurosci. (2008) 28(4):788-797.
Nimmrich, V. et al., "Is Alzheimer's disease a result of presynaptic failure?—Synaptic dysfunctions induced by oligomeric p-amyloid," Rev. Neurosci. (2009) 20(1):1-12.
Ning, S. et al., "Intratumoral radioimmunotherapy of a human colon cancer xenograft using a sustained-release gel," Radiotherapy & Oncology (1996) 39:179-189.
Nomura, I. et al., "Mechanism of impairment of long-term potentiation by amyloid beta is independent of NMDA receptors or voltage-dependent calcium channels in hippocampal CA1 pyramidal neurons," Neurosci. Lett. (2005) 391(1-2):1-6.
Oi, V.T. et al., "Chimeric antibodies," BioTechniques (1985) 4(3):214-215.
Okamuro et al., The Biochemistry of Plants—A comprehensive Treatise, V. 15, 1-82 (1989).
Ono, K. et al., "Effects of grape seed-derived polyphenols on amyloid beta-protein self-assembly and cytotoxicity," J. Biol. Chem. (2008) 283(47):32176-32187.
Opazo, C. et al., "Metalloenzyme-like activity of Alzheimer's disease beta-amyloid: Cu-dependent catalytic conversion of dopamine, cholesterol, and biological reducing agents to neurotoxic H SUB 20 SUB 2," J. Biol. Chem. (2002) 277(43):40302-40308.
Orgogozo et al., "Subacute meningoencephalitis in a subset of patients with AD after Abeta42 immunization," Neurology (2003) 61:46-54.
Origlia, N. et al., "Abeta-dependent inhibition of LTP in different intracortical circuits of the visual cortex: the role of RAGE," J. Alzheimer's Disease (2009) 17(1):59-68.
Otto, M. et al., "Neurochemical approaches of cerebrospinal fluid diagnostics in neurogenerative diseases," Methods (2008) 44(4):289-298.
Padlan et al., "Structure of an antibody-antigen complex: crystal structure of the HyHEL-10 Fab-lysozyme complex," Proc. Natl. Acad. Sci USA (1989) 86:5938-5942.
Padlan, E.A. et al., "Identification of specificity-determining residues in antibodies," FASEB (1995) 9:133-139.
Padlan, E.A., "A possible procedure for recucing the immunogenicity of antibody variable domains while preserving their ligand-binding properties," Molec. Immunol. (1991) 28(4/5):489-498.
Palmer, J. et al., "Endothelin-converting enzyme-2 is increased in Alzheimer's disease and up-regulated by Abeta," Am. J. Path. (2009) 175(1):262-270.
Pan, X.D. et al., "Tripchlorolide protects neuronal cells from microglia-mediated beta-amyloid neurotoxicity through inhibiting NF-kappa B and JNK signaling," GLIA (2009) 57:1227-1238.
Pan, X-D. et al., "Effect of inflammatory responses in microglia induced by oligomeric beta-amyloid SUB 1-42 on neuronal cells," Acta Anatomica Sinica (2008) 39(6):804-809.
Partis, M.D. et al., "Crosslinking of proteins by omega-maleimido alkanoyl N-hydroxysuccinimide esters," J. Protein Chem. (1983) 2:263-277.
Pastor, M.T. et al., "Amyloid toxicity is independent of polypeptide sequence, length and chirality," J. Mol. Biol. (2008) 375:695-707.
Paul, W.E., editor, Fundamental Immunology, Third Edition, Raven Press, New York (1993) 292-295.
Peacock, M.L. et al., "Novel amyloid precursor protein gene mutation (codon 665Asp) in a patient with late-onset Alzheimer's disease," Ann. Neurol. (1994) 35(4):432-438.
Peacock, M.L. et al., "Novel polymorphism in the A4 region of the amyloid precursor protein gene in a patient without Alzheimer's disease," Neurol. (1993) 43(6):1254-1256.
Pearson, W.R. et al., "Improved tools for biological sequence comparison," PNAS (1988) 85:2444-2448.

Pellicano, M. et al., "The sea urchin embryo: a mdoel to study Alzheimer's beta amyloid induced toxicity," Archives of Biochem. Biophys. (2009) 483:120-126.
Perouansky, M., "Liaisons dangereuses? General anaesthetics and long-term toxicity in the CNS," Eur. J. Anaesthesiol. (2007) 24(2):107-115.
Persic, L. et al., "An integrated vector system for the eukaryotic expression of antibodies or their fragments after selection from phage display libraries," Gene (1997) 187:9-18.
Petrushina, I., "Alzheimer's disease peptide epitope vaccine reduces insoluble but not soluble/oligomeric Abeta species in amyloid precursor protein transgenic mice," J. Neurosci. (2007) 27(46):12721-12731.
Pfeifer, M. et al., "Cerebral hemorrhage after passitve anti-Abeta immunotherapy," Science (2002) 298:1379.
Phu, M-J et al., "Fluorescence resonance energy transfer analysis of apolipoprotein e C-terminal domain and amyloid beta peptide (1-42) interaction," J. Neurosci. Res. (2005) 80(6):877-886.
Pike, C.J. et al., "Structure—activity analyses of B-amyloid peptides: contributions of the B25-35 region to aggregation and neurotoxicity," J. Neurochem. (1995) 64(1):253-265.
Plant, LD. Et al., "The production of amyloid beta peptide is a critical requirement for the viablility of central neurons," J. Neurosci. (2003) 23(13):5531-5535.
Podlisny, M.B. et al., "Aggreagation of secreted amyloid beta-protein into sodium dodecyl sufate-stable oligomers in cell culture," J. Biol. Chem. (1995) 270(16):9564-9570.
Poljak, R.J., "Production and structure of diabodies," Structure (1994) 2:1121-1123.
Portelius, E. et al., "Targeted proteomics in Alzheimer's disease: focus on amyloid-beta," Exp. Rev. Proteomics (2008) 5(2):225-237.
Portolano, S. et al., "High affinity, thyroid-specific human autoantibodies displayed on the surface of filamentous phage use V genes similar to other autoantibodies," J. Immunol. (1993) 151(5):L2839-2851.
Presta, LG. et al., "Humanization of an antibody directed against IgE," J. Immunol. (1993) 151(5):2623-2632.
Putney, P.W., Calcium Signaling, CRC Press Inc. (2005).
Puzzo, D. et al., "Picomolar amyloid-beta positively modulates synaptic plasticity and memory in hippocampus," J. Neurosci. (2008) 28:14537-14545.
Qian, J. et al., "Presynaptic Ca2+ channels and neurotransmitter release at the terminal of a mouse cortical neuron," J. Neurosci. (2001) 21(11):3721-3728.
Qiu, W. et al., "Convenient, large-scale asymmetric synthesis of eriantiomerically pure trans-cinnamylglycine and -alpha-alamine," Tetrahedron (2000) 56:2577-2582.
Qiu, W.Q. et al., "Degradation of amyloid beta-protein by a metalloprotease secreted by microglia and other neural and non-neural cells," J. Biol. Chem. (1997) 272(10):6641-6646.
Qiu, W.Q. et al., "Insulin-degrading enzyme regulates extracellular levels of amyloid beta-protein by degradation," J. Biol. Chem. (1998) 273(49):32730-32738.
Qiu, W., "Facile synthesis of hydrocarbon-stapled peptides," Anaspec poster at 20th American Peptide Society Annual Meeting (2008).
Racke, M.M. et al., "Exacerbation of cerebral amyloid angiopathy-associated microhemmorrhage in amyloid precursor protein transgenic mice by immunotherapy is dependent on antibody recognition of deposited forms of amyloid beta," J. Neurosci. (2005) 25(3):629-636.
Rahimi, F. et al., "Photo-induced cross-linking of unmodified proteins (PICUP) applied to amyloidogenic peptides," J. Visualized Exp. (2009) 23.
Rahimi, F. et al., "Structure-function relationships of pre-fibrillar protein assemblies in Alzheimer's disease and related disorders," Curr. Alzheimer Res. (2008) 5(3):319-341.
Rambaldi, D.C. et al., "In vitro amyloid A beta(1-42) peptide aggregation monitoring by asymmetrical flow field-flow fractionation with multi-angle light scattering detection," Anal. Bioanal. Chem. (2009) 394:2145-2149.

(56) References Cited

OTHER PUBLICATIONS

Rangachari, V. et al., "Amyloid beta(1-42) rapidly forms protofibrils and oligomers by distinct pathways in low concentrations of sodium dodecylsulfatet," Biochem. (2007) 46:12451-12462.

Rangachari, V. et al., "Rationally designed dehydroalanine (Delta Ala)-containing peptides inhibit amyloid-beta (A beta) peptide aggregation," Biopolymers (2009) 91:456-465.

Rangachari, V. et al., "Secondary structure and interfacial aggregation of Amyloid beta(1-40) on sodium dodecyl sulfate micelles," Biochem. (2006) 45:8639-8648.

Ravault, S. et al., "Fusogenic Alzheimer's peptide fragment Abeta (29-42) in interaction with lipid bilayers: secondary structure, dynamics, and specific interaction with phosphatidyl ethanolamine polar heads as revealed by solid-state NMR," Protein Sci. (2005) 14(5):1181-1189.

Ravetch, J.V. et al., "Structure of the human immunoglobulin µ locus: characterization of embryonic and rearranged J and D genes," Cell (1981) 27:583-591.

Reisner, Y. et al., "The trimera mouse: generating human monoclonal antibodies and an animal model for human diseases," Trends in Biotech. (1998) 16:242-246.

Remington: The Science and Practice of Pharmacy, Mack Publishing (1995) 19th Edition: Table of Contents.

Resende, R. et al., "ER stress is involved in Abeta-induced GSK-3 beta activation and tau phosphorylation," J. Neurosci. Res. (2008) 86(9):2091-2099.

Resende, R. et al., "Neurotoxic effect of oligomeric and fibrillar species of amyloid-beta peptide 1-42: involvement of endoplasmic reticulum calcium release in oligomer-induced cell death," Neurosci. (2008) 155(3):725-737.

Riechman, L. et al., "Reshaping human antibodies for therapy," Nature (1988) 332:323-327.

Robert, R. et al., "Engineered antibody intervention strategies for Alzheimer's disease and related dementias by targeting amyloid and toxic oligomers," Protein Engineering, Design and Selection (2009) 22(3):199-208.

Roberts, R.W. et al., "RNA-peptide fusions for the in vitro selection of peptides and proteins," Proc. Natl. Acad. Sci. USA (1997) 94:12297-12302.

Robinson, J.R. et al., Sustained and Controlled Release Drug Delivery Systems, (1978) Table of Contents.

Roes, J. et al., "Mouse anti-mouse IgD monoclonal antibodies generated in IgD-deficient mice," J. Immunol. Meth. (1995) 183:231-237.

Roguska, M.A. et al., "Humanization of murine monclonal antibodies through variable domain resurfacing," Proc. Natl. Acad. Sci. (1994) 91:969-973.

Roher, A.A. et al., "Oligomerization and fibril assembly of the amyloid-beta protein," Biochimica et Biophysica Acta (2000) 1502(1):31-43.

Roher, A.E. et al., "Morphology and toxicity of Abeta-(1-42) dimer derived from neuritic and vascular amyloid deposits of Alzheimer's disease," J. Biol. Chem. (1996) 271(34):20631-20635.

Ronicke, R. et al., Abeta mediated diminution of MTT reduction—an artefact or single cell culture? PLoS One (2008) 3(9) e3236.

Rossi, G. et al., "A family with Alzheimer disease and strokes associated with A713T mutation of the APP gene," Neurology (2004) 63(5):910-912.

Rouillard, J-M et al., "Gene2Oligo: oligonucleotide design for in vitro gene synthesis," Nucl. Acids. Res. (2004) 32:W176-180.

Rudikoff et al., "Single amino acid substitution altering antigen-binding specificity," Proc. Natl. Acad. Sci. USA (1982) 79(6):1979-1983.

Russo, C. et al., "Presenilin-1 mutatiosn in Alzheimer's disease," Nature (2000) 405:531-532.

Sabella, S. et al., "Capillary electrophoresis studies on the aggregation process of beta-amyloid 1-42 and 1-40 peptides," Electrophoresis (2004) 25:3186-3194.

Saido, T.C. et al., "Dominant and differential deposition of distinct beta-amyloid peptide species, AbetaN3 in senile plaques," Neuron (1995) 14:457-486.

Sakmann, B. et al., "Single-channel recording" in Antibodies, 2nd edition, Springer, Table of Contents (1995).

Salomon, A.R. et al., "Nicotine inhibits amyloid formation by the beta-peptide," Biochem. (1996) 35(42):13568-78.

Sambamurti, K. et al., "A partial failure of membrane protein turnover may cause Alzheimer's disease: a new hypothesis," Curr. Alzheimer Res. (2006) 3:81-90.

Sambrook, J. et al., Molecular Cloning—A Laboratory Manual, 2nd Edition (1989) Table of Contents 17.2-17.9.

Samoszuk, M.K. et al., "A peroxide-generating immunoconjugate directed to eosinophil peroxidase is cytotoxic to Hodgkin's disease cells in vitro," Antibody, Immunoconjugates and Radiopharmaceuticals (1989) 2:37-45.

Sandberg, A. et al., "Stabilization of neurotoxic Alzheimer amyloid-beta oligomers by protein engineering," Proc. Natl. Acad. Sci. (2010) 107(35):15595-15600.

Sankaranarayanan, S., "Genetically modified mice models for Alzheimer's disease," Curr. Top. Med. Chem. (2006) 6(6):609-627.

Santos, a.N. et al., "A method for the detection of amyloid-beta SUB 1-40, amyloid-beta SUB 1-42 and amyloid-beta oligomers in blood using magnetic beads in combination with flow cytometry and its application in the diagnostics of Alzheimer's disease," J. Alzheimer's Dis. (2008) 14(2):127-131.

Sanz-Blasco, S. et al., "Mitochondrial Ca2+ overload underlies a beta oligomers neurotoxicity providing an unexpected mechanism of neuroprotection by NSAIDs," PloS One (2008) 3 Article No. e2718.

Sato, J. et al., "Design of peptides that form amyloid-like fibrils capturing amyloid beta 1-42 peptides," Chemistry A Eur. J. (2007) 13:7745-7752.

Sato, N. et al., "Development of new screening system for Alzheimer disease, in vitro Abeta sink assay, to identify the dissocation of soluble Abeta from fibrils," Neurobiol. Dis. (2006) 22(3):487-495.

Saudek, C.D. et al., "A preliminary trail of the programmable implantable medication system for insulin delivery," New Engl. J. Med. (1989) 321(9):574-579.

Sawai, H. et al., "Direct production of the fab fragment derived from the sperm immobilizing antibody using polymerase chain reaction and cDNA expression vectors," Amer. J. Reproduc. Immunol. (1995) 34:26-34.

Schafmeister et al., "An all-hydrocarbon cross-linking system for enhancing the helicity and metabolilc stability of peptides," J. Am. Chem. Soc. (2000) 122:5891-5892.

Schenk et al., "Current progress in beta-amyloid immunotherapy," Curr. Opin. Immun. (2004) 16:599-606.

Schenk, D., "Amyloid-beta immunotherapy for Alzheimer's disease: the end of the beginning," Nature (2002) 3:824-828.

Schilling, S. et al., "On the seeding and oligomerization of pGlu-amyloid peptides (in vitro)," Biochem. (2006) 45(41):12393-12399.

Scholtzova, H. et al., "Induction fo toll-like receptor 9 signaling as a method for ameliorating Alzheimer's disease-related pathology," J. Neurosci. (2009) 291846-1854.

Schott, J.M. et al., "New developments in mild cognitive impairment and Alzheimer's disease," Curr. Opin. Neurol. (2006) 19(6):552-558.

Schuck, P., "Size distribution analysis of macromolecules by sedimentation velocity ultracentrifugation and Lamm equation modeling," Biophys. J. (2000) 78:1606-1619.

Sciaretta et al., "Abeta40-Lactam (D23/K28) models a conformation highly favorable for nucleation of amyloid," Biochem. (2005) 44:6003-6014.

Sefton, M.V., "Implantable pumps," Critical Reviews in Biomedical Engineering (1987) 14(3):201-240.

Selenica, M.L. et al., "Cystatin C reduces the in vitro formation of soluble Abeta1-42 oligomers and protofibrils," Scan. J. Clin. Lab. Invest. (2007) 67(2):179-190.

Selkoe, D.J., "Alzheimer's disease: genes, proteins and therapy," Physiol. Reviews, American Physiological Society (2001) 81(2):741-766.

(56) References Cited

OTHER PUBLICATIONS

Selkoe, D.J., Clearing the brain's amyloid cobwebs, Neuron (2001) 32:177-180.
Sergeant, N. et al., "Truncated beta-amyloid peptide species in pre-clinical Alzheimer's disease as new targets for the vaccination approach," J. Neurochem. (2003) 85:1581-1591.
Shapiro, .S. et al., "DNA target motifs of somatic mutagenesis in antibody genes," Crit. Rev. in Immunol (2002) 22(3):183-200.
Shields, R.L. et al., "Lack of fucose on human IgG1 N-linked oligosaccharide improves binding to human FcγRIII and antibody-dependent cellular toxiciy," J. Biol. Chem. (2002) 277(30):26733-26740.
Shimizu, E. et al., "IL-4- induced selective clearance of oligomeric beta-amyloid peptide(1-42) by rat primary type 2 microglia," J. Immun. (2008) 181(9):6503-6513.
Shu, L. et al., "Secretion of a single-gene-encoded immunoglobulin from myeloma cells," Proc. Natl. Acad. Sci.(1993) 90:7995-7999.
Shughrue et al., "Anti=ADDL antibodies differentially block oligomer binding to hippocampal neurons," Neurobiol. Aging (2010) 31:189-202.
Sikorski, P. et al., "Structure and texture of fibrous crystals formed by Alzheimer's abeta(11-25) peptide fragment," Structure (London) (2003) 11(8):915-926.
Sims, M.J. et al., "A humanized CD18 antibody can block function without cell destruction," J. Immunol. (1993) 151(4):2296-2308.
Sinz, A., "Chemical cross-linking and mass spectrometry for mapping three-dimensional structures of proteins and protein complexes," J. Mass Spectrom. (2003) 38:1225-1237.
Sjogren, M. et al., "Cholesterol and Alzheimer's disease—is there a relation?," Mechanisms of Aging and Development (2006) 127:138-147.
Sjogren, M. et al., "The link between cholesterol and Alzheimer's disease," World J. Biol. Psych. (2005) 6(2):85-97.
Skerra, A. et al., "Assembly of a functional immunoglobulin F fragment in *Escherichia coli*," Science (1988) 240:1038-1040.
Smith, D.P. et al., "Concentration dependent Cu SUP 2+ induced aggregation and dityrosine formation of the Alzheimer's disease amyloid-betapeptide," Biochem. (2007) 46(10):2881-2891.
Smith, N.W. et al., "Amphotericin B interactions with soluble oligomers of amyloid A beta 1-42 peptide," Bioorg. Med. Chem. (2009) 17:2366-2370.
Smith, T.F. et al., "Comparison of biosequences," Adv. in Applied Math (1981) 2:482-489.
Smith-Gill et al., "Contributions of immunoglobulin heavy and light chains to antibody specificity for lysozyme and two haptens," J. Immunol. (1987) 139:4135-4144.
Smithson, S.L. et al., "Molecular analysis of the heavy chain of antibodies that recognize the capsular polysaccharide of Neisseria meningitides in hu-PBMC reconstituted SCID mice and in the immunized human donor," Molec. Immunol. (1999) 36:113-124.
Smolen, V.F. et al., editors, Controlled Drug Bioavailability (1984) 1:Table of Contents.
Solorzano-Vargas, R.S. et al., "Epitope mapping and neuroprotective properties of a human single chain FV antibody that binds an internal epitope of amyloid-beta 1-42," Molecular Immunol. (2008) 45(4):881-886.
Sondag, C.M. et al., "Beta amyloid oligomers and fibrils stimulate differential activation of primary microglia," J. Neuroinflamm. (2009) 6 article No. 1.
Song et al., Biochem. Biophys. Res. Comm. (2000) 268:390-394.
Song, Y.K. et al., "Antibody mediated lung targeting of long-circulating emulsions," PDA J. of Pharm. Sci Tech. (1995) 50:372-397.
Soos, K. et al., "An improved synthesis of beta-amyloid peptides for in vitro and in vivo experiments," J. Peptide Science (2004) 10:136.
Sorensen, K. et al., "ApoE counteracts the impairment of mitochondrial activity induced by oligomeric A beta 1-42," Eur. J. Neurol. (2008) 15:45.

Spatola, A.F. et al., "Structure-activity relationships of enkephalins containing serially replaced thiomethylene amide bond surrogates," Life Sci. (1986) 38:1243-1249.
Spatola, A.F. et al., in Chemistry and Biochemistry of Amino Acids, Peptides and Proteins, B. Weinstein editor, Marcel Dekker, New York (1983) vol. VII, 267-357.
Spencer, B. et al., "Novel strategies for Alzheimer's disease treatment," Exp. Opin. Biol. Ther. (2007) 7(12): 1853-1867.
Stan, R.V., "Multiple PV1 dimers reside in the same stomatal or fesestral diaphragm," Am. J. Physiol. Heart Circ. Physiol. (2004) 286(4):H1347-1353.
Standridge, J.B., "Vicious cycles within the neuropathophysiologic mechanisms of Alzheimer's disease," Curr. Alzheimer Res. (2006) 3(2):95-107.
Staros et al., "Enhancement by N-hydroxysulfosuccinimide of water-soluble carbodilimide-mediated coupling reactions," Anal. Biochem. (1986) 156(1):220-222.
Stewart, J.M. et al., Solid-Phase Peptide Synthesis, 2nd Edition, Pierce Chemical Company (1984) Table of Contents.
Stine, W. et al., "In vitro characterization of conditions for amyloid-beta peptide oligomerization and fibrillogenesis," J. Biol. Chem. (2003) 278(13):11612-11622.
Stine, W.B. et al., "Antibodies specific for toxic Abeta oligomers," Abst. Viewer/Itinerary Planner, Soc. of Neurosci. (2003) 1.
Studnicka, G.M. et al., "Human-engineered monoclonal antibodies retain full specific binding activity by preserving non-CDR complementarity-modulating residues," Protein Eng. (1994) 7(6):805-814.
Suram, A. et al., "A new evidence for DNA nicking property of amyloid beta-peptide (1-42): relevance of Alzheimer's disease," Archives of Biochem. Biophys. (2007) 463(2):245-252.
Tabaton, M. et al., "Role of water-soluble amyloid-beta in the pathogenesis of Alzheimer's disease: role of amyloid-beta in Alzheimer's disease," Int. J. Exp. Path. (2005) 3(85):139-145.
Tabaton, M., "Coffee 'breaks' Alzheimer's disease," J. Alzheimer's Disease (2009) 17/3:699-700.
Taguchi, J. et al., "Different expresison of calreticulin and immunoglobulin binding protein in Alzheimer's disease brain," Acta Neuropathologica (2000) 100(2):153-160.
Takano, K., "Amyloid beta conformation in aqueous environment," Curr. Alzheimer Res. (2008) 5(6):540-547.
Takata, K. et al., "High mobility group box protein-1 enhances amyloid-beta neurotoxicity," J. Pharm. Sci. (2006) 100154P, 79th Annual Meeting of the Japanese Pharmacological Society, Yokohama, Japan, Mar. 8-10, 2006.
Takata, K. et al., "Possible involvement of small oligomers of amyloid-beta peptides in 15-deoxyDELTA12, 14 prostaglandin J2-sensitive microglial activation," J. Pharm. Sci. (2003) 91:330-333.
Takeda, S.I. et al., "Construction of chimaeric processed immunoglobulin genes containing mouse variable and human constant region sequences," Nature (1985) 314:452-454.
Tamagno, E. et al., "The various aggregation states of beta-amyloid 1-42 mediate different effects on oxidative stress, neurodegeneration, and BACE-1 expression," Free Radic. Biol. Med. (2006) 41(2):202-212.
Tamura, M. et al., "Structural correleates of an anticarcinoma antibody: identification of specificity-determining residues (SDRs) and development of a minimally immunogenic antibody variant by retention of SDRs only," J. Immunol. (2000) 164(3):1432-1441.
Taniguchi, A. et al., "'Click peptide': pH-triggered in situ production and aggregation of monomer Abeta1-42," Chembiochem. (2009) 10(4);710-715.
Taniuchi, M. et al., "Induction of nerve growth factor receptor in Schwann cells after axotomy," Proc. Natl. Acad. Sci. (1986) 83:4094-4098.
Tanzi, R., "Alzheimer research forum discussion: gain or loss of function—time to shake up assumptions on gamma-secretase in Alzheimer disease? Commentary," J. Alzheimer's Dis. 92007) 11(3):409.
Tanzi, R.E., "Novel therapeutics for Alzheimer's disease," Neurotherapeutics (2008) 5(3):377-380.

(56) References Cited

OTHER PUBLICATIONS

Tarozzi, A. et al., "Cyanidin 3-O-glucopyranoside protects and rescues SH-Sy5Y cells against amyloid-beta peptide-induced toxicity," Neuroreport (2008) 19(15):1483-1486.
Taylor, L.D. et al., "A transgenic mouse that expresses a diversity of human sequence heavy and light chain immunoglobulins," Nucl. Acids. Rse. (1992) 20(23):6287-6295.
Teplow, D.B. et al., "Effects of structural modifications in a beta on its oligomer size distribution," Soc. for Neurosci. Abstract Viewer and Itinerary Planner (2002), Abstract No. 19.6, 32nd Annual meeting of the Society for Neuroscience, Orlando, FL, Nov. 2-7, 2002.
Terry, R.D. et al., "Physical basis of cognitive alterations in Alzheimer's disease: synapse loss is the major correlate of cognitive impairment," Am. Neurol. Assoc. (1991) 572-580.
Terryberry, J.W. et al., "Autoantibodies in neurodegenerative diseases: antigen-specific frequencies and intrathecal analysis," Neurobiology of Aging (1998) 19(3):205-216.
Tew, D.J. et al., "Stabilization of neurotoxic soluble beta-sheet-rich conformations of the Alzheimer's disease amyloid-beta peptide," Biophys. J. (2008) 974752-2766.
Thal, D.R. et al., "Fleecy amyloid deposits in the internal layers of the human entorhinal cortex are comprised of N-terminal truncated fragments of A13," J. Neuropath. Exp. Neurol. (1999) 58:210-216.
Tijssen, P.., editor, "Hybridization with nucleic acid probes—Part II: Probe labeling and hybridzation techniques," Laboratory Techniques in Biochemistry and Molecular Biology, (1993) 24:iii-vi, 269-613, table of contents.
Tolstoshev, P., "Gene therapy, concentps, current trials and future directions," Ann. Rev. Pharmacol. Toxicol. (1993) 32:573-596.
Tomaselli, S. et al., "The alpha-to-beta conformational transition of Alzheimer's Abeta-(1-42) peptide in aqueous media is reversible: a step by step conformational analysis suggests the location of beta conformation seeding," ChemBioChem. (2006) 7(2):257-267.
Tomidokoro, Y. et al., "Familial Danish dementia: co-existence of Danish and Alzheimer amyloid subunits (Adan AND Abeta) in the absence of compact plaques," J. Biol. Chem. (2005) 280(44):36883-36894.
Tomidokoro, Y. et al., "Familial Danish dementia: the relationship of two different amyloids (ADAN/ABETA) deposited in the brain," Society for Neuroscience Abstract Viewer and Itinerary Planner (2002) 2002Abstract No. 328.9, 32nd Annual Meeting of the Society of Neuroscience, Orlando, FL, Nov. 2-7, 2002.
Tomiyama, T. et al., "A new amyloid beta variant favoring oligomerization in Alzheimer's-type dementia," Ann. Neurol. (2008) 63(3):377-387.
Tsubuki, S. et al., "Dutch, Flemish, Italian and Arctic mutations of APP and resistance of Abeta to physiologically relevant proteolytic degradation," Lancet (2003) 361(9373):1957-1958.
Turner, R. et al., "The potential exploitation of plant viral translational enhancers in biotechnology for increased gene expression," Mol. Biotech. (1995) 3:225-236.
Tusell, J.M. et al., "upregulation of p21Cip1 in activated glial cells," Glia (2009) 57(5):524-534.
Ueki et al., "Solid phase synthesis and biological activities of (Arg8)-vasopressin methylenedithioether," Bioorg. Med. Chem. Lett. (1999) 9:1767-1772.
Umana, P. et al., "Engineered glycoforms of an antieuro-blastoma IgG1 with optimized antibody-dependent cellular cytotoxic activity," Nature Biotech. (1999) 17:176-180.
Urbanc, B. et al., "Computer simulations of Alzheimer's amyloid beta-protein folding and assembly," Curr. Alzheimer Res. (2006) 3(5):493-504.
Urbanc, B. et al., "In silico study of amyloid beta-protein folding and oligomerization," Proc. Natl. Acad. Sci. USA (2004) 101:17345-17350.
Urbanc, B. et al., "Molecular dynamics simulation of amyloid beta dimer formation," Biophys. J. (2004) 87(4):2310-2321.
Urlaub et al., "Isolation of Chinese hamster cell mutants deficient in dihydrofolate reductase activity," Proc. Natl. Acad. Sci. (1980) 77:4216-4220.
Uto, L. et al., "Determination of urinary Tamm-Horsfall protein by ELISA using a maleimide method for enzyme-antibody conjugation," J. Immunol. Methods (1991) 138:87-94.
Vajdos et al., J. Mol. Biol. (2002) 320(2):415-428.
Valincius, G. et al., "Soluble amyloid beta-oligomers affect dielectric membrane properties by bilayer insertion and domain formation: implications for cell toxicity," Biophys. J. (2008) 95(10):4845-4851.
Van Broeck, B. et al., "Current insights into molecular mechanisms of Alzheimer disease and their implications for therapeutic approaches," Neurdegenerative Dis. (2007) 4(5):349-365.
Van Broeckhoven et al., "Amyloid beta protein precursor gene and hereditary cerebral hemorrhage with amyloidosis (Dutch)" Science (1990) 248(4959):1120-1122.
Vattemi, G. et al., "Amyloid-beta42 is preferentially accumulated in muscle fibers of patients with sporadic inclusion-body myositis," Acta Neuropathol. (2009) 117(5):569-574.
Veber, D.F. et al., "The design of metabolically-stable peptide analogs," TINS (1985) 392-396.
Vestergaard, M. et al., "Detection of Alzheimer's amyloid beta aggregation by capturing molecular trails of individual assemblies," Biochem. Biophys. Res. Comm. (2008) 377(2):725-728.
Vickers, "A vaccine against Alzheimer's disease," Drugs Aging (2002) 19:487-494.
Viola, K.L. et al., "Addls bind selectively to nerve cell surfaces in receptor-like puncta," Soc. For Neurosci. Abstract Viewer and Itinerary Planner (2002), Abstract No. 91.9, 32nd Annual meeting of the Society for Neuroscience, Orlando, FL, Nov. 2-7, 2002.
Viola, K.L. et al , "Immunolocalization of oligomeric Abeta42 bindnig to primary mouse hippocampal cells and B103 rat neuroblastoma cells," Society for Neuroscience Abstracts (1999), 29th Annual Meeting of the Society for Neuroscience, Miami Beach, FL, Oct. 23-28, 1999.
Wahlstrom, A. et al., "Secondary structure conversions of Alzheimer's a beta(1-40) peptide induced by membrane-mmimicking detergents," FEBS J. (2008) 275:5117-5128.
Wakutani, Y. et al., "Novel amyloid precursor protein gene missense mutation (D678N) in probable familial Alzheimer's disease," J. Neurol. Neurosurg. Psychiatry (2004) 75(7):1039-1042.
Walensky et al., "Activation of apoptosis in vivo by a hydrocarbon-stapled BH3 helix," Science (2004) 305:1466-1470.
Wallick, S.C. et al., "Glycosylation of a V(H) residue of a monoclonal antibody against alpha-1-6) dextran increases its affinity for antigen," J. Exp. Med. (1988) 168:1099-1109.
Wang, H. et al, "Soluble oligomers of Abeta(1-42) impair LTP in rat hippocampal dentate gyms," Society for Neuroscience Abstracts (2000) Abstract No. 663.18, 30th Annual Meeting of the Society of Neuroscience, New Orleans, LA, Nov. 4-9, 2000.
Wang, H. et al., "Direct and selective elimination of specific prions and amyloids by 4,5-dianilinophthalimide and analogs," Proc. Natl. Acad. Sci. USA (2008) 105:7159-7164.
Wang, H.W. et al., "Differential effect of Abeta1-42 conformation and apoE isoform on LTP," Society for Neurosci. Abstracts (2001) 752.18, 31st Annual meeting of the Society for Neurosci., San Diego, CA, Nov. 10-15, 2001.
Wang, H-W. et al., "Soluble oligomers of beta amyloid (1-42) inhibito long-term potentiation but not long-term depression in rat dentate gyms," Brain Res. (2002) 924(2):133-140.
Wang, J. et al., "Development and characterization of a TAPIR-like mouse monoclonal antibody to amyloid-beta," J. Alzheimer's Disease (2008) 14(2):161-173.
Wang, R. et la., "The profile of soluble amyloid beta protein in cultured cell medicine . . . " J. Biol. Chem. (1996) 271(50):31894-31902.
Wang, Z. et al., "Per-6-substituted-per-6-deoxy beta-cyclodextrins inhibit the formation of beta-amyloid peptide derived soluble oligomers," J. Med. Chem. (2004) 47:3329-3333.
Ward, E.S. et al., "Binding activities of a repetoire of single immunoglobulin varialbe domains secreted from *Escherichia coli*," Nature (1989) 341:544-546.

(56) References Cited

OTHER PUBLICATIONS

Weggen, S. et al., "Evidence that nonsteroidal anti-inflammatory drugs decrease amyloid beta-42 production by direct moculation of y-secretase activity," J. Biol. Chem. (2003) 276(34):31831-31837.
Weksler et al., "Patients with Alzheimer disease have lower levels of serum anti-amyloid peptide antibodies than healthy elderly individuals," Gerontology (2002) 37:943-948.
Wels, B. et al., "Synthesis of a novel potent cyclic peptide MC4-ligand by ring-closing metathesis," Bioorg. Med. Chem. (2005) 13:4221-4227.
Wermuth, C.G. et al., "Glossary of terms used in medicinal chemistry," Pure and Applied Chem. (1998) 70:1129-1143.
Westlind-Danielsson, A. et la., "Spontaneous in vitro formation of supramolecular beta-amyloid structures, 'betaamy balls' by beta-amyloid 1-40 peptide," Biochem. (2001) 40(49):14736-43.
White, J.A. et al., "Differential effects of oligomeric and fibrillar amyloid-beta 1-42 on astrocyte-mediated inflammation," Neurbiol. of Disease 92005) 18(3):459-465.
Wilcock et al., "Passive immunotherapy against Abeta in aged APP-transgenic mice reverses cognitive deficits and depletes parenchymal amyloid deposits in spite of increased vascular amyloid and microhemorrhage," J. Neuroinflammation (2004) 1(24):1-11.
Wilcock, D.M. et al., "Intracranially administered anti- A-beta antobodies reduce beta-amyloid depsoition by mechanisms both independent of and associated with microglial activation," J. Neurosci. (2003) 23(9):3745-3751.
Williamson, M.P. et al., "Binding of amyloid beta-peptide to ganglioside micelles is dependent on histidine-13," Biochem. J. (2006) 397:483-490.
Wilson, D.M. et al., "Free fatty acids stimulate the polymerization of tau and amyloid beta peptides in vitro evidence for a common effector in pathogenesis in Alzheimer's disease," Am. J. Path. (1997) 150(6):2181-2195.
Wiltfang, J. et al., "Highly conserved and disease-specific patterns of carboxyterminally truncated A-beta peptides 1-37/38/39 in addition to 1-40/42 in Alzheimer's disease and in patients with chronic neuroinflammation," J. Neurochem. (2002) 81:481-495.
Windisch, M. et al., "The role of alpha-synuclein in neurodegenerative diseases: a potential target for new treatment strategies," Neuro-Degenerative Diseases (2008) 5(3-4):218-221.
Winnacker, E-L., From Genes to Clones: Introduction to Gene Technology (1987) Table of Contents.
Wong, P.T. et al., "Amyloid-beta membrane binding and permeabilization are distinct processes influenced separately by membrane charge and fluidity," J. Mol. Biol. (2009) 286(1):81-96.
Woodhouse, A. et al., "Vaccination strategies for Alzheimer's disease: a new hope?" Drugs Aging (2007) 24(2): 107-119.
Wright, A. et al., "Antibody variable region glycosylation: position effects on antigen binding and carbohydrate structure," EMBO J. (1991) 10(10):2717-2723.
Wu et al., "Humanization of a murine monoclonal antibody by simultaneous optimization of framework and CDR residues," J. Mol. Biol. (1999) 294:151-162.
Wu, C. et al., "The structure of Abeta42 C-terminal fragments probed by a combined experimental and theoretical study," J. Mol. Biol. (2009) 287(2):492-501.
Wu, G.Y. et al., "Delivery systems for gene therapy," Biotherapy (1991) 3:87-95.
Wu, G.Y. et al., "Receptor-mediated in vitro ene transformation by a soluble DNA carrier system," J. Biol. Chem. (1987) 262:4429-4432.
Wurth, C. et al., "Mutations that reduce aggregation of the Alzheimer's Abeta42 peptide: an unbiased search for the sequence determinants of Abeta amyloidogenesis," J. Mol. Biol. (2002) 319(5):1279-1290.
Xia, W. et al., "A specific enzyme-linked immunosorbent assay for measuring beta-amyloid protein oligomers in human plasma and brain tissue of patients with Alzheimer disease," Archives of Neurology (2009) 66190-199.

Xia, W. et al., "Enhanced production and oligomerization fo the 42-residue amyloid beta-protein by Chinese hamster ovary cells stably expressing mutant presenilins," J. Biol. Chem. (1997) 272(12):7977-7982.
Xu, X. et al., "gamma-secretase catalyzes sequential cleavages of the A beta PP transmembrane domain," J. Alzheimer's Disease (2009) 16:211-224.
Yamamoto, N. et al., "Environment- and mutation-dependent aggregation behavior of Alzheimer amyloid beta-protein," J. Neurochem. (2004) 90:62-69.
Yamin, G. et al., "Amyloid beta-protein assembly as a therapeutic target of Alzheimer's disease," Curr. Pharm. Design (2008) 14:3231-3246.
Yamin, G. et al., "NMDA receptor-dependent signaling pathways that underlie amyloid beta-protein disruption of LTP in the hippocampus," J. Neuroscience Res. (2009) 87(8):1729-1736.
Yan, Y. et al., "Protection mechanisms against Abeta42 aggregation," Curr. Alzheimer Res. (2008) 5(6):548-554.
Yan, Z. et al., "Roscovitine: a novel regulator of P/Q-type calcium channels and transmitter release in central neurons," J. Physiol. (2002) 540(3):761-770.
Yang, M. et al., "Amyloid beta-protein monomer folding: free-energy surfaces reveal alloform-specific differences," J. Mol. Biol. (2008) 384(2):450-464.
Yang, X.D. et al., "Fully human anti-interleukin-8 monoclonal antibodies: potential therapeutics for the treatment of inflammatory disease status," J. Leukocyte Biol. (1999) 66:401-410.
Yeh, M.Y. et al., "A cell-surface antigen which is present in the ganglioside fraction and shared by human melanomas," Int. J. Cancer (1982) 29:269-275.
Yeh, M.Y. et al., "Cell surface antigens of human melanoma identified by monoclonal antibody," Proc. Natl. Acad. Sci. USA (1979) 76(6):2927-2931.
Yoshinari, K. et al., "Differential effects of immunosuppressants and antibiotics on human monoclonal antibody production is SCID mouse ascites by five heterohybridomas," Hybridoma (1998) 17(1):41-45.
Yoshitake et al., "Mild and efficient conjugation of rabbit Fab and horseradish peroxide using a maleimide compound and its use for enzyme immunoassay," J. Biochem. (1982) 92:1413-1424.
Young, K.F. et al., "Oligomeric amyloid-beta 1-42 activates extracellular signal regulated kinases ERK1 and ERK2 of the mitogen activated protein kinase pathway in SH-SY5YCELLS," Neurobiol of Aging (2004) 25:S150.
Youssef, I. et al., "N-truncated amyloid-beta oligomers induce learning impairment and neuronal apoptosis," Neurobiol of Aging (2008) 29:1319-1333.
Yu, L. et al., "Structural characterization of a soluble amyloid beta-peptide oligomer," Biochem. (2009) 48:1870-1877.
Yun, S. et al., "Role of electrostatic interactions in amyloid beta-protein (Abeta) oligomer formation: a discrete molecular dynamics study," Biophys. J. (2007) 92(11):4064-4077.
Yun, S.H. et al., "Amyloid-beta 1-42 reduces neuronal excitability I nmouse dentate gyms," Neurosci. Lett. 92006) 403:162-165.
Zameer, A. et al., "Anti-oligomeric abeta single-chain variable domain antibody blocks abeta-induced toxicity against human neuroblastoma cells," J. Mol. Biol. (2008) 384(4):917-928.
Zarandi, M. et al., "Synthesis of Abeta[1-42] and its derivatives with improved efficiency," J. Peptide Sci. (2007) 13(2):94-99.
Zhao, J-H. et al., "Molecular dynamics simulations to investigate the aggregation behaviors of the Abeta(17-42) oligomers," J. Biomol. Struct. Dyn. (2009) 26(4):481-490.
Zhao, W. et al., "Identification of antihypertensive drugs which inhibit amyloid-beta protein oligomerization," J. Alzheimer's Dis. (2009) 16(1):49-57.
Zheng, J. et al., "Annular structures as intermediates in fibril formation of Alzheimer Abeta17-42," J. Phys. Chem. (2008) 112(22):6856-6865.
Zhu, D. et la., "Phospholipases A2 mediate amyloid-beta peptide-induced mitochondrial dysfunction," J. Neurosci. (2006) 26(43):11111-11119.
Zlokovic, B.V., "Clearing amyloid through the blood-brain barrier," J. neurochem. (2004) 89(40:807-811.

(56) References Cited

OTHER PUBLICATIONS

Zou, K et al., "A novel function of monomeric amyloid beta-protein serving as an antioxidant molecule against metal-induced oxidative damage," J. Neurosci. (2002) 22:4833-4841.
Zou, K. et al., "Amyloid beta-protein (Abeta)1-40 protects neurons from damage induced by Abeta1-42 in culture and in rat brain," J. Neurochem. (2003) 87(3):609-619.
European Patent Office Search Report for Application No. 09180982 dated May 31, 2010 (4 pages).
Notice of Opposition for European Application No. 06707413/Patent No. 1861422 dated Nov. 24, 2010.
Supplemental European Patent Office Search Report for Application No. 07864914 dated Apr. 28, 2010 (5 pages).
Supplemental European Search Report from European Patent Publication No. 2303920 dated Sep. 26, 2011.
International Preliminary Report on Patentability and Written Opinion for Application No. PCT/EP2004/000927 dated Aug. 5, 2005 (11 pages).
International Preliminary Report on Patentability and Written Opinion for Application No. PCT/EP2006/011530 dated Jun. 3, 2008 (11 pages).
International Preliminary Report on Patentability and Written Opinion for Application No. PCT/EP2008/001548 dated Sep. 1, 2008 (11 pages).
International Preliminary Report on Patentability and Written Opinion for Application No. PCT/IB2009/006636 dated Jan. 25, 2011 (7 pages).
International Preliminary Report on Patentability and Written Opinion for Application No. PCT/US2006/046043 dated Jun. 30, 2008 (32 pages).
International Preliminary Report on Patentability and Written Opinion for Application No. PCT/US2006/046148 dated Jun. 3, 2008 (8 pages).
International Preliminary Report on Patentability and Written Opinion for Application No. PCT/US2007/085932 dated Jun. 3, 2009 (5 pages).
International Preliminary Report on Patentability and Written Opinion for Application No. PCT/US2008/065199 dated Dec. 1, 2009 (10 pages).
International Preliminary Report on Patentability and Written Opinion for Application No. PCT/US2008/065205 dated Dec. 1, 2009 (6 pages).
International Preliminary Report on Patentability and Written Opinion for Application No. PCT/US2009/051721 dated Jan. 25, 2011 (7 pages).
International Search Report for Application No. PCT/EP2004/000927 dated Jun. 14, 2004 (4 pages).
International Search Report for Application No. PCT/EP2008/001548 dated Jul. 4, 2008 (3 pages).
International Search Report for Application No. PCT/EP2008/001549 mailed on Dec. 23, 2008 (6 pages).
International Search Report for Application No. PCT/IB2009/006636 dated Jan. 22, 2010 (6 pages).
International Search Report for Application No. PCT/PCT/EP2006/011530 dated Jun. 6, 2007 (7 pages).
International Search Report for Application No. PCT/US2006/046043 dated Jun. 21, 2008 (16 pages).
International Search Report for Application No. PCT/US2006/046148 dated Jun. 19, 2007 (5 pages).
International Search Report for Application No. PCT/US2007/085932 dated Spetember 22, 2008 (3 pages).
International Search Report for Application No. PCT/US2008/065199 dated Sep. 26, 2008 (4 pages).
International Search Report for Application No. PCT/US2008/065205 dated Oct. 31, 2008 (3 pages).
International Search Report for Application No. PCT/US2009/051721 mailed on Mar. 16, 2010 (6 pages).
United States Patent Office Action for U.S. Appl. No. 11/574,844 dated Feb. 10, 2011 (11 pages).
United States Patent Office Action for U.S. Appl. No. 11/574,847 dated Jul. 14, 2011 (22 pages).
United States Patent Office Action for U.S. Appl. No. 11/574,876 dated Jan. 23, 2012 (17 pages).
United States Patent Office Action for U.S. Appl. No. 11/574,876 dated Nov. 15, 2012 (9 pages).
United States Patent Office Action for U.S. Appl. No. 11/885,362 dated Jul. 22, 2010 (10 pages).
United States Patent Office Action for U.S. Appl. No. 11/885,362 dated Mar. 29, 2011 (8 pages).
United States Patent Office Action for U.S. Appl. No. 11/945,124 dated Mar. 3, 2010 (15 pages).
United States Patent Office Action for U.S. Appl. No. 11/945,124 dated Oct. 14, 2010 (8 pages).
United States Patent Office Action for U.S. Appl. No. 12/509,315 dated Jun. 6, 2012 (10 pages).
United States Patent Office Action for U.S. Appl. No. 12/509,325 dated Jun. 6, 2012 (14 pages).
United States Patent Office Action for U.S. Appl. No. 12/529,467 dated Dec. 6, 2011 (24 pages).
United States Patent Office Action for U.S. Appl. No. 12/529,467 dated May 24, 2012 (19 pages).
United States Patent Office Action for U.S. Appl. No. 13/102,713 dated Apr. 19, 2012 (20 pages).
United States Patent Office Action for U.S. Appl. No. 13/102,713 dated Oct. 1, 2012 (14 pages).
United States Patent Office Action for U.S. Appl. No. 13/188,034 dated Jan. 3, 2012 (35 pages).
United States Patent Office Action for U.S. Appl. No. 13/188,034 dated Sep. 11, 2012 (18 pages).
United States Patent Office Action for U.S. Appl. No. 13/195,533 dated Nov. 13, 2012 (23 pages).
United States Patent Office Notice of Allowance for U.S. Appl. No. 11/574,844 dated Aug. 11, 2011 (14 pages).
United States Patent Office Notice of Allowance for U.S. Appl. No. 11/574,844 dated May 9, 2012 (8 pages).
United States Patent Office Notice of Allowance for U.S. Appl. No. 11/574,847 dated Feb. 10, 2012 (12 pages).
United States Patent Office Notice of Allowance for U.S. Appl. No. 11/574,847 dated Oct. 4, 2012 (8 pages).
United States Patent Office Notice of Allowance for U.S. Appl. No. 11/945,124 dated Apr. 4, 2011 (8 pages).
United States Patent Office Notice of Allowance for U.S. Appl. No. 11/945,124 dated Mar. 5, 2012 (7 pages).
United States Patent Office Notice of Allowance for U.S. Appl. No. 11/945,124 dated Oct. 9, 2012 (7 pages).
Barghorn, S. et al., "Abeta-oligomer selective antibody A-887755 exhibits a favorable profile for Alzheimer's disease immunotherapy compared to Abeta-peptide unselective antibodies," Alzheimer's & Dementia: The Journal of the Alzheimer's & Association (2009) 5(4):P424.
Bendig, "Humanization of rodent monoclonal antibodies by CDR grafting," Methods: A Companion to Methods in Enzymology (1995) 8:83-93.
Benevenuti et al., "Crystallization of soluble proteins in vapor diffusion for xray crystallography," Nature Protocols (2007) 2(7):1633-1651.
Citron, M., "Alzheimer's disease: strategies for disease modification," Nature Reviews Drug Discovery (2010) 9:387-398.
Kundrot, C.E. et al., "Which strategy for a protein crystallization project?" Cell. Mol. Life Sci. (2004) 61:525-536.
McPherson, A., "Current approaches to macromolecular crystallization," Eur. J. Biochem. (1990) 189:1-23.
Verhoeven, M. et al., "Engineering of antibodies," Bioessays (1988) 8(2):74-78.
European Patent Office Action for Application No. 087160818 dated Dec. 22, 2011 (6 pages).
European Patent Office Action for Application No. 101783942 dated Mar. 2, 2012 (4 pages).
European Patent Office Action for Application No. 101783942 dated Aug. 22, 2012 (4 pages).
International Search Report for Application No. PCT/US2011/047622 dated Jan. 2, 2012 (6 pages).

(56) References Cited

OTHER PUBLICATIONS

Written Opinion for Application No. PCT/US2011/047622 dated Jan. 2, 2012 (8 pages).
United States Patent Office Action for U.S. Appl. No. 13/195,533 dated Jul. 11, 2013 (21 pages).
United States Patent Office Action for U.S. Appl. No. 13/085,891 dated Apr. 18, 2013 (16 pages).
Co-pending U.S. Appl. No. 13/862,865, filed Apr. 15, 2013.
United States Patent Office Notice of Allowance for U.S. Appl. No. 12/529,467 dated Jul. 9, 2014.
United States Patent Office Notice of Allowance for U.S. Appl. No. 13/102,713 dated Jun. 24, 2014.
U.S. Patent Office Notice of Allowance for U.S. Appl. No. 13/102,713 dated Mar. 14, 2014 (9 pages).
Chen, C., "Beta-amyloid increases dendritic Ca2+ influx by inhibiting the A-type K+ current in hippocampal CA1 pyramidal neurons," Biochem. Biophys. Res. Comm. (2005) 338:1913-1919.
Jeon, D. et al., "Impaired long-term memory and long-term potentiation in N-type Ca2+ channel-deficient mice," Genes, Brain Behavior (2007) 6:375-388.
Lipscombe, D. et al., "Functional diversity in neuronal voltage-gated calcium channels by alternative splicing of Cav. alpha1," Mol. Neurobiol. (2002) 26(1):21-44.
Rovira, C. et al., "Abeta(25-35) and Abeta(1-40) act on different calcium channels in CA1 hippocampal neurons," Biochem. Biophys. Res. Comm. (2002) 296:1317-1321.
Shankar, G.M. et al., "Natural oligomers of the Alzheimer amyloid-beta protein induce reversible synapse loss by modulating an NMDA-type glutamate receptor-dependent signaling pathway," J. Neurosci. (2007) 27(11):2866-2875.
Ye, C.P. et al., "Protofibrils of amyloid beta-protein inhibit specific K+ currents in neocortical cultures," Neurobiol. Disease (2003) 13:177-190.
United States Patent Office Action for U.S. Appl. No. 12/529,467 dated Feb. 14, 2014 (17 pages).
United States Patent Office Action for U.S. Appl. No. 13/195,533 dated Feb. 24, 2014 (9 pages).
Acha-Orbea et al., "Anti-T-cell receptor V beta antibodies in autoimmunity," Immunol. Ser. (1993) 59:193-202.
Anderson et al., "Characterization of beta amyloid assemblies in drusen: the deposits associated with aging and age-related macular degeneration," Experimental Eye Research (2004) 78:243-256.
Bard et al., "Epitope and isotype specificities of antibodies to beta-amyloid peptide for protection against Alzheimer's disease-like neuropathology," Proc. Natl. Acad. Sci. (2003) 100(4):2023-2028.
Bard et al., "Peripherally administered antibodies against amyloid bipeptide enter the central nervous system and reduce pathology in a mouse model of Alzheimer disease," Nature Med. (2000) 6:916-919.
Brown, M. et al., "Tolerance to single, but not multiple, amino acid replacements in antibody V-H CDR2: a means of minimizing B cell wastage from somatic hypermutation?" J. Immunol. (1996) 156(9):3285-3291.
Campbell et al., "General properties and applications of monoclonal antibodies," Elsevier Science Publishers B.V. (1984) pp. 1-32.
Celli et al., "Origin and pathogenesis of antiphospholipid antibodies," Braz. J. Med. Biol. Res. (1998) 31(6):723-732.
Database EMBL, "Mouse immunoglobulin rearranged kappa-chain V-region V105 gene from, C.AL20-TEPC-105 myeloma, exons 1 and 2," Jul. 16, 1988, Database Accession No. M12183.
Database EMBL, "Mus musculus F5.20G3 low-affinity anti-phosphorylcholine IgG antibody mRNA, partial cds," Feb. 8, 1999, Database Accession No. AF044238.
Database Geneseq, "Anti-human Fas monoclonal antibody CH11 light chain cDNA," retrieved from EBI Accession No. GSN:AAV66736, Jan. 18, 1999, Database Accession No. AAV66736.
Database Geneseq, "Mouse DNA encoding antibody 3D8 heavy chain variable region," Apr. 22, 2003, Database Accession No. ABX16569.
Database Geneseq, "Mouse monoclonal antibody 4785 heavy chain SEQ ID 38", retrieved from EBI Accession No. GSP:ADX39137, 2005) Database Accession No. ADX39137.
Database Geneseq., Humanized monoclonal antibody H74785-2 heavy chain, retrieved from EBI accession No. GSP:ADX39139, 2005, Database Accession No. ADX39139.
Database Geneseq., "Humanized monoclonal antibody Hu4785-2 partial protein," retrieved from EBI Accession No. GSP:ADX39104 (2005) Database Accession No. ADX39104.
Database Geneseq., "Humanized monoclonal antibody Hu4785-2 VH region," retrieved from EBI accession No. GSP:ADX39143 (2005), Database Accession No. ADX39143.
Database Geneseq., "Mouse monoclonal antibody 4785 heavy chain SEQ ID 1," retrieved from EBI Accession No. GSP:ADX39100 (2005) Database Accession No. ADX39100.
Database NCBI Protein dated Apr. 11, 1996, Accession No. AAA96779.
Database NCBI Protein dated Mar. 23, 2002, Accession No. AAA92933.
Database NCBI Protein, dated Mar. 23, 2002, Accession No. AAL92941.
Database NCBL Protein, dated Aug. 30, 1993, Accession No. AAA38584.
David et al., A significant reduction in the incidence of collagen induced arthritis in mice treated with anti-TCRV-beta antibodies, J. Cell Biochem. (1991) 179.
DeGiorgi et al., "Induction of foetal lethality in AKR offspring after repeated inoculations into AKR females of anti-TCR/V beta 6 monoclonal antibody," Res. Immunol. (1993) 144(4):245-255.
DeGirogi et al., "Murine hybridomas secreting monoclonal antibodies reacting with Misa antigens," Exp. Clin. Immunogenet. (1993) 10(4):219-223.
Ding et al., "Targeting age-related macular degeneration with Alzheimer's disease based immunotherapies: anti-amyloid-beta antibody attenuates pathologies in an age-related macular degeneration mouse model," Vision Research, Pergamon Press, Oxford, GB (2007) 48(3):339-345.
Dorronsoro et al., "Peripheral and dual binding site inhibitors of acetylcholinesterase as neurodegenerative disease-modifying agents," Exp. Opin. Ther. Pat. (2003) 13(11):1725-1732.
Frenkel et al., "Modulation of Alzheimer's beta-amyloid neurotoxicity by site-directed single-chain antibody," J. Neuroimmunol. (2000) 106(1-2):23-31.
Fujimoro et al., "Production and characterization of monoclonal antibodies specific to multi-ubiquitin chains of polyubiquitinated proteins," FEBS (1994) 349:173-180.
Fujimoro et al., "Production of antipolyubiquitin monoclonal antibodies and their use for characterization and isolation of polyubiquitinated proteins," Meth. Enzymol. (2005) 399:75-86.
Fukuchi et al., "Amelioration of amyloid load by anti-Abeta single-chain antibody in Alzheimer mouse model," Biochem. Biophys. Res. Commun. (2006) 344(1):79-86.
Guo et al., "Targeting amyloid-beta in glaucoma treatment," Proc. Natl. Acad. Sci. USA (2007) 104(33):13444-13449.
Hicke, "Protein regulation by monoubiquitin," Nat. Rev. (2001) 2:196-201.
Kim et al., "Development of conformation-specific antibodies for neutralization of beta-amyloid oligomers," Neurobiol. Aging (2004) 25(1):S145, P1-175 Abstract.
Kisilevsky et al., "Arresting amyloidosis in vivo using small-molecule anionic sulphonates or sulphates: implications for Alzheimer's disease," Nat. Med. (1995) 1(2):143-148.
Kisilevsky, "Anti-amyloid drugs potential in the treatment of diseases associated with aging," Drugs Aging (1996) 8(2):75-83.
Langdon et al., "Germline sequences of VH7183 gene family members in C57BL/6 mice demonstrate natural selection of particular sequences during recent evolution," Immunogen (2000) 51:241-245.

(56) References Cited

OTHER PUBLICATIONS

Lee et al., "Molecular cloning of agonistic and antagonistic monoclonal antibodies against human 4-IBB," Eur. J. Immunogenet. (2002) 29(5):449-452.
LeVine, H, III., "4,4'-dianilino-1,1"-binaphthyl-5'-disulfonate (bis-ANS) reports on non-beta-sheet conformers of Alzheimer's peptide beta (1-40)," Arch Biochem. Biophys. (2002) 404:106-115.
Liu, et al., "Single chain variable fragments against beta-amyloid (Abeta) can inhibit Abeta aggregation and prevent Abeta-induced neurotoxicity," Biochem. (2004) 43:6959-6967.
Lund et al., "Oligosaccharide-protein interactions in IgG can modulate recognition by Fc-gamma receptors," FASEB J. (1995) 9(1):115-119.
McKinnon et al., "Caspase activation and amyloid precursor protein cleavage in rat ocular hypertension," Investigative Ophthalmology & Visual Science (2002) 43(4):1077-1087.
McLaurin et al., "therapeutically effective antibodies against amyloid-beta peptide target amyloid-beta residues 4-10 and inhibit cytotoxicity and fibrillogenesis," Nat. Med. (2002) 8(11):1263-1269.
Moretto et al., "Conformation-sensitive antibodies against Alzheimer amyloid-beta by immunization with a thioredoxin-constrained B-cell epitope peptide," J. Biol. Chem. (2007) 282(15):11436-11445.
Nemes et al., "Cross-linking of obiquitin, HSP27, parkin, and alpha-synuclein by gamma-glutamyl-ε-lysine bonds in Alzheimer's neurofibrillary tangles," FASEB J. (2004) 18:1135-1137.
Nicolau et al., "A liposome-based therapetuci vaccine against beta-amyloid plaques on the pancreas of transgenic NORBA mice," Proc. Natl. Acad. Sci. USA (2002) 99(4):2332-2337.
Rzepecki et al., "Prevention of Alzheimer's disease-associated Abeta aggregation by rationally designed non-peptide beta-sheet ligands," J. Biol. Chem. (2004) 279(46):47497-47505.
Schable et al., "Characteristics of the immunoglobulin V kappa genes, pseudogenes, relics and orphons in the mouse genome," Eur. J. Immunol. (1999) 29:2082-2086.
Schenk et al , "Immunization with amyloid-beta attenuates Alzheimer'disease-like pathology in the PDAPP mouse," Nature (1999) 400:173-177.
Solomon et al., "disaggregation of Alzheimer beta-amyloid by site-directed mAb," Proc. Natl. Acad. Sci. USA (1997) 94:4109-4112.
Solomon et al., "Monoclonal antibodies inhibit in vitro fibrillar aggregation fo the Alzheimer beta-amyloid peptide," Proc. Natl. Acad. Sci. USA (1996) 93:452-455.
Tenno et al., "Structural basis for distinct roles of Lys63- and Lys48-linked polyubiquitin chains," Genes to Cells (1994) 9:865-875.
Van Gool et al., "Concentrations of amyloid-beta protein in cerebrospinal fluid increase with age in patients free from neurodegenerative disease," Neurosci Lett. (1994) 172(1-2):122-124.
Weaver-Feldhaus et al., "Yeast mating for combinatorial Fab library generation and surface display," FEBS Lett. (2004) 564(2):24-34.
European Opposition of EP 06838873.5 (Patent No. 1976877) by Genentech, Inc. and AC Immune SA dated Oct. 15, 2014 (35 pages).
Declaration of Andreas Muhs in support of opposition dated Oct. 10, 2014, with attachments.
Declaration of Hartmut Engelmann in support of opposition dated Oct. 14, 2014, with attachments.
United States Patent Office Action for U.S. Appl. No. 13/195,533 dated Dec. 3, 2014 (13 pages).
United States Patent Office Notice of Allowance for U.S. Appl. No. 13/085,891 dated Oct. 29, 2014 (10 pages).
U.S. Patent Office Notice of Allowance for U.S. Appl. No. 13/988,307 dated Feb. 11, 2015 (17 pages).
Dodel, R. et al., "Naturally occurring autoantibodies against beta-amyloid: investigating their role in transgenic animal and in vitro models of Alzheimer's disease," J. Neurosci. (2011) 31(15):5847-5854.
United States Patent Office Action for U.S. Appl. No. 13/862,865 dated Jun. 4, 2015 (14 pages).
United States Patent Office Notice of Allowance for U.S. Appl. No. 13/195,533 dated Jun. 25, 2015 (8 pages).
United States Patent Office Action for U.S. Appl. No. 14/303,300 dated Jul. 31, 2015 (12 pages).
European Patent Office Action for Application No. 11745902.4 dated Jul. 14, 2015 (5 pages).
U.S. Appl. No. 14/864,526, filed Sep. 24, 2015, Heinz Hillen.
United States Patent Office Action for U.S. Appl. No. 14/513,837 dated Nov. 9, 2015 (11 pages).
Co-pending U.S. Appl. No. 14/792,500, Stefan Barghorn, filed Jul. 6, 2015.
Klyubin, I. et al., "Amyloid beta protein immunotherapy neutralizes Abeta oligomers that disrupt synaptic plasticity in vivo," Nature Med. (2005) 11(5):556-561.
Invitation to Pay Fees for Application No. PCT/EP2015/065362 dated Dec. 10, 2015 (10 pages).
United States Patent Office Notice of Allowance for U.S. Appl. No. 13/862,865 dated Feb. 3, 2016 (9 pages).
United States Patent Office Notice of Allowance for U.S. Appl. No. 14/513,837 dated Feb. 10, 2016 (7 pages).
United States Patent Office Action for U.S. Appl. No. 14/514,168 dated Feb. 1, 2016 (8 pages).

\* cited by examiner

FIG. 8 (D-H)
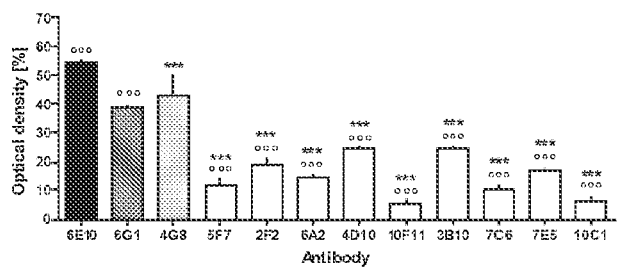
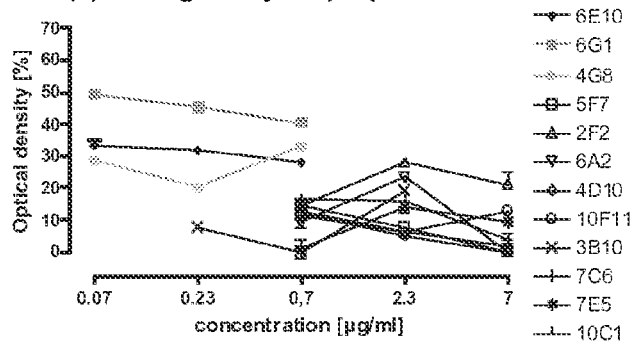
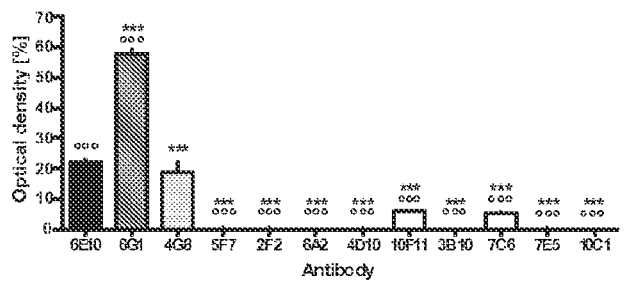
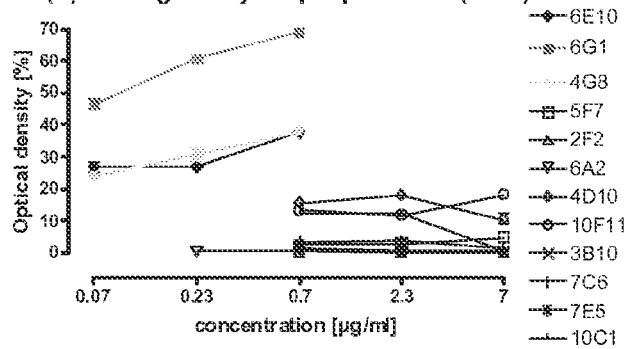

FIG. 10

|  | 7C6 ->BA199 Aβ(20-42) globulomer [pmol/g] brain tissue | 10F11->BA199 Aβ(20-42) globulomer [pmol/g] brain tissue | 5F7 ->BA199 Aβ(20-42) globulomer [pmol/g] brain tissue |
|---|---|---|---|
| RZ16 (AD) | 50,1 | 10,6 | 10,2 |
| RZ 52 (AD) | 43,9 | 14,3 | 13,9 |
| RZ 55 (AD) | 13,9 | 2,9 | 3,6 |
| RZ 92 (control) | < 0,2 | < 0,06 | < 0,06 |

SEQ ID NO:1

CAGGTCCAGCTGAAGCAGTCTGGAGCTGAGCTGGTGAGGCCTGGGACTTC
AGTGAAGATGTCCTGCAAGGCTTCTGGCTACACCTTCACTACCTTCTATAT
ACACTGGGTGAAGCAGAGGCCTGGACAGGGCCTTGAGTGGATTGGAATG
ATTGGTCCTGGAAGTGGTAATACTTACTACAATGAGATGTTCAAGGACAA
GGCCACATTGACTGTAGACACATCCTCCAGCACAGCCTACATGCAGCTCA
GCAGCCTCACATCTGAGGACTCTGCGGTCTATTTCTGTGCAAGAGCAAAG
TCAGCTCGGGCGGCCTGGTTTGCTTACTGGGGCCAAGGGACTCTGGTCAC
TGTCTCTGCA

SEQ ID NO:3

QVQLKQSGAELVRPGTSVKMSCKASGYTFT<u>TFYIH</u>WVKQRPGQGLEWIG<u>MI
GPGSGNTYYNEMFKD</u>KATLTVDTSSSTAYMQLSSLTSEDSAVYFCAR<u>AKSAR
AAWFAY</u>WGQGTLVTVSA

A2) VL ML15-5F7

SEQ ID NO:2

GATGTTTTGATGACCCAAACTCCACTCTCCCTGCCTGTCAGTCTTGGAGAT
CAAGCCTCCATCTCTTGCAGATCTAGTCAGAGCGTTGTACAGAGTAATGG
AAACACCTATTTAGAATGGTACCTGCAGAAACCAGGCCAGTCTCCAAAGC
TCCTGATCTACAAAGTTTCCAACCGATTTTCTGGGGTCCCAGACAGGTTCA
GTGGCAGTGGATCAGGGACAGATTTCACACTCAAGATCAGCAGAGTGGA
GGCTGAGGATCTGGGAGTTTATTACTGCTTCAAGGTTCACATGTTCCTCC
CACGTTCGGAGGGGGGACCAAGCTGGAAATAAAACGG

SEQ ID NO:4

DVLMTQTPLSLPVSLGDQASISC<u>RSSQSVVQSNGNTYLE</u>WYLQKPGQSPKLLI
Y<u>KVSNRFS</u>GVPDRFSGSGSGTDFTLKISRVEAEDLGVYYC<u>FQGSHVPPT</u>FGGG
TKLEIKR

SEQ ID NO:5

CAGGTCCAGCTGCAGCAGTCTGGACCTGAGCTGGTAAAGCCTGGGGCTTC
AGTGAAGATGTCCTGCAAGGCTTCTGGATACACATTCACTAGCTATGTTAT
GCACTGGGTGAAGCAGAGGCCTGGGCAGGGCCTTGAGTGGATTGGATATA
TTTATCCTTACAATGATGGTACTAAGTACAATGAGAAGTTCAAAGGCAAG
GCCACACTGACTTCAGACAAATCCTCCAGCACAGTATATGGAGCTCAG
CAGCCTGACCTCTGAGGACTCTACAGTCTATTACTGTACAGTAGAGGGTG
CTACCTGGGACGGGTACTTCGATGTCTGGGGCACAGGGACCACGGTCACC
GTCTCCTCA

SEQ ID NO:7

QVQLQQSGPELVKPGASVKMSCKASGYTFTSYVMHWVKQRPGQGLEWIGYI
YPYNDGTKYNEKFKGKATLTSDKSSSTVYMELSSLTSEDSTVYYCTVEGATW
DGYFDVWGTGTTVTVSS

B2)  VL ML15-10F11

SEQ ID NO:6

GATGTTGTGATGACCCAGACTCCACTCACTTTGTCGGTTACCATTGGACAA
TCAGCCTCTATCTCTTGCAAGTCAAGTCAGAGCCTCTTATATAGTAAAGGA
AAAACCTATTTGAATTGGTTATTACAGAGGCCAGGCCAGTCTCCAAAGCG
CCTAATCTATCTGGTGTCTAAACTGGACTCTGGAGTCCCTGACAGGTTCAC
TGGCAGTGGATCAGGAACAGATTTTACACTGAAAATCAGCAGAGTGGAG
GCTGAGGATTTGGGAGTTTATTACTGCGTGCAAGGTACACATTTTCCTCAC
ACGTTCGGAGGGGGGACCAAGCTGGAAATAAAACGG

SEQ ID NO:8

DVVMTQTPLTLSVTIGQSASISCKSSQSLLYSKGKTYLNWLLQRPGQSPKRLI
YLVSKLDSGVPDRFTGSGSGTDFTLKISRVEAEDLGVYYCVQGTHFPHTFGG
GTKLEIKR

SEQ ID NO:9

GAAGTGAAGCTGGTGGAGTCTGGGGGAGGCTTAGTGAAGCCTGGAGGGT
CCCTGAAACTCTCCTGTGCAGCCTCTGGATTCACTTTCAGTAGCTATGCCA
TGTCTTGGGTTCGCCAGACTCCAGCGAAGAGGCTAGAGTGGGTCGCGTCC
ATTCATAATAGAGGTACTATCTTCTATCTAGACAGTGTGAAGGGCCGATTC
ACCATCTCCAGAGATAATGTCAGGAACACCCTGTACCTGCAAATGAGCAG
TCTGAGGTCTGAGGACACGGCCATATATTACTGTACAAGAGGCCGGAGTA
ACTCCTATGCTATGGACTACTGGGGTCAAGGAACCTCAGTCACCGTCTCCT
CG

SEQ ID NO:11

EVKLVESGGGLVKPGGSLKLSCAASGFTFS<u>SYAMS</u>WVRQTPAKRLEWVA<u>SIH
NRGTIFYLDSVKG</u>RFTISRDNVRNTLYLQMSSLRSEDTAIYYC<u>TRGRSNSYAM
DY</u>WGQGTSVTVSS

<u>C2)    VL ML13-7C6</u>

SEQ ID NO:10

GATGTTTTGGTGACCCAATCTCCACTCTCCCTGCCTGTCAGGCTTGGAGAT
CAAGCCTCCATCTCTTGCCGATCTACTCAGACCCTTGTACATCGTAATGGA
GACACCTATTTAGAATGGTACCTGCAGAAACCAGGCCAGTCTCCAAAGTC
CCTGATCTACAAAGTTTCCAACCGATTTTCTGGGGTCCCAGACAGGTTCAG
CGGCAGTGGATCAGGGACAGATTTCACACTCAAGATCAGCAGAGTGGAG
GCTGAGGATCTGGGAGTTTATTACTGCTTTCAAGGTTCACATGTTCCGTAC
ACGTTCGGAGGGGGGACCAAGCTGGAAATAAAACGG

SEQ ID NO:12

DVLVTQSPLSLPVRLGDQASISC<u>RSTQTLVHRNGDTYLE</u>WYLQKPGQSPKSLI
Y<u>KVSNRFS</u>GVPDRFSGSGSGTDFTLKISRVEAEDLGVYYC<u>FQGSHVPYT</u>FGGG
TKLEIKR

SEQ ID NO:13

GAGGTGAAGCTGGTGGAGTCTGGGGGAGGCTTAGTGCAGCCTGGAGGCTC
CCGGAAACTCTCCTGTGCAGCCTCTGGATTCACTTTCAGTGACTACGAAAT
GGTGTGGGTTCGACAGGCTCCAGGGGAGGGGCTGGAGTGGGTTGCATACA
TTAGTAGTGGCAGTCGTACCATCCACTATGCAGACACAGTGAAGGGCCGA
TTCACCATCTCCAGAGACAATCCCAAGAACACCCTGTTCCTGCAAATGAG
CAGTCTGAGGTCTGAGGACACGGCCATGTATTACTGTGCAAGGACATTAC
TACGGCTACACTTTGACTACTGGGGCCAAGGCACCATTCTCACAGTCTCCT
CA

SEQ ID NO:15

EVKLVESGGGLVQPGGSRKLSCAASGFTFS<u>DYEMV</u>WVRQAPGEGLEWVA<u>YI
SSGSRTIHY</u>ADTVKGRFTISRDNPKNTLFLQMSSLRSEDTAMYYCAR<u>TLLRLH
FDY</u>WGQGTILTVSS

D2) VL ML15-4B7

SEQ ID NO:14

GACATTGTGATGTCACAGTCTCCATCCTCCCTAGCTGTGTCAGTTGGAGAG
AAGGTTACTATGAGCTGCAGGTCCAGTCAGAGCCTTTTCTATAGGAGCAA
TCAAAAGAACTTCTTGGCCTGGTACCAGCAGAAACCAGGGCAGTCTCCTA
AACTGCTGATTTACTGGGCATCCACTAGGGAATCTGGGGTCCCTGATCGCT
TCACAGGCAGTGGATCTGGGACAGATTTCACTCTCACCATCAGCAGTGTG
AAGGCTGAAGACCTGGCAGTTTATTACTGTCAGCAATATTATAGCTATCC
GTGGACGTTCGGTGGAGGCACCAAGCTGGAAATCAAACGG

SEQ ID NO:16

DIVMSQSPSSLAVSVGEKVTMSC<u>RSSQSLFYRSNQKNFLA</u>WYQQKPGQSPKL
LIY<u>WASTRES</u>GVPDRFTGSGSGTDFTLTISSVKAEDLAVYYC<u>QQYYSYPWT</u>FG
GGTKLEIKR

SEQ ID NO:17

CAGGTCCAGCTGAAGCAGTCTGGAGCTGAGCTGGTGAGGCCTGGGACTTC
AGTGAAGATGTCCTGCAAGGCTTCTGGCTACACCTTCACTACCTTCTATAT
ACACTGGGTGAAGCAGAGGCCTGGACAGGGCCTTGAGTGGATTGGAATG
ATTGGTCCTGGAAGTGGTAATACTTACTACAATGAGATGTTCAAGGACAA
GGCCACATTGACTGTAGACACATCCTCAGCACAGCCTACATGCAGCTCA
GCAGCCTCACATCTGAGGACTCTGCGGTCTATTTCTGTGCAAGAGCAAAG
TCAGCTCGGGCGGCCTGGTTTGCTTACTGGGGCCAAGGGACTCTGGTCAC
TGTCTCTGCA

SEQ ID NO:19

QVQLKQSGAELVRPGTSVKMSCKASGYTFT<u>TFYIH</u>WVKQRPGQGLEWIG<u>MI
GPGSGNTYYNEMFKDK</u>ATLTVDTSSSTAYMQLSSLTSEDSAVYFCAR<u>AKSAR
AAWFAY</u>WGQGTLVTVSA

E2) VL ML15-2F2

SEQ ID NO:18

GATGTTTTGATGACCCAAACTCCACTCTCCCTGCCTGTCAGTCTTGGAGAT
CAAGCCTCCATCTCTTGCAGATCTAGTCAGAGCGTTGTACAGAGTAATGG
AAACACCTATTTAGAATGGTACCTGCAGAAACCAGGCCAGTCTCCAAAGC
TCCTGATCTACAAAGTTTCCAACCGATTTTCTGGGGTCCCAGACAGGTTCA
GTGGCAGTGGATCAGGGACAGATTTCACACTCAAGATCAGCAGAGTGGA
GGCTGAGGATCTGGGAGTTTATTACTGCTTTCAAGGTTCACATGTTCCTCC
CACGTTCGGAGGGGGGACCAAGCTGGAAATAAAACGG

SEQ ID NO:20

DVLMTQTPLSLPVSLGDQASISC<u>RSSQSVVQSNGNTYLE</u>WYLQKPGQSPKLLI
Y<u>KVSNRFS</u>GVPDRFSGSGSGTDFTLKISRVEAEDLGVYYC<u>FQGSHVPPT</u>FGGG
TKLEIKR

SEQ ID NO:21

CAGGTCCAGCTGCAGCAGTCTGGAGCTGAGCTGGTGAGGCCTGGGACTTC
AGTGAAGATGTCCTGCAAGGCTTCTGGCTACACCTTCACTACCTTCTATAT
ACACTGGGTGAGGCAGAGGCCTGGACAGGGCCTTGAGTGGATTGGAATG
ATTGGTCCTGGAAGTGGTAATACTTACTACAATGAGATGTTCAAGGACAA
GGCCACATTGACTGTAGACACATCCTCCAGCACAGCCTACATGCAGCTCA
GCAGCCTCACATCTGAGGACTCTGCGGTCTATTTCTGTGCAAGAGCAAAG
TCACATCGGGCGGCCTGGTTTGCTTACTGGGGCCAAGGGACTCTGGTCAC
TGTCTCTGCA

SEQ ID NO:23

QVQLQQSGAELVRPGTSVKMSCKASGYTFT<u>TFYIH</u>WVRQRPGQGLEWIG<u>MI
GPGSGNTYYNEMFKD</u>KATLTVDTSSSTAYMQLSSLTSEDSAVYFCAR<u>AKSHR
AAWFAY</u>WGQGTLVTVSA

F2) VL ML15-6A2

SEQ ID NO:22

GATGTTTTGATGACCCAAACTCCACTCTCCCTGCCTGTCAGTCTTGGAGAT
CAAGCCTCCATCTCTTGCAGATCTAGTCAGAGCGTTGTACAGAGTAATGG
AAACACCTATTTAGAATGGTACCTGCAGAAACCAGGCCAGTCTCCAAAGC
TCCTGATCTACAAAGTTTCCAACCGATTTTTTGGGGTCCCAGACAGGTTCA
GTGGCAGTAGATCAGGGACAGATTTCACACTCAAGATCAGCAGAGTGGA
GGCTGAGGATCTGGGAGTTTATTACTGCTTTCAAGGTTCACATGTTCCTCC
CACGTTCGGAGGGGGGACCAAGCTGGAAATAAAACGG

SEQ ID NO:24

DVLMTQTPLSLPVSLGDQASISC<u>RSSQSVVQSNGNTYLE</u>WYLQKPGQSPKLLI
Y<u>KVSNRFF</u>GVPDRFSGSRSGTDFTLKISRVEAEDLGVYYC<u>FQGSHVPPT</u>FGGG
TKLEIKR

SEQ ID NO:25

CAGGTGCAGCTGAAGCAGTCAGGACCTAGCCTAATACAGCCCTCACAGAG
CCTGTCCATAACCTGCACAGTCTCTGGTTTCTCATTAACTAGCTATGGTGT
ACACTGGGTTCGCCAGTCTCCAGGAAAGGGTCTGGAGTGGCTGGGAGTGA
TATGGAGAGGTGGAAGGATAGACTATAATGCAGCTTTCATGTCCAGACTG
AGCATCACCAAGGACAACTCCAAGAGCCAAGTTTTCTTTAAAATGAACAG
TCTGCAAGCTGATGACACTGCCATATACTACTGTGCCAGAAACTCCGATG
TCTGGGGCACAGGGACCACGGTCACCGTCTCCTCA

SEQ ID NO:27

QVQLKQSGPSLIQPSQSLSITCTVSGFSLTSYGVHWVRQSPGKGLEWLGVIWR
GGRIDYNAAFMSRLSITKDNSKSQVFFKMNSLQADDTAIYYCARNSDVWGT
GTTVTVSS

G2) VL ML13-4D10

SEQ ID NO:26

GATGTTGTGATGACCCAGACTCCACTCACTTTGTCGGTTACCATTGGACAA
CCAGCCTCCATCTCTTGCAAGTCAAGTCAGAGCCTCTTAGATATTGATGGA
AAGACATATTTGAATTGGTTGTTACAGAGGCCAGGCCAGTCTCCAAAGCG
CCTAATCTATCTGGTGTCTAAACTGGACTCTGGAGTCCCTGACAGGTTCAC
TGGCAGTGGATCAGGGACAGATTTCACACTGAAAATCAGCAGAGTGGAG
GCTGAGGATTTGGGAGTTTATTATTGCTGGCAAGGTACACATTTTCCGTAC
ACGTTCGGAGGGGGGACCAAGCTGGAAATAAAACGG

SEQ ID NO:28

DVVMTQTPLTLSVTIGQPASISCKSSQSLLDIDGKTYLNWLLQRPGQSPKRLIY
LVSKLDSGVPDRFTGSGSGTDFTLKISRVEAEDLGVYYCWQGTHFPYTFGGG
TKLEIKR

SEQ ID NO:29

GAGGTGAAGCTGGTGGAGTCTGGGGGAGGCTTAGTGCAGCCTGGAGGCTC
CCGGAAACTCTCCTGTGCAGCCTCTGGATTCACTTTCAGTGACTACGAAAT
GGTGTGGGTTCGACAGGCTCCAGGGGAGGGGCTGGAGTGGGTTGCATACA
TTAGTAGTGGCAGTCGTACCATCCACTATGCAGACACAGTGAAGGGCCGG
TTCACCATCTCCAGAGACAATCCCAAGAACACCTGTTCCTGCAAATGAG
CAGTCTGAGGTCTGAGGACACGGCCATGTATTACTGTGCAAGGACATTAC
TACGGCTACACTTTGACTACTGGGGCCAAGGCACCATTCTCACAGTCCTCT
CA

SEQ ID NO:31

EVKLVESGGGLVQPGGSRKLSCAASGFTFS<u>DYEMV</u>WVRQAPGEGLEWVA<u>YI
SSGSRTIHYADTVKG</u>RFTISRDNPKNTLFLQMSSLRSEDTAMYYCAR<u>TLLRLH
FDY</u>WGQGTILTVSS

H2) VL ML15-7E5

SEQ ID NO:30

GACATTGTGATGTCACAGTCTCCATCCTCCCTAGCTGTGTCAGTTGGAGAG
AAGGTTACTATGAGCTGCAGGTCCAGTCAGAGCCTTTTCTATAGGAGCAA
TCAAAAGAACTTCTTGGCCTGGTACCAGCAGAAACCAGGGCAGTCTCCTA
AACTGCTGATTTACTGGGCATCCACTAGGGAATCTGGGGTCCCTGATCGCT
TCACAGGCAGTGGATCTGGGACAGATTTCACTCTCACCATCAGCAGTGTG
AAGGCTGAAGACCTGGCAGTTTATTACTGTCAGCAATATTATAGCTATCC
GTGGACGTTCGGTGGAGGCACCAAGCTGGAAATCAAACGG

SEQ ID NO:32

DIVMSQSPSSLAVSVGEKVTMSC<u>RSSQSLFYRSNQKNFLA</u>WYQQKPGQSPKL
LIY<u>WASTRES</u>GVPDRFTGSGSGTDFTLTISSVKAEDLAVYYC<u>QQYYSYPWT</u>FG
GGTKLEIKR

SEQ ID NO:33

GAGGTGAAGCTGGTGGAGTCTGGGGGAGGTTTAGTGCAGCCTGGAGGCTC
CCGGAAACTCTCCTGTCAGCCTCTGGATTCACTTTCAGTGACTACGAAAT
GGTGTGGGTTCGACAGGCTCCAGGGAAGGGGCTGGAGTGGGTTGCATACA
TTAATAGTGGCAGTGGTACCATCCACTATGCAGACACAGTGAAGGGCCGA
TTCACCATCTCCAGAGACAATCCCAAGAACACCCTGTTCCTGCAAATGAG
CAGTCTAAGGTCTGAGGACACGGCCATGTATTACTGTGCAAGGACATTAC
TACGGCTACACTTTGACTACTGGGGCCAAGGCACCATTCTCACTGTCTCCT
CA

SEQ ID NO:35

EVKLVESGGGLVQPGGSRKLSCAASGFTFS<u>DYEMV</u>WVRQAPGKGLEWVA<u>YI
NSGSGTIHYADTVKG</u>RFTISRDNPKNTLFLQMSSLRSEDTAMYYCAR<u>TLLRLH
FDY</u>WGQGTILTVSS

I2) VL ML15-10C1

SEQ ID NO:34

GACATTGTGATGTCACAGTCTCCATCCTCCCTAGCTGTGTCAGTTGGAGAG
AAGGTTACTATGAGCTGCAAGTCCAGTCAGAGCCTTTTCTATAGTCGCAAT
CAAAAGAACTTCTTGGCCTGGTACCAGCAGAAACCAGGGCAGTCTCCTAA
ACTGCTGATTTACTGGGCATCCACTGGGGAATCTGGGGTCCCTGATCGCTT
CACAGGCAGTGGATCTGGGACAGATTTCACTCTCACCATCAGCAGTGTGA
AGGCTGAAGACCTGGCAGTTTATTACTGTCAGCAATATTTTAGCTATCCGT
GGACGTTCGGTGGAGGCACCAAGCTGGAAATCAAACGG

SEQ ID NO:36

DIVMSQSPSSLAVSVGEKVTMSC<u>KSSQSLFYSRNQKNFLA</u>WYQQKPGQSPKL
LIY<u>WASTGES</u>GVPDRFTGSGSGTDFTLTISSVKAEDLAVYYC<u>QQYFSYPWT</u>FG
GGTKLEIKR

SEQ ID NO:37

CAGGTCCAGCTGCAGCAGTCTGGACCTGAGCTGGTAAAGCCTGGGGCTTC
AGTGAAGATGTCCTGCAAGGCTTCTGGATACACATTCACTGACTATGTTAT
ACACTGGGTGAAGCAGAAGCCTGGGCAGGGCCTTGAGTGGATTGGATATA
TTAATCCTTACAATGATGGTACTCAGTACAATGAGAAGTTCAAAGGCAAG
GCCACACTGACTTCAGACAAATCCTCCAGCACAGTCTACATGGAGCTCAG
CAGTCTGACCTCTGAGGACTCTACAGTCTACTACTGTACAGTAGAGGGTG
GTACCTGGGACGGGTATTTCGATGTCTGGGGCACAGGGACCACGGTCACC
GTCTCCTCA

SEQ ID NO:38

QVQLQQSGPELVKPGASVKMSCKASGYTFTDYVIHWVKQKPGQGLEWIGYI
NPYNDGTQYNEKFKGKATLTSDKSSSTVYMELSSLTSEDSTVYYCTVEGGTW
DGYFDVWGTGTTVTVSS

SEQUENCE LISTING

<160> NUMBER OF SEQ ID NOS: 42

<210> SEQ ID NO 1
<211> LENGTH: 360
<212> TYPE: DNA
<213> ORGANISM: Artificial Sequence
<220> FEATURE:
<223> OTHER INFORMATION: Description of Artificial Sequence: Synthetic
      VH ML15-5F7 polynucleotide

<400> SEQUENCE: 1

```
caggtccagc tgaagcagtc tggagctgag ctggtgaggc ctgggacttc agtgaagatg      60
tcctgcaagg cttctggcta caccttcact accttctata tacactgggt gaagcagagg     120
cctggacagg gccttgagtg gattggaatg attggtcctg gaagtggtaa tacttactac     180
aatgagatgt tcaaggacaa ggccacattg actgtagaca catcctccag cacagcctac     240
atgcagctca gcagcctcac atctgaggac tctgcggtct atttctgtgc aagagcaaag     300
```

```
tcagctcggg cggcctggtt tgcttactgg ggccaaggga ctctggtcac tgtctctgca    360
```

<210> SEQ ID NO 2
<211> LENGTH: 339
<212> TYPE: DNA
<213> ORGANISM: Artificial Sequence
<220> FEATURE:
<223> OTHER INFORMATION: Description of Artificial Sequence: Synthetic
      VH ML15-5F7 polynucleotide

<400> SEQUENCE: 2

```
gatgttttga tgacccaaac tccactctcc ctgcctgtca gtcttggaga tcaagcctcc     60
atctcttgca gatctagtca gagcgttgta cagagtaatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttcct    300
cccacgttcg gagggggac caagctggaa ataaaacgg                            339
```

<210> SEQ ID NO 3
<211> LENGTH: 120
<212> TYPE: PRT
<213> ORGANISM: Artificial Sequence
<220> FEATURE:
<223> OTHER INFORMATION: Description of Artificial Sequence: Synthetic
      VH ML15-5F7 polypeptide

<400> SEQUENCE: 3

```
Gln Val Gln Leu Lys Gln Ser Gly Ala Glu Leu Val Arg Pro Gly Thr
1               5                   10                  15

Ser Val Lys Met Ser Cys Lys Ala Ser Gly Tyr Thr Phe Thr Thr Phe
            20                  25                  30

Tyr Ile His Trp Val Lys Gln Arg Pro Gly Gln Gly Leu Glu Trp Ile
        35                  40                  45

Gly Met Ile Gly Pro Gly Ser Gly Asn Thr Tyr Tyr Asn Glu Met Phe
    50                  55                  60

Lys Asp Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ala Lys Ser Ala Arg Ala Ala Trp Phe Ala Tyr Trp Gly Gln
            100                 105                 110

Gly Thr Leu Val Thr Val Ser Ala
        115                 120
```

<210> SEQ ID NO 4
<211> LENGTH: 113
<212> TYPE: PRT
<213> ORGANISM: Artificial Sequence
<220> FEATURE:
<223> OTHER INFORMATION: Description of Artificial Sequence: Synthetic
      VH ML15-5F7 polypeptide

<400> SEQUENCE: 4

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Val Val Gln Ser
            20                  25                  30

Asn Gly Asn Thr Tyr Leu Glu Trp Tyr Leu Gln Lys Pro Gly Gln Ser
        35                  40                  45
```

-continued

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 5
<211> LENGTH: 360
<212> TYPE: DNA
<213> ORGANISM: Artificial Sequence
<220> FEATURE:
<223> OTHER INFORMATION: Description of Artificial Sequence: Synthetic
      VH ML15-10F11 polynucleotide

<400> SEQUENCE: 5
caggtccagc tgcagcagtc tggacctgag ctggtaaagc ctggggcttc agtgaagatg       60
tcctgcaagg cttctggata cacattcact agctatgtta tgcactgggt gaagcagagg     120
cctgggcagg gccttgagtg gattggatat atttatcctt acaatgatgg tactaagtac     180
aatgagaagt tcaaaggcaa ggccacactg acttcagaca atcctccag cacagtatat      240 atggagctca gcagcctgac ctctgaggac tctacagtct attactgtac agtagagggt     300
gctacctggg acgggtactt cgatgtctgg ggcacaggga ccacggtcac cgtctcctca     360

<210> SEQ ID NO 6
<211> LENGTH: 339
<212> TYPE: DNA
<213> ORGANISM: Artificial Sequence
<220> FEATURE:
<223> OTHER INFORMATION: Description of Artificial Sequence: Synthetic
      VH ML15-10F11 polynucleotide

<400> SEQUENCE: 6
gatgttgtga tgacccagac tccactcact ttgtcggtta ccattggaca atcagcctct       60
atctcttgca gtcaagtca gagcctctta tatagtaaag gaaaaaccta tttgaattgg      120
ttattacaga ggccaggcca gtctccaaag cgcctaatct atctggtgtc taaactggac     180
tctggagtcc ctgacaggtt cactggcagt ggatcaggaa cagattttac actgaaaatc     240
agcagagtgg aggctgagga tttgggagtt tattactgcg tgcaaggtac acattttcct    300
cacacgttcg gaggggggac caagctggaa ataaaacgg                            339

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      VH ML15-10F11 polypeptide

<400> SEQUENCE: 7

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Arg Pro Gly Gln Gly Leu Glu Trp Ile
```

```
                35                  40                  45
Gly Tyr Ile Tyr Pro Tyr Asn Asp Gly Thr Lys Tyr Asn Glu Lys Phe
 50                  55                  60

Lys Gly Lys Ala Thr Leu Thr Ser Asp Lys Ser Ser Thr Val Tyr
 65                  70                  75                  80

Met Glu Leu Ser Ser Leu Thr Ser Glu Asp Ser Thr Val Tyr Tyr Cys
                 85                  90                  95

Thr Val Glu Gly Ala Thr Trp Asp Gly Tyr Phe Asp Val Trp Gly Thr
                100                 105                 110

Gly Thr Thr Val Thr Val Ser Ser
        115                 120

<210> SEQ ID NO 8
<211> LENGTH: 113
<212> TYPE: PRT
<213> ORGANISM: Artificial Sequence
<220> FEATURE:
<223> OTHER INFORMATION: Description of Artificial Sequence: Synthetic
      VH ML15-10F11 polypeptide

<400> SEQUENCE: 8

Asp Val Val Met Thr Gln Thr Pro Leu Thr Leu Ser Val Thr Ile Gly
 1               5                  10                  15

Gln Ser Ala Ser Ile Ser Cys Lys Ser Ser Gln Ser Leu Leu Tyr Ser
                20                  25                  30

Lys Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Val Gln Gly
                 85                  90                  95

Thr His Phe Pro His Thr Phe Gly Gly Gly Thr Lys Leu Glu Ile Lys
                100                 105                 110

Arg

<210> SEQ ID NO 9
<211> LENGTH: 354
<212> TYPE: DNA
<213> ORGANISM: Artificial Sequence
<220> FEATURE:
<223> OTHER INFORMATION: Description of Artificial Sequence: Synthetic
      VH ML13-7C6 polynucleotide

<400> SEQUENCE: 9
gaagtgaagc tggtggagtc tgggggaggc ttagtgaagc ctggagggtc cctgaaactc      60
tcctgtgcag cctctggatt cactttcagt agctatgcca tgtcttgggt tcgccagact     120
ccagcgaaga ggctagagtg gtcgcgtcc attcataata gaggtactat cttctatcta     180
gacagtgtga aggccgatt caccatctcc agagataatg tcaggaacac cctgtacctg     240
caaatgagca gtctgaggtc tgaggacacg gccatatatt actgtacaag aggccggagt     300
aactcctatg ctatggacta ctggggtcaa ggaacctcag tcaccgtctc ctcg            354

<210> SEQ ID NO 10
<211> LENGTH: 339
<212> TYPE: DNA
<213> ORGANISM: Artificial Sequence
```

<220> FEATURE:
<223> OTHER INFORMATION: Description of Artificial Sequence: Synthetic
      VH ML13-7C6 polynucleotide

<400> SEQUENCE: 10
gatgttttgg tgacccaatc tccactctcc ctgcctgtca ggcttggaga tcaagcctcc     60
atctcttgcc gatctactca gacccttgta catcgtaatg gagacaccta tttagaatgg    120
tacctgcaga aaccaggcca gtctccaaag tccctgatct acaaagtttc caaccgattt    180
tctggggtcc cagacaggtt cagcggcagt ggatcaggga cagatttcac actcaagatc    240
agcagagtgg aggctgagga tctgggagtt tattactgct ttcaaggttc acatgttccg    300
tacacgttcg gagggggggac caagctggaa ataaaacgg                          339

<210> SEQ ID NO 11
<211> LENGTH: 118
<212> TYPE: PRT
<213> ORGANISM: Artificial Sequence
<220> FEATURE:
<223> OTHER INFORMATION: Description of Artificial Sequence: Synthetic
      VH ML13-7C6 polypeptide

<400> SEQUENCE: 11

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Ala Lys Arg Leu Glu Trp Val
        35                  40                  45

Ala Ser Ile His Asn Arg Gly Thr Ile Phe Tyr Leu Asp Ser Val Lys
    50                  55                  60

Gly Arg Phe Thr Ile Ser Arg Asp Asn Val Arg Asn Thr Leu Tyr Leu
65                  70                  75                  80

Gln Met Ser Ser Leu Arg Ser Glu Asp Thr Ala Ile Tyr Tyr Cys Thr
                85                  90                  95

Arg Gly Arg Ser Asn Ser Tyr Ala Met Asp Tyr Trp Gly Gln Gly Thr
            100                 105                 110

Ser Val Thr Val Ser Ser
        115

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic
      VH ML13-7C6 polypeptide

<400> SEQUENCE: 12

Asp Val Leu Val Thr Gln Ser Pro Leu Ser Leu Pro Val Arg Leu Gly
1               5                   10                  15

Asp Gln Ala Ser Ile Ser Cys Arg Ser Thr Gln Thr Leu Val His Arg
            20                  25                  30

Asn Gly Asp Thr Tyr Leu Glu Trp Tyr Leu Gln Lys Pro Gly Gln Ser
        35                  40                  45

Pro Lys Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg

<210> SEQ ID NO 13
<211> LENGTH: 354
<212> TYPE: DNA
<213> ORGANISM: Artificial Sequence
<220> FEATURE:
<223> OTHER INFORMATION: Description of Artificial Sequence: Synthetic
      VH ML15-4B7 polynucleotide

<400> SEQUENCE: 13
gaggtgaagc tggtggagtc tgggggaggc ttagtgcagc ctggaggctc ccggaaactc      60
tcctgtgcag cctctggatt cactttcagt gactacgaaa tggtgtgggt cgacaggct     120 ccaggggagg gctggagtg gttgcatac attagtagtg gcagtcgtac catccactat      180
gcagacacag tgaagggccg attcaccatc tccagagaca atcccaagaa caccctgttc      240
ctgcaaatga gcagtctgag gtctgaggac acggccatgt attactgtgc aaggacatta      300
ctacggctac actttgacta ctggggccaa ggcaccattc tcacagtctc ctca             354

<210> SEQ ID NO 14
<211> LENGTH: 342
<212> TYPE: DNA
<213> ORGANISM: Artificial Sequence
<220> FEATURE:
<223> OTHER INFORMATION: Description of Artificial Sequence: Synthetic
      VH ML15-4B7 polynucleotide

<400> SEQUENCE: 14
gacattgtga tgtcacagtc tccatcctcc ctagctgtgt cagttggaga aaggttact       60 atgagctgca ggtccagtca gagccttttc tataggagca atcaaaagaa cttcttggcc     120
tggtaccagc agaaaccagg gcagtctcct aaactgctga tttactgggc atccactagg      180
gaatctgggg tccctgatcg cttcacaggc agtggatctg ggacagattt cactctcacc      240
atcagcagtg tgaaggctga agacctggca gtttattact gtcagcaata ttatagctat      300
ccgtggacgt tcggtggagg caccaagctg gaaatcaaac gg                           342

<210> SEQ ID NO 15
<211> LENGTH: 118
<212> TYPE: PRT
<213> ORGANISM: Artificial Sequence
<220> FEATURE:
<223> OTHER INFORMATION: Description of Artificial Sequence: Synthetic
      VH ML15-4B7 polypeptide

<400> SEQUENCE: 15

Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asp Tyr
            20                  25                  30

Glu Met Val Trp Val Arg Gln Ala Pro Gly Glu Gly Leu Glu Trp Val
        35                  40                  45

Ala Tyr Ile Ser Ser Gly Ser Arg Thr Ile His Tyr Ala Asp Thr Val
    50                  55                  60

Lys Gly Arg Phe Thr Ile Ser Arg Asp Asn Pro Lys Asn Thr Leu Phe
65                  70                  75                  80
```

Leu Gln Met Ser Ser Leu Arg Ser Glu Asp Thr Ala Met Tyr Tyr Cys
                85                  90                  95

Ala Arg Thr Leu Leu Arg Leu His Phe Asp Tyr Trp Gly Gln Gly Thr
            100                 105                 110

Ile Leu Thr Val Ser Ser
        115

<210> SEQ ID NO 16
<211> LENGTH: 114
<212> TYPE: PRT
<213> ORGANISM: Artificial Sequence
<220> FEATURE:
<223> OTHER INFORMATION: Description of Artificial Sequence: Synthetic
      VH ML15-4B7 polypeptide

<400> SEQUENCE: 16

Asp Ile Val Met Ser Gln Ser Pro Ser Ser Leu Ala Val Ser Val Gly
1               5                   10                  15

Glu Lys Val Thr Met Ser Cys Arg Ser Ser Gln Ser Leu Phe Tyr Arg
            20                  25                  30

Ser Asn Gln Lys Asn Phe Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
            100                 105                 110

Lys Arg

<210> SEQ ID NO 17
<211> LENGTH: 360
<212> TYPE: DNA
<213> ORGANISM: Artificial Sequence
<220> FEATURE:
<223> OTHER INFORMATION: Description of Artificial Sequence: Synthetic
      VH ML15-2F2 polynucleotide

<400> SEQUENCE: 17
caggtccagc tgaagcagtc tggagctgag ctggtgaggc ctgggacttc agtgaagatg      60
tcctgcaagg cttctggcta caccttcact accttctata tacactgggt gaagcagagg     120
cctggacagg gccttgagtg gattggaatg attggtcctg aagtggtaa tacttactac      180 aatgagatgt tcaaggacaa ggccacattg actgtagaca catcctccag cacagcctac     240
atgcagctca gcagcctcac atctgaggac tctgcggtct atttctgtgc aagagcaaag     300
tcagctcggg cggcctggtt tgcttactgg ggccaaggga ctctggtcac tgtctctgca     360

<210> SEQ ID NO 18
<211> LENGTH: 339
<212> TYPE: DNA
<213> ORGANISM: Artificial Sequence
<220> FEATURE:
<223> OTHER INFORMATION: Description of Artificial Sequence: Synthetic
      VH ML15-2F2 polynucleotide

<400> SEQUENCE: 18
gatgttttga tgacccaaac tccactctcc ctgcctgtca gtcttggaga tcaagcctcc      60

```
atctcttgca gatctagtca gagcgttgta cagagtaatg gaaacaccta tttagaatgg      120
tacctgcaga aaccaggcca gtctccaaag ctcctgatct acaaagtttc caaccgattt      180
tctggggtcc cagacaggtt cagtggcagt ggatcaggga cagatttcac actcaagatc      240
agcagagtgg aggctgagga tctgggagtt tattactgct ttcaaggttc acatgttcct      300
cccacgttcg gaggggggac caagctggaa ataaaacgg                             339
```

```
<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic
      VH ML15-2F2 polypeptide

<400> SEQUENCE: 19

Gln Val Gln Leu Lys Gln Ser Gly Ala Glu Leu Val Arg Pro Gly Thr
1               5                   10                  15

Ser Val Lys Met Ser Cys Lys Ala Ser Gly Tyr Thr Phe Thr Thr Phe
                20                  25                  30

Tyr Ile His Trp Val Lys Gln Arg Pro Gly Gln Gly Leu Glu Trp Ile
            35                  40                  45

Gly Met Ile Gly Pro Gly Ser Gly Asn Thr Tyr Tyr Asn Glu Met Phe
        50                  55                  60

Lys Asp Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ala Lys Ser Ala Arg Ala Ala Trp Phe Ala Tyr Trp Gly Gln
            100                 105                 110

Gly Thr Leu Val Thr Val Ser Ala
        115                 120
```

```
<210> SEQ ID NO 20
<211> LENGTH: 113
<212> TYPE: PRT
<213> ORGANISM: Artificial Sequence
<220> FEATURE:
<223> OTHER INFORMATION: Description of Artificial Sequence: Synthetic
      VH ML15-2F2 polypeptide

<400> SEQUENCE: 20

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Val Val Gln Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

Arg
```

<210> SEQ ID NO 21
<211> LENGTH: 360
<212> TYPE: DNA
<213> ORGANISM: Artificial Sequence
<220> FEATURE:
<223> OTHER INFORMATION: Description of Artificial Sequence: Synthetic
      VH ML15-6A2 polynucleotide

<400> SEQUENCE: 21

```
caggtccagc tgcagcagtc tggagctgag ctggtgaggc ctgggacttc agtgaagatg      60
tcctgcaagg cttctggcta caccttcact accttctata tacactgggt gaggcagagg     120
cctggacagg gccttgagtg gattggaatg attggtcctg aagtggtaa tacttactac      180 aatgagatgt tcaaggacaa ggccacattg actgtagaca catcctccag cacagcctac     240
atgcagctca gcagcctcac atctgaggac tctgcggtct atttctgtgc aagagcaaag     300
tcacatcggg cggcctggtt tgcttactgg ggccaaggga ctctggtcac tgtctctgca     360
```

<210> SEQ ID NO 22
<211> LENGTH: 339
<212> TYPE: DNA
<213> ORGANISM: Artificial Sequence
<220> FEATURE:
<223> OTHER INFORMATION: Description of Artificial Sequence: Synthetic
      VH ML15-6A2 polynucleotide

<400> SEQUENCE: 22

```
gatgttttga tgacccaaac tccactctcc ctgcctgtca gtcttggaga tcaagcctcc      60
atctcttgca gatctagtca gagcgttgta cagagtaatg gaaacaccta tttagaatgg     120
tacctgcaga aaccaggcca gtctccaaag ctcctgatct acaaagtttc caaccgattt     180
tttggggtcc cagacaggtt cagtggcagt agatcaggga cagatttcac actcaagatc     240
agcagagtgg aggctgagga tctgggagtt tattactgct ttcaaggttc acatgttcct     300
cccacgttcg agggggggac caagctggaa ataaaacgg                            339
```

<210> SEQ ID NO 23
<211> LENGTH: 120
<212> TYPE: PRT
<213> ORGANISM: Artificial Sequence
<220> FEATURE:
<223> OTHER INFORMATION: Description of Artificial Sequence: Synthetic
      VH ML15-6A2 polypeptide

<400> SEQUENCE: 23

Gln Val Gln Leu Gln Gln Ser Gly Ala Glu Leu Val Arg Pro Gly Thr
1               5                   10                  15

Ser Val Lys Met Ser Cys Lys Ala Ser Gly Tyr Thr Phe Thr Thr Phe
            20                  25                  30

Tyr Ile His Trp Val Arg Gln Arg Pro Gly Gln Gly Leu Glu Trp Ile
        35                  40                  45

Gly Met Ile Gly Pro Gly Ser Gly Asn Thr Tyr Tyr Asn Glu Met Phe
    50                  55                  60

Lys Asp Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ala Lys Ser His Arg Ala Ala Trp Phe Ala Tyr Trp Gly Gln
            100                 105                 110

```
Gly Thr Leu Val Thr Val Ser Ala
        115                 120
```

<210> SEQ ID NO 24
<211> LENGTH: 113
<212> TYPE: PRT
<213> ORGANISM: Artificial Sequence
<220> FEATURE:
<223> OTHER INFORMATION: Description of Artificial Sequence: Synthetic
      VH ML15-6A2 polypeptide

<400> SEQUENCE: 24

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Val Val Gln Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Phe Gly Val Pro
    50                  55                  60

Asp Arg Phe Ser Gly Ser Arg Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

Arg
```

<210> SEQ ID NO 25
<211> LENGTH: 336
<212> TYPE: DNA
<213> ORGANISM: Artificial Sequence
<220> FEATURE:
<223> OTHER INFORMATION: Description of Artificial Sequence: Synthetic
      VH ML13-4D10 polynucleotide

<400> SEQUENCE: 25

```
caggtgcagc tgaagcagtc aggacctagc ctaatacagc cctcacagag cctgtccata      60
acctgcacag tctctggttt ctcattaact agctatggtg tacactgggt tcgccagtct     120
ccaggaaagg gtctggagtg gctgggagtg atatggagag gtggaaggat agactataat     180
gcagctttca tgtccagact gagcatcacc aaggacaact ccaagagcca gttttctttt     240
aaaatgaaca gtctgcaagc tgatgacact gccatatact actgtgccag aaactccgat     300
gtctggggca cagggaccac ggtcaccgtc tcctca                               336
```

<210> SEQ ID NO 26
<211> LENGTH: 339
<212> TYPE: DNA
<213> ORGANISM: Artificial Sequence
<220> FEATURE:
<223> OTHER INFORMATION: Description of Artificial Sequence: Synthetic
      VH ML13-4D10 polynucleotide

<400> SEQUENCE: 26

```
gatgttgtga tgacccagac tccactcact ttgtcggtta ccattggaca accagcctcc      60
atctcttgca agtcaagtca gagcctctta gatattgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
```

```
agcagagtgg aggctgagga tttgggagtt tattattgct ggcaaggtac acattttccg    300
tacacgttcg gagggggac caagctggaa ataaaacgg                            339
```

<210> SEQ ID NO 27
<211> LENGTH: 112
<212> TYPE: PRT
<213> ORGANISM: Artificial Sequence
<220> FEATURE:
<223> OTHER INFORMATION: Description of Artificial Sequence: Synthetic
    VH ML13-4D10 polypeptide

<400> SEQUENCE: 27

```
Gln Val Gln Leu Lys Gln Ser Gly Pro Ser Leu Ile Gln Pro Ser Gln
1               5                   10                  15

Ser Leu Ser Ile Thr Cys Thr Val Ser Gly Phe Ser Leu Thr Ser Tyr
                20                  25                  30

Gly Val His Trp Val Arg Gln Ser Pro Gly Lys Gly Leu Glu Trp Leu
            35                  40                  45

Gly Val Ile Trp Arg Gly Gly Arg Ile Asp Tyr Asn Ala Ala Phe Met
        50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asn Ser Asp Val Trp Gly Thr Gly Thr Thr Val Thr Val Ser Ser
                100                 105                 110
```

<210> SEQ ID NO 28
<211> LENGTH: 113
<212> TYPE: PRT
<213> ORGANISM: Artificial Sequence
<220> FEATURE:
<223> OTHER INFORMATION: Description of Artificial Sequence: Synthetic
    VH ML13-4D10 polypeptide

<400> SEQUENCE: 28

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ile
                20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
                100                 105                 110

Arg
```

<210> SEQ ID NO 29
<211> LENGTH: 354
<212> TYPE: DNA
<213> ORGANISM: Artificial Sequence
<220> FEATURE:
<223> OTHER INFORMATION: Description of Artificial Sequence: Synthetic
    VH ML15-7E5 polynucleotide

<400> SEQUENCE: 29

```
gaggtgaagc tggtggagtc tgggggaggc ttagtgcagc ctggaggctc ccggaaactc      60
tcctgtgcag cctctggatt cactttcagt gactacgaaa tggtgtgggt tcgacaggct     120 ccagggagg ggctggagtg ggttgcatac attagtagtg gcagtcgtac catccactat     180
gcagacacag tgaagggccg gttcaccatc tccagagaca atcccaagaa caccctgttc     240
ctgcaaatga gcagtctgag gtctgaggac acggccatgt attactgtgc aaggacatta     300
ctacggctac actttgacta ctggggccaa ggcaccattc tcacagtctc ctca           354
```

<210> SEQ ID NO 30
<211> LENGTH: 342
<212> TYPE: DNA
<213> ORGANISM: Artificial Sequence
<220> FEATURE:
<223> OTHER INFORMATION: Description of Artificial Sequence: Synthetic
VH ML15-7E5 polynucleotide

<400> SEQUENCE: 30

```
gacattgtga tgtcacagtc tccatcctcc ctagctgtgt cagttggaga aaggttact      60 atgagctgca ggtccagtca gagccttttc tataggagca atcaaaagaa cttcttggcc     120
tggtaccagc agaaaccagg gcagtctcct aaactgctga tttactgggc atccactagg     180
gaatctgggg tccctgatcg cttcacaggc agtggatctg ggacagattt cactctcacc     240
atcagcagtg tgaaggctga agacctggca gtttattact gtcagcaata ttatagctat     300
ccgtggacgt tcggtggagg caccaagctg gaaatcaaac gg                        342
```

<210> SEQ ID NO 31
<211> LENGTH: 118
<212> TYPE: PRT
<213> ORGANISM: Artificial Sequence
<220> FEATURE:
<223> OTHER INFORMATION: Description of Artificial Sequence: Synthetic
VH ML15-7E5 polypeptide

<400> SEQUENCE: 31

```
Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asp Tyr
            20                  25                  30

Glu Met Val Trp Val Arg Gln Ala Pro Gly Glu Gly Leu Glu Trp Val
        35                  40                  45

Ala Tyr Ile Ser Ser Gly Ser Arg Thr Ile His Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Ser Ser Leu Arg Ser Glu Asp Thr Ala Met Tyr Tyr Cys
                85                  90                  95

Ala Arg Thr Leu Leu Arg Leu His Phe Asp Tyr Trp Gly Gln Gly Thr
            100                 105                 110

Ile Leu Thr Val Ser Ser
        115
```

<210> SEQ ID NO 32
<211> LENGTH: 114
<212> TYPE: PRT
<213> ORGANISM: Artificial Sequence
<220> FEATURE:
<223> OTHER INFORMATION: Description of Artificial Sequence: Synthetic VH ML15-7E5 polypeptide

<400> SEQUENCE: 32

Asp Ile Val Met Ser Gln Ser Pro Ser Ser Leu Ala Val Ser Val Gly
1               5                   10                  15

Glu Lys Val Thr Met Ser Cys Arg Ser Ser Gln Ser Leu Phe Tyr Arg
            20                  25                  30

Ser Asn Gln Lys Asn Phe Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
                100                 105                 110

Lys Arg

<210> SEQ ID NO 33
<211> LENGTH: 354
<212> TYPE: DNA
<213> ORGANISM: Artificial Sequence
<220> FEATURE:
<223> OTHER INFORMATION: Description of Artificial Sequence: Synthetic
      VH ML15-10C1 polynucleotide

<400> SEQUENCE: 33
gaggtgaagc tggtggagtc tgggggaggt ttagtgcagc ctggaggctc ccggaaactc      60
tcctgtgcag cctctggatt cactttcagt gactacgaaa tggtgtgggt tcgacaggct     120
ccagggaagg ggctggagtg ggttgcatac attaatagtg gcagtggtac catccactat     180
gcagacacag tgaagggccg attcaccatc tccagagaca tcccaagaa cacccctgttc    240 ctgcaaatga gcagtctaag gtctgaggac acggccatgt attactgtgc aaggacatta     300
ctacggctac actttgacta ctggggccaa ggcaccattc tcactgtctc ctca           354

<210> SEQ ID NO 34
<211> LENGTH: 342
<212> TYPE: DNA
<213> ORGANISM: Artificial Sequence
<220> FEATURE:
<223> OTHER INFORMATION: Description of Artificial Sequence: Synthetic
      VH ML15-10C1 polynucleotide

<400> SEQUENCE: 34
gacattgtga tgtcacagtc tccatcctcc ctagctgtgt cagttggaga gaaggttact      60
atgagctgca agtccagtca gagccttttc tatagtcgca atcaaaagaa cttcttggcc     120
tggtaccagc agaaaccagg gcagtctcct aaactgctga tttactgggc atccactggg    180
gaatctgggg tccctgatcg cttcacaggc agtggatctg ggacagattt cactctcacc     240
atcagcagtg tgaaggctga agacctggca gtttattact gtcagcaata ttttagctat    300
ccgtggacgt tcggtggagg caccaagctg gaaatcaaac gg                       342

<210> SEQ ID NO 35
<211> LENGTH: 118
<212> TYPE: PRT
<213> ORGANISM: Artificial Sequence
<220> FEATURE:

<223> OTHER INFORMATION: Description of Artificial Sequence: Synthetic
VH ML15-10C1 polypeptide

<400> SEQUENCE: 35

Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asp Tyr
            20                  25                  30

Glu Met Val Trp Val Arg Gln Ala Pro Gly Lys Gly Leu Glu Trp Val
        35                  40                  45

Ala Tyr Ile Asn Ser Gly Ser Gly Thr Ile His Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Ser Ser Leu Arg Ser Glu Asp Thr Ala Met Tyr Tyr Cys
                85                  90                  95

Ala Arg Thr Leu Leu Arg Leu His Phe Asp Tyr Trp Gly Gln Gly Thr
            100                 105                 110

Ile Leu Thr Val Ser Ser
        115

<210> SEQ ID NO 36
<211> LENGTH: 114
<212> TYPE: PRT
<213> ORGANISM: Artificial Sequence
<220> FEATURE:
<223> OTHER INFORMATION: Description of Artificial Sequence: Synthetic
VH ML15-10C1 polypeptide

<400> SEQUENCE: 36

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Phe Tyr Ser
            20                  25                  30

Arg Asn Gln Lys Asn Phe Leu Ala Trp Tyr Gln Gln Lys Pro Gly Gln
        35                  40                  45

Ser Pro Lys Leu Leu Ile Tyr Trp Ala Ser Thr Gly Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Phe Ser Tyr Pro Trp Thr Phe Gly Gly Gly Thr Lys Leu Glu Ile
            100                 105                 110

Lys Arg

<210> SEQ ID NO 37
<211> LENGTH: 360
<212> TYPE: DNA
<213> ORGANISM: Artificial Sequence
<220> FEATURE:
<223> OTHER INFORMATION: Description of Artificial Sequence: Synthetic
VH ML15-3B10 polynucleotide

<400> SEQUENCE: 37
caggtccagc tgcagcagtc tggacctgag ctggtaaagc ctggggcttc agtgaagatg      60
tcctgcaagg cttctggata cacattcact gactatgtta cactgggt gaagcagaag      120 cctgggcagg gccttgagtg gattggatat attaatcctt acaatgatgg tactcagtac      180
aatgagaagt tcaaaggcaa ggccacactg acttcagaca atcctccag cacagtctac    240 atggagctca gcagtctgac ctctgaggac tctacagtct actactgtac agtagagggt    300
ggtacctggg acgggtattt cgatgtctgg ggcacaggga ccacggtcac cgtctcctca    360

<210> SEQ ID NO 38
<211> LENGTH: 120
<212> TYPE: PRT
<213> ORGANISM: Artificial Sequence
<220> FEATURE:
<223> OTHER INFORMATION: Description of Artificial Sequence: Synthetic
      VH ML15-3B10 polypeptide

<400> SEQUENCE: 38

```
Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Thr Gln Tyr Asn Glu Lys Phe
    50                  55                  60

Lys Gly Lys Ala Thr Leu Thr Ser Asp Lys Ser Ser Ser Thr Val Tyr
65                  70                  75                  80

Met Glu Leu Ser Ser Leu Thr Ser Glu Asp Ser Thr Val Tyr Tyr Cys
                85                  90                  95

Thr Val Glu Gly Gly Thr Trp Asp Gly Tyr Phe Asp Val Trp Gly Thr
            100                 105                 110

Gly Thr Thr Val Thr Val Ser Ser
        115                 120
```

<210> SEQ ID NO 39
<211> LENGTH: 330
<212> TYPE: PRT
<213> ORGANISM: Artificial Sequence
<220> FEATURE:
<223> OTHER INFORMATION: Description of Artificial Sequence: Synthetic
      Ig gamma-1 constant region polypeptide

<400> SEQUENCE: 39

```
Ala Ser Thr Lys Gly Pro Ser Val Phe Phe Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 40
<211> LENGTH: 330
<212> TYPE: PRT
<213> ORGANISM: Artificial Sequence
<220> FEATURE:
<223> OTHER INFORMATION: Description of Artificial Sequence: Synthetic
      Ig gamma-1 constant region mutant polypeptide

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu

```
                    165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 41
<211> LENGTH: 106
<212> TYPE: PRT
<213> ORGANISM: Artificial Sequence
<220> FEATURE:
<223> OTHER INFORMATION: Description of Artificial Sequence: Synthetic
      Ig Kappa constant region polypeptide

<400> SEQUENCE: 41

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 42
<211> LENGTH: 105
<212> TYPE: PRT
<213> ORGANISM: Artificial Sequence
<220> FEATURE:
<223> OTHER INFORMATION: Description of Artificial Sequence: Synthetic
      Ig Lambda constant region polypeptide

<400> SEQUENCE: 42

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
```

-continued

```
                    20                  25                  30
Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
                100                 105
```

ANTI-Aβ GLOBULOMER 7C6 ANTIBODIES

CROSS-REFERENCE TO RELATED APPLICATIONS

This application is a continuation of Ser. No. 11/574,876, filed on Feb. 25, 2009, now U.S. Pat. No. 8,691,224, which is a U.S. national stage entry of International Patent Application No. PCT/EP2006/011530, filed on Nov. 30, 2006, which claims priority to U.S. Patent Application No. 60/740,866, filed on Nov. 30, 2005, U.S. Patent Application No. 60/779,171, filed on Mar. 3, 2006, U.S. Patent Application No. 60/787,361, filed on Mar. 30, 2006, and U.S. Patent Application No. 60/842,400, filed on Sep. 5, 2006, the contents of all of which are fully incorporated herein by reference.

BRIEF DESCRIPTION OF THE SEQUENCE LISTING

A sequence listing in accordance with 37 C.F.R. par 1.821-1.825 is attached to the present invention and contained in a file named "8126USC1-029996-1511-US04-SEQ-LIST-05-14-13.txt" (43,083 bytes, created May 14, 2013) and is incorporated herein by reference.

The present invention relates to anti-Aβ globulomer antibodies, antigen-binding moieties thereof, hybridomas producing said antibodies, nucleic acids encoding said antibodies, vectors comprising said nucleic acids, host cells comprising said vectors, methods of producing said antibodies, compositions comprising said antibodies, therapeutic and diagnostic uses of said antibodies and corresponding methods relating to Alzheimer's disease and other amyloidoses.

In 1907 the physician Alois Alzheimer first described the neuropathological features of a form of dementia subsequently named in his honour (Alzheimer 1907). Alzheimer's disease (AD) is the most frequent cause for dementia among the aged with an incidence of about 10% of the population above 65 years. With increasing age, the probability of disease also rises. Globally, there are about 15 million people affected and further increases in life expectancy are expected to increase the number of diseased people to about threefold over the next decades.

From a molecular point of view Alzheimer's disease (AD) is characterized by a deposit of abnormally aggregated proteins. In the case of extra-cellular amyloid plaques these deposits consist mostly of amyloid-β-peptide filaments, in the case of the intracellular neurofibrillary tangles (NFTs) of the tau protein. The amyloid β (Aβ) peptide arises from the β-amyloid precursor protein by proteolytic cleavage. This cleavage is effected by the cooperative activity of several proteases named α-, β- and γ-secretase. Cleavage leads to a number of specific fragments of differing length. The amyloid plaques consist mostly of peptides with a length of 40 or 42 amino acids (Aβ40, Aβ342) The dominant cleavage product is Aβ40; however, Aβ42 has a much stronger toxic effect.

Cerebral amyloid deposits and cognitive impairments very similar to those observed in Alzheimer's disease are also hallmarks of Down's syndrome (trisomy 21), which occurs at a frequency of about 1 In 800 births.

The amyloid cascade hypothesis of Hardy and Higgins postulated that increased production of Aβ(1-42) would lead to the formation of protofibrils and fibrils, the principal components of Aβ plaques, these fibrils being responsible for the symptoms of Alzheimer's disease. Despite the poor correlation between severity of dementia and Aβ plaque burden deposited this hypothesis was favoured until recently. The discovery of soluble Aβ forms in AD brains, which correlates better with AD symptoms than plaque load does, has led to a revised amyloid-cascade-hypothesis.

Active immunization with Aβ peptides leads to a reduction in the formation as well as to partial dissolution of existing plaques. At the same time it leads to alleviation of cognitive defects in APP transgenic mouse models.

For passive immunization with antibodies directed to Aβ peptides a reduction of an Aβ plaque burden was also found.

The results of a phase IIa trial (ELAN Corporation Plc, South San Francisco, Calif., USA and Dublin, UK) of active immunization with AN-1792 (Aβ(1-42) peptide in fibrillary condition of aggregation) suggest that immunotherapy directed to Aβ peptide was successful. In a subgroup of 30 patients the progression of disease was significantly reduced in patients with positive anti-Aβ antibody titer, measured by MMSE and DAD index. However, this study was stopped because of serious side effects in form of a meningoencephalitis (Bennett and Holtzman, 2005, Neurology, 64, 10-12).

Meningoencephalitis was characterized by neuroinflammation and infiltration of T-cells into the brain. Presumably, this was due to a T-cell immune response induced by injection of Aβ(1-42) as antigen. Such an immune response is not to be expected after passive immunization. To date, there are no clinical data with reference to this available yet. However, with reference to such a passive approach to immunization concerns about the side effect profile were voiced because of preclinical studies in very old APP23 mice which received an antibody directed against an N-terminal epitope of Aβ(1-42) once a week over 5 months. These mice showed an increase in the number and severity of microhaemorrhages compared to control animals treated with saline (Pfeffer et al., 2002, Science, 298, 1379). A comparable increase in microhaemorrhages was also described in very old (>24 months) Tg2576 and PDAPP mice (Racke et al., 2005, J Neuroscl, 25, 629-636; Wilcock et al. 2004, J. Neuroinflammation, 1(1):24; De Mattos et al., 2004, Neurobiol. Aging 25(S2):577). In both mouse strains antibody injection led to a significant increase in microhaemorrhages. In contrast, an antibody directed against the central region of the Aβ(1-42) peptide did not induce microhaemorrhages (de Mattos et al., supra). The lack of inducing microhaemorrhages was associated with an antibody treatment which did not bind to aggregated Aβ peptide in the form of CAA (Racke et al., J Neuroscl, 25, 629-636). But, the exact mechanism leading to microhaemorrhages in mice transgenic for APP has not been understood. Presumably, cerebral amyoid angiopathy (CAA) induces or at least aggravates cerebral haemorrhages. CAA is present in nearly every Alzheimer's disease brain and about 20% of the cases are regarded as "severe CAA". Passive immunization should therefore aim at avoiding microhaemorrhages by selecting an antibody which recognizes the central or the carboxy terminal region of the Aβ peptide.

WO2004/067561 describes stable Aβ(1-42) oligomers (Aβ(1-42) globulomers) and antibodies directed specifically against the globulomers. Digestion with unspecific proteases shows that the Aβ globulomer may be digested beginning with the hydrophilic N-terminus protruding from the globular core structure (Barghorn et al., 2005, J Neurochem, 95, 834-847). Such N-terminal truncated Aβ globulomers (Aβ(12-42) and Aβ(20-42) globulomers) represent the basic structural unit of this oligomeric Aβ They are a very potent antigen for active immunization of rabbits and mice leading to high antibody titers (WO2004/067561). The putative pathological role of N-terminally truncated Aβ forms in vivo has been suggested by several recent reports of their existence in AD brains (Sergeant at al., 2003, J Neurochem, 85, 1581-1591; Thal et al., 1999, J Neuropathol. Exp Neurol, 58, 210-216). During in vivo digestion certain proteases found in brain, e.g. neprilysin (NEP 24.11) or insulin degrading enzyme (IDE), may be involved (Selkoe, 2001, Neuron, 32, 177-180).

It was an object of the present invention to provide antibodies directed against A, globulomers which improve the cognitive performance of a patient in immunotherapy while at the same time reacting only with a small portion of the entire amount of Aβ peptide in brain. This is expected to prevent a substantial disturbance of cerebral Aβ balance and lead to less side effects. (For instance, a therapeutically questionable reduction of brain volume has been observed in the study of active immunization with Aβ peptides in fibrillary condition of aggregation (ELAN trial with AN1792). Moreover, in this trial severe side effects in form of a meningoencephalitis were observed.

The present invention solves this problem by providing globulomer-specific antibodies possessing high affinity for truncated forms of AB globulomers. These antibodies are capable of discriminating not only other forms of Aβ peptides, particularly monomers and fibrils, but also untruncated forms of Aβ globulomers.

Thus, the present invention relates to an antibody having a binding affinity to an Aβ(20-42) globulomer that is greater than the binding affinity of this antibody to an Aβ(1-42) globulomer.

Further, the present invention relates to an antibody having a binding affinity to an Aβ(20-42) globulomer that is greater than the binding affinity of this antibody to an Aβ(12-42) globulomer.

According to a particular embodiment, the invention thus relates to antibodies having a binding affinity to the Aβ(20-42) globulomer that is greater than the binding affinity of the antibody to both the Aβ(1-42) globulomer and the Aβ(12-42) globulomer.

The term "Aβ(X-Y)" here refers to the amino acid sequence from amino acid position X to amino acid position Y of the human amyloid 1 protein including both X and Y, in particular to the amino acid sequence from amino acid position X to amino acid position Y of the amino acid sequence DAEFRHDSGY EVHHQKLVFF AEDVGSNKGA IIGLMVGGW IAT (corresponding to amino acid positions 1 to 43) or any of its naturally occurring variants, in particular those with at least one mutation selected from the group consisting of A2T, H6R, D7N, A21G ("Flemish"), E22G ("Arctic"), E22Q ("Dutch"), E22K ("Italian"), D23N ("Iowa"), A42T and A42V wherein the numbers are relative to the start of the Aβ peptide, including both position X and position Y or a sequence with up to three additional amino acid substitutions none of which may prevent globulomer formation, preferably with no additional amino acid substitutions in the portion from amino acid 12 or X, whichever number is higher, to amino acid 42 or Y, whichever number is lower, more preferably with no additional amino acid substitutions in the portion from amino acid 20 or X, whichever number is higher, to amino acid 42 or Y, whichever number Is lower, and most preferably with no additional amino acid substitutions in the portion from amino acid 20 or X, whichever number is higher, to amino acid 40 or Y, whichever number is lower, an "additional" amino acid substation herein being any deviation from the canonical sequence that is not found in nature.

More specifically, the term "Aβ(1-42)" here refers to the amino acid sequence from amino acid position 1 to amino acid position 42 of the human amyloid β protein including both 1 and 42, in particular to the amino acid sequence DAEFRHDSGY EVHHQKLVFF AEDVGSNKGA IIGLM-VGGW IA or any of its naturally occurring variants, in particular those with at least one mutation selected from the group consisting of A2T, H6R, D7N, A21G ("Flemish"), E22G ("Arctic"), E22Q ("Dutch"), E22K ("Italian"), D23N ("Iowa"), A42T and A42V wherein the numbers are relative to the start of the Aβ peptide, including both 1 and 42 or a sequence with up to three additional amino acid substitutions none of which may prevent globulomer formation, preferably with no additional amino acid substitutions in the portion from amino acid 20 to amino acid 42. Likewise, the term "Aβ(1-40)" here refers to the amino acid sequence from amino acid position 1 to amino acid position 40 of the human amyloid β protein including both 1 and 40, in particular to the amino acid sequence DAEFRHDSGY EVHHQKLVFF AEDVGSNKGA IIGLMVGGW or any of Its naturally occurring variants, in particular those with at least one mutation selected from the group consisting of A2T, H6R, D7N, A21G ("Flemish"), E22G ("Arctic"), E22Q ("Dutch"), E22K ("Italian"), and D23N ("Iowa") wherein the numbers are relative to the start of the Aβ peptide, including both 1 and 40 or a sequence with up to three additional amino acid substitutions none of which may prevent globulomer formation, preferably with no additional amino acid substitutions in the portion from amino acid 20 to amino acid 40.

More specifically, the term "Aβ(12-42)" here refers to the amino acid sequence from amino acid position 12 to amino acid position 42 of the human amyloid β protein including both 12 and 42, in particular to the amino acid sequence VHHQKLVFF AEDVGSNKGA IIGLMVGGW IA or any of its naturally occurring variants, in particular those with at least one mutation selected from the group consisting of A21G ("Flemish"), E22G ("Arctic"), E22Q ("Dutch"), E22K ("Italian"), D23N ("Iowa"), A42T and A42V wherein the numbers are relative to the start of the Aβ peptide, including both 12 and 42 or a sequence with up to three additional amino acid substitutions none of which may prevent globulomer formation, preferably with no additional amino acid substitutions in the portion from amino acid 20 to amino acid 42.

More specifically, the term "Aβ(20-42)" here refers to the amino acid sequence from amino add position 20 to amino acid position 42 of the human amyloid β protein including both 20 and 42, in particular to the amino acid sequence F AEDVGSNKGA IIGLMVGGW IA or any of its naturally occurring variants, in particular those with at least one mutation selected from the group consisting of A21G ("Flemish"), E22G ("Arctic"), E22Q ("Dutch"), E22K ("Italian"), D23N ("Iowa"), A42T and A42V wherein the numbers are relative to the start of the Aβ peptide, including both 20 and 42 or a sequence with up to three additional amino acid substitutions none of which may prevent globulomer formation, preferably without any additional amino acid substitutions.

The term "Aβ(X-Y) globulomer" (Aβ(X-Y) globular oligomer) here refers to a soluble, globular, non-covalent association of Aβ(X-Y) peptides as defined above, possessing homogeneity and distinct physical characteristics. According to one aspect, Aβ(X-Y) globulomers are stable, non-fibrillar, oligomeric assemblies of Aβ(X-Y) peptides which are obtainable by incubation with anionic detergents. In contrast to monomer and fibris, these globulomers are characterized by defined assembly numbers of subunits (e.g. early assembly forms, n=4-6, "oligomers A", and late assembly forms, n=12-14, "oligomers B", as described in WO2004/067561). The globulomers have a 3-dimensional globular type structure ("molten globule", see Barghorn et al., 2005, J Neurochem, 95, 834-847) They may be further characterized by one or more of the following features:

cleavability of N-terminal amino acids X-23 with promiscuous proteases (such as thermolysin or endoproteinase GluC) yielding truncated forms of globulomers;

non-accessibility of C-terminal amino acids 24-Y with promiscuous proteases and antibodies;

truncated forms of these globulomers maintain the 3-dimensional core structure of said globulomers with a better accessibility of the core epitope Aβ(20-Y) in its globulomer conformation.

According to the Invention and in particular for the purpose of assessing the binding affinities of the antibodies of the present invention, the term "Aβ(X-Y) globulomer" here refers in particular to a product which is obtainable by a process as described in WO 2004/067561, which is incorporated herein by reference.

Said process comprises unfolding a natural, recombinant or synthetic Aβ(X-Y) peptide or a derivative thereof, exposing the at least partially unfolded Aβ(X-Y) peptide or derivative thereof to a detergent, reducing the detergent action and continuing incubation.

For the purpose of unfolding the peptide, hydrogen bond-breaking agents such as, for example, hexafluoroisopropanol (HFIP) may be allowed to act on the protein. Times of action of a few minutes, for example about 10 to 60 minutes, are sufficient when the temperature of action is from about 20 to 50° C. and in particular about 35 to 40° C. Subsequent dissolution of the residue evaporated to dryness, preferably in concentrated form, in suitable organic solvents miscible with aqueous buffers, such as, for example, dimethyl sulfoxide (DMSO), results in a suspension of the at least partially unfolded peptide or derivative thereof, which can be used subsequently. If required, the stock suspension may be stored at low temperature, for example at about −20° C., for an interim period.

Alternatively, the peptide or the derivative thereof may be taken up in slightly acidic, preferably aqueous, solution, for example an about 10 mM aqueous HCl solution. After an incubation time of usually a few minutes, insoluble components are removed by centrifugation. A few minutes at 10000 g is expedient. These method steps are preferably carried out at room temperature, i.e. a temperature in the range from 20 to 30° C. The supernatant obtained after centrifugation contains the Aβ(X-Y) peptide or the derivative thereof and may be stored at low temperature, for example at about −20° C., for an interim period.

The following exposure to a detergent relates to the oligomerization of the peptide or the derivative thereof to give an intermediate type of oligomers (in WO 2004/067561 referred to as oligomers A). For this purpose, a detergent is allowed to act on the at least partially unfolded peptide or derivative thereof until sufficient intermediate oligomer has been produced.

Preference is given to using ionic detergents, in particular anionic detergents.

According to a particular embodiment, a detergent of the formula (I):

is used, in which
the radical R is unbranched or branched alkyl having from 6 to 20 and preferably 10 to 14 carbon atoms or unbranched or branched alkenyl having from 6 to 20 and preferably 10 to 14 carbon atoms,
the radical X is an acidic group or salt thereof, with X being preferably selected from among —COO$^-$M$^+$, —SO$_3^-$M$^+$, and especially
—OSO$_3^-$M$^+$ and M$^+$ is a hydrogen cation or an inorganic or organic cation preferably selected from alkali metal and alkaline earth metal cations and ammonium cations.

Advantageous are detergents of the formula (I), in which R is unbranched alkyl of which alk-1-yl radicals must be mentioned in particular. Particular preference is given to sodium dodecyl sulfate (SDS). Lauric acid and oleic acid can also be used advantageously. The sodium salt of the detergent lauroylsarcosin (also known as sarkosyl NL-30 or Gardol®) is also particularly advantageous.

The time of detergent action in particular depends on whether—and if yes, to what extent—the peptide or the derivative thereof subjected to oligomerization has unfolded. If, according to the unfolding step, the peptide or derivative thereof has been treated beforehand with a hydrogen bond-breaking agent, i.e. in particular with hexafluoroisopropanol, times of action in the range of a few hours, advantageously from about 1 to 20 and in particular from about 2 to 10 hours, are sufficient when the temperature of action is about 20 to 50° C. and in particular about 35 to 40° C. If a less unfolded or an essentially not unfolded peptide or derivative thereof is the starting point, correspondingly longer times of action are expedient. If the peptide or the derivative thereof has been pretreated, for example, according to the procedure indicated above as an alternative to the HFIP treatment or said peptide or derivative thereof is directly subjected to oligomerization, times of action in the range from about 5 to 30 hours and in particular from about 10 to 20 hours are sufficient when the temperature of action is about 20 to 50° C. and in particular about 35 to 40° C. After incubation, insoluble components are advantageously removed by centrifugation. A few minutes at 10000 g is expedient.

The detergent concentration to be chosen depends on the detergent used. If SDS is used, a concentration in the range from 0.01 to 1% by weight, preferably from 0.05 to 0.5% by weight, for example of about 0.2% by weight, proves expedient. If lauric acid or oleic acid are used, somewhat higher concentrations are expedient, for example in a range from 0.05 to 2% by weight, preferably from 0.1 to 0.5% by weight, for example of about 0.5% by weight.

The detergent action should take place at a salt concentration approximately in the physiological range. Thus, in particular NaCl concentrations in the range from 50 to 500 mM, preferably from 100 to 200 mM and particularly at about 140 mM are expedient.

The subsequent reduction of the detergent action and continuation of incubation relates to a further oligomerization to give the Aβ(X-Y) globulomer of the invention (In WO 2004/067561 referred to as oligomers B). Since the composition obtained from the preceding step regularly contains detergent and a salt concentration in the physiological range it is then expedient to reduce detergent action and, preferably, also the salt concentration. This may be carried out by reducing the concentration of detergent and salt, for example, by diluting, expediently with water or a buffer of lower salt concentration, for example Tris-HCl, pH 7.3. Dilution factors in the range from about 2 to 10, advantageously in the range from about 3 to 8 and in particular of about 4, have proved suitable. The reduction in detergent action may also be achieved by adding substances which can neutralize said detergent action Examples of these include substances capable of complexing the detergents, like substances capable of stabilizing cells in the course of purification and extraction measures, for example particular EO/PO block copolymers, in particular the block copolymer under the trade name Pluronic® F 68. Alkoxylated and, in particular, ethoxylated alkyl phenols such as the ethoxylated t-octylphenols of the Triton® X series, in particular Triton® X100, 3-(3-cholamidopropydimethylammonio)-1-propanesulfonate (CHAPS®) or alkoxylated and, in particular, ethoxylated sorbitan fatty esters such as those of the Tween® series, in particular Tween® 20, in concentration ranges around or above the particular critical micelle concentration, may be equally used.

Subsequently, the solution is incubated until sufficient Aβ(X-Y) globulomer of the invention has been produced. Times of action in the range of several hours, preferably in the range from about 10 to 30 hours and in particular in the range from about 15 to 25 hours, are sufficient when the temperature of action is about 20 to 50° C. and in particular about 35 to 40° C. The solution may then be concentrated and possible residues may be removed by centrifugation. Here too, a few minutes at 10000 g proves expedient. The supernatant obtained after centrifugation contains an Aβ(X-Y) globulomer of the invention.

An Aβ(X-Y) globulomer of the invention can be finally recovered in a manner known per se, e. g. by ultrafiltration, dialysis, precipitation or centrifugation.

It is further preferred if electrophoretic separation of the Aβ(X-Y) globulomers under denaturing conditions, e. g. by SDS-PAGE, produces a double band (e. g. with an apparent molecular weight of 38/48 kDa for Aβ(1-42)), and especially preferred if upon glutardialdehyde treatment of the globulomers before separation these two bands are merged into one. It is also preferred if size exclusion chromatography of the globulomers results in a single peak (e. g. corresponding to a molecular weight of approximately 100 kDa for Aβ(1-42) globulomer or of approximately 60 kDa for glutardialdehyde cross-linked Aβ(1-42) globulomer), respectively.

Starting out from Aβ(1-42) peptide, Aβ(12-42) peptide, and Aβ(20-42) peptide said processes are in particular suitable for obtaining Aβ(1-42) globulomers, Aβ(12-42) globulomers, and Aβ(20-42) globulomers.

In a particular embodiment of the invention, Aβ(X-Y) globulomers wherein X is selected from the group consisting of the numbers 2 . . . 24 and Y is as defined above, are those which are obtainable by truncating Aβ(1-Y) globulomers into shorter forms wherein X is selected from the group consisting of the numbers 2 . . . 24, with X preferably being 20 or 12, and Y is as defined above, which can be achieved by treatment with appropriate proteases. For instance, an Aβ(20-42) globulomer can be obtained by subjecting an Aβ(1-42) globulomer to thermolysin proteolysis, and an Aβ(12-42) globulomer can be obtained by subjecting an Aβ(1-42) globulomer to endoproteinase GluC proteolysis. When the desired degree of proteolysis is reached, the protease is inactivated in a generally known manner. The resulting globulomers may then be isolated following the procedures already described herein and, if required, processed further by further work-up and purification steps. A detailed description of said processes is disclosed in WO 2004/067561, which is incorporated herein by reference.

For the purposes of the present invention, an Aβ(1-42) globulomer is in particular the Aβ(1-42) globulomer as described in example 1a herein; an Aβ(20-42) globulomer is in particular the Aβ(20-42) globulomer as described in examples 1c herein, and an Aβ(12-42) globulomer is in particular the Aβ(12-42) globulomer as described in examples 1d herein.

Preferably, the globulomer shows affinity to neuronal cells. Preferably, the globulomer also exhibits neuromodulating effects.

According to another aspect of the invention, the globulomer consists of 11 to 16, and most preferably, of 12 to 14 Aβ(X-Y) peptides.

According to another aspect of the invention, the term "Aβ(X-Y) globulomer" here refers to a globulomer consisting essentially of Aβ(X-Y) subunits, where it is preferred if on average at least 11 of 12 subunits are of the Aβ(X-Y) type, more preferred if less than 10% of the globulomers comprise any non-Aβ(X-Y) peptides, and most preferred if the content of non-Aβ(X-Y) peptides is below the detection threshold.

More specifically, the term "Aβ(1-42) globulomer" here refers to a globulomer consisting essentially of Aβ(1-42) units as defined above; the term "Aβ(12-42) globulomer" here refers to a globulomer consisting essentially of Aβ(12-42) units as defined above; and the term "Aβ(20-42) globulomer" here refers to a globulomer consisting essentially of Aβ(20-42) units as defined above.

The term "cross-linked Aβ(X-Y) globulomer" here refers to a molecule obtainable from an Aβ(X-Y) globulomer as described above by cross-linking, preferably chemically cross-linking, more preferably aldehyde cross-linking, most preferably glutardialdehyde cross-linking of the constituent units of the globulomer. In another aspect of the invention, a cross-linked globulomer is essentially a globulomer in which the units are at least partially joined by covalent bonds, rather than being held together by non-covalent interactions only. For the purposes of the present invention, a cross-linked Aβ(1-42) globulomer is in particular the cross-linked Aβ(1-42) oligomer as described in example 1b herein.

The term "Aβ(X-Y) globulomer derivative" here refers in particular to a globulomer that is labelled by being covalently linked to a group that facilitates detection, preferably a fluorophore, e. g. fluorescein isothiocyanate, phycoerythrin, *Aequorea victoria* fluorescent protein, Dictyosoma fluorescent protein or any combination or fluorescence-active derivative thereof; a chromophore; a chemoluminophore, e. g. luciferase, preferably *Photinus pyralis* luciferase, *Vibrio fischeri* luciferase, or any combination or chemoluminescence-active derivative thereof; an enzymatically active group, e. g. peroxidase, e. g. horseradish peroxidase, or any enzymatically active derivative thereof; an electron-dense group, e. g. a heavy metal containing group, e.g. a gold containing group; a hapten, e. g. a phenol derived hapten; a strongly antigenic structure, e. g. peptide sequence predicted to be antigenic, e. g. predicted to be antigenic by the algorithm of Kolaskar and Tongaonkar; an aptamer for another molecule; a chelating group, e. g. hexahistidinyl; a natural or nature-derived protein structure mediating further specific protein-protein interactions, e. g. a member of the fos/jun pair; a magnetic group, e. g. a ferromagnetic group; or a radioactive group, e. g. a group comprising $^1$H, $^{14}$C, $^2$P, $^3$S or $^{125}$I or any combination thereof; or to a globulomer flagged by being covalently or by non-covalent high-affinity interaction, preferably covalently linked to a group that facilitates inactivation, sequestration, degradation and/or precipitation, preferably flagged with a group that promotes in vivo degradation, more preferably with ubiquitin, where is particularly preferred if this flagged oligomer is assembled in vivo; or to a globulomer modified by any combination of the above. Such labelling and flagging groups and methods for attaching them to proteins are known in the art. Labelling and/or flagging may be performed before, during or after globulomerisation. In another aspect of the invention, a globulomer derivative is a molecule obtainable from a globulomer by a labelling and/or flagging reaction.

Correspondingly, term "Aβ(X-Y) monomer derivative" here refers in particular to an Aβ monomer that is labelled or flagged as described for the globulomer.

Expediently, the antibody of the present invention binds to an Aβ(20-42) globulomer with a $K_D$ in the range of $1 \times 10^{-6}$ M to $1 \times 10^{-12}$ M. Preferably, the antibody binds to an Aβ(20-42) globulomer with high affinity, for instance with a $K_D$ of $1 \times 10^{-7}$ M or greater affinity, e.g. with a $K_D$ of $3 \times 10^{-8}$ M or greater affinity, with a $K_D$ of $1 \times 10^{-8}$ M or greater affinity, e.g. with a $K_D$ of $3 \times 10^{-9}$ M or greater affinity, with a $K_D$ of $1 \times 10^{-9}$ M or greater affinity, e.g. with a $K_D$ of $3 \times 10^{-10}$ M or greater affinity, with a $K_D$ of $1 \times 10^{-10}$ M or greater affinity, e.g. with a $K_D$ of $3 \times 10^{-11}$ M or greater affinity, or with a $K_D$ of $1 \times 10^{-11}$ M or greater affinity.

The term "greater affinity" here refers to a degree of interaction where the equilibrium between unbound antibody and unbound globulomer on the one hand and antibody-globulomer complex on the other is further in favour of the antibody-globulomer complex. Likewise, the term "smaller affinity" here refers to a degree of interaction where the equilibrium between unbound antibody and unbound globulomer on the one hand and antibody-globulomer complex on the other is further in favour of the unbound antibody and unbound globulomer. The term "greater affinity" is synonymous with the term "higher affinity" and term "smaller affinity" is synonymous with the term "lower affinity".

According to a particular embodiment, the invention relates to an antibody which binds to the Aβ(20-42) globulomer with a $K_D$ in the range of $1 \times 10^{-6}$ M to $1 \times 10^{-12}$ M, to the Aβ(1-42) globulomer with a $K_D$ of $10^{-12}$ M or smaller affinity, the binding affinity to the Aβ(20-42) globulomer being greater than the binding affinity to the Aβ(1-42) globulomer.

It is preferred that the binding affinity of the antibody of the present invention to the Aβ(20-42) globulomer is at least 2 times, e. g. at least 3 times or at least 5 times, preferably at least 10 times, e. g. at least 20 times, at least 30 times or at least 50 times, more preferably at least 100 times, e. g. at least 200 times, at least 300 times or at least 500 times, and even more preferably at least 1000 times, e. g. at least 2000 times, at least 3000 times or at least 5000 times, even more preferably at least 10000 times, e. g. at least 20000 times, at least 30000 or at least 50000 times, and most preferably at least 100000 times greater than the binding affinity of the antibody to the Aβ(1-42) globulomer.

According to a particular embodiment, the invention relates to an antibody which binds to the Aβ(12-42) globulomer with a $K_D$ with a $K_D$ of $10^{-12}$ M or smaller affinity, the binding affinity to the Aβ(20-42) globulomer being greater than the binding affinity to the Aβ(12-42) globulomer.

It is also preferred that the binding affinity of the antibody of the present invention to the Aβ(20-42) globulomer is at least 2 times, e. g. at least 3 times or at least 5 times, preferably at least 10 times, e. g. at least 20 times, at least 30 times or at least 50 times, more preferably at least 100 times, e. g. at least 200 times, at least 300 times or at least 500 times, and even more preferably at least 1000 times, e. g. at least 2000 times, at least 3000 times or at least 5000 times, even more preferably at least 10000 times, e. g. at least 20000 times, at least 30000 or at least 50000 times, and most preferably at least 100000 times greater than the binding affinity of the antibody to the Aβ(12-42) globulomer.

Preferably, the antibodies of the present invention bind to at least one Aβ globulomer, as defined above, and have a comparatively smaller affinity for at least one non-globulomer form of Aβ.

Antibodies of the present invention having a comparatively smaller affinity for at least one non-globulomer form of Aβ than for at least one Aβ globulomer include antibodies having a binding affinity to the Aβ(20-42) globulomer that is greater than to an Aβ(1-42) monomer. Further, it is preferred that, alternatively or additionally, the binding affinity of the antibody to the Aβ(20-42) globulomer is greater than to an Aβ(1-40) monomer.

In a preferred embodiment of the invention, the affinity of the antibody to the Aβ(20-42) globulomer is greater than its affinity to both the Aβ(1-40) and the Aβ(1-42) monomer.

The term "Aβ(X-Y) monomer" here refers to the isolated form of the Aβ(X-Y) peptide, preferably a form of the Aβ(X-Y) peptide which is not engaged in essentially non-covalent interactions with other Aβ peptides Practically, the Aβ(X-Y) monomer is usually provided in the form of an aqueous solution. In a particularly preferred embodiment of the invention, the aqueous monomer solution contains 0.05% to 0.2%, more preferably about 0.1% $NH_4OH$. In another particularly preferred embodiment of the invention, the aqueous monomer solution contains 0.05% to 0.2%, more preferably about 0.1% NaOH. When used (for instance for determining the binding affinities of the antibodies of the present invention), it may be expedient to dilute said solution in an appropriate manner. Further, it is usually expedient to use said solution within 2 hours, in particular within 1 hour, and especially within 30 minutes after its preparation.

More specifically, the term "Aβ(1-40) monomer" here refers to an Aβ(1-40) monomer preparation as described in example 2 herein, and the term "Aβ(1-42) monomer" here refers to an Aβ(1-42) preparation as described in example 2 herein.

Expediently, the antibody of the present invention binds to one or, more preferably, both monomers with low affinity, most preferably with a $K_D$ of $1 \times 10$ M or smaller affinity, e. g. with a $K_D$ of $3 \times 10^4$ M or smaller affinity, with a $K_D$ of $1 \times 10^{-7}$ M or smaller affinity, e. g. with a $K_D$ of $3 \times 10^{-7}$ M or smaller affinity, or with a $K_D$ of $1 \times 10^{-7}$ M or smaller affinity, e. g. with a $K_D$ of $3 \times 10^{-7}$ M or smaller affinity, or with a $K_D$ of $1 \times 10^{-5}$ M or smaller affinity.

It is especially preferred that the binding affinity of the antibody of the present invention to the Aβ(20-42) globulomer is at least 2 times, e. g. at least 3 times or at least 5 times, preferably at least 10 times, e. g. at least 20 times, at least 30 times or at least 50 times, more preferably at least 100 times, e. g. at least 200 times, at least 300 times or at least 500 times, and even more preferably at least 1000 times, e. g. at least 2000 times, at least 3000 times or at least 5000 times, even more preferably at least 10000 times, e. g. at least 20000 times, at least 30000 or at least 50000 times, and most preferably at least 100000 times greater than the binding affinity of the antibody to one or, more preferably, both monomers.

Antibodies of the present invention having a comparatively smaller affinity for at least one non-globulomer form of Aβ than for at least one Aβ globulomer further include antibodies having a binding affinity to the Aβ(20-42) globulomer that is greater than to Aβ(1-42) fibrils. Further, it is preferred that, alternatively or additionally, the binding affinity of the antibody to the Aβ(20-42) globulomer is greater than to Aβ(1-40) fibrils.

The term "fibril" here refers to a molecular structure that comprises assemblies of noncovalently associated, individual Aβ(X-Y) peptides, which show fibrillary structure in the electron microscope, which bind Congo red and then exhibit birefringence under polarized light and whose X-ray diffraction pattern is a cross-R structure.

In another aspect of the invention, a fibril is a molecular structure obtainable by a process that comprises the self-induced polymeric aggregation of a suitable Aβ peptide in the absence of detergents, e. g. In 0.1 M HCl, leading to the formation of aggregates of more than 24, preferably more than 100 units. This process is well known in the art. Expediently, Aβ(X-Y) fibrils are used in the form of an aqueous solution. In a particularly preferred embodiment of the invention, the aqueous fibril solution is made by dissolving the Aβ peptide in 0.1% $NH_4OH$, diluting it 1:4 with 20 mM $NaH_2PO_4$, 140 mM NaCl, pH 7.4, followed by readjusting the pH to 7.4, incubating the solution at 37° C. for 20 h, followed by centrifugation at 10000 g for 10 min and resuspension in 20 mM $NaH_2PO_4$, 140 mM NaCl, pH 7.4.

The term "Aβ(X-Y) fibril" here refers to a fibril consisting essentially of Aβ(X-Y) subunits, where it is preferred if on average at least 90% of the subunits are of the Aβ(X-Y) type, more preferred if at least 98% of the subunits are of the Aβ(X-Y) type, and most preferred if the content of non-Aβ(X-Y) peptides is below the detection threshold.

More specifically, the term "Aβ(1-42) fibril" here refers to a Aβ(1-42) fibril preparation as described in example 3 herein.

Expediently, the antibody of the present invention binds to one or, more preferably, both fibrils with low affinity, most preferably with a $K_D$ of $1 \times 10^{-8}$ M or smaller affinity, e. g. with a $K_D$ of $3 \times 10^{-8}$ M or smaller affinity, with a $K_D$ of $1 \times 10^{-7}$ M or smaller affinity, e. g. with a $K_D$ of $3 \times 10^{-7}$ M or smaller affinity, or with a $K_D$ of $1 \times 10^{-6}$ M or smaller affinity, e. g. with a $K_D$ of $3 \times 10^{-5}$ M or smaller affinity, or with a $K_D$ of $1 \times 10^{-5}$ M or smaller affinity.

It is especially preferred that the binding affinity of the antibody of the present invention to Aβ(20-42) globulomer is at least 2 times, e. g. at least 3 times or at least 5 times, preferably at least 10 times, e. g. at least 20 times, at least 30 times or at least 50 times, more preferably at least 100 times, e. g. at least 200 times, at least 300 times or at least 500 times, and even more preferably at least 1000 times, e. g. at least 2000 times, at least 3000 times or at least 5000 times, even more preferably at least 10000 times, e. g. at least 20000 times, at least 30000 or at least 50000 times, and most preferably at least 100000 times greater than the binding affinity of the antibody to one or, more preferably, both fibrils.

According to one particular embodiment, the invention relates to antibodies having a binding affinity to the Aβ(20-42) globulomer which is greater than its binding affinity to both Aβ(1-40) and Aβ(1-42) fibrils.

According to a particularly preferred embodiment, the present invention relates to antibodies having a comparatively smaller affinity for both the monomeric and fibrillary forms of Aβ than for at least one Aβ globulomer, in particular Aβ(20-42) globulomer. These antibodies hereinafter are referred to globulomer-specific antibodies.

Antibodies of the present invention further include antibodies having a binding affinity to the Aβ(20-42) globulomer that is greater than to a cross-linked Aβ(1-42) globulomer, in particular to a glutardialdehyde cross-linked Aβ(1-42) globulomer, such as that described in example 1b herein.

In a particularly preferred embodiment of the invention, the binding affinity of the antibody to Aβ(20-42) globulomer is at least 2 times, e. g. at least 3 times or at least 5 times, preferably at least 10 times, e. g. at least 20 times, at least 30 times or at least 50 times, more preferably at least 100 times, e. g. at least 200 times, at least 300 times or at least 500 times, and even more preferably at least 1000 times, e. g. at least 2000 times, at least 3000 times or at least 5000 times, even more preferably at least 10000 times, e. g. at least 20000 times, at least 30000 or at least 50000 times, and most preferably at least 100000 times greater than the binding affinity of the antibody to cross-linked Aβ(1-42) globulomer.

The antibodies of the present invention are preferably isolated, in particular monoclonal and more particularly recombinant.

The present invention also relates to a monoclonal antibody (5F7) that is obtainable from a hybridoma designated by American Type Culture Collection deposit number PTA-7241.

The present invention also relates to a monoclonal antibody (10F11) that is obtainable from a hybridoma designated by American Type Culture Collection deposit number PTA-7239.

The present invention also relates to a monoclonal antibody (7C6) that is obtainable from a hybridoma designated by American Type Culture Collection deposit number PTA-7240.

The present invention also relates to a monoclonal antibody (4B7) that is obtainable from a hybridoma designated by American Type Culture Collection deposit number PTA-7242.

The present invention also relates to a monoclonal antibody (6A2) that is obtainable from a hybridoma designated by American Type Culture Collection deposit number PTA-7409.

The present invention also relates to a monoclonal antibody (2F2) that is obtainable from a hybridoma designated by American Type Culture Collection deposit number PTA-7408

The present invention also relates to a monoclonal antibody (4D10) that is obtainable from a hybridoma designated by American Type Culture Collection deposit number PTA-7405.

The present invention also relates to a monoclonal antibody (7E5) that is obtainable from a hybridoma designated by American Type Culture Collection deposit number PTA-7809.

The present invention also relates to a monoclonal antibody (10C1) that is obtainable from a hybridoma designated by American Type Culture Collection deposit number PTA-7810.

The present invention also relates to a monoclonal antibody (3B10) that is obtainable from a hybridoma designated by American Type Culture Collection deposit number PTA-7851.

These antibodies of the present Invention, 5F7, 10F11, 7C6, 4B7, 6A2, 2F2, 4D10, 7E5, 10C1 and 3B10, are characterized by having a binding affinity to an Aβ(20-42)

globulomer that is greater than the binding affinity of the antibody to an Aβ(1-42) globulomer.

The present invention also relates to antibodies having a similar binding profile to that of any one of said monoclonal antibodies, 5F7, 10F11, 7C6, 4B7, 6A2, 2F2, 4D10, 7E5, 10C1 and 3B10. Antibodies having a similar binding profile to that of any one of said monoclonal antibodies should be understood as not being limited to antibodies having a binding affinity to an Aβ(20-42) globulomer that is greater than the binding affinity of the antibody to an Aβ(1-42) globulomer.

Antibodies having a binding profile similar to that of any one of said monoclonal antibodies, 5F7, 10F11, 7C6, 4B7, 6A2, 2F2, 4D10, 7E5, 10C1 and 3B10, include antibodies which bind to the same epitope as monoclonal antibody 5F7, 10F11, 7C6, 4B7, 6A2, 2F2, 4D10, 7E5, 10C1 and 3B10.

All monoclonal antibodies from the group consisting of 5F7, 10F11, 7C6, 4B7, 6A2, 2F2, 4D10, 7E5, 10C1 and 3B10 bind to an epitope contained within the 20 and 42 Aβ sequence range, in particular within the 20-30 Aβ sequence range. Without being bound to theory, said epitope is believed to be a structural, non-linear epitope in between subunits in the region of amino acids 20 and 42, in particular in the region of amino acids 20 and 30.

The present invention also relates to antibodies which are capable of competing with at least one, preferably all, antibodies selected from the group consisting of 5F7, 10F11, 7C6, 4B7, 6A2, 2F2, 4D10, 7E5, 10C1 and 3B10.

The term "competing antibodies" herein refers to any number of antibodies targeting the same molecular or stably but non-covalently linked supermolecular entity, preferably the same molecule, wherein at least one is capable of specifically reducing the measurable binding of another, preferably by sterically hampering the other's access to its target epitope or by inducing and/or stabilizing a conformation in the target entity that reduces the target's affinity for the other antibody, more preferably by directly blocking access to the other's target epitope by binding to an epitope in sufficiently close vicinity of the former, overlapping with the former or identical to the former, most preferably overlapping or identical, in particular identical. Two epitopes are herein said to be "overlapping" if they share part of their chemical structures, preferably their amino acid sequences, and to be "identical", if their chemical structures, preferably their amino acid sequences, are identical.

Thus, the present invention also relates to antibodies whose target epitopes are overlapping with, preferably identical to, the target epitope of at least one of the antibodies selected from the group consisting of 5F7, 10F11, 7C6, 4B7, 6A2, 2F2, 4D10, 7E5, 10C1 and 3B10.

Antibodies having a similar binding profile to that of any one of said monoclonal antibodies, 5F7, 10F11, 7C6, 4B7, 6A2, 2F2, 4D10, 7E5, 10C1 and 3B10, thus further include antibodies which comprise at least a portion of the antigen-binding moiety of any one of said monoclonal antibodies, 5F7, 10F11, 7C6, 4B7, 6A2, 2F2, 4D10, 7E5, 10C1 and 3B10. Preferably, said portion comprises at least one complementary determining region (CDR) of any one of said monoclonal antibodies, 5F7, 10F11, 7C06, 4B7, 6A2, 2F2, 4D10, 7E5, 10C1 and 3B10.

Thus, according to a further particular embodiment, the present invention relates to antibodies comprising the amino acid sequence of the heavy chain CDR3 and/or the amino acid sequence of the right chain CDR3 of monoclonal antibody 5F7, 10F11, 7C6, 4B7, 6A2, 2F2, 4D10, 7E5, 10C1 or 3B10. Specific examples of such antibodies include those which also comprise the amino acid sequence of the heavy chain CDR2 and/or the amino acid sequence of the light chain CDR2 of monoclonal antibody 5F7, 10F11, 7C6, 487, 6A2, 2F2, 4D10, 7E5, 10C1 or 3B10, respectively. Even more specifically, such antibodies include those which also comprise the amino acid sequence of the heavy chain CDR1 and/or the amino acid sequence of the light chain CDR1 of monoclonal antibody 5F7, 10F11, 7C6, 487, 6A2, 2F2, 4D10, 7E5, 10C1 or 3B10, respectively.

In one aspect, the present invention thus relates to antibodies comprising a heavy chain wherein the CDR3, CDR2 and/or CDR1 domain comprises the amino acid sequence of the heavy chain CDR3, CDR2 and/or CDR1 of monoclonal antibody 5F7, 10F11, 7C6, 487, 6A2, 2F2, 4D10, 7E5, 10C1 or 3B10.

In a further aspect, the present invention thus relates to antibodies comprising a light chain wherein the CDR3, CDR2 and/or CDR1 domain comprises the amino acid sequence of the light chain CDR3, CDR2 and/or CDR1, respectively, of monoclonal antibody 5F7, 10F11, 7C6, 4B7, 6A2, 2F2, 4D10, 7E5, 10C1 or 3B10.

Preferably, the antibody comprises at least one CDR comprising an amino acid sequence selected from the group consisting of: amino acid residues 31-35 of SEQ ID NO:3, amino acid residues 50-66 of SEQ ID NO:3, amino acid residues 99-109 of SEQ ID NO:3, amino acid residues 24-39 of SEQ ID NO:4, amino acid residues 55-61 of SEQ ID NO:4, amino acid residues 94-102 of SEQ ID NO:4, amino acid residues 31-35 of SEQ ID NO:7, amino acid residues 50-66 of SEQ ID NO:7, amino acid residues 97-109 of SEQ ID NO:7, amino acid residues 24-39 of SEQ ID NO:8, amino acid residues 55-61 of SEQ ID NO:8, amino add residues 94-102 of SEQ ID NO:8, amino acid residues 31-35 of SEQ ID NO:11, amino acid residues 50-65 of SEQ ID NO:11, amino acid residues 98-107 of SEQ ID NO: 11, amino add residues 24-39 of SEQ ID NO:12, amino acid residues 55-61 of SEQ ID NO:12, amino acid residues 94-102 of SEQ ID NO:12, amino acid residues 31-35 of SEQ ID NO:15, amino acid residues 50-66 of SEQ ID NO:15, amino acid residues 99-107 of SEQ ID NO:15, amino add residues 24-40 of SEQ ID NO:16, amino acid residues 56-62 of SEQ ID NO:16, amino acid residues 95-103 of SEQ ID NO:16, amino acid residues 31-35 of SEQ ID NO:19, amino acid residues 50-66 of SEQ ID NO:19, amino acid residues 99-109 of SEQ ID NO:19, amino acid residues 24-39 of SEQ ID NO:20, amino acid residues 55-61 of SEQ ID NO:20, amino acid residues 94-102 of SEQ ID NO:20, amino acid residues 31-35 of SEQ ID NO:23, amino acid residues 50-66 of SEQ ID NO:23, amino acid residues 99-109 of SEQ ID NO:23, amino acid residues 24-39 of SEQ ID NO:24, amino acid residues 55-61 of SEQ ID NO:24, amino acid residues 94-102 of SEQ ID NO:24, amino acid residues 31-35 of SEQ ID NO:27, amino acid residues 50-65 of SEQ ID NO:27, amino acid residues 98-101 of SEQ ID NO:27, amino acid residues 24-39 of SEQ ID NO:28, amino acid residues 55-61 of SEQ ID NO:28, amino acid residues 94-102 of SEQ ID NO:28, amino acid residues 31-35 of SEQ ID NO:31, amino acid residues 50-66 of SEQ ID NO:31, amino acid residues 99-107 of SEQ ID NO:31, amino acid residues 24-40 of SEQ ID NO:32, amino acid residues 56-62 of SEQ ID NO:32, amino acid residues 95-103 of SEQ ID NO:32, amino acid residues 31-35 of SEQ ID NO:35, amino acid residues 50-66 of SEQ ID NO:35, amino acid residues 99-107 of SEQ ID NO:35, amino acid residues 24-40 of SEQ ID NO:36, amino acid residues 56-62 of SEQ ID NO:36, amino acid residues 95-103 of SEQ ID NO:36, amino acid residues 31-35 of SEQ ID NO:38, amino acid residues 50-66 of SEQ ID NO:38, and amino acid residues 98-109 of SEQ ID NO:38.

In a preferred embodiment, the antibody comprises at least 3 CDRs selected from the group consisting of the sequences disclosed above. More preferably the 3 CDRs selected are from sets of variable domain CDRs selected from the group consisting of:

| VH 5F7 CDR Set | |
|---|---|
| VH 5F7 CDR-H1 | TFYIH: residues 31-35 of SEQ ID NO: 3 |
| VH 5F7 CDR-H2 | MIGRGSGNTYYNEHFKD: residues 50-66 of SEQ ID NO: 3 |
| VH 5F7 CDR-H3 | AKSARAAWFAY: residues 99-109 of SEQ ID NO: 3 |

| VL 5F7 CDR Set | |
|---|---|
| VL 5F7 CDR-L1 | RSSQSVVQSNGNTYLE: residues 24-39 of SEQ ID NO: 4 |
| VL 5F7 CDR-L2 | KVSNRFS: residues 55-61 of SEQ ID NO: 4 |
| VL 5F7 CDR-L3 | FQGSHVPPT: residues 94-102 of SEQ ID NO: 4 |

| VH 10F11 CDR Set | |
|---|---|
| VH 10F11 CDR-H1 | SYVMH: residues 31-35 of SEQ ID NO: 7 |
| VH 10F11 CDR-H2 | YIYPYNDGTKYNEKFKG: residues 50-66 of SEQ ID NO: 7 |
| VH 10F11 CDR-H3 | TVEGATWDGYFDV: residues 97-109 of SEQ ID NO: 7 |

| VL 10F11 CDR Set | |
|---|---|
| VL 10F11 CDR-L1 | KSSQSLLYSKGKTYLN: residues 24-39 of SEQ ID NO: 8 |
| VL 10F11 CDR-L2 | LVSKLDS: residues 55-61 of SEQ ID NO: 8 |
| VL 10F11 CDR-L3 | VQGTHFPHT: residues 94-102 of SEQ ID NO: 8 |

| VH 7C6 CDR Set | |
|---|---|
| VH 7C6 CDR-L1 | SYAMS: residues 31-35 of SEQ ID NO: 11 |
| VH 7C6 CDR-L2 | SIHNRGTIFYLDSVKG: residues 50-65 of SEQ ID NO: 11 |
| VH 7C6 CDR-L3 | GRSNSYAMDY: residues 98-107 of SEQ ID NO: 11 |

| VL 7C6 CDR Set | |
|---|---|
| VL 7C6 CDR-L1 | RSTQTLVHRNGDTYLE: residues 24-39 of SEQ ID NO: 12 |
| VL 7C6 CDR-L2 | KVSNRFS: residues 55-61 of SEQ ID NO: 12 |
| VL 7C6 CDR-L3 | FQGSHVPYT: residues 94-102 of SEQ ID NO: 12 |

| VH 4B7 CDR Set | |
|---|---|
| VS 4B7 CDR-H1 | DYEMV: residues 31-35 of SEQ ID NO: 15 |
| VH 4B7 CDR-H2 | YISSGSRTIHYADTVKG: residues 50-66 of SEQ ID NO: 15 |
| VH 4B7 CDR-H3 | TLLRLHFDY: residues 99-107 of SEQ ID NO: 15 |

| VI 4B7 CDR Set | |
|---|---|
| VL 4B7 CDR-L1 | RSSQSLFYRSNQKNFLA: residues 24-40 of SEQ ID NO: 16 |
| VL 4B7 CDR-L2 | WASTRES: residues 56-62 of SEQ ID NO: 16 |
| VL 4B7 CDR-L3 | QQYYSYPST: residues 95-103 of SEQ ID NO: 16 |

| VH 2F2 CDR Set | |
|---|---|
| VH 2F2 CDR-H1 | TFYIH: residues 31-35 of SEQ ID NO: 19 |
| VH 2F2 CDR-S2 | MIGPGSGNTYYNEMFKD: residues 50-66 of SEQ ID NO: 19 |
| VH 2F2 CDR-S3 | AKSARAAWFAY: residues 99-109 of SEQ ID NO: 19 |

| VL 2F2 CDR Set | |
|---|---|
| VL 2F2 CDR-L1 | PSSQSVVQSNGNTYLE: residues 24-39 of SEQ ID NO: 20 |
| VL 2F2 CDR-L2 | KVSNRFS: residues 55-61 of SEQ ID NO: 20 |
| VL 2F2 CDR-L3 | FQGSHVPPT: residues 94-102 of SEQ ID NO: 20 |

| VH 6A2 CDR Set | |
|---|---|
| VH 6A2 CDR-H1 | TFYIH: residues 31-35 of SEQ ID NO: 23 |
| VH 6A2 CDR-H2 | MIGPGSGNTYYNEMFKD: residues 50-66 of SEQ ID NO: 23 |
| VH 6A2 CDR-H3 | AKSHRAAWFAY: residues 99-109 of SEQ ID NO: 23 |

| VL 6A2 CDR Set | |
|---|---|
| VL 6A2 CDR-L1 | RSSQSVVQSNGNTYLE: residues 24-39 of SEQ ID NO: 24 |
| VL 6A2 CDR-L2 | KVSNRFF: residues 55-61 of SEQ ID NO: 24 |
| VL 6A2 CDR-L3 | FQGSHVPPT: residues 94-102 of SEQ ID NO: 24 |

| VH 4D10 CDR Set | |
|---|---|
| VH 4D10 CDR-H1 | SYGVH: residues 31-35 of SEQ ID NO: 27 |
| VH 4D10 CDR-H2 | VIWRGGRIDYNAAFMS: residues 50-65 of SEQ ID NO: 27 |
| VH 4D10 CDR-H3 | NSDV: residues 98-101 of SEQ ID NO: 27 |

| VL 4D10 CDR Set | |
|---|---|
| VL 4D10 CDR-L1 | KSSQSLLDIDGKTYLN: residues 24-39 of SEQ ID NO: 28 |
| VL 4D10 CDR-L2 | LVSKLDS: residues 55-61 of SEQ ID NO: 28 |
| VL 4D10 CDR-L3 | WQGTHFPYT: residues 94-102 of SEQ ID NO: 28 |

| VH 7E5 CDR Set | |
|---|---|
| VH 7E5 CDR-H1 | DYEMV: residues 31-35 of SEQ ID NO: 31 |
| VH 7E5 CDR-H2 | YISSGSRTIHYADTVKG: residues 50-66 of SEQ ID NO: 31 |
| VH 7E5 CDR-H3 | TLLRLHFDY: residues 99-107 of SEQ ID NO: 31 |

| VL 7E5 CDR Set | |
|---|---|
| VL 7E5 CDR-L1 | RSSQSLFYRSNQKNFLA: residues 24-40 of SEQ ID NO: 32 |
| VL 7E5 CDR-L2 | WASTRES: residues 56-62 of SEQ ID NO: 32 |
| VL 7E5 CDR-L3 | QQYYSYPWT: residues 95-103 of SEQ ID NO: 32 |

| VH 10C1 CDR Set | |
|---|---|
| VH 10C1 CDR-H1 | DYEMV: residues 31-35 of SEQ ID NO: 35 |
| VH 10C1 CDR-H2 | YINSGSGTIHYADTVKG: residues 50-66 of SEQ ID NO: 35 |

-continued

| | |
|---|---|
| VH 10C1 CDR-H3 | TLLRLHFDY:<br>residues 99-107 of SEQ ID NO: 35 |
| VL 10C1 CDR Set | |
| VL 10C1 CDR-L1 | KSSQEFYSRNQKNFLA:<br>residues 24-40 of SEQ ID NO: 36 |
| VL 10C1 CDR-L2 | WASTGES:<br>residues 56-62 of SEQ ID NO: 36 |
| VL 10C1 CER-L3 | QQYFSYWT:<br>residues 95-103 of SEQ ID NO: 36 |
| VH 3B10 CDR Sat | |
| VH 3B10 CDR-H1 | DYVIH:<br>residues 31-35 of SEQ ID NO: 38 |
| VH 3B10 CDR-H2 | YINPYNDGTQYNEKFKG:<br>residues 50-66 of SEQ ID NO: 38 |
| VH 3B10 CDR-H3 | VEGGTWDGYFDV:<br>residues 98-109 of SEQ ID NO: 38 |

In one embodiment the antibody of the invention comprises at least two variable domain CDR sets. More preferably, the two variable domain CDR sets are selected from the group consisting of: VH 5F7 CDR Set & VL 5F7 CDR Set; VH 10F11 CDR Set & VL 10F11 CDR Set; VH 7C6 CDR Set & VL 7C6 CDR Set; VH 4B7 CDR Set & VL 4B7 CDR Set; VH 2F2 CDR Set & VL 2F2 CDR Set; VH 6A2 CDR Set & VL 6A2 CDR Set; VH 4D10 CDR Set & VL 4010 CDR Set; VH 7E5 CDR Set & VL 7E5 CDR Set; and VH 10C1 CDR Set & VL 10C1 CDR Set.

In another embodiment the antibody disclosed above further comprises a human acceptor framework.

In a preferred embodiment the antibody is a CDR grafted antibody. Preferably the CDR grafted antibody comprises one or more of the CDRs disclosed above.

Preferably the CDR grafted antibody comprises a human acceptor framework.

In a preferred embodiment the antibody is a humanized antibody. Preferably the humanized antibody comprises one or more of the CDRs disclosed above. More preferably the humanized antibody comprises three or more of the CDRs disclosed above. Most preferably the humanized antibody comprises six CDRs disclosed above. In a particular embodiment, the CDRs are incorporated into a human antibody variable domain of a human acceptor framework. Preferably the human antibody variable domain is a consensus human variable domain. More preferably the human acceptor framework comprises at least one Framework Region amino acid substitution at a key residue, wherein the key residue is selected from the group consisting of a residue adjacent to a CDR; a glycosylation site residue; a rare residue; a residue capable of interacting with Aβ(20-42) globulomer; a residue capable of interacting with a CDR; a canonical residue; a contact residue between heavy chain variable region and light chain variable region; a residue within a Vernier zone; and a residue in a region that overlaps between a Chothia-defined variable heavy chain CDR1 and a Kabat-defined first heavy chain framework. Preferably the human acceptor framework human acceptor framework comprises at least one Framework Region amino acid substitution, wherein the amino acid sequence of the framework is at least 65% identical to the sequence of said human acceptor framework and comprises at least 70 amino acid residues identical to said human acceptor framework.

In yet a further aspect, the present invention relates to antibodies comprising both the heavy and light chain as defined above.

Preferably, the antibody comprises at least one variable domain having an amino acid sequence selected from the group consisting of: SEQ ID NO:3, SEQ ID NO:4, SEQ ID NO:7, SEQ ID NO:8, SEQ ID NO:11, SEQ ID NO:12, SEQ ID NO:15, SEQ ID NO:16, SEQ ID NO:19, SEQ ID NO:20, SEQ ID NO:23, SEQ ID NO:24, SEQ ID NO:27, SEQ ID NO:28, SEQ ID NO:31, SEQ ID NO:32, SEQ ID NO:35, SEQ ID NO:36, and SEQ ID NO:38. More preferably, the antibody comprises two variable domains, wherein said two variable domains have amino acid sequences selected from the group consisting of: SEQ ID NO:3 & SEQ ID NO:4, SEQ ID NO:7 & SEQ ID NO:8 & SEQ ID NO:11 & SEQ ID NO:12, SEQ ID NO:15 & SEQ ID NO:16, SEQ ID NO:19 & SEQ ID NO:20, SEQ ID NO:23 & SEQ ID NO:24, SEQ ID NO:27 & SEQ ID NO:28, SEQ ID NO:31 & SEQ ID NO:32, and SEQ ID NO:35 & SEQ ID NO:36.

In another aspect, the antibodies of the present invention comprise a heavy chain constant region selected from the group consisting of IgG1, IgG2, IgG3, IgG4, IgM, IgA, IgD, IgE and human IgG1 Ala234 Ala235 mutant constant regions. In particular, the antibodies comprise a human constant region. More preferably, the antibodies comprise an amino add sequence selected from the group consisting of SEQ ID NOs:39-42. Antibodies comprising an IgG 1 heavy chain constant region are preferred.

In another embodiment the antibody is glycosylated. Preferably the glycosylation pattern is a human glycosylation pattern or a glycosylation pattern produced by any one of the eukaryotic cells disclosed herein, in particular CHO cells.

The present invention also relates to an antigen-binding moiety of an antibody of the present invention. Such antigen-binding moieties include, but are not limited to, Fab fragments, F(ab')$_2$ fragments and single chain Fv fragments of the antibody. Further antigen-binding moieties are Fab' fragments, Fv fragments, and disulfide linked Fv fragments.

The invention also provides an isolated nucleic acid encoding any one of the antibodies disclosed herein. A further embodiment provides a vector comprising the isolated nucleic acid disclosed herein. Said vector may in particular be selected from the group consisting of pcDNA; pTT (Durocher et al., *Nucleic Acids Research* 2002, Vol 30, No. 2); pTT3 (pTT with additional multiple cloning site; pEFBOS (Mizushima, S. and Nagata, S., (1990) *Nucleic Acids Research Vol* 18, No. 17); pBV; pJV; and pBJ.

In another aspect a host cell is transformed with the vector disclosed herein. Preferably the host cell is a prokaryotic cell. More preferably the host cell is E coli. In a related embodiment the host cell is a eukaryotic cell. Preferably the eukaryotic cell is selected from the group consisting of a protist cell, an animal cell (e g. a mammalian cell, an avian cell, and an insect cell), a plant cell and a fungal cell. More preferably the host cell is a mammalian cell including, but not limited to, CHO and COS; or a fungal cell, eg., a yeast cell, such as *Saccharomyces cerevisiae*; or an insect cell such as Sf9.

Another aspect of the invention provides a method of producing an antibody of the invention, comprising culturing any one of the host cells or a hybridoma disclosed herein in a culture medium under conditions suitable to produce the antibody. Another embodiment provides an antibody that is obtainable by the method disclosed herein.

Antibodies of the present invention can be obtained in a manner known per se.

B lymphocytes which, in totality, contain an antibody repertoire composed of hundreds of billions of different antibody specificities are a part of the mammalian immune system. A normal immune response to a particular antigen means selection of one or more antibodies of said repertoire which specifically bind to said antigen, and the success of an immune response is based at least partially on the ability of said antibodies to specifically recognize (and ultimately to eliminate) the stimulating antigen and to ignore other molecules in the environment of said antibodies.

The usefulness of antibodies which specifically recognize one particular target antigen has led to the development of monoclonal antibody technology. Standardized hybridoma technology now allows the production of antibodies with a single specificity for an antigen of interest More recently, recombinant antibody techniques such as in-vitro screening of antibody libraries have been developed. These techniques likewise allow antibodies having a single specificity for an antigen of interest to be produced.

In the method of the invention, the antigen of interest may be allowed to act on the antibody repertoire either in vivo or in vitro.

According to one embodiment, the antigen is allowed to act on the repertoire by immunizing an animal in vivo with said antigen. This in-vivo approach may furthermore comprise establishing from the lymphocytes of an animal a number of hybridomas and selecting a particular hybridoma which secretes an antibody specifically binding to said antigen. The animal to be immunized may be, for example, a mouse, rat, rabbit, chicken, camelid or sheep or may be a transgenic version of any of the animals mentioned above, for example a transgenic mouse with human immunoglobulin genes, which produces human antibodies after an antigenic stimulus. Other types of animals which may be immunized include mice with severe combined immunodeficiency (SCID) which have been reconstituted with human peripheral mononuclear blood cells (chimeric hu-PBMC SCID mice) or with lymphoid cells or precursors thereof, as well as mice which have been treated with a lethal total body irradiation, then protected against radiation with bone marrow cells from a mouse with severe combined immunodeficiency (SCID) and subsequently transplanted with functional human lymphocytes (the "Trimera" system). Another type of an animal to be immunized is an animal (e.g. a mouse) in whose genome an endogenous gene encoding the antigen of interest has been switched off (knocked out), for example by homologous recombination, so that, after immunization with the antigen, said animal recognizes said antigen as foreign. It is obvious to the skilled worker that the polyclonal or monoclonal antibodies produced by this method are characterized and selected by using known screening methods which include, but are not limited to, ELISA and dot blot techniques.

According to another embodiment, the antigen is allowed to act on the antibody repertoire in vitro by screening a recombinant antibody library with said antigen. The recombinant antibody library may be expressed, for example, on the surface of bacteriophages or on the surface of yeast cells or on the surface of bacterial cells. In a variety of embodiments, the recombinant antibody library is an scFv library or an Fab library, for example. According to another embodiment, antibody libraries are expressed as RNA-protein fusions.

Another approach to producing antibodies of the Invention comprises a combination of in vivo and in vitro approaches. For example, the antigen may be allowed to act on the antibody repertoire by immunizing an animal in vivo with said antigen and then screening in vitro with said antigen a recombinant antibody library prepared from lymphoid cells of said animal or a single domain antibody library (e.g. containing heavy and/or light chains). According to another approach, the antigen is allowed to act on the antibody repertoire by immunizing an animal in vivo with said antigen and then subjecting a recombinant antibody library or single domain library produced from lymphoid cells of said animal to affinity maturation. According to another approach, the antigen is allowed to act on the antibody repertoire by immunizing an animal in vivo with said antigen, then selecting individual antibody-producing cells secreting an antibody of interest and obtaining from said selected cells cDNAs for the variable region of the heavy and light chains (e.g. by means of PCR) and expressing said variable regions of the heavy and light chains in mammalian host cells in vitro (this being referred to as selected lymphocyte antibody method or SLAM), thereby being able to further select and manipulate the selected antibody gene sequences. Moreover, monoclonal antibodies may be selected by expression cloning by expressing the antibody genes for the heavy and light chains in mammalian cells and selecting those mammalian cells which secrete an antibody having the desired binding affinity.

The present invention provides defined antigens for screening and counter screening. Thus it is possible, according to the invention, to select those polyclonal and monoclonal antibodies which bind to an Aβ(20-42) globulomer with the binding affinities as defined above.

The methods of the invention for producing antibodies can be used to produce various types of antibodies. These include monoclonal, in particular recombinant antibodies, especially essentially human antibodies, chimeric antibodies, humanized antibodies and CDR graft antibodies, and also antigen-binding moieties thereof.

The present invention further relates to a hybridoma that is capable of producing (secreting) a monoclonal antibody of the present invention. Hybridomas of the present invention include those designated by an American Type Culture Collection deposit number selected from the group consisting of PTA-7241, PTA-7239, PTA-7240, PTA-7242, PTA-7408, PTA-7409, PTA-7405, PTA-7809, PTA-7810 and PTA-7851.

It is noted that the antibodies of the present invention may also be reactive with, i.e. bind to, AP forms other than the Aβ globulomers described herein. These antigens may or may not be oligomeric or globulomeric. Thus, the antigens to which the antibodies of the present invention bind include any Aβ form that comprises the globulomer epitope with which the antibodies of the present invention are reactive. Such Aβ forms include truncated and non-truncated Aβ(X-Y) forms (with X and Y being defined as above), such as Aβ(20-42), Aβ(20-40), Aβ(12-42), Aβ(12-40), Aβ(1-42), and Aβ(1-40) forms, provided that said forms comprise the globulomer epitope.

The present invention also relates to a composition comprising an antibody of the invention or an antigen-binding moiety thereof, as defined above.

According to a particular embodiment, said composition is a pharmaceutical composition which comprises the antibody of the Invention or the antigen-binding moiety and a pharmaceutical acceptable carrier.

The antibody of the invention or the antigen-binding moiety as defined above is preferably capable of neutralizing, both in vitro and in vivo, the activity of Aβ globulomer or a derivative thereof to which it binds. Said antibody or antigen-binding moiety may therefore be used for Inhibiting the activity of said globulomer or derivative thereof, for example in a preparation containing said globulomer or derivative thereof or in human individuals or other mammals in which said globulomer or derivative thereof is present.

According to one embodiment, the invention relates to a method of inhibiting the activity of said globulomer or derivative thereof, which method comprises allowing an antibody of the invention or an antigen-binding moiety thereof to act on a globulomer or derivative thereof so as to inhibit the activity of said globulomer or derivative thereof. Said activity may be inhibited in vitro, for example. For instance, the antibody of the invention or the antigen-binding moiety may be added to a preparation such as a sample derived from a subject or a cell culture which contains or is suspected to contain said globulomer or derivative thereof, in order to inhibit the activity of said globulomer or derivative thereof in said sample. Alternatively, the activity of the globulomer or derivative thereof may be Inhibited in an individual in vivo.

Thus the present invention further relates to the use of an antibody or an antigen-binding moiety as defined above for preparing a pharmaceutical composition for treating or preventing an amyloidosis, in particular an amyloidosis selected from the group consisting of Alzheimer's disease and the amyloidosis of Down's syndrome. One aspect of said use of the invention is therefore a method of treating or preventing an amyloidosis, in particular Alzheimer's disease or the amyloidosis of Down's syndrome, in a subject in need thereof, which comprises administering an antibody or an antigen-binding moiety as defined above to the subject. Using said antibody or antigen-binding moiety for treating and especially preventing the amyloidosis, in particular Alzheimer's disease or the amyloidosis of Down's syndrome, is in particular for passive immunization. Accordingly, in the method of treating or preventing an amyloidosis, in particular Alzheimer's disease or the amyloidosis of Down's syndrome, in a subject in need thereof one purpose of administering the antibody or antigen-binding moiety to the subject is passively immunizing the subject against the amyloidosis, in particular Alzheimer's disease or the amyloidosis of Down's syndrome.

The antibody of the Invention or the antigen-binding moiety as defined above is preferably capable of detecting, both in vitro and in vivo, an Aβ globulomer or derivative thereof to which it binds. Said antibody or the antigen-binding moiety may therefore be used for detecting said globulomer or derivative thereof, for example in a preparation containing said globulomer or derivative thereof or in human individuals or other mammals in which said globulomer or derivatives thereof is present.

According to one embodiment, the invention relates to a method of detecting said globulomer or derivative thereof, which method comprises allowing an antibody of the invention or an antigen-binding moiety thereof to act on a globulomer or derivative thereof so as to bind to said globulomer or derivative thereof (and thereby preferably forming a complex comprising the antibody or antigen-binding moiety thereof and the globulomer or derivative thereof). Said globulomer may be detected in vitro, for example. For example, the antibody of the invention or the antigen-binding moiety may be added to a preparation, for instance a sample derived from a subject or a cell culture which contains or is suspected to contain said globulomer or derivative thereof, in order to detect said globulomer or derivative thereof in said preparation. Alternatively, the globulomer or derivative thereof may be detected in an individual in vivo.

Thus the present invention further relates to the use of an antibody or an antigen-binding moiety as defined above for preparing a composition for diagnosing an amyloidosis, in particular Alzheimer's disease or the amyloidosis of Down's syndrome. One aspect of said use of the invention is a method of diagnosing an amyloidosis, in particular Alzheimer's disease or the amyloidosis of Down's syndrome, in a subject suspect of having the amyloidosis, in particular Alzheimer's disease or the amyloidosis of Down's syndrome, which comprises administering to the subject an antibody or an antigen-binding moiety as defined above and detecting the formation of a complex comprising the antibody or the antigen-binding moiety with the antigen, the presence of the complex Indicating the amyloidosis, in particular Alzheimer's disease or the amyloidosis of Down's syndrome, In the subject. A second aspect of said use of the invention is a method of diagnosing an amyloidosis, in particular Alzheimer's disease or the amyloidosis of Down's syndrome, in a subject suspect of having the amyloidosis, in particular Alzheimer's disease or the amyloidosis of Down's syndrome, which comprises providing a sample from the subject, contacting the sample with an antibody or an antigen-binding moiety as defined above and detecting the formation of a complex comprising the antibody or the antigen-binding moiety with the antigen, the presence of the complex indicating the amyloidosis, in particular Alzheimer's disease or the amyloidosis of Down's syndrome, in the subject

DETAILED DESCRIPTION OF THE INVENTION

The binding affinities of the antibodies of the invention may be evaluated by using standardized in-vitro immunoassays such as ELISA, dot blot or BIAcore analyses (Pharmacia Biosensor AB, Uppsala, Sweden and Piscataway, N.J.). For further descriptions, see Jönsson, U., et al. (1993) Ann. Biol. Clin. 51:19-26; Jönsson, U., et al. (1991) Bio-Techniques 11:620-627; Johnsson, B., et al. (1995) J. Mol. Recognit. 8:125-131; and Johnsson, B., et al. (1991) Anal. Biochem. 198:268-277.

According to a particular embodiment, the affinities defined herein refer to the values obtained by performing a dot blot as described in example 8 and evaluating it by densitometry. According to a particular embodiment of the invention, determining the binding affinity by dot blot comprises the following: a certain amount of the antigen (e.g. the Aβ(X-Y) globulomer, Aβ(X-Y) monomer or Aβ(X-Y) fibrils, as defined above) or, expediently, an appropriate dilution thereof, for instance in 20 mM NaH$_2$PO$_4$, 140 mM NaCl, pH 7.4, 0.2 mg/ml BSA to an antigen concentration of, for example, 100 pmol/μl, 10 pmol/μl, 1 pmol/μl, 0.1 pmol/μl and 0.01 pmol/μl, is dotted onto a nitrocellulose membrane, the membrane is then blocked with milk to prevent unspecific binding and washed, then contacted with the antibody of interest followed by detection of the latter by means of an enzyme-conjugated secondary antibody and a colorimetric reaction; at defined antibody concentrations, the amount of antibody bound allows affinity determination. Thus the relative affinity of two different antibodies to one target, or of one antibody to two different targets, is here defined as the relation of the respective amounts of target-bound antibody observed with the two antibody-target combinations under otherwise identical dot blot conditions. Unlike a similar approach based on Western blotting, the dot blot approach will determine an antibody's affinity to a given target in the latter's natural conformation; unlike the ELISA approach, the dot blot approach does not suffer from differences in the affinities between different targets and the matrix, thereby allowing for more precise comparisons between different targets.

The term "$K_d$", as used herein, is Intended to refer to the dissociation constant of a particular antibody-antigen interaction as is known in the art.

The antibodies of the present invention are preferably isolated antibodies. An "isolated antibody" means an antibody having the binding affinities as described above and which is essentially free of other antibodies having different binding affinities. The term "essentially free" here refers to an antibody preparation in which at least 95% of the antibodies, preferably at least 98% of the antibodies and more preferably at least 99% of the antibodies have the desired binding affinity. Moreover, an isolated antibody may be substantially free of other cellular material and/or chemicals.

The isolated antibodies of the present invention include monoclonal antibodies. A "monoclonal antibody" as used herein is intended to refer to a preparation of antibody molecules, antibodies which share a common heavy chain and common light chain amino acid sequence, in contrast with "polyclonal" antibody preparations which contain a mixture of antibodies of different amino acid sequence. Monoclonal antibodies can be generated by several novel technologies like phage, bacteria, yeast or ribosomal display, as well as by classical methods exemplified by hybridoma-derived antibodies (e.g., an antibody secreted by a hybridoma prepared by hybridoma technology, such as the standard Kohler and Milstein hybridoma methodology ((1975) Nature 256:495-497). Thus, a non-hybridoma-derived antibody with uniform sequence is still referred to as a monoclonal antibody herein although it may have been obtained by nonclassical methodologies, and the term "monoclonal" is not restricted to hybridoma-derived antibodies but used to refer to all antibodies derived from one nucleic acid clone.

Thus, the monoclonal antibodies of the present invention include recombinant antibodies. The term "recombinant" herein refers to any artificial combination of two otherwise separated segments of sequence, e.g., by chemical synthesis or by the manipulation of isolated segments of nucleic acids by genetic engineering techniques. In particular, the term "recombinant antibody" refers to antibodies which are produced, expressed, generated or isolated by recombinant means, such as antibodies which are expressed using a recombinant expression vector transfected into a host cell; antibodies isolated from a recombinant combinatorial antibody library; antibodies isolated from an animal (e.g. a mouse) which is transgenic due to human immunoglobulin genes (see, for example, Taylor, L. D., et al. (1992) *Nucl Acids Res* 20:6287-6295); or antibodies which are produced, expressed, generated or isolated in any other way in which particular immunoglobulin gene sequences (such as human immunoglobulin gene sequences) are assembled with other DNA sequences. Recombinant antibodies include, for example, chimeric, CDR graft and humanized antibodies. The person skilled in the art will be aware that expression of a conventional hybridoma-derived monoclonal antibody in a heterologous system will require the generation of a recombinant antibody even if the amino acid sequence of the resulting antibody protein is not changed or Intended to be changed.

In a particular embodiment of the invention, the antibody is a humanized antibody.

According to a multiplicity of embodiments, the antibody may comprise an amino acid sequence derived entirely from a single species, such as a human antibody or a mouse antibody. According to other embodiments, the antibody may be a chimeric antibody or a CDR graft antibody or another form of a humanized antibody.

The term "antibody" is intended to refer to immunoglobulin molecules consisting of 4 polypeptide chains, two heavy (H) chains and two light (L) chains. The chains are usually linked to one another via disulfide bonds. Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

The term "antigen-binding moiety" of an antibody (or simply "antibody moiety") refers to one or more fragments of an antibody of the invention, said fragment(s) still having the binding affinities as defined above. Fragments of a complete antibody have been shown to be able to carry out the antigen-binding function of an antibody. In accordance with the term "antigen-binding moiety" of an antibody, examples of binding fragments include (i) an Fab fragment, i.e. a monovalent fragment composed of the VL, VH, CL and CH1 domains; (ii) an F(ab')$_2$ fragment, i.e. a bivalent fragment comprising two Feb fragments linked to one another in the hinge region via a disulfide bridge; (iii) an Fd fragment composed of the VH and CH1 domains; (iv) an Fv fragment composed of the FL and VH domains of a single arm of an antibody; (v) a dAb fragment (Ward et al., (1989) *Nature* 341:544-546) consisting of a VH domain or of VH, CH1, CH2, DH3, or VH, CH2, CH3; and (vi) an isolated complementarity-determining region (CDR). Although the two domains of the Fv fragment, namely VL and VH, are encoded by separate genes, they may further be linked to one another using a synthetic linker, e.g. a poly-G$_4$S amino acid sequence, and recombinant methods, making it possible to prepare them as a single protein chain in which the VL and VH regions combine in order to form monovalent molecules (known as single chain Fv (ScFv); see, for example, Bird et al. (1988) *Science* 242:423-426; and Huston et al. (1988) *Proc. Nat. Acad. Sci. USA* 85:5879-5883). The term "antigen-binding moiety" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites (see, for example, Holliger, P., et al. (1993) *Proc. Natl. Acad. Sc. USA* 90:6444-6448; Poljak, R. J., et a. (1994) *Structure* 2:1121-1123). An immunoglobulin constant domain refers to a heavy or light chain constant domain. Human IgG heavy chain and light chain constant domain amino acid sequences are known in the art and are represented in Table 1.

TABLE 1

Sequence of human IgG heavy chain constant domain and light chain constant domain

| Protein | Sequence ID | Sequence 123456789012345678901223456789012 |
|---|---|---|
| Ig gamma-1 constant region | SEQ ID NO: 39 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig gamma-1 constant region mutant | SEQ ID NO: 40 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPEAAGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig Kappa constant region | SEQ ID NO: 41 | TVAAPSVFIFPPSDEQLKSGTASVVCLLNNFY PREAKVQWKVDNALQSGNSQESVTEQDSKDST YSLSSTLTLSKADYEKHKVYACEVTHQGLSSP VTKSFNRGEC |
| Ig Lambda constant region | SEQ ID NO: 42 | QPKAAPSVTLFPPSSEELQANKATLVCLISDF YPGAVTVAWKADSSPVKAGVETTTPSKQSNNK YAASSYLSLTPEQWKSHRSYSCQVTHEGSTVE KTVAPTECS |

Furthermore, an antibody of the present invention or antigen-binding moiety thereof may be part of a larger immunoadhesion molecule formed by covalent or noncovalent association of said antibody or antibody moiety with one or more further proteins or peptides. Relevant to such immunoadhesion molecules are the use of the streptavidin core region in order to prepare a tetrameric scFv molecule (Kipriyanov, S. M., et at (1995) *Human Antibodies and Hybridomas* 6:93-101) and the use of a cystein residue, a marker peptide and a C-terminal polyhistidinyl, e. g. hexahistidinyl, tag in order to produce bivalent and biotinylated scFv molecules (Kipriyanov, S. M., et al. (1994) *Mol. Immunol.* 31:1047-1058).

The term "human antibody" refers to antibodies whose variable and constant regions correspond to or are derived from immunoglobulin sequences of the human germ line, as described, for example, by Kabat et al. (see Kabat, et al. (1991) *Sequences of Proteins of Immunological Interest, Fifth Edition*, U.S. Department of Health and Human Services, NIH Publication No. 91-3242). However, the human antibodies of the invention may contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies of the invention have variable regions and may also contain constant regions derived from immunoglobulin sequences of the human germ line (see Kabat, E A., et al. (1991) *Sequences of Proteins of Immunological Interest, Fifth Edition*, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and Vl regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody.

The term "chimeric antibody" refers to antibodies which contain sequences for the variable region of the heavy and light chains from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e g., CDR3) has been replaced with human CDR sequences.

The term "humanized antibody" refers to antibodies which contain sequences of the variable region of heavy and light chains from a nonhuman species (e.g. mouse, rat, rabbit, chicken, camelid, sheep or goat) but in which at least one part of the VH and/or VL sequence has been altered in order to be more "human-like", i.e. to be more similar to variable sequences of the human germ line. One type of a humanized antibody is a CDR graft antibody in which human CDR sequences have been inserted into nonhuman VH and VL sequences to replace the corresponding nonhuman CDR sequences.

The terms "Kabat numbering", "Kabat definitions" and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad, Sci.* 190:382-391 and Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues not occurring at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences There are three CDRs in each of the variable regions of the heavy chain and of the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, in spite of great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol. 227:799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a spades different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined using different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200

(2002); Marchalonis et al., Adv Exp Med Biol. 484:13-30 (2001)). One of the advantages provided by various embodiments of the present invention stems from the finding that germline antibody genes are more likely than mature antibody genes are to conserve essential amino acid sequence structures characteristic of individuals in the species, hence less likely to be recognized as non-self when used in that species.

As used herein, the term "key" residues refers to certain residues within the variable region that have more impact on the binding specificity and/or affinity of an antibody, in particular a humanized antibody. A key residue Includes, but is not limited to, one or more of the following: a residue that is adjacent to a CDR, a potential glycosylation site (which can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" specifically refers to an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR A humanized antibody comprises substantially all of at least one, and typically two, variable domains (Fab, Fab', F(ab') 2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of Immunoglobulins, including IgM, IgG, IgD, IgA and IgE, and any subclass, including without limitation IgG1, IgG2, IgG3 and IgG4.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond exactly to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus Immunoglobulin sequence" refers to the sequence formed from the most frequently occurring amino acids (or nucleotides) in a family of related immunoglobulin sequences (see e.g., Winnaker, From Genes to Clones (Veriagsgesellschaft, Weinheim, Germany 1987). In a family of immunoglobulins, each position in the consensus sequence is occupied by the amino acid occurring most frequently at that position in the family. Where two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

The term "epitope" includes any polypeptide determinant capable of specific binding to an immunoglobulin. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or any combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is connected in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription Initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence Is advantageous, for example, leader sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, also to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the kingdoms of life. Preferred eukaryotic cells include protist, fungal, plant and animal cells. Most preferably host cells include but are not limited to the prokaryotic cell line *E. coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

Methods of producing antibodies of the invention are described below. A distinction is made here between in-vivo approaches, in-vitro approaches or a combination of both.

Some methods of producing antibodies of the invention are described below. A distinction is made here between in-vivo approaches, in-vitro approaches or a combination of both.

In-Vivo Approaches

Depending on the type of the desired antibody, various host animals may be used for in-vivo immunization. A host expressing Itself an endogenous version of the antigen of interest may be used. Alternatively, it is possible to use a host which has been made deficient in an endogenous version of the antigen of interest. For example, mice which had been made deficient in a particular endogenous protein via homologous recombination at the corresponding endogenous gene (i.e. knockout mice) have been shown to generate a humoral response to the protein with which they have been immunized and therefore to be able to be used for production of high-affinity monoclonal antibodies to the protein (see, for example, Roes, J. et al. (1995) *J. Immunol. Methods* 183:231-237; Lunn, M. P. et al. (2000) *J. Neurochem.* 75:404-412).

A multiplicity of nonhuman mammals are suitable hosts for antibody production in order to produce nonhuman antibodies of the invention. They include mice, rats, chickens, camelids, rabbits, sheep and goats (and knockout versions thereof), although preference is given to mice for the production of hybridomas. Furthermore, a nonhuman host animal expressing a human antibody repertoire may be used for producing essentially human antibodies to a human antigen with dual specificity. Nonhuman animals of this kind include transgenic animals (e.g. mice) bearing human immunoglobulin transgenes (chimeric hu-PBMC SCID mice) and human/mouse irradiation chimeras which are described in more detail below.

According to one embodiment, the animal immunized with Aβ(20-42) globulomer or derivative thereof is a nonhuman mammal, preferably a mouse, which is transgenic due to human immunoglobulin genes so that said nonhuman mammal makes human antibodies upon antigenic stimulation. Typically, immunoglobulin transgenes for heavy and light chains with human germ line configuration are introduced into such animals which have been altered such that their endogenous heavy and light chain loci are Inactive. If such animals are stimulated with antigen (e.g. with a human antigen), antibodies derived from the human immunoglobulin sequences (human antibodies) are produced. It Is possible to make from the lymphocytes of such animals human monoclonal antibodies by means of standardized hybridoma technology. For a further description of transgenic mice with human immunoglobulins and their use in the production of human antibodies, see, for example, U.S. Pat. No. 5,939, 598, WO 96/33735, WO 96/34096, WO 98/24893 and WO 99/53049 (Abgenix Inc.), and U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, U.S. Pat. No. 5,814,318, U.S. Pat. No. 5,877,397 and WO 99/45962 (Genpharm Inc.); see also MacQuitty, J. J. and Kay, R. M. (1992) *Science* 257:1188; Taylor, L. D. et al. (1992) *Nucleic Acids Res.* 20:6287-6295; Lonberg, N. et al. (1994) *Nature* 368:856-859; Lonberg, N. and Huszar, D. (1995) *Int. Rev. Immunol.* 13:65-93; Harding, F. A. and Lonberg, N. (1995) *Ann. N.Y. Aced. Sc.* 764:536-546; Fishwild, D. M. et al. (1996) *Nature Biotechnology* 14:845-851; Mendez, M. J. et al. (1997) *Nature Genetics* 15:146-156; Green, L. L. and Jakobovits, A. (1998) *J. Exp. Med.* 188: 483-495; Green, L L. (1999) *J. Immunol. Methods* 231:11-23; Yang, X. D. et al. (1999) *J. Leukoc. Biol.* 66:401-410; Gallo, M. L. et al. (2000) *Eur. J. Immunol.* 30:534-540.

According to another embodiment, the animal which is immunized with Aβ(20-42) globulomer or derivative thereof may be a mouse with severe combined immunodeficiency (SCID), which has been reconstituted with human peripheral mononuclear blood cells or lymphoid cells or precursors thereof. Such mice which are referred to as chimeric hu-PBMC SCID mice produce human immunoglobulin responses upon antigenic stimulation, as has been proved. For a further description of these mice and of their use for generating antibodies, see, for example, Leader, K. A. et al. (1992) *Immunology* 76:229-234; Bombil, F. et al. (1996) *Immunobiol.* 195:360-375; Murphy, W. J. et al. (1996) *Semin. Immunol.* 8:233-241; Herz, U. et al. (1997) *Int. Arch. Allergy Immunol.* 113:150-152; Albert, S. E. et al. (1997) *J. Immunol.* 159:1393-1403; Nguyen, H. et al. (1997) *Microbiol Immunol.* 41:901-907; Arai, K. et al. (1998) *J. Immunol. Methods* 217:79-85; Yoshinarl, K. and Arai, K. (1998) *Hybridoma* 17:41-45; Hutchins, W. A. et al. (1999) *Hybridoma* 18:121-129; Murphy, W. J. et al. (1999) *Clin. Immunol* 90:22-27; Smithson, S. L. et al. (1999) *Mol. Immunol.* 36:113-124; Chamat, S et al. (1999) *J. Infect. Diseases* 180:268-277; and Heard, C. et al. (1999) *Molec. Med.* 5:35-45.

According to another embodiment, the animal which is immunized with Aβ(20-42) globulomer or a derivative thereof is a mouse which has been treated with a lethal dose of total body irradiation, then protected from radiation with bone marrow cells from mice with severe combined immunodeficiency (SCID) and subsequently transplanted with functional human lymphocytes. This type of chimera, referred to as the Trimera system, is used in order to produce human monoclonal antibodies by immunizing said mice with the antigen of interest and then producing monoclonal antibodies by using standardized hybridoma technology. For a further description of these mice and of their use for generating antibodies, see, for example, Eren, R et al. (1998) *Immunology* 93:154-161; Reisner, Y and Dagan, S. (1998) *Trends Biotechnol.* 16:242-246; Ilan, E. et al. (1999) *Hepatology* 29:553-562; and Bocher, W. O. et al. (1999) *Immunology* 96:634-641.

Starting from the in-vivo generated antibody-producing cells, monoclonal antibodies may be produced by means of standardized techniques such as the hybridoma technique originally described by Kohler and Milstein (1975, *Nature* 256:495-497) (see also Brown et al. (1981) *J. Immunol* 127:539-46; Brown et al. (1980) *J Biol Chem* 255:4980-83; Yeh et al. (1976) *PNAS* 76:2927-31; and Yeh et a. (1982) *Int. J. Cancer* 29:269-75). The technology of producing monoclonal antibody hybridomas is sufficiently known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). Briefly, an immortalized cell line (typically a myeloma) is fused with lymphocytes (typically splenocytes or lymph node cells or peripheral blood lymphocytes) of a mammal immunized with the Aβ globulomer of the invention or derivative thereof, and the culture supernatants of the resulting hybridoma cells are screened in order to identify a hybridoma which produces a monoclonal antibody of the present invention. Any of the many well known protocols for fusing lymphocytes and immortalized cell lines can be applied for this purpose (see also G. Galfre et al. (1977) *Nature* 266:550-52; Gefter et al. *Somatic Cell Genet.*, cited supra; Lemer, *Yale J. Biol. Med.*, cited supra; Kenneth, Monoclonal Antibodies, cited supra). Moreover, the skilled worker will appreciate that there are diverse variations of such methods, which are likewise useful. Typically, the Immortalized cell line (e.g. a myeloma cell line) is derived from the same mammalian species as the lymphocytes. For example, murine hybridomas may be established by fusing lymphocytes from a mouse immunized with an immunogenic preparation of the invention with an immortalized mouse cell line. Preferred immortalized cell lines are mouse myeloma cell lines which are sensitive to culture medium containing hypoxanthine, aminopterine and thymidine (HAT medium). Any of a number of myeloma cell lines may be used by default as fusion partner, for example the P3-NS1/1-Ag4-1, P3-x63-Ag8.653 or Sp2/O-Ag14 myeloma lines. These myeloma cell lines are available from the American Type Culture Collection (ATCC), Rockville, Md. Typically, HAT-sensitive mouse myeloma cells are fused to mouse splenocytes using polyethylene glycol (PEG). Hybridoma cells resulting from the fusion are then selected using HAT medium, thereby killing unfused and unproductively fused myeloma cells (unfused splenocytes die after several days because they are not transformed). Hybridoma cells producing monoclonal antibodies of the invention are identified by screening the hybridoma culture supernatants for such antibodies, for example by using a dot blot assay as described above and in example 8 in order to select those antibodies which have the binding affinities as defined above.

The monoclonal antibodies 5F7, 10F11, 7C6, 4B7, 6A2, 2F2, 4D10, 7E5, 10C1, and 3B10 all have been generated using the above-described in-vivo approach and thereof are obtainable from a hybridoma as defined herein.

Likewise, said hybridoma can be used as a source of nucleic acid encoding light and/or heavy chains in order to recombinantly produce antibodies of the present Invention, as is described below in further detail.

In-Vitro Approaches

As an alternative to producing antibodies of the invention by immunization and selection, antibodies of the invention may be identified and isolated by screening recombinant combinatorial immunoglobulin libraries with Aβ(20-42) globulomer or derivative thereof to thereby isolate immunoglobulin library members which have the required binding affinity. Kits for generating and screening display libraries are commercially available (e.g. the Pharmacia Recombinant Phage Antibody System, catalog No. 27-9400-01; and the Stratagene SurfZAP® Phage Display Kit, catalog No. 240612). In many embodiments, the display library is an scFv library or an Fab library. The phage display technique for screening recombinant antibody libraries has been adequately described. Examples of methods and compounds which can be used particularly advantageously for generating and screening antibody display libraries can be found, for example, in McCafferty et al. WO 92/01047, U.S. Pat. No. 5,969,108 and EP 589 877 (describes in particular scFv display), Ladner et al. U.S. Pat. No. 5,223,409, U.S. Pat. No. 5,403,484, U.S. Pat. No. 5,571,698, U.S. Pat. No. 5,837,500 and EP 436 597 (describes pill fusion, for example); Dower et al. WO 91/17271, U.S. Pat. No. 5,427,908, U.S. Pat. No. 5,580,717 and EP 527 839 (describes in particular Fab display); Winter et al. International Publication WO 92/20791 and EP 368,684 (describes in particular the cloning of sequences for variable immunoglobulin domains); Griffiths et al. U.S. Pat. No. 5,885,793 and EP 589 877 (describes in particular isolation of human antibodies to human antigens by using recombinant libraries); Garrard et al. WO 92/09690 (describes in particular phage expression techniques); Knappik et al. WO 97/08320 (describes the human recombinant antibody library HuCal); Salfeld et al. WO 97/29131, (describes production of a recombinant human antibody to a human antigen (human tumor necrosis factor alpha) and also in-vitro affinity maturation of the recombinant antibody) and Salfeld et al U.S. Provisional Application No. 60/126,603 and the patent applications based hereupon (likewise describes production of recombinant human antibodies to human antigen (human interleukin-12), and also in-vitro affinity maturation of the recombinant antibody).

Further descriptions of screenings of recombinant antibody libraries can be found in scientific publications such as Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Bo* 226:889-896; Clarkson et ael. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; Barbas et al. (1991) *PNAS* 88:7978-7982; McCafferty et al. *Nature* (1990) 348:552-554; and Knappik at al. (2000) *J. Mol. Biol.* 296:57-86.

As an alternative to using bacteriophage display systems, recombinant antibody libraries may be expressed on the surface of yeast cells or of bacterial cells. WO 99/36569 describes methods of preparing and screening libraries expressed on the surface of yeast cells. WO 98/49286 describes in more detail methods of preparing and screening libraries expressed on the surface of bacterial cells.

In all in vitro approaches, a selection process for enriching recombinant antibodies with the desired properties form an integral part of the process, which is generally referred to as "panning" and often takes the form of affinity chromatography over columns to whose matrix the target structure has been attached. Promising candidate molecules are then subjected to individual determination of their absolute and/or relative affinities, preferably by means of a standardized dot blot assay, as described above and in example 8.

Once an antibody of Interest of a combinatorial library has been identified and sufficiently characterized, the DNA sequences encoding the light and heavy chains of said antibody are isolated by means of standardized molecular-biological techniques, for example by means of PCR amplification of DNA from the display package (e.g. the phage) which has been isolated during library screening. Nucleotide sequences of genes for light and heavy antibody chains, which may be used for preparing PCR primers, are known to the skilled worker. A multiplicity of such sequences are described, for example, in Kabat, E. A., et al. (1991) *Sequences of Proteins of Immunological Interest, Fifth Edition*, U.S. Department of Health and Human Services, NIH Publication No. 91-3242 and in the database of sequences of the human germ line VBASE.

An antibody or antibody moiety of the invention may be produced by recombinantly expressing the genes for light and heavy immunoglobulin chains in a host cell. In order to recombinantly express an antibody, a host cell is transfected with one or more recombinant expression vectors carrying DNA fragments encoding the light and heavy immunoglobulin chains of said antibody, thereby expressing the light and heavy chains in the host cell and secreting them preferably into the medium in which said host cells are cultured. The antibodies can be isolated from this medium. Standardized recombinant DNA methods are used in order to obtain genes for heavy and light antibody chains, to insert said genes into recombinant expression vectors and to introduce said vectors into host cells. Methods of this kind are described, for example, in Sambrook, Fritsch and Maniatis (eds.), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816, 397 by Boss et al.

Once DNA fragments encoding VH and VL segments of the antibody of interest have been obtained, said DNA fragments may be further manipulated using standardized recombinant DNA techniques, for example in order to convert the genes for variable regions to genes for full length antibody chains, to genes for Fab fragments or to an scFv gene. These manipulations comprise linking a VL- or VH-encoding DNA fragment operatively to another DNA fragment encoding another protein, for example a constant antibody region or a flexible linker. The term "operatively linked" is to be understood here as meaning that the two DNA fragments are linked in such a way that the amino acid sequences encoded by said two DNA fragments remain in frame.

The isolated DNA encoding the VH region may be converted to a gene for a full length heavy chain by operatively linking the VH-region encoding DNA with another DNA molecule encoding heavy chain constant regions (CH1, CH2 and CH3). The sequences of human heavy chain constant region genes are well known (see, for example, Kabat, E. A., et al. (1991) *Sequences of Proteins of Immunological Interest, Fifth Edition*, U.S. Department of Health and Human Services, NIH Publication No. 91-3242), and DNA fragments spanning said regions may be obtained by means of standardized PCR amplification. The heavy chain constant region may be a constant region from IgG1, IgG2, IgG3, IgG4, IgM, IgA, IgE or IgD, with preference being given to a constant region from IgG, in particular IgG1 or IgG4. To obtain a gene for a heavy chain Fab fragment, the VH-encoding DNA may be operatively linked to another DNA molecule encoding merely the heavy chain constant region CH1.

The isolated DNA encoding the VL region may be converted to a gene for a full length light chain (and a gene for an Fab light chain) by operatively linking the VL-encoding DNA to another DNA molecule encoding the light chain constant region CL. The sequences of genes of the constant region of human light chain are well known (see Kabat, E. A., et al. (1991) *Sequences of Proteins of Immunological Interest, Fifth Edition*, U.S. Department of Health and Human Services, NIH Publication No. 91-3242), and DNA fragments spanning said regions may be obtained by means of standardized PCR amplification. The light chain constant region may be a constant kappa or lambda region, a constant kappa region being preferred.

In order to generate an scFv gene, the VH- and VL-encoding DNA fragments may be operatively linked to another fragment encoding a flexible linker, for example the amino acid sequence $(Gly_4-Ser)_3$ so that the VH and VL sequences are expressed as a continuous single-chain protein, with the VL and VH regions being linked to one another via said flexible linker (see Bird et al. (1988) *Science* 242:423-426; Huston et al. (1988) *Proc. Natl. Acad. Sci. USA* 85:5879-5883; McCafferty et al., *Nature* (1990) 348: 552-554).

Single domain VH and VL having the binding affinities as described above may be isolated from single domain libraries by the above-described methods. Two VH single-domain chains (with or without CH1) or two VL chains or a pair of one VH chain and one VL chain with the desired binding affinity may be useful as described herein for the antibodies of the invention.

In order to express the recombinant antibodies or antibody moieties of the invention, the DNAs encoding partial or full length light and heavy chains may be inserted into expression vectors so as to operatively link the genes to appropriate transcriptional and translational control sequences. In this context, the term "operatively linked" is to be understood as meaning that an antibody gene is ligated in a vector in such a way that transcriptional and translational control sequences within the vector fulfill their intended function of regulating transcription and translation of said antibody gene.

Expediently, the expression vector and the expression control sequences are chosen so as to be compatible with the expression host cell used. The gene for the antibody light chain and the gene for the antibody heavy chain may be inserted into separate vectors or both genes are inserted into the same expression vector, this being the usual case. The antibody genes are inserted into the expression vector by means of standardized methods (for example by ligation of complementary restriction cleavage sites on the antibody gene fragment and the vector, or by ligation of blunt ends, if no restriction cleavage sites are present). The expression vector may already carry sequences for antibody constant regions prior to insertion of the sequences for the light and heavy chains. For example, one approach is to convert the VH and VL sequences to full length antibody genes by inserting them into expression vectors already encoding the heavy and, respectively, light chain constant regions, thereby operatively linking the VH segment to the CH segment(s) within the vector and also operatively linking the VL segment to the CL segment within the vector.

Additionally or alternatively, the recombinant expression vector may encode a signal peptide which facilitates secretion of the antibody chain from the host cell. The gene for said antibody chain may be cloned into the vector, thereby linking the signal peptide in frame to the N terminus of the gene for the antibody chain. The signal peptide may be an immunoglobulin signal peptide or a heterologous signal peptide (i.e. a signal peptide from a non-immunoglobulin protein). In addition to the genes for the antibody chain, the expression vectors of the invention may have regulatory sequences controlling expression of the genes for the antibody chain in a host cell.

The term "regulatory sequence" is intended to include promoters, enhancers and further expression control elements (e.g. polyadenylation signals) which control transcription or translation of the genes for the antibody chain. Regulatory sequences of this kind are described, for example, in Goeddel; *Gene Expression Technology: Methods in Enzymology* 185, Academic Press, San Diego, Calif. (1990). The skilled worker will appreciate that the expression vector design which includes selection of regulatory sequences may depend on factors such as the choice of the host cell to be transformed, the desired strength of expression of the protein, etc. Preferred regulatory sequences for expression in mammalian host cells include viral elements resulting in strong and constitutive protein expression in mammalian cells, such as promoters and/or enhancers derived from cytomegalovirus (CMV) (such as the CMV promoter/enhancer), simian virus 40 (SV40) (such as the SV40 promoter/enhancer), adenovirus (e.g. the adenovirus major late promoter (AdMLP)) and polyoma. For a further description of viral regulatory elements and sequences thereof, see, for example, U.S. Pat. No. 5,168,062 to Stinski, U.S. Pat. No. 4,510,245 to Bell et a. and U.S. Pat. No. 4,968,615 to Schaffner et al.

Apart from the genes for the antibody chain and the regulatory sequences, the recombinant expression vectors of the invention may have additional sequences such as those which regulate replication of the vector in host cells (e.g. origins of replication) and selectable marker genes. The selectable marker genes facilitate the selection of host cells into which the vector has been introduced (see, for example, U.S. Pat. Nos. 4,399,216, 4,634,665 and 5,179,017, all to Axel et al.). For example, it is common for the selectable marker gene to render a host cell into which the vector has been inserted resistant to cytotoxic drugs such as G418, hygromycin or methotrexate. Preferred selectable marker genes include the gene for dihydrofolate reductase (DHFR) (for use in dhfr⁻ host cells with methotrexate selection/amplification) and the neo gene (for G418 selection).

For expression of the light and heavy chains, the expression vector(s) encoding said heavy and light chains is(are) transfected into a host cell by means of standardized techniques. The various forms of the term "transfection" are intended to comprise a multiplicity of techniques customarily used for introducing exogenous DNA into a prokaryotic or eukaryotic host cell, for example electroporation, calcium phosphate precipitation, DEAE-dextran transfection, and the like. Although it is theoretically possible to express the antibodies of the invention either in prokaryotic or eukaryotic host cells, preference is given to expressing the antibodies in eukaryotic cells and, in particular, in mammalian host cells, since the probability of a correctly folded and immunologically active antibody being assembled and secreted is higher in such eukaryotic cells and in particular mammalian cells than in prokaryotic cells Prokaryotic expression of antibody genes has been reported as being ineffective for production of high yields of active antibody (Boss, M. A. and Wood, C R. (1985) *Immunology Today* 6:12-13).

Preferred mammalian host cells for expressing recombinant antibodies of the invention include CHO cells (including dhfr⁻ CHO cells described in Urfaub and Chasin, (1980)

*Proc. Natl. Acad. Sci. USA* 77:4216-4220, which are used together with a DHFR-selectable marker, as described, for example, in R. J. Kaufman and P. A. Sharp (1982) *Mol. Biol.* 159:601-621), NS0 myeloma cells, COS cells and SP2 cells. When introducing recombinant expression vectors encoding the antibody genes into mammalian host cells, the antibodies are produced by culturing the host cells until the antibody is expressed in said host cells or, preferably, the antibody is secreted into the culture medium in which the host cells grow. The antibodies may then be isolated from the culture medium by using standardized protein purification methods.

It is likewise possible to use host cells in order to produce moieties of intact antibodies, such as Fab fragments or scFv molecules. Variations of the above-described procedure are of course included in the invention. For example, it may be desirable to transfect a host cell with DNA encoding either the light chain or the heavy chain (but not both) of an antibody of the invention. If either light or heavy chains are present which are not required for binding of the antigen of interest, then the DNA encoding either such a light or such a heavy chain or both may be removed partially or completely by means of recombinant DNA technology. Molecules expressed by such truncated DNA molecules are likewise included in the antibodies of the invention. In addition, it is possible to produce bifunctional antibodies in which a heavy chain and a light chain are an antibody of the invention and the other heavy chain and the other light chain have specificity for an antigen different from the antigen of interest, by crosslinking an antibody of the Invention to a second antibody by means of standardized chemical methods.

In a preferred system for recombinant expression of an antibody of the invention or an antigen-binding moiety thereof, a recombinant expression vector encoding both the antibody heavy chain and the antibody light chain is introduced into dhfr⁻ CHO cells by means of calcium phosphate-mediated transfection. Within the recombinant expression vector, the genes for the heavy and light antibody chains are in each case operatively linked to regulatory CMV enhancer/AdMLP-promoter elements in order to effect strong transcription of said genes. The recombinant expression vector also carries a DHFR gene which can be used for selecting dhfr CHO cells transfected with the vector by using methotrexate selection/amplification. The selected transformed host cells are cultured so that the heavy and light antibody chains are expressed, and intact antibody is isolated from the culture medium. Standardized molecular-biological techniques are used in order to prepare the recombinant expression vector, to transfect the host cells, to select the transformants, to culture said host cells, and to obtain the antibody from the culture medium. Thus the invention relates to a method of synthesizing a recombinant antibody of the invention by culturing a host cell of the invention in a suitable culture medium until a recombinant antibody of the invention has been synthesized. The method may furthermore comprise isolating said recombinant antibody from said culture medium.

As an alternative to screening recombinant antibody libraries by phage display, other methods known to the skilled worker may be used for screening large combinatorial libraries to identify the antibodies of the invention. Basically, any expression system in which a close physical linkage between a nucleic acid and the antibody encoded thereby is established and may be used to select a suitable nucleic acid sequence by virtue of the properties of the antibody it encodes may be employed.

In one type of an alternative expression system, the recombinant antibody library is expressed in the form of RNA-protein fusions, as described in WO 98/31700 to Szostak and Roberts, and in Roberts, R. W. and Szostak, J. W. (1997) *Proc. Natl. Acad. Sci. USA* 94:12297-12302. In this system, in-vitro translation of synthetic mRNAs carrying on their 3' end puromycin, a peptidyl acceptor antibiotic, generates a covalent fusion of an mRNA and the peptide or protein encoded by it. Thus a specific mRNA of a complex mixture of mRNAs (e.g. a combinatorial library) may be concentrated on the basis of the properties of the encoded peptide or protein (e.g. of the antibody or a moiety thereof), such as binding of said antibody or said moiety thereof to Aβ(20-42) globulomer or a derivative thereof. Nucleic acid sequences which encode antibodies or moieties thereof and which are obtained by screening of such libraries may be expressed by recombinant means in the above-described manner (e.g. in mammalian host cells) and may, in addition, be subjected to further affinity maturation by either screening in further rounds mRNA-peptide fusions, introducing mutations into the originally selected sequence(s), or using other methods of in-vitro affinity maturation of recombinant antibodies in the above-described manner.

Combinations of In-Vivo and In-Vitro Approaches

The antibodies of the invention may likewise be produced by using a combination of in-vivo and in-vitro approaches such as methods in which Aβ(20-42) globulomer or a derivative thereof is first allowed to act on an antibody repertoire in a host animal in vivo to stimulate production of Aβ(20-42) globulomer- or derivative-binding antibodies and then further antibody selection and/or antibody maturation (i.e. optimization) are accomplished with the aid of one or more in-vitro techniques. According to one embodiment, a combined method of this kind may comprise firstly immunizing a nonhuman animal (e.g. a mouse, rat, rabbit, chicken, camelid, sheep or goat or a transgenic version thereof or a chimeric mouse) with said Aβ(20-42) globulomer or derivative thereof to stimulate an antibody response to the antigen and then preparing and screening a phage display antibody library by using immunoglobulin sequences of lymphocytes which have been stimulated in vivo by the action of said Aβ(20-42) globulomer or derivative. The first step of this combined procedure may be carded out in the manner described above in connection with the in-vivo approaches, while the second step of this procedure may be carried out in the manner described above in connection with the in-vitro approaches. Preferred methods of hyperimmunizing nonhuman animals with subsequent in-vitro screening of phage display libraries prepared from said stimulated lymphocytes include those described by BioSite Inc., see, for example, WO 98/47343, WO 91/17271, U.S. Pat. No. 5,427,908 and U.S. Pat. No. 5,580,717.

According to another embodiment, a combined method comprises firstly immunizing a nonhuman animal (e.g. a mouse, rat, rabbit, chicken, camelid, sheep, goat or a knockout and/or transgenic version thereof, or a chimeric mouse) with an Aβ(20-42) globulomer of the invention or derivative thereof to stimulate an antibody response to said Aβ(20-42) globulomer or derivative thereof and selecting the lymphocytes which produce the antibodies having the desired specificity by screening hybridomas (prepared, for example, from the immunized animals). The genes for the antibodies or single domain antibodies are Isolated from the selected clones (by means of standardized cloning methods such as reverse transcriptase polymerase chain reaction) and subjected to in-vitro affinity maturation in order to improve thereby the binding properties of the selected antibody or the selected antibodies. The first step of this procedure may be conducted in the manner described above in connection with the in-vivo approaches, while the second step of this procedure may be conducted in the manner described above in connection with the in-vitro approaches, in particular by using methods of in-vitro affinity maturation, such as those described in WO 97/29131 and WO 00/56772.

In a further combined method, the recombinant antibodies are generated from individual isolated lymphocytes by using a procedure which is known to the skilled worker as selected lymphocyte antibody methods (SLAM) and which is described in U.S. Pat. No. 5,627,052, WO 92/02551 and Babcock, J. S. et al. (1996) *Proc. Natl. Acad. Sci. USA* 93:7843-7848. In this method, a non-human animal (e.g. a mouse, rat, rabbit, chicken, camelid, sheep, goat, or a transgenic version thereof, or a chimeric mouse) is firstly immunized in vivo with Aβ(20-42) globulomer or a derivative thereof to stimulate an immune response to said oligomer or derivative, and then individual cells secreting antibodies of interest are selected by using an antigen-specific haemolytic plaque assay. To this end, the globulomer or derivative thereof or structurally related molecules of interest may be coupled to sheep erythrocytes, using a linker such as biotin, thereby making it possible to identify individual cells secreting antibodies with suitable specificity by using the haemolytic plaque assay. Following the identification of cells secreting antibodies of interest, cDNAs for the variable regions of the light and heavy chains are obtained from the cells by reverse transcriptase PCR, and said variable regions may then be expressed in association with suitable immunoglobulin constant regions (e g. human constant regions) in mammalian host cells such as COS or CHO cells. The host cells transfected with the amplified immunoglobulin sequences derived from in vivo-selected lymphocytes may then be subjected to further in-vitro analysis and in-vitro selection by spreading out the transfected cells, for example, in order to isolate cells expressing antibodies with the binding affinity. The amplified immunoglobulin sequences may furthermore be manipulated in vitro.

Antibodies having the required affinities defined herein can be selected by performing a dot blot essentially as described above. Briefly, the antigen is attached to a solid matrix, preferably dotted onto a nitrocellulose membrane, in serial dilutions. The immobilized antigen is then contacted with the antibody of interest followed by detection of the latter by means of an enzyme-conjugated secondary antibody and a colorimetric reaction; at defined antibody and antigen concentrations, the amount of antibody bound allows affinity determination. Thus the relative affinity of two different antibodies to one target, or of one antibody to two different targets, is here defined as the relation of the respective amounts of target-bound antibody observed with the two antibody-target combinations under otherwise identical dot blot conditions.

Antibodies which bind to the same epitope as monoclonal antibody 5F7, 10F11, 7C6, 4B7, 6A2, 2F2, 4D10, 7E5, 10C1, or 3B10 can be obtained in a manner known per se.

In the same way as antibodies may be competing, described above, different target structures are herein said to be "competing" for a particular antibody if at least one of these structures is capable of specifically reducing the measurable binding of another, preferably by offering an overlapping or identical epitope, more preferably an identical epitope.

Competing target entities are useful for directly selecting antibodies by virtue of their relative affinity to such target structures. Relative affinities may thus be determined directly by using a competition assay in which distinguishable forms of the competing entities, e. g. differently labelled competing structures, are contacted with the antibody of interest, and the relative affinity of the antibody to each of these entities is deduced from the relative amounts of these entities which are bound by the antibody.

Such competition may be used to directly enrich for antibodies possessing a desired relative affinity to the target entity, by attaching the entity towards which greater affinity is desired to a solid matrix support and adding a suitable amount, preferably a molar excess, of the competing entity towards which smaller affinity is desired to the medium. Thus, the antibodies displaying the desired relative affinities will tend to bind to the matrix more strongly than others and may be obtained after washing out the less desirable forms, e. g. by washing out at low salt concentrations and then harvesting the bound antibody by reversibly detaching it from its target by using high salt concentrations. If desired, several rounds of enrichment may be performed. In a particular embodiment of the invention, where the genotype underlying an antibody is physically linked to this antibody, e. g. in a pool of hybridomas or antigen-displaying phages or yeast cells, the corresponding phenotype may be rescued.

In another embodiment of the invention, a modified dot blot is used where the immobilized antigen competes with a solved entity for antibody binding, so that the relative affinity of the antibody can be deduced from the percentage bound to the immobilized antigen.

Antibody moieties such as Fab and F(ab')$_2$ fragments may be produced from whole antibodies by using conventional techniques such as digestion with papain or pepsin. In addition, antibodies, antibody moieties and immunoadhesion molecules may be obtained by using standardized recombinant DNA techniques.

The present invention also relates to pharmaceutical agents (compositions) comprising an antibody of the invention and, optionally, a pharmaceutically suitable carrier. Pharmaceutical compositions of the invention may furthermore contain at least one additional therapeutic agent, for example one or more additional therapeutic agents for the treatment of a disease for whose relief the antibodies of the invention are useful. If, for example, the antibody of the Invention binds to a globulomer of the invention, the pharmaceutical composition may furthermore contain one or more additional therapeutic agents useful for the treatment of disorders in which the activity of said globulomer is important.

Pharmaceutically suitable carriers include any solvents, dispersing media, coatings, antibacterial and antifungal agents, isotonic and absorption-delaying agents, and the like, as long as they are physiologically compatible. Pharmaceutically acceptable carriers include, for example, water, saline, phosphate-buffered saline, dextrose, glycerol, ethanol and the like, and combinations thereof. In many cases, preference is given to using isotonic agents, for example sugars, polyalcohols such as mannitol or sorbitol, or sodium chloride in addition. Pharmaceutically suitable carriers may furthermore contain relatively small amounts of auxiliary substances such as wetting agents or emulsifiers, preservatives or buffers, which increase the half life or efficacy of the antibodies.

The pharmaceutical compositions may be suitable for parenteral administration, for example. Here, the antibodies are prepared preferably as Injectable solutions with an antibody content of 0.1-250 mg/ml. The injectable solutions may be prepared in liquid or lyophilized form, the dosage form being a flint glass or vial, an ampoule or a filled syringe. The buffer may contain L-histidine (1-50 mM, preferably 5-10 mM) and have a pH of 5.0-7.0, preferably of 6.0. Further suitable buffers include, without being limited thereto, sodium succinate, sodium citrate, sodium phosphate or potassium phosphate buffers. Sodium chloride may be used in order to adjust the tonicity of the solution to a concentration of 0-300 mM (preferably 150 mM for a liquid dosage form). Cryoprotectants, for example sucrose (e g. 0-10%, preferably 0.5-1.0%) may also be included for a lyophilized dosage form. Other suitable cryoprotectants are trehalose and lactose. Fillers, for example mannitol (e.g. 1-10%, preferably 2-4%) may also be included for a lyophilized dosage form. Stabilizers, for example L-methionine (e.g. 51-50 mM, preferably 5-10 mM) may be used both in liquid and lyophilized dosage forms. Further suitable fillers are glycine and arginine. Surfactants, for example polysorbate 80 (e. g. 0-0.05%, preferably 0.005-0.01%), may also be used. Further surfactants are polysorbate 20 and BRIJ surfactants.

The compositions of the invention may have a multiplicity of forms. These Include liquid, semi-solid and solid dosage forms, such as liquid solutions (e.g. injectable and Infusible solutions), dispersions or suspensions, tablets, pills, powders, liposomes and suppositories. The preferred form depends on the intended type of administration and on the therapeutic application. Typically, preference is given to compositions in the form of injectable or infusible solutions, for example compositions which are similar to other antibodies for passive immunization of humans. The preferred route of administration is parenteral (e.g. intravenous, subcutaneous, intraperitoneal or intramuscular). According to a preferred embodiment, the antibody is administered by intravenous infusion or injection. According to another preferred embodiment, the antibody is administered by Intramuscular or subcutaneous injection.

Therapeutic compositions must typically be sterile and stable under preparation and storage conditions. The compositions may be formulated as solutions, microemulsions, dispersions, liposomes or other ordered structures suitable for high concentrations of active substance. Sterile injectable solutions may be prepared by introducing the active compound (i.e. the antibody) in the required amount into a suitable solvent, where appropriate with one or a combination of the abovementioned ingredients, as required, and then sterile-filtering said solution. Dispersions are usually prepared by introducing the active compound into a sterile vehicle containing a basic dispersion medium and, where appropriate, other required ingredients. In the case of a sterile lyophilized powder for preparing sterile injectable solutions, vacuum drying and spray drying are preferred methods of preparation, which produces a powder of the active ingredient and, where appropriate, of further desired ingredients from a previously sterile-filtered solution. The correct flowability of a solution may be maintained by using, for example, a coating such as lecithin, by maintaining, in the case of dispersions the required particle size or by using surfactants. A prolonged absorption of injectable compositions may be achieved by additionally introducing into the composition an agent which delays absorption, for example monostearate salts and gelatine.

The antibodies of the invention may be administered by a multiplicity of methods known to the skilled worker, although the preferred type of administration for many therapeutic applications is subcutaneous injection, Intravenous injection or infusion. The skilled worker will appreciate that the route and/or type of administration depend on the result desired According to particular embodiments, the active compound may be prepared with a carrier which protects the compound against rapid release, such as, for example, a formulation with sustained or controlled release, which includes implants, transdermal plasters and microencapsulated release systems. Biologically degradable biocompatible polymers such as ethylene vinyl acetate, polyanhydrides, polyglycolic acid, collagen, polyorthoesters and polylactic acid may be used. The methods of preparing such formulations are well known to the skilled worker; see, for example, *Sustained and Controlled Release Drug Delivery Systems*, J. R. Robinson, ed., Marcel Dekker, Inc., New York, 1978.

According to particular embodiments, an antibody of the invention may be administered orally, for example in an inert diluent or a metabolizable edible carrier. The antibody (and further ingredients, if desired) may also be enclosed in a hard or soft gelatine capsule, compressed to tablets or added directly to food. For oral therapeutic administration, the antibodies may be mixed with excipients and used in the form of oral tablets, buccal tablets, capsules, elixirs, suspensions, syrups and the like. If it is intended to administer an antibody of the invention via a route other than the parenteral one, it may be necessary to choose a coating from a material which prevents its inactivation.

The present invention also relates to a method of inhibiting the activity of globulomers of the invention in an individual which suffers from a disorder in which the amyloid β protein is involved and in which in particular the activity of said globulomers of the invention is important Said method comprises the administration of at least one antibody of the invention to the individual with the aim of inhibiting the activity of the globulomer to which the antibody binds. Said individual is preferably a human being. An antibody of the invention may be administered for therapeutic purposes to a human individual. In addition, an antibody of the invention may be administered to a nonhuman mammal for veterinary purposes or within the framework of an animal model for a particular disorder. Such animal models may be useful for evaluating the therapeutic efficacy of antibodies of the invention (for example for testing dosages and time courses of administration).

Disorders in which the globulomers of the invention play a part include in particular disorders in whose development and/or progression a globulomer of the invention is involved. These are in particular those disorders in which globulomers of the invention are evidently or presumably responsible for the pathophysiology of said disorder or are a factor which contributes to the development and/or progression of said disorder. Accordingly, those disorders are included here in which inhibition of the activity of globulomers of the Invention can relieve symptoms and/or progression of the disorder. Such disorders can be verified, for example, by an increased concentration of globulomers of the invention in a biological fluid of an individual suffering from a particular disorder (e g. Increased concentration in serum, plasma, CSF, urine, etc.). This may be detected, for example, by using an antibody of the invention. The globulomers of the invention play an important part in the pathology associated with a multiplicity of disorders in which neurodegenerative elements, cognitive deficiencies, neurotoxic elements and inflammatory elements are involved.

In another aspect of the Invention, disorders that can be treated or prevented include those associated with amyloidoses. The term "amyloidoses" here denotes a number of disorders characterized by abnormal folding, dumping, aggregation and/or accumulation of particular proteins (amyloids, fibrous proteins and their precursors) in various tissues of the body. In Alzheimer's disease and Down's syndrome, nerve tissue is affected, and in cerebral amyloid angiopathy (CAA) blood vessels are affected.

The pharmaceutical compositions of the invention may include a "therapeutically effective amount" or a "prophylactically effective amount" of an antibody or antibody moiety of the invention. A "therapeutically effective amount" refers to an amount effective, at dosages and for periods of time necessary, to achieve the desired therapeutic result. A therapeutically effective amount of the antibody or antibody moiety may be determined by a person skilled in the art and may vary according to factors such as the disease state, age, sex, and weight of the individual, and the ability of the antibody or antibody moiety to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result Typically, since a prophylactic dose is used in subjects prior to or at an earlier stage of disease, the prophylactically effective amount will be less than the therapeutically effective amount.

Moreover, the present invention includes a further method of preventing or treating Alzheimer's disease in a patient in need of such prevention or treatment. This method comprises the step of administering the vaccine noted above to the patient in an amount sufficient to effect the prevention or treatment.

Further, the present invention encompasses a method of identifying compounds suitable for active immunization of a patient predicted to develop an amyloidosis, e.g. Alzheimer's disease. This method comprises: 1) exposing one or more compounds of interest to one or more of the antibodies described above for a time and under conditions sufficient for the one or more compounds to bind to the antibody or antibodies; 2) identifying those compounds which bind to the antibody or antibodies, the identified compounds to be used in active immunization in a patient predicated to develop an amyloidosis, e.g. Alzheimer's disease.

Within the framework of diagnostic usage of the antibodies, qualitative or quantitative specific globulomer determination serves in particular to diagnose disease-relevant amyloid β forms In this context, specificity means the possibility of being able to detect a particular globulomer or a derivative thereof, or a mixture thereof with sufficient sensitivity. The antibodies of the invention advantageously have detection threshold concentrations of less than 10 ng/ml of sample, preferably of less than 1 ng/ml of sample and particularly preferably of less than 100 pg/ml of sample, meaning that at least the concentration of globulomer per ml of sample, indicated in each case, advantageously also lower concentrations, can be detected by the antibodies of the invention.

The detection is carried out immunologically. This may be carried out in principle by using any analytical or diagnostic assay method in which antibodies are used, including agglutination and precipitation techniques, immunoassays, immunohistochemical methods and immunoblot techniques, for example Western blotting or, preferably, dot blot methods. In vivo methods, for example imaging methods, are also included here.

The use in immunoassays is advantageous. Competitive immunoassays, i.e. assays where antigen and labelled antigen (tracer) compete for antibody binding, and sandwich immunoassays, i.e. assays where binding of specific antibodies to the antigen is detected by a second, usually labelled antibody, are both suitable. These assays may be either homogeneous, i.e. without separation into solid and liquid phases, or heterogeneous, i.e. bound labels are separated from unbound ones, for example via solid phase-bound antibodies. Depending on labelling and method of measurement, the various heterogeneous and homogeneous immunoassay formats can be classified into particular classes, for example RIAs (radioimmunoassays), ELISA (enzyme-linked Immunosorbent assay), FIA (fluorescence immunoassay), LIA (luminescence immunoassay), TRFIA (time-resolved FIA), IMAC (immunoactivation), EMIT (enzyme-multiplied immune test), TIA (turbidometric immunoassay), I-PCR (immuno-PCR).

For the globulomer quantification of the invention, preference is given to competitive immunoassays in which a defined amount of labelled globulomer derivative serving as tracer competes with the globulomer of the sample (containing an unknown amount of unlabelled globulomers) to be quantified for binding to the antibody used. The amount of antigen, i.e. the amount of globulomer, in the sample can be determined from the amount of the displaced tracer with the aid of a standard curve.

Of the labels available for these purposes, enzymes have proved advantageous. Systems based on peroxidases, in particular horseradish peroxidase, alkaline phosphatase and β-D-galactosidase, may be used, for example. Specific substrates whose conversion can be monitored photometrically, for example, are available for these enzymes. Suitable substrate systems are based on p-nitrophenyl phosphate (p-NPP), 5-bromo-4-chloro-3-indolyl phosphate/nitroblue tetrazolium (BCIP/NPT), Fast-Red/naphthol-AS-TS phosphate for alkaline phosphatase; 2,2-azinobis(3-ethylbenzothiazoline-6-sulfonic acid) (ABTS), o-phenylenediamine (OPT), 3,3',5,5'-tetramethylbenzidine (TMB), o-dianisidine, 5-aminosalicylic acid, 3-dimethylaminobenzoic acid (DMAB) and 3-methyl-2-benzothiazolinehydrazone (MBTH) for peroxidases; o-nitrophenyl-β-galactoside (o-NPG), p-nitrophenyl-β-D-galactoside and 4-methylumbelliphenyl-β-D-galactoside (MUG) for β-D-galactosidase. In many cases, these substrate systems are commercially available in a ready-to-use form, for example in the form of tablets which may also contain further reagents such as appropriate buffers and the like.

The tracers used may be labelled globulomers. In this sense, a particular globulomer can be determined by labelling the globulomer to be determined and using it as tracer.

The coupling of labels to globulomers for preparing tracers may be carried out in a manner known per se. The comments above on derivatization of globulomers of the invention are referred to by analogy. In addition, a number of labels appropriately modified for conjugation to proteins are available, for example biotin-, avidin-, extravidin- or streptavidin-conjugated enzymes, maleimide-activated enzymes and the like. These labels may be reacted directly with the oligomer or, if required, with the appropriately derivatized globulomer to give the tracer. If, for example, a streptavidin-peroxidase conjugate is used, then this firstly requires biotinylation of the globulomer. This applies correspondingly to the reverse order. Suitable methods to this end are also known to the skilled worker.

If a heterogeneous immunoassay format is chosen, the antigen-antibody complex may be separated by binding it to the support, for example via an anti-idiotypical antibody coupled to said support, e.g. an antibody directed against rabbit IgG. Appropriate supports, in particular microtiter plates coated with appropriate antibodies, are known and partly commercially available.

The present invention further relates to immunoassay sets having at least one antibody as described above and further components. Said sets are, usually in the form of a packaging unit, a combination of means for carrying out a globulomer determination of the invention. For the purpose of as easy handling as possible, said means are preferably provided in an essentially ready-to-use form. An advantageous arrangement offers the immunoassay in the form of a kit. A kit usually comprises multiple containers for separate arrangement of components. All components may be provided in a ready-to-use dilution, as a concentrate for diluting or as a dry substance or lyophilisate for dissolving or suspending; individual or all components may be frozen or stored at room temperature until use. Sera are preferably shock-frozen, for example at −20° C. so that in these cases an immunoassay has to be kept preferably at temperatures below freezing prior to use.

Further components supplied with the immunoassay depend on the type of said immunoassay. Usually, standard protein, tracer which may or may not be required and control serum are supplied together with the antiserum. Furthermore, microtiter plates, preferably antibody-coated, buffers, for example for testing, for washing or for conversion of the substrate, and the enzyme substrate itself may also be included.

General principles of immunoassays and generation and use of antibodies as auxiliaries in laboratory and hospital can be found, for example, in Antibodies, A Laboratory Manual (Harlow, E., and Lane, D., Ed., Cold Spring Harbor Laboratory, Cold Spring Harbor, N.Y., 1988).

Thus, the present invention also includes a method of diagnosing an amyloidosis, e.g. Alzheimer's disease, in a patient suspected of having this disease. This method comprises the steps of: 1) Isolating a biological sample from the patient; 2) contacting the biological sample with at least one of the antibodies described above for a time and under conditions sufficient for formation of antigen/antibody complexes; and 3) detecting presence of the antigen/antibody complexes in said sample, presence of the complexes indicating a diagnosis of an amyloidosis, e.g. Alzheimer's disease, in the patient. The antigen may be, for example, an globulomer or a portion or fragment thereof which has the same functional properties as the full globulomer (e.g., binding activity).

Further, the present invention includes another method of diagnosing an amyloidosis, e.g. Alzheimer's disease in a patient suspected of having this disease. This method comprising the steps of: 1) isolating a biological sample from the patient; 2) contacting the biological sample with an antigen for a time and under conditions sufficient for the formation of antibody/antigen complexes; 3) adding a conjugate to the resulting antibodylantigen complexes for a time and under conditions sufficient to allow the conjugate to bind to the bound antibody, wherein the conjugate comprises one of the antibodies described above, attached to a signal generating compound capable of generating a detectable signal; and 4) detecting the presence of an antibody which may be present in the biological sample, by detecting a signal generated by the signal generating compound, the signal indicating a diagnosis of an amyloidosis, e.g. Alzheimer's disease in the patient. The antigen may be a globulomer or a portion or fragment thereof having the same functional properties as the full globulomer (e.g., binding activity).

The present invention includes an additional method of diagnosing an amyloidosis, e.g. Alzheimer's disease in a patient suspected of having an amyloidosis, e g. Alzheimer's disease. This method comprises the steps of: 1) isolating a biological sample from said patient; 2) contacting the biological sample with anti-antibody, wherein the anti-antibody is specific for one of the antibodies described above, for a time and under conditions sufficient to allow for formation of anti-antibody/antibody complexes, the complexes containing antibody present in the biological sample; 2) adding a conjugate to resulting anti-antibody/antibody complexes for a time and under conditions sufficient to allow the conjugate to bind to bound antibody, wherein the conjugate comprises an antigen, which binds to a signal generating compound capable of generating a detectable signal; and 3) detecting a signal generated by the signal generating compound, the signal indicating a diagnosis of an amyloidosis, e.g. Alzheimer's disease in the patient.

Also, the present invention includes a kit comprising: a) at least one of the antibodies described above and b) a conjugate comprising an antibody attached to a signal-generating compound, wherein the antibody of the conjugate is different from the isolated antibody.

The present invention also encompasses a kit comprising: a) an anti-antibody to one of the antibodies described above and b) a conjugate comprising an antigen attached to a signal-generating compound. The antigen may be a globulomer or a fragment or portion thereof having the same functional characteristics as the globulomer (e.g., binding activity).

In one diagnostic embodiment of the present invention, an antibody of the present invention, or a portion thereof, is coated on a solid phase (or is present in a liquid phase). The test or biological sample (e.g., whole blood, cerebrospinal fluid, serum, etc.) is then contacted with the solid phase. If antigen (e.g., globulomer) is present in the sample, such antigens bind to the antibodies on the solid phase and are then detected by either a direct or indirect method. The direct method comprises simply detecting presence of the complex itself and thus presence of the antigens. In the indirect method, a conjugate is added to the bound antigen. The conjugate comprises a second antibody, which binds to the bound antigen, attached to a signal-generating compound or label. Should the second antibody bind to the bound antigen, the signal-generating compound generates a measurable signal. Such signal then indicates presence of the antigen in the test sample.

Examples of solid phases used in diagnostic immunoassays are porous and non-porous materials, latex particles, magnetic particles, microparticles (see U.S. Pat. No. 5,705, 330), beads, membranes, microtiter wells and plastic tubes. The choice of solid phase material and method of labeling the antigen or antibody present in the conjugate, if desired, are determined based upon desired assay format performance characteristics.

As noted above, the conjugate (or indicator reagent) will comprise an antibody (or perhaps anti-antibody, depending upon the assay), attached to a signal-generating compound or label. This signal-generating compound or "label" is itself detectable or may be reacted with one or more additional compounds to generate a detectable product. Examples of signal-generating compounds include chromogens, radioisotopes (e.g., 125I, 131I, 32P, 3H, 35S and 14C), chemiluminescent compounds (e g., acridinium), particles (visible or fluorescent), nucleic acids, complexing agents, or catalysts such as enzymes (e.g., alkaline phosphatase, acid phosphatase, horseradish peroxidase, beta-galactosidase and ribonuclease). In the case of enzyme use (e.g., alkaline phosphatase or horseradish peroxidase), addition of a chromo-, fluro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

Examples of biological fluids which may be tested by the above immunoassays include plasma, whole blood, dried whole blood, serum, cerebrospinal fluid or aqueous or organo-aqueous extracts of tissues and cells.

The present invention also encompasses a method for detecting the presence of antibodies in a test sample. This method comprises the steps of: (a) contacting the test sample suspected of containing antibodies with anti-antibody specific for the antibodies in the patient sample under time and conditions sufficient to allow the formation of anti-antibody/antibody complexes, wherein the anti-antibody is an antibody of the present invention which binds to an antibody in the patient sample; (b) adding a conjugate to the resulting anti-antibody/antibody complexes, the conjugate comprising an antigen (which binds to the anti-antibody) attached to a signal generating compound capable of detecting a detectable signal; and (d) detecting the presence of the antibodies which may be present in the test sample by detecting the signal generated by the signal generating compound. A control or calibrator may be used which comprises antibody to the anti-antibody.

Kits are also included within the scope of the present invention. More specifically, the present invention includes kits for determining the presence of antigens (e.g., globulomers) in a patient suspected of having Alzheimer's disease or another condition characterized by cognitive impairment. In particular, a kit for determining the presence of antigens in a test sample comprises a) an antibody as defined herein or moiety thereof; and b) a conjugate comprising a second antibody (having specificity for the antigen) attached to a signal generating compound capable of generating a detectable signal. The kit may also contain a control or calibrator which comprises a reagent which binds to the antigen.

The present invention also includes a kit for detecting antibodies in a test sample. The kit may comprise a) an anti-antibody specific (for example, one of the subject invention) for the antibody of interest, and b) an antigen or portion thereof as defined above. A control or calibrator comprising a reagent which binds to the antigen may also be included. More specifically, the kit may comprise a) an anti-antibody (such as the one of the present invention) specific for the antibody and b) a conjugate comprising an antigen (e.g., globulomer) attached to a signal generating compound capable of generating a detectable signal. Again, the kit may also comprise a control of calibrator comprising a reagent which binds to the antigen.

The kit may also comprise one container such as vial, bottles or strip, with each container with a pre-set solid phase, and other containers containing the respective conjugates. These kits may also contain vials or containers of other reagents needed for performing the assay, such as washing, processing and indicator reagents.

It should also be noted that the subject invention not only includes the full length antibodies described above but also moieties or fragments thereof, for example, the Fab portion thereof. Additionally, the subject invention encompasses any antibody having the same properties of the present antibodies in terms of, for example, binding specificity, structure, etc.

Advantages of the Invention:

By immunization with Aβ(20-42) globulomer different monoclonal antibodies may be obtained which differ in their tolerance or recognition of different Aβ(1-42) oligomers and Aβ(X-42) oligomers, as determined by comparative dot blotting as described above. This allows development of an antibody directed to N-terminally truncated Aβ oligomers which possesses an optimal relation between cognition enhancing effect, desired specificity over other Aβ forms and minimal side effect profile. Surprisingly, the Aβ(1-42) and Aβ(12-42) globulomers, in spite of containing the structural element, are only partly recognized by antibodies obtained by using the further truncated Aβ(20-42) globulomer as antigen.

By restriction of the specific oligomeric Aβ form to the basic structural principle (i.e. use of the N-terminally truncated Aβ globulomers) an antibody profile is generated in active immunization which is highly specific for oligomeric Aβ forms. The same holds true for monoclonal antibodies for use in passive immunization. The advantage of such a specific strategy for immunization (active and passive) is that it will not induce an immune response against Aβ monomers, Aβ peptides in fibrillary states of aggregation or sAPPα. This is advantageous in several ways:

1) In the form of insoluble Aβ plaques Aβ peptides in fibrillary states of aggregation amount to the major part of the entire Aβ peptide pool in AD brains. A massive release of Aβ by dissolution of Aβ plaques induced by reaction of anti-Aβ antibodies with these plaques is to be regarded as detrimental. This massive release of Aβ would then cross the blood-brain barrier, enter the bloodstream and potentially increase the risk of microhaemorrhages. In addition, in the ELAN trial this very strategy of immunization with fibrillary Aβ peptide forms required cancellation of the trial due to 6% of cases with an onset of meningoencephalitis.

2) Immune responses directed to monomeric Aβ peptide forms are undesirable, as it was possible to show that the latter may exert cognition-enhancing effects.

3) Immune responses directed to sAPPα are likewise undesirable, as this might lead to a reaction with the physiologically occurring precursor protein APP and thus to an auto-immune reaction. Moreover, sAPPα was also shown to exert cognition-enhancing effects.

4) A response directed to vascular Aβ peptide in the form of CAA is to be avoided in order to eschew the undesirable side effect of microhaemorrhages (antibodies against the central portion of Aβ and which in addition do not bind to AP-peptides aggregated in the form of CAA induce fewer microhaemorrhages when compared to such against the N-terminus, see above).

5) Antibodies which specifically react with Aβ oligomers will have higher bioavailability with regard to the pathophysiologically relevant Aβ species, as they will not be bound to, e.g., fibrillary Aβ and thus made unavailable for therapeutic effect.

Deposit Information: The hybridoma which produces monoclonal antibody 5F7 was deposited with the American Type Culture Collection, 10801 University Boulevard, Manassas, Va. 20110 on Dec. 1, 2005 under the terms of the Budapest Treaty and received designation PTA-7241. Further, the hybridoma which produces monoclonal antibody 10F11 was deposited with the American Type Culture Collection, 10801 University Boulevard, Manassas, Va. 10801 on Dec. 1, 2005 under the terms of the Budapest Treaty and received designation PTA-7239. Additionally, the hybridoma which produces monoclonal antibody 4B7 was deposited with the American Type Culture Collection, 10801 University Boulevard, Manassas, Va. 10801 on Dec. 1, 2005 under the terms of the Budapest Treaty and received designation PTA-7242, and the hybridoma which produces monoclonal antibody 7C6 was deposited with the American Type Culture Collection, 10801 University Boulevard, Manassas, Va. 10801 on Dec. 1, 2005 under the terms of the Budapest Treaty and received designation PTA-7240. Additionally, the hybridoma which produces monoclonal antibody 6A2 was deposited with the American Type Culture Collection, 10801 University Boulevard, Manassas, Va. 10801 on Feb. 28, 2006 under the terms of the Budapest Treaty and received designation PTA-7409, and the hybridoma which produces monoclonal antibody 2F2 was deposited with the American Type Culture Collection, 10801 University Boulevard, Manassas, Va. 10801 on Feb. 28, 2006 under the terms of the Budapest Treaty and received designation PTA-7408 The hybridoma which produces monoclonal antibody 4D10 was deposited with the American Type Culture Collection, 10801 University Boulevard, Manassas, Va. 10801 on Feb. 28, 2006 under the terms of the Budapest Treaty and received designation PTA-7405. The hybridoma which produces monoclonal antibody 7E5 was deposited with the American Type Culture Collection, 10801 University Boulevard, Manassas, Va. 10801 on Aug. 16, 2006 under the terms of the Budapest Treaty and received designation PTA-7809. The hybridoma which produces monoclonal antibody 10C1 was deposited with the American Type Culture Collection, 10801 University Boulevard, Manassas, Va. 10801 on Aug. 16, 2006 under the terms of the Budapest Treaty and received designation PTA-7810. The hybridoma which produces monoclonal antibody 3B10 was deposited with the American Type Culture Collection, 10801 University Boulevard, Manassas, Va. 10801 on Sep. 1, 2006 under the terms of the Budapest Treaty and received designation PTA-7851. A1 deposits have been made on behalf of Abbott Laboratories, 100 Abbott Park Road, Abbott Park, Ill. 60064 (US).

In the drawings:

FIG. 1 shows size-exclusion chromatograms of Aβ(1-42) and Aβ(1-40). Aβ(1-42) monomer was dissolved in A) 0.1% NH$_4$OH, B) 70% formic acid C) 0.1% NaOH and in D) Aβ(1-40) was dissolved in 0.1% NaOH. Subsequently, the samples were further diluted 1:10 in 20 mM NaH$_2$PO$_4$, 140 mM NaCl, pH 7.4 These samples were incubated for 5 min (left column) or 1 hour (right column) after dissolution at ambient temperature, then applied to the size exclusion column;

FIG. 2 A) shows an SDS PAGE of standard proteins (molecular marker proteins, lane 1); Aβ(1-42) fibril preparation; control (lane 2); Aβ(1-42) fibril preparation+mAb 5F7, 20 h, 37° C., supernatant (lane 3); Aβ(1-42) fibril preparation+mAb 5F7, 20 h, 37° C., pellet (lane 4); Aβ(1-42) fibril preparation+mAb 6E10, 20 h, 37° C., supernatant (lane 5); Aβ(1-42) fibril preparation+mAb 6E10, 20 h 37° C., pellet (lane 6););

B) shows the results of the quantitative analysis of mAbs bound to Aβ-fibrils in percent of total antibody;

FIG. 3 is a bar diagram which shows the results of the object recognition test with APP/L transgenic mice after active immunization with Aβ(1-42) monomers in 0.1% NH$_4$OH, Aβ(1-42) globulomers and Aβ(20-42) globulomers as compared to wild-type mice (positive control) and PBS-treated APP/L mice (negative control), where circles indicate significant differences to PBS-treated APP/L mice and asterisks indicate highly significant differences to chance level (50%) according to post-hoc t-test after P<0.05 in ANOVA for differences among groups;

FIG. 4 shows dot blots of the reactivity of 100 pmol/µl (row A); 10 pmol/µl (row B); 1 pmol/µl (row C), 0.1 pmol/µl (row D) and 0.01 pmol/µl (row E) of Aβ(1-42) globulomer (column 1), of HFIP pretreated Aβ(1-42) monomer in Pluronic F68 (column 2), of Aβ(20-42) globulomer (column 3), of Aβ(12-42) globulomer (column 4); of HFIP pretreated Aβ(1-40) monomer in DMSO (column 5); of Aβ(1-42) monomer, NH$_4$OH (column 6); of an Aβ(1-42) fibril preparation (column 7); and of sAPPα from Sigma (column 8) with various antisera obtained after an active immunization of APP/IL Tg mice with Aβ(20-42) globulomer;

Figure 7:
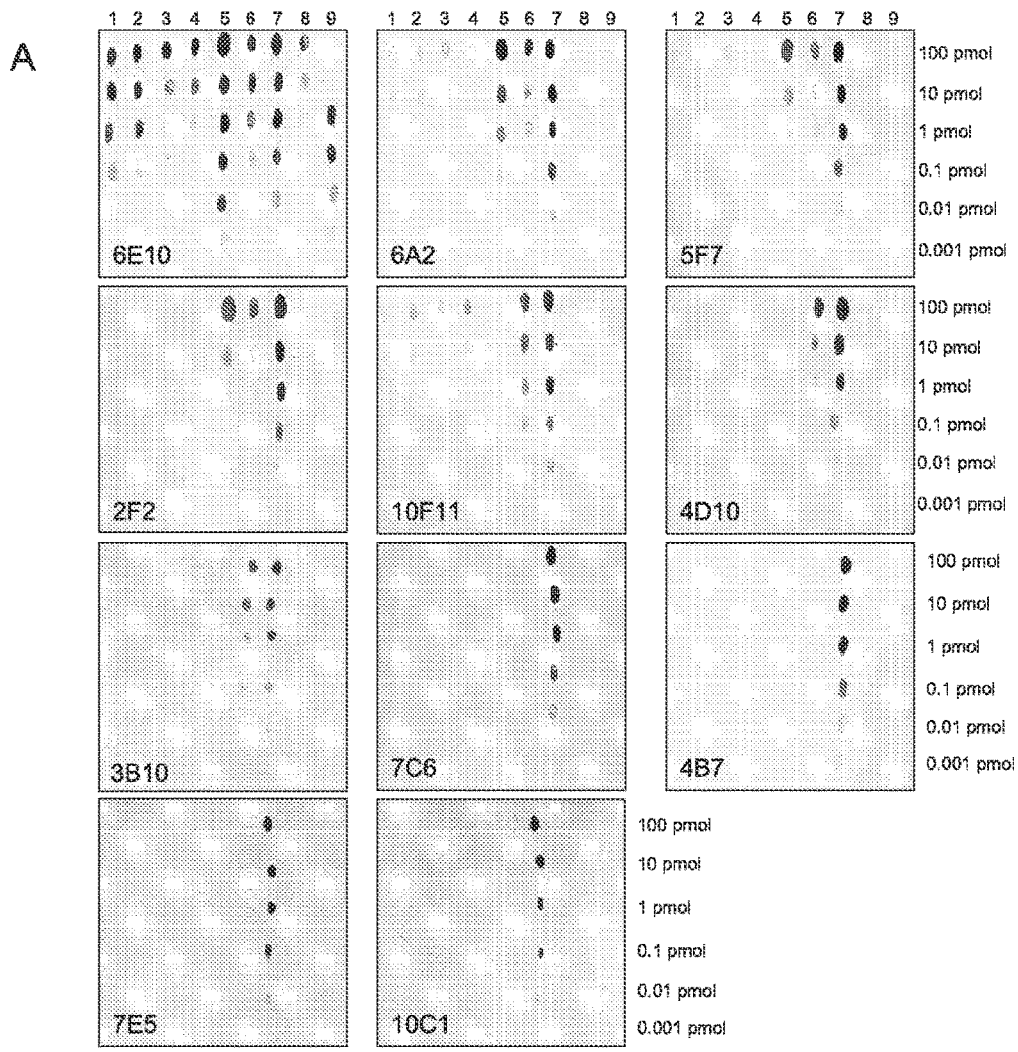

FIG. 7 A) shows a dot blot analysis of the specificity of different anti-Aβ antibodies (−6E10, −5F7, −4B7, −10F11, −6A2, −4D10, −3B10, −2F2, −7C6, −7E5, −10C1). The monoclonal antibodies tested here were obtained by active immunization of mice with Aβ(20-42) globulomer followed by selection of the fused hybridoma cells (except for the commercial available 6E10, Signet No 9320). The individual Aβ forms were applied in serial dilutions and incubated with the respective monoclonal antibodies for immune reaction:

1. Aβ(1-42) monomer, 0.1% NH$_4$OH
2. Aβ(1-40) monomer, 0.1% NH$_4$OH
3. Aβ(1-42) monomer, 0.1% NaOH
4. Aβ(1-40) monomer, 0.1% NaOH
5. Aβ(1-42) globulomer
6. Aβ(12-42) globulomer
7. Aβ(20-42) globulomer
8. Aβ(1-42) fibril preparation
9. sAPPα (Sigma) (first dot: 1 pmol)

Figure 8:
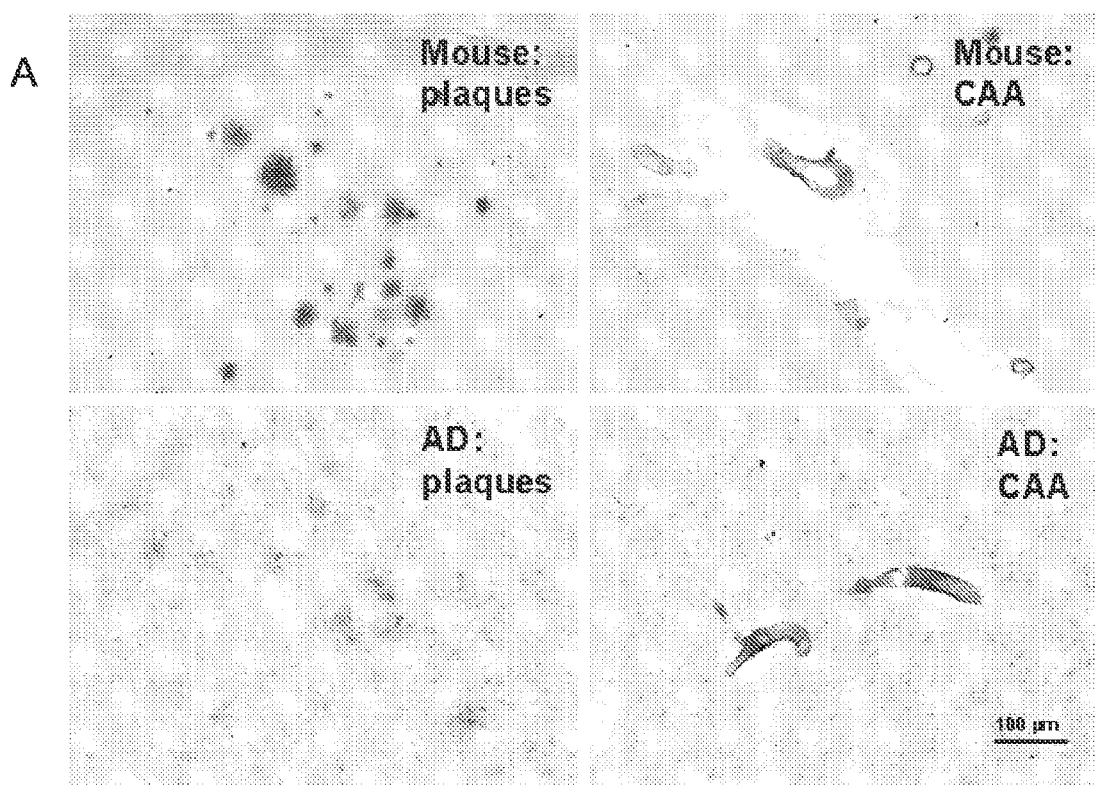
Figure 8:
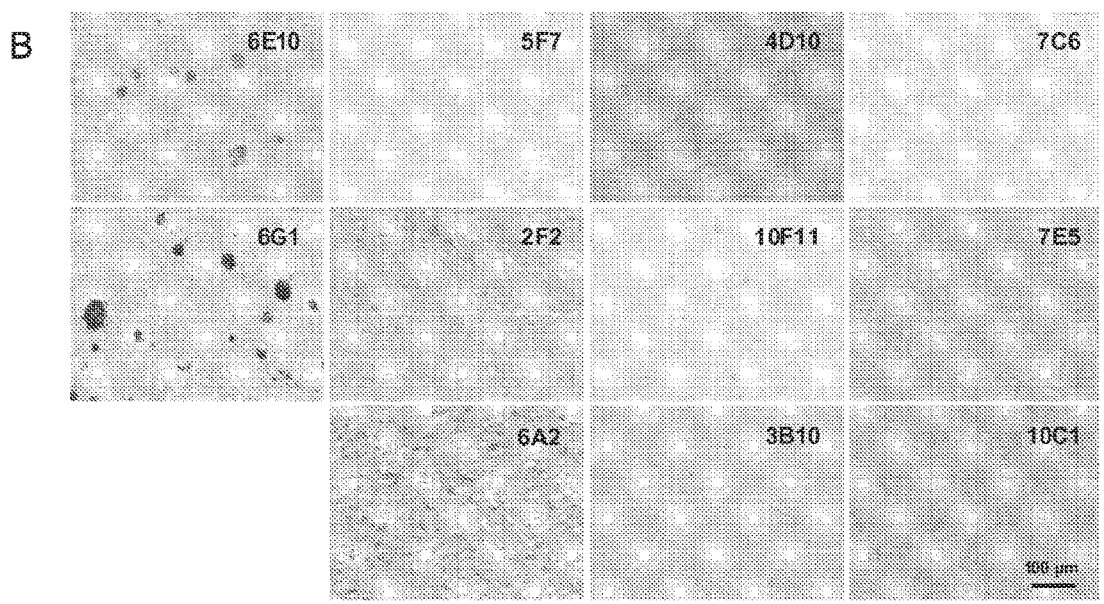
Figure 8:
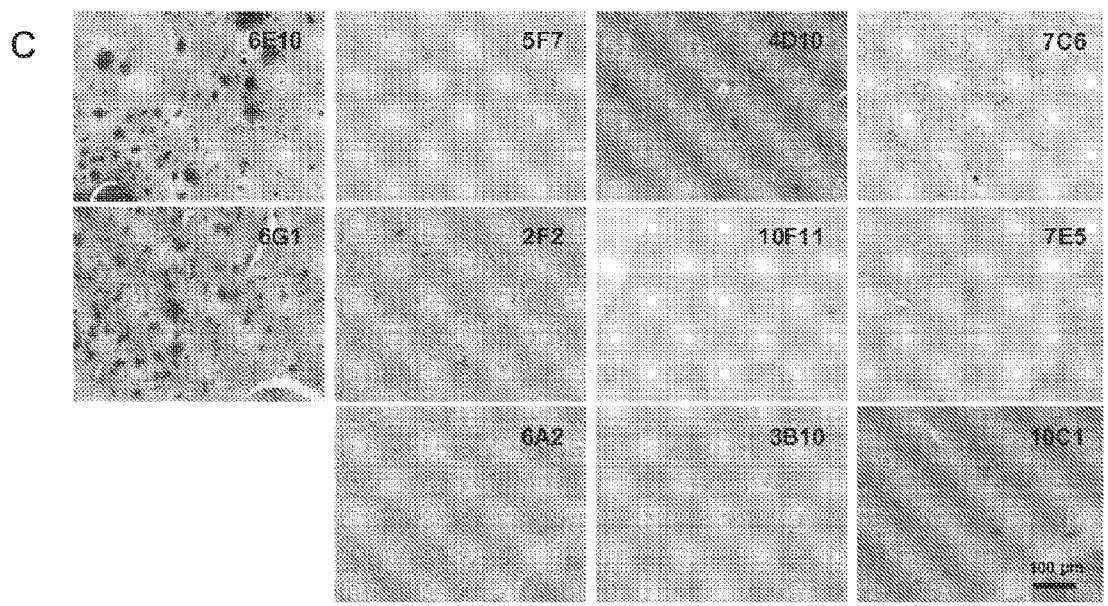
Figure 8:
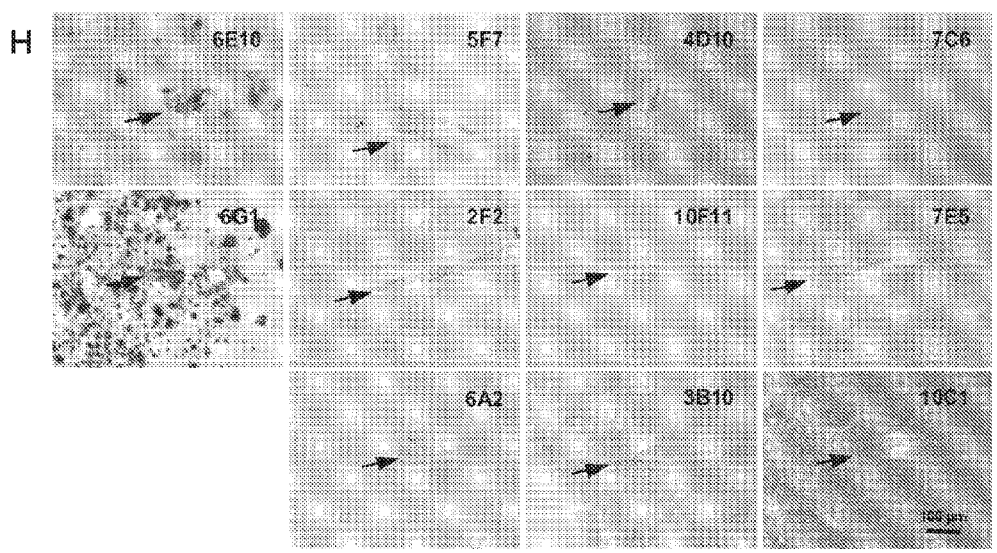

B) Quantitative evaluation was done using a densitometric analysis of the intensity. For each Aβ form, only the dot corresponding to the lowest antigen concentration was evaluated provided that it had a relative density of greater than 20% of the relative density of the last optically unambiguously Identified dot of the Aβ(20-42) globulomer (threshold). This threshold value was determined for every dot-blot independently. The value indicates the relation between recognition of Aβ(20-42) globulomer and the respective Aβ form for the antibody given;

FIG. 8 shows the binding of antibodies at different concentrations to transversal sections of the neocortices of Alzheimer's disease (AD) patients or old APP transgenic mice:

A) Verification of amyloid deposits by Congo Red staining as plaques in brain tissue and as cerebral amyloid angiopathy (CAA) in brain vessels in the APP transgenic mouse line Tg2576 and in an AD patient (RZ55);

B) Strong staining of parenchymal deposits of Aβ(amyloid plaques) in an AD patient (RZ16) occurs only with 6G1 and the commercially available antibody 6E10

(left column) while antibodies 5F7, 2F2, and 6A2 (second column), 4D10, 10F11, and 3B10 (third column) and 7C6, 7E5, and 10C1 (right column) show no staining. All antibodies were used at a concentration of 0.7 μg/ml;

C) Strong staining of parenchymal deposits of Aβ(amyloid plaques) in 19 month old Tg2576 occurs only with 6G1 and the commercially available antibody 6E10 (left column) while antibodies 5F7, 2F2, and 6A2 (second column), 4D10, 10F11, and 3B10 (third column) and 7C6, 7E5, and 10C1 (right column) show no staining. All antibodies were used at a concentration of 0.7 μg/ml;

D)-G) Quantification of the analysis of Aβ plaque staining in the histological images using image analysis. Optical density values (0%=no staining) were calculated from the greyscale values of plaques subtracted by greyscale values of background tissue: D) Staining at 0.7 μg/ml antibody in old Tg2576 mice, E) staining at 3 different concentrations of antibodies in APP/L mice, F) staining at 0.7 μg/ml antibody in an AD patient (RZ55), and G) staining at 3 different concentrations of antibodies in an AD patient (RZ16). The differences between staining of the commercially available antibodies 6E10 (asterisks) and 4G8 (circles) and all other antibodies (three asterisks/circles: p<0.001 versus control; post-hoc Bonferroni's t-test after ANOVA with p<0.001) were statistically evaluated (D, F). In E) and G) all antibodies except 6G1 showed always significantly less staining than the commercially available antibodies 6E10 and 4G8 (p<0.001 in post-hoc t-test after p<0.001 In ANOVA).

Figure 9:
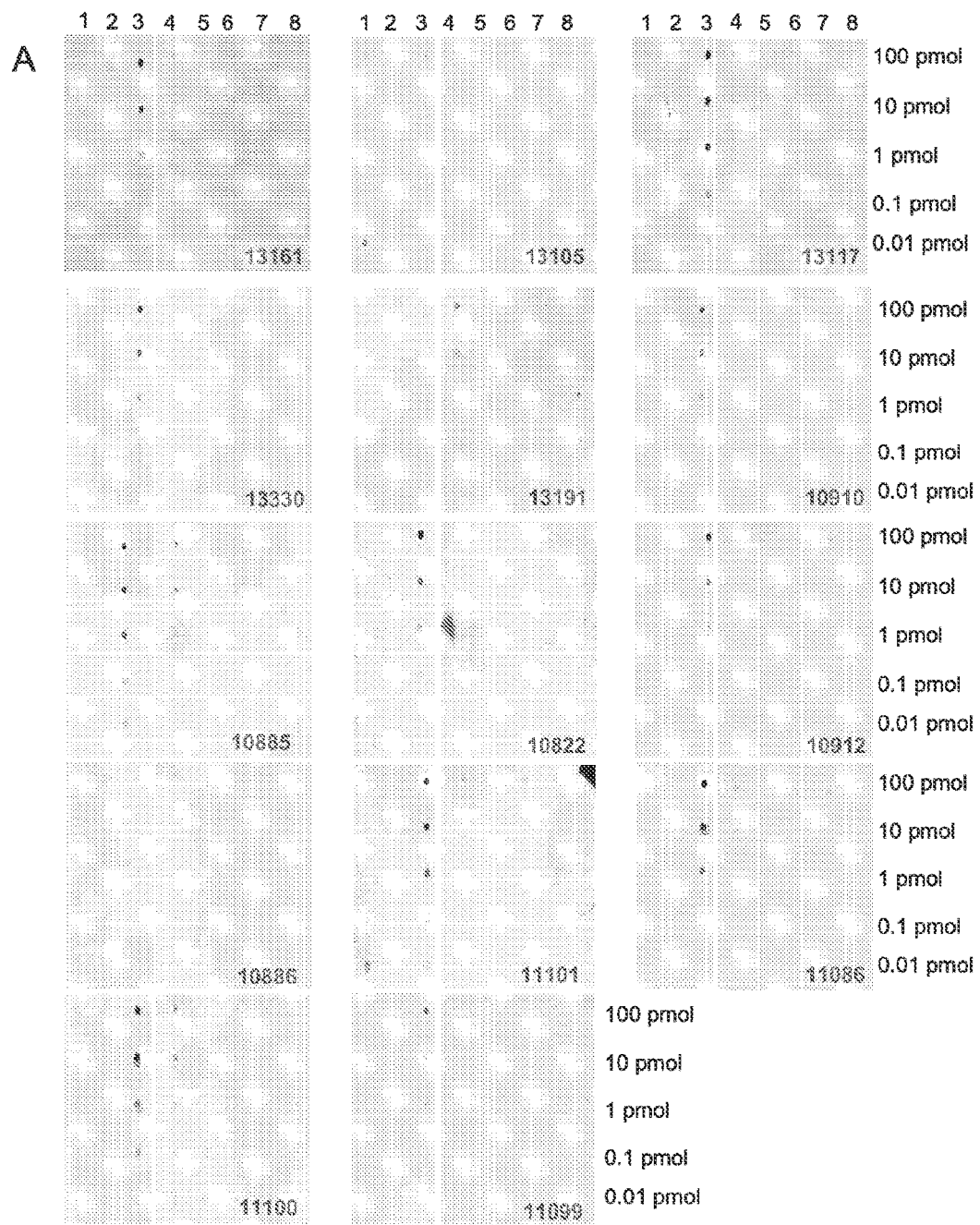
Figure 9:
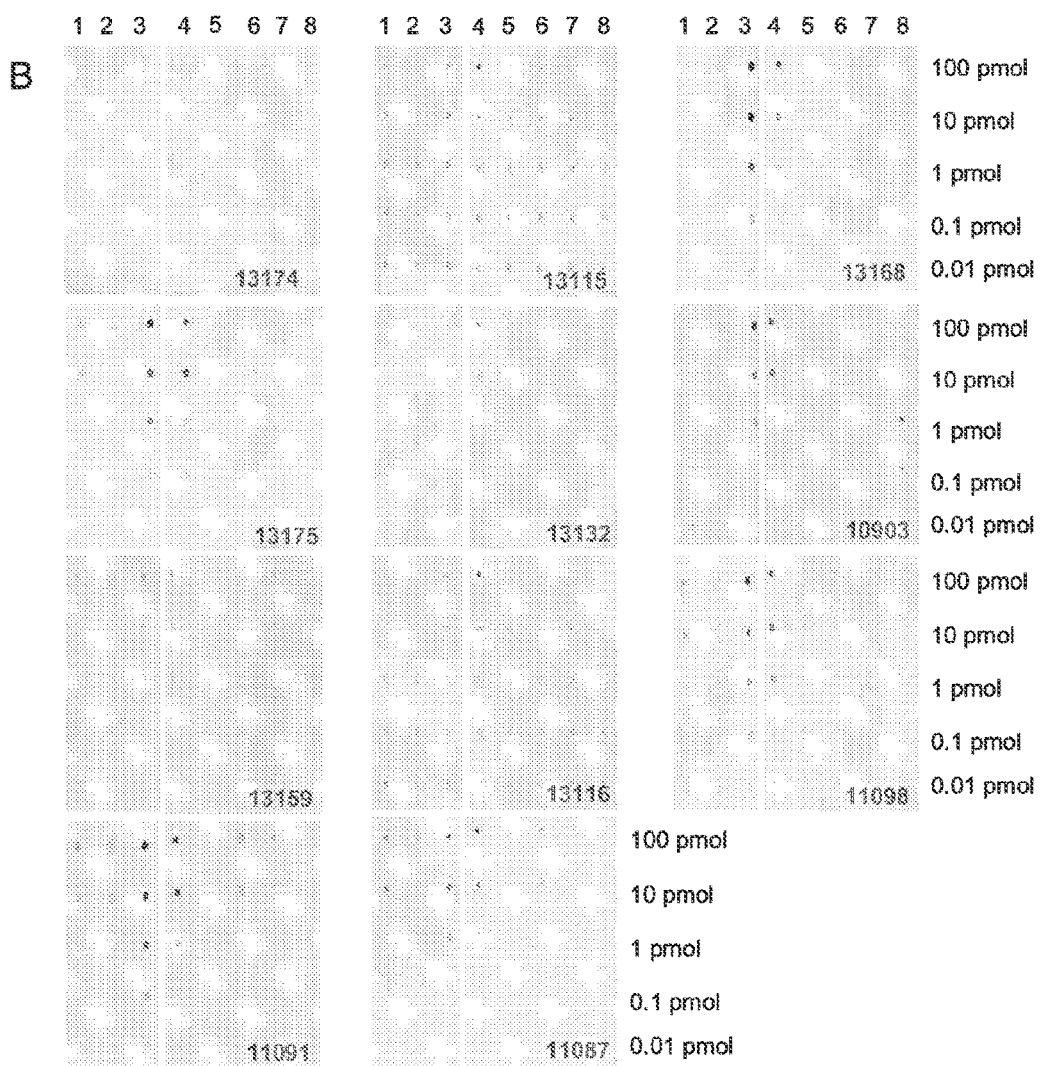
Figure 9:
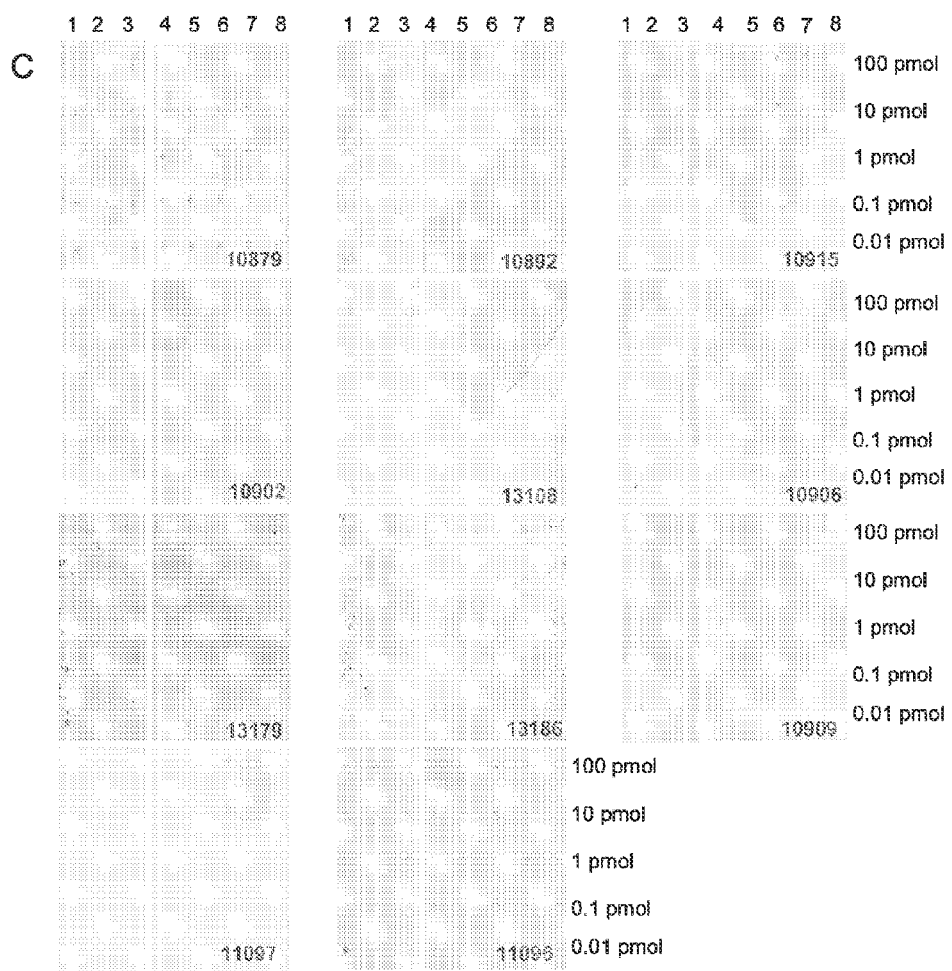
Figure 9:
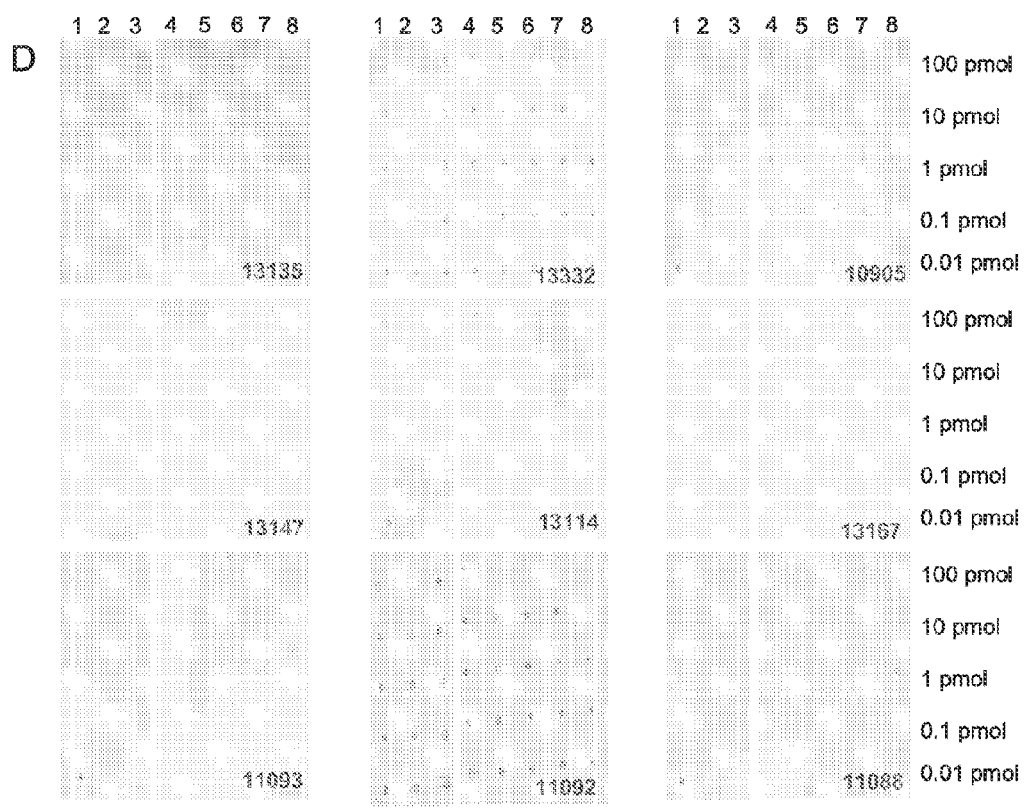

H) Strong staining of vascular deposits of Aβ (arrows) occurs only with 6G1 and the commercially available antibody 6E10 (left column) while antibodies 5F7, 2F2, and 6A2 (second column), 4D10, 10F11, and 3B10 (third column) and 7C6, 7E5, and 10C1 (right column) show no staining. All antibodies were used at a concentration of 0.7 μg/ml. A qualitatively similar situation was found in Tg2576 mice (not shown here);

FIG. 9 Anti-Aβ-antibody titer and dot-blot selectivity profile in plasma of TG2576 mice approximately one year after active immunization. Plasma samples of Tg2576-mice approximately one year after the last immunization with A) Aβ (20-42) globulomer, B) Aβ (12-42) globulomer, C) Aβ (1-42) monomer and D) vehicle, were assessed for anti-Aβ antibodies produced and still present by dot-blot.

1. Aβ (1-42) globulomer
2. Aβ (1-42) monomer, HFIP pretreated, in 0.1% Pluronic F68
3. Aβ (20-42) globulomer
4. Aβ (12-42) globulomer
5. Aβ (1-40) monomer, HFIP pre-treated, 5 mM in DMSO
6. Aβ (1-42) monomer, 0.1% NH₄OH
7. Aβ (1-42) fibril preparation
8. sAPPα (Sigma); (first dot: 1 pmol);

FIG. 10 shows a table summarizing the levels of Aβ(20-42) globulomer in brain tissue of human beings having Alzheimer's disease and a non demented control;

FIG. 11 illustrates nucleotide and amino acid sequences of the variable heavy and light chains of monoclonal antibodies (mAbs) as follows (complementarity determining regions (CDRs) are underlined in each amino acid sequence):

| FIG. 11 | SEQ ID NO: | Sequence Type | Chain | mAb |
|---|---|---|---|---|
| A1 | 1 | nucleotide | variable heavy (VH) | 5F7 |
| A2 | 2 | nucleotide | variable light (VL) | 5F7 |
| A1 | 3 | amino acid | variable heavy (VH) | 5F7 |
| A2 | 4 | amino acid | variable light (VL) | 5F7 |
| B1 | 5 | nucleotide | variable heavy (VH) | 10F11 |
| B2 | 6 | nucleotide | variable light (VL) | 10F11 |
| B1 | 7 | amino acid | variable heavy (VH) | 10F11 |
| B2 | 8 | amino acid | variable light (VL) | 10F11 |
| C1 | 9 | nucleotide | variable heavy (VH) | 7C6 |
| C2 | 10 | nucleotide | variable light (VL) | 7C6 |
| C1 | 11 | amino acid | variable heavy (VH) | 7C6 |
| C2 | 12 | amino acid | variable light (VL) | 7C6 |
| D1 | 13 | nucleotide | variable heavy (VH) | 4B7 |
| D2 | 14 | nucleotide | variable light (VL) | 4B7 |
| D1 | 15 | amino acid | variable heavy (VH) | 4B7 |
| D2 | 16 | amino acid | variable light (VL) | 4B7 |
| E1 | 17 | nucleotide | variable heavy (VH) | 2F2 |
| E2 | 18 | nucleotide | variable light (VL) | 2F2 |
| E1 | 19 | amino acid | variable heavy (VH) | 2F2 |
| E2 | 20 | amino acid | variable light (VL) | 2F2 |
| F1 | 21 | nucleotide | variable heavy (VH) | 6A2 |
| F2 | 22 | nucleotide | variable light (VL) | 6A2 |
| F1 | 23 | amino acid | variable heavy (VH) | 6A2 |
| F2 | 24 | amino acid | variable light (VL) | 6A2 |
| G1 | 25 | nucleotide | variable heavy (VH) | 4D10 |
| G2 | 26 | nucleotide | variable light (VL) | 4D10 |
| G1 | 27 | amino acid | variable heavy (VH) | 4D10 |
| G2 | 28 | amino acid | variable light (VL) | 4D10 |
| H1 | 29 | nucleotide | variable heavy (VH) | 7E5 |
| H2 | 30 | nucleotide | variable light (VL) | 7E5 |
| H1 | 31 | amino acid | variable heavy (VH) | 7E5 |
| H2 | 32 | amino acid | variable light (VL) | 7E5 |
| I1 | 33 | nucleotide | variable heavy (VH) | 10C1 |
| I2 | 34 | nucleotide | variable light (VL) | 10C1 |
| I1 | 35 | amino acid | variable heavy (VH) | 10C1 |
| I2 | 36 | amino acid | variable light (VL) | 10C1 |
| J1 | 37 | nucleotide | variable heavy (VH) | 3B10 |
| J1 | 38 | amino acid | variable heavy (VH) | 3B10 |

The following examples are intended to illustrate the invention, without limiting its scope Example 1

Preparation of Globulomers a) Aβ(1-42) Globulomer

The Aβ(1-42) synthetic peptide (H-1368, Bachem, Bubendorf, Switzerland) was suspended in 100% 1,1,1,3,3,3-hexafluoro-2-propano (HFIP) at 6 mg/mL and incubated for complete solubilization under shaking at 37° C. for 1.5 h. The HFIP acts as a hydrogen-bond breaker and is used to eliminate pre-existing structural inhomogeneities in the Aβ peptide. HFIP was removed by evaporation in a SpeedVac and Aβ(1-42) resuspended at a concentration of 5 mM in dimethylsulfoxide and sonicated for 20 s. The HFIP-pretreated Aβ(1-42) was diluted in phosphate-buffered saline (PBS) (20 mM $NaH_2PO_4$, 140 mM NaCl, pH 7.4) to 400 μM and 1/10 volume 2% sodium dodecyl sulfate (SDS) (in $H_2O$) added (final concentration of 0.2% SDS). An incubation for 6 h at 37° C. resulted in the 16/20-kDa Aβ(1-42) globulomer (short form for globular oligomer) intermediate. The 38/48-kDa Aβ(1-42) globulomer was generated by a further dilution with three volumes of $H_2O$ and incubation for 18 h at 37° C. After centrifugation at 3000 g for 20 min the sample was concentrated by ultrafiltration (30-kDa cut-off), dialysed against 5 mM $NaH_2PO_4$, 35 mM NaCl, pH 7.4, centrifuged at 10000 g for 10 min and the supernatant comprising the 38/48-kDa Aβ(1-42) globulomer withdrawn. As an alternative to dialysis the 38/48-kDa Aβ(1-42) globulomer could also be precipitated by a ninefold excess (v/v)

of ice-cold methanol/acetic acid solution (33% methanol, 4% acetic acid) for 1 h at 4° C. The 38/48-kDa Aβ(1-42) globulomer is then pelleted (10 min at 16200 g), resuspended in 5 mM $NaH_2PO_4$, 35 mM NaCl, pH 7.4, and the pH adjusted to 7.4.

b) Cross-Linked Aβ(1-42) Globulomer

The Aβ(1-42) synthetic peptide (H-1368, Bachem, Bubendorf, Switzerland) was suspended in 100% 1,1,1,3,3,3-hexafluoro-2-propanol (HFIP) at 6 mg/mL and incubated for complete solubilization under shaking at 37° C. for 1.5 h. The HFIP acts as a hydrogen-bond breaker and was used to eliminate pre-existing structural inhomogeneities in the Aβ peptide. HFIP was removed by evaporation in a Speed-Vac and Aβ(1-42) resuspended at a concentration of 5 mM in dimethylsulfoxide and sonicated for 20 s. The HFIP-pretreated Aβ(1-42) was diluted in phosphate-buffered saline (PBS) (20 mM $NaH_2PO_4$, 140 mM NaCl, pH 7.4) to 400 μM and 1/10 volume 2% sodium dodecyl sulfate (SDS) (in $H_2O$) added (final concentration of 0.2% SDS). An incubation for 6 h at 37° C. resulted in the 16/20-kDa Aβ(1-42) globulomer (short form for globular oligomer) intermediate. The 38/48-kDa Aβ(1-42) globulomer was generated by a further dilution with three volumes of $H_2O$ and incubation for 18 h at 37° C. Cross-linking of the 38/48-kDa Aβ(1-42) globulomer was now performed by incubation with 1 mM glutaraldehyde for 2 h at 21° C. room temperature (RT) followed by ethanolamine (5 mM) treatment for 30 min at RT.

c) Aβ(20-42) Globulomer 1.59 ml of Aβ(1-42) globulomer preparation prepared according to example 1a were admixed with 38 ml of buffer (50 mM MES/NaOH, pH 7.4) and 200 μl of a 1 mg/ml thermolysin solution (Roche) in water. The reaction mixture was stirred at RT for 20 h. Then 80 μl of a 100 mM EDTA solution, pH 7.4, in water were added and the mixture was furthermore adjusted to an SDS content of 0.01% with 400 μl of a 1% strength SDS solution. The reaction mixture was concentrated to approx. 1 ml via a 15 ml 30 kDa Centriprep tube. The concentrate was admixed with 9 ml of buffer (50 mM MES/NaOH, 0.02% SDS, pH 7.4) and again concentrated to 1 ml. The concentrate was dialyzed at 6° C. against 1 l of buffer (5 mM sodium phosphate, 35 mM NaCl) in a dialysis tube for 16 h. The dialysate was adjusted to an SDS content of 0.1% with a 2% strength SDS solution in water. The sample was centrifuged at 10000 g for 10 min and the Aβ(20-42) globulomer supernatant was withdrawn d) Aβ(12-42) Globulomer 2 ml of an Aβ(1-42) globulomer preparation prepared according to example 1a were admixed with 38 ml buffer (5 mM sodium phosphate, 35 mM sodium chloride, pH 7.4) and 150 μl of a 1 mg/ml GluC endoproteinase (Roche) In water. The reaction mixture was stirred for 6 h at RT, and a further 150 μl of a 1 mg/ml GluC endoproteinase (Roche) in water were subsequently added. The reaction mixture was stirred at RT for another 16 h, followed by addition of 8 μl of a 5 M DIFP solution. The reaction mixture was concentrated to approx. 1 ml via a 15 ml 30 kDa Centriprep tube. The concentrate was admixed with 9 ml of buffer (5 mM sodium phosphate, 35 mM sodium chloride, pH 7.4) and again concentrated to 1 ml. The concentrate was dialyzed at 6° C. against 1 l of buffer (5 mM sodium phosphate, 35 mM NaCl) In a dialysis tube for 16 h. The dialysate was adjusted to an SDS content of 0.1% with a 1% strength SDS solution in water. The sample was centrifuged at 10000 g for 10 min and the Aβ(12-42) globulomer supernatant was withdrawn.

Example 2

Size-Exclusion Chromatography of Different Aβ(1-42) Monomer and Aβ(1-40) Monomer Preparations

Aβ(1-42), 0.1% $NH_4OH$:

1 mg of Aβ(1-42) (Bachem, catalogue no. H-1368) were dissolved in 500 μl of 0.1% $NH_4OH$ in $H_2O$ and agitated for 1 min at ambient temperature. The sample was centrifuged for 5 min at 10,000 g. The supernatant was collected. Aβ(1-42) concentration in the supernatant was determined according to Bradford's method (BIO-RAD).

5 min sample:

20 μl of Aβ(1-42) in the 0.1% $NH_4OH$ containing supernatant were diluted with 20 mM $NaH_2PO_4$, 140 mM NaCl, pH 7.4 to an Aβ(1-42) concentration of 0.2 mg/ml. The sample was incubated for 5 min at ambient temperature. Then 100 μl were analyzed by size exclusion chromatography (SEC).

1 hour sample:

20 μl of Aβ(1-42) in the 0.1% $NH_4OH$ containing supernatant were diluted with 20 mM $NaH_2PO_4$, 140 mM NaCl, pH 7.4 to an Aβ(1-42) concentration of 0.2 mg/ml. The sample was incubated for 1 hour at ambient temperature. Then 100 μl were analyzed by size exclusion chromatography (SEC).

Aβ(1-42), 70% HCOOH:

1 mg of Aβ(1-42) were dissolved in 50 μl 70% HCOOH in $H_2O$ and agitated 1 min at ambient temperature. The sample was centrifuged for 5 min at 10,000 g. The supernatant was collected. Aβ(1-42) concentration in the supernatant is determined according to Bradford's method (BIO-RAD).

5 min sample:

2 μl of Aβ(1-42) in 70% HCOOH were diluted to a concentration of 0.2 mg/ml Aβ(1-42) with 20 mM $NaH_2PO_4$, 140 mM NaCl, pH 7.4 and adjusted to pH 7.4 with 1 M NaOH. The sample was incubated for 5 min at ambient temperature. Then 100 μl were analyzed by size exclusion chromatography.

1 hour sample:

2 μl of Aβ(1-42) in 70% HCOOH were diluted to a concentration of 0.2 mg/ml Aβ(1-42) with 20 mM $NaH_2PO_4$, 140 mM NaCl, pH 7.4 and adjusted to pH 7.4 with 1 M NaOH. The sample was incubated for 1 hour at ambient temperature. Then 100 μl were analyzed by size exclusion chromatography.

Aβ(1-42), 0.1% NaOH:

1 mg of Aβ(1-42) (Bachem, catalogue no. H-1368) were dissolved in 500 μl of 0.1% NaOH in $H_2O$ and agitated 1 min at ambient temperature. The sample was centrifuged for 5 min at 10,000 g. The supernatant was collected. Aβ(1-42) concentration in the supernatant is determined according to Bradford's method (BIO-RAD).

5 min sample:

20 μl of Aβ(1-42) in 0.1% NaOH were diluted to a concentration of 0.2 mg/ml Aβ(1-42) with 20 mM $NaH_2PO_4$, 140 mM NaCl, pH 7.4. The sample was incubated for 5 min at ambient temperature. Then 100 μl were analyzed by size exclusion chromatography.

1 hour sample:

20 μl of Aβ(1-42) in 0.1% NaOH were diluted to a concentration of 0.2 mg/ml Aβ(1-42) with 20 mM $NaH_2PO_4$, 140 mM NaCl, pH 7.4. The sample was incubated for 1 hour at ambient temperature. Then 100 μl were analyzed by size exclusion chromatography.

Aβ(1-40), 0.1% NaOH:

1 mg of Aβ(1-40) (Bachem, catalogue no. H-1194) were dissolved in 500 µl of 0.1% NaOH in H$_2$O and agitated 1 min at ambient temperature. The sample is was centrifuged for 5 min at 10,000 g. The supernatant was collected. Aβ(1-42) concentration in the supernatant was determined according to Bradford's method (BIO-RAD).

5 min sample:

20 µl of Aβ(1-40) in 0.1% NaOH were diluted to a concentration of 0.2 mg/ml Aβ(1-40) with 20 mM NaH$_2$PO$_4$, 140 mM NaCl, pH 7.4. The sample was incubated for 5 min at ambient temperature. Then 100 µl were analyzed by size exclusion chromatography.

1 hour sample:

20 µl of Aβ(1-40) in 0.1% NaOH were diluted to a concentration of 0.2 mg/ml Aβ(1-40) with 20 mM NaH$_2$PO$_4$, 140 mM NaCl, pH 7.4. The sample was incubated for 1 hour at ambient temperature. Then 100 µl were analyzed by size exclusion chromatography.

Conditions for size exclusion chromatography (SEC):

SEC column: Superose 12 HR 10/300 GL (Amersham, catalogue no. 17-5173-01)

Flow: 0.5 ml/min

Paper feed: 0.2 cm/min

Extinction at 214 nm: 0-0.2 absorption units

Figure 1:
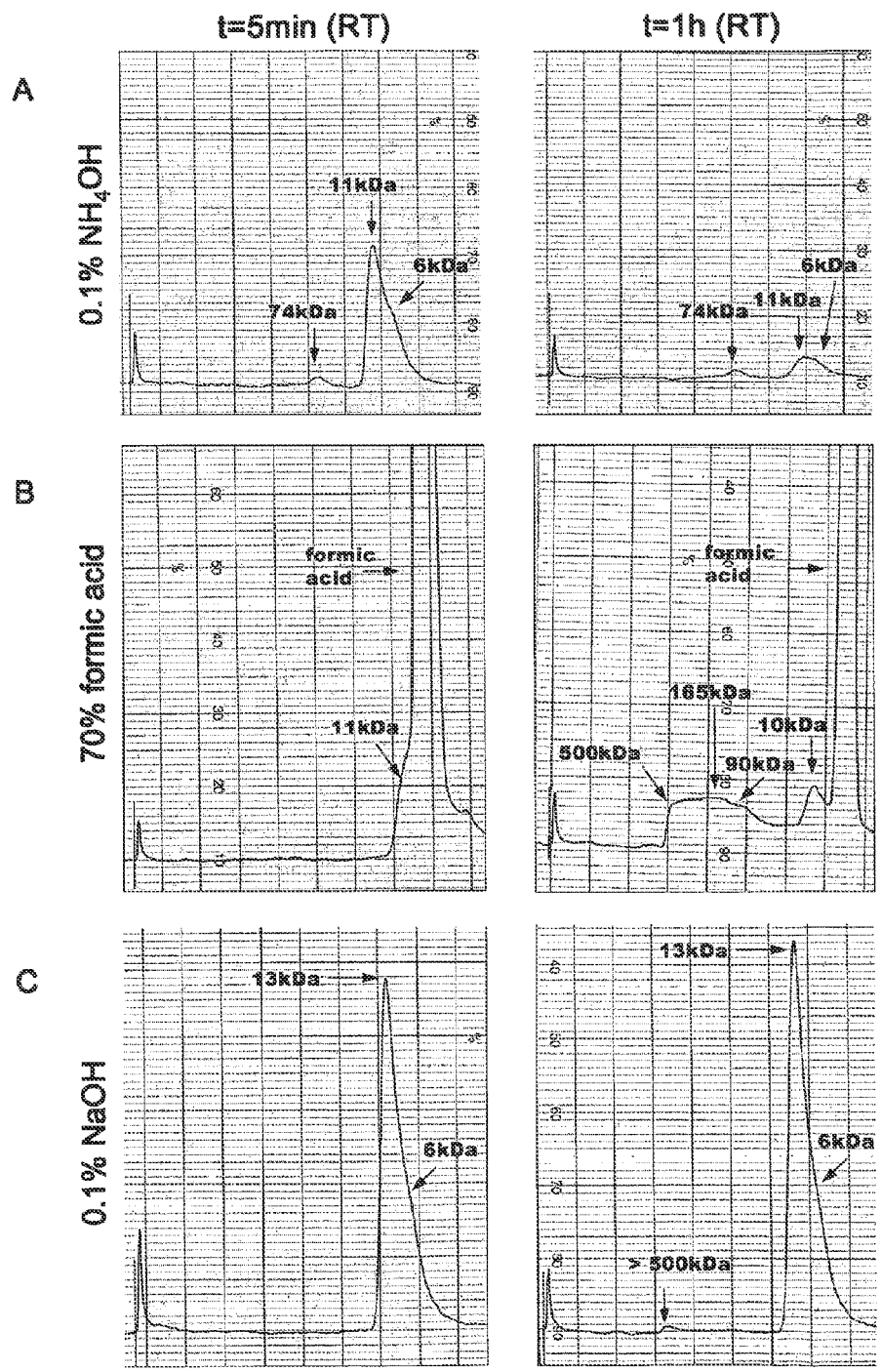
Figure 1:
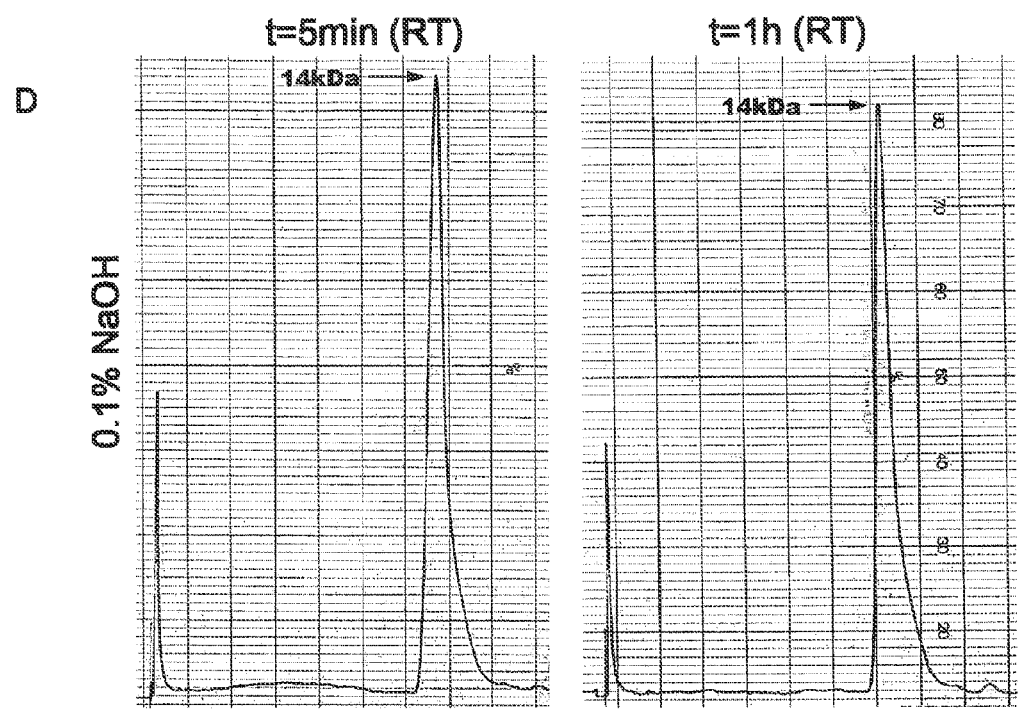

Mobile phase: 20 mM NaH$_2$PO$_4$, 140 mM NaCl, pH 7.4
Results are shown in FIG. 1.

The preparation of a purely monomeric Aβ-solution is a great challenge due to the strong tendency of the Aβ peptide, especially the Aβ(1-42) monomer, to aggregate into fibrils. Nevertheless, for the screening and characterization of anti-Aβ(20-42) globulomers that discriminate Aβ(1-42)-monomers and Aβ(1-40)-monomers the best technically achievable Aβ-monomeric preparation should be used. Here the effect of the initial solvent of the Aβ peptide on the aggregation effect after further dilution into 20 mM NaH$_2$PO$_4$, 140 mM NaCl, pH 7.4 was tested. The Aβ peptide supplier (Bachem) states in their technical information that the Aβ(1-42) should be solubilized in 0.1% NH$_4$OH. Five minutes at room temperature (RT) after solubilizing the Aβ(1-42) in NH$_4$OH and immediate further 1:10 dilution in 20 mM NaH$_2$PO$_4$, 140 mM NaCl, pH 7.4 a size-exclusion chromatography shows first signs of Aβ(1-42) aggregation to fibrillary precursors with a minor peak at 74 kD. Monomeric Aβ(1-42) runs at a major peak with 11 kD and a shoulder at 6 kD. After incubation for one hour at room temperature (RT) the Aβ(1-42) peptide in NH$_4$OH has already aggregated to a high extent to Aβ(1-42) fibrils leading to a loss of detectable material that did not enter the size-exclusion chromatographic column. If 70% formic acid is used as the initial solvent for Aβ(1-42) peptide a high extent of aggregation after 1 h at RT occurs with only a minor fraction Aβ(1-42) monomer left (note that the formic acid itself leads to a high background absorption at the protein detection wavelength). The best initial solvent for Aβ(1-42) to prevent aggregation is 0.1% NaOH which even after 1 h incubation of solubilization and further dilution shows only a minor fraction of aggregated Aβ(1-42) with the majority of Aβ(1-42) being still monomeric. Aβ(1-40) solubilized initially in 0.1% NaOH shows no signs at all of aggregation even after 1 h at RT incubation.

Example 3

Semi-Quantitative Analysis Visualized by SDS-PAGE of the Discrimination of Aβ(20-42) Globulomer Selective Antibodies for Aβ(1-42) Fibrils Aβ(1-42) fibril preparation:

1 mg of Aβ(1-42) (Bachem, Cat. no.: H-1368) were dissolved in 500 µl 0.1% NH$_4$OH in H$_2$O and agitated for 1 min at ambient temperature. The sample was centrifuged for 5 min at 10,000 g. The supernatant was collected. Aβ(1-42) concentration in the supernatant was determined according to Bradford's method (BIO-RAD).

100 µl of Aβ(1-42) in 0.1% NH$_4$OH were mixed with 300 µl of 20 mM NaH$_2$PO$_4$, 140 mM NaCl, pH 7.4 and adjusted to pH 7.4 with 2% HCl. The sample was then incubated at 37° C. for 20 hours. Following which the sample was centrifuged for 10 min at 10,000 g. The supernatant was discarded, and the residue was mixed with 400 µl of 20 mM NaH$_2$PO$_4$, 140 mM NaCl, pH 7.4, resuspended by vigorous agitation ("vortexing") for 1 min and centrifuged for 10 min at 10,000 g. The supernatant was discarded and the residue was mixed with 400 µl of 20 mM NaH$_2$PO$_4$, 140 mM NaCl, pH 7.4, resuspended by vigorous agitation ("vortexing") for 1 min and centrifuged for 10 min at 10,000 g once more. The supernatant was discarded. The residue was resuspended in 380 µl of 20 mM NaH$_2$PO$_4$, 140 mM NaCl, pH 7.4 and prompted by vigorous agitation ("vortexing").

Binding of anti-Aβ antibodies to Aβ(1-42) fibrils:

40 µl of Aβ(1-42) fibril preparation were diluted with 160 µl of 20 mM NaH$_2$PO$_4$, 140 mM NaCl, 0.05% Tween 20, pH 7.4 and agitated 5 min at ambient temperature, then the sample was centrifuged for 10 min at 10,000 g. The supernatant was discarded, and the residue was resuspended in 95 µl of 20 mM NaH$_2$PO$_4$, 140 mM NaCl, 0.05% Tween 20, pH 7.4. Resuspension was prompted by vigorous agitation ("vortexing").

Aliquots of 10 µl of the fibril preparation were each mixed with:

a) 10 µl 20 mM NaH$_2$PO$_4$, 140 mM NaCl, pH 7.4
b) 10 µl 0.5 µg/µl of 5F7 in 20 mM NaH$_2$PO$_4$, 140 mM NaCl, pH 7.4
c) 10 µl 0.5 µg/µl of 6E10 (Signet Nr.: 9320) in 20 mM NaH$_2$PO$_4$, 140 mM NaCl, pH 7.4

The samples were incubated at 37° C. for 20 hours, then centrifuged for 10 min at 10,000 g. The supernatants were collected and mixed with 20 µl of SDS-PAGE sample buffer. The residues were mixed with 50 µl of 20 mM NaH$_2$PO$_4$, 140 mM NaCl, 0.025% Tween 20, pH 7.4 and resuspended by "vortexing", then the samples were centrifuged for 10 min at 10,000 g. The supernatants were discarded, and the residues were mixed with 20 µl 20 mM NaH$_2$PO$_4$, 140 mM NaCl, 0.025% Tween 20, pH 7.4, then with 20 µl of SDS-PAGE sample buffer. The samples were applied to a 4-20% Tris/glycine gel for electrophoresis.

Parameters for SDS-PAGE:

SDS sample buffer. 0.3 g SDS
    4 ml 1 M Tris/HCl pH 6.8
    8 ml glycerine
    1 ml 1% bromphenol blue in ethanol
    Fill with H$_2$O ad 50 ml
4-20% Tris/Glycine Gel: (Invitrogen, Cat. no.: EC6025BOX)

Figure 2:
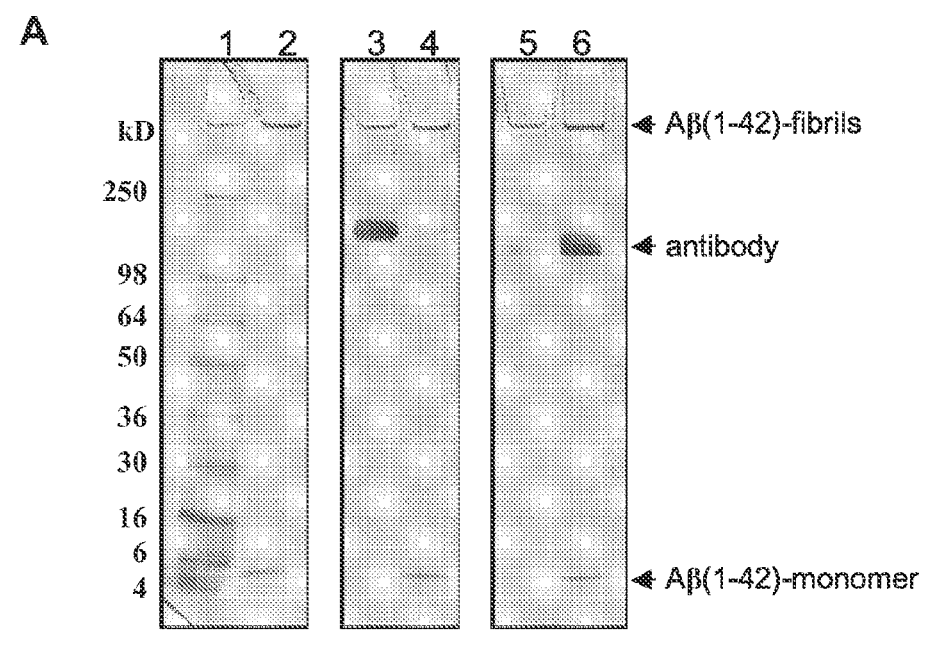

Electrophoresis buffer: 7.5 g Tris
  36 g Glycine
  2.5 g SDS
  Fill with H$_2$O ad 2.5 l
The gel is run at a constant current of 20 mA.
Staining of the gels: Coomassie Blue R250
Results are shown in FIG. 2.

Semiquantitative analysis of different anti-Aβ antibodies and their discrimination of Aβ(1-42) fibrils. Positions of antibodies, Aβ(1-42) fibrils and Aβ(1-42) monomers are marked at the edge of the gel. Due to their size, Aβ(1-42) fibrils cannot enter the SDS-PAGE gel and can be seen in the gel slot.
  1. Marker
  2. Aβ(1-42) fibril preparation; control
  3. Aβ(1-42) fibril preparation; +mAb 5F7; 20 h 37° C.; supernatant
  4. Aβ(1-42) fibril preparation; +mAb 5F7; 20 h 37° C.; pellet
  5. Aβ(1-42) fibril preparation; +mAb 6E10; 20 h 37° C.; supernatant
  6. Aβ(1-42) fibril preparation; +mAb 6E10; 20 h 37° C.; pellet The relative binding to fibril type Aβ was evaluated from SDS-PAGE analysis by measuring the Optical Density (OD) values from the Heavy Chain of the antibodies in the fibril bound (pellet-fraction) and the supernatant fractions after centrifugation. Antibodies that have bound to the Aβ fibrils should be co-pelleted with the Aβ-fibrils and therefore are found in the pellet fraction whereas non-Aβ-fibril bound (free) antibodies are found in the supernatant. The percentage of antibody bound to Aβ-fibrils was calculated according to the following formula:

Percent antibody bound to $A\beta$-fibrils=OD$_{fibril\ fraction}$× 100%/(OD$_{fibril\ fraction}$+OD$_{supernatant\ fraction}$).

This procedure was performed for the mAbs 6E10 (Signet, Cat. no.: 9320), 5F7, 2F2, 6A2, 4D10, 10F11, 3B10, 7C6, 7E5 and 10C1.

In the Alzheimer disease brain the Aβ fibrils are a major component of the total Aβ peptide pool. By attacking these fibrils by anti Aβ-antibodies the risk of negative side effects is elevated due to a liberation of high amounts of Aβ which subsequently may increase the risk of microhaemorrhages. An increased risk for microhaemorrhages was observed in an active Immunization approach with fibrillar aggregates of the Aβ peptide (Bennett and Holtzman, 2005, Neurology, 64, 10-12; Orgogozo J, Neurology, 2003, 61, 46-54; Schenk et al., 2004, Curr Opin Immunol, 16, 599-606).

In contrast to the commercially available antibody 6E10 (Signet 9320) which recognizes a linear Aβ-epitope between AA1-17, the Aβ(20-42) globulomer selective antibody 5F7 (which actually has the lowest selectivity for Aβ(20-42) globulomers over other Aβ-forms) does not bind to Aβ(1-42) fibrils in an co-pelleting experiment. This is shown by the fact that the 5F7 antibody after an incubation with Aβ(1-42) fibrils remains after a pelleting step in the supernatant and is not co-pelleted because of being bound to the Aβ(1-42) fibrils.

Example 4

Analysis of Cognitive Performance in Mice by Means of an Object Recognition Test after Active Immunization with Aβ(1-42) Monomer (0.1% NH$_4$OH), Aβ(1-42) Globulomer or Aβ(20-42) Globulomer in Comparison to Wild Type In these experiments mice overexpressing human APP with a point mutation were used. The point mutation refers to amino acid 717 (substitution of isoleucine for valine) and has been found in a London family where it leads to onset of AD before the beginning of the sixth decade of life (Mullan et al., Nature Genetics 2 (1992) 340-342). The transgenic mice, herein referred to as APP/L, were created by and first described in Leuven (Moechars et al., J. Biol Chem. 274 (1999) 6483-6492). Female APP/L mice were subjected to active immunization at 6 weeks of age.

The mice received either 100 μg of Aβ(1-42) monomer (0.1% NH$_4$OH), Aβ(1-42) globulomer or Aβ(20-42) globulomer in phosphate-buffered saline (PBS) mixed with an equal amount of complete Freund's adjuvant intraperitoneally, followed by booster injections with the same a mount of antigene in incomplete Freund's adjuvant every third week for three months. Throughout the time course of the experiment the animals were kept under standard conditions in a reverted day/night cycle (14 hours of light beginning at 7 pm/10 hours of darkness). Body weight gain over the time of the experiment was as expected and did not differ from a control group which received PBS/adjuvant alone, suggesting that the antigen treatments were well tolerated.

At 4.5 month of age cognitive ability of the mice was tested by an object recognition test as described in the art (Dewachter et al. Journal of Neuroscience 22 (2002) 3445-3453). To this end, mice were accustomed to an arena and then exposed for 10 minutes to an acquisition phase during which they were individually placed in the arena which now contained two identical elements (blue pyramid, green cube, yellow cylinder of similar size, ca. 4 cm). The duration and frequency with which the mouse explored the objects were recorded. During retention phase, 2.5 h later, mice were returned to the arena which now contained, in addition to the known object, an unknown object randomly selected from the other objects. Recognition of the new object was recorded as the time during which the mouse was exploring the old object relative to total time (exploration of old and new object). The "recognition index" expresses this relation (time for new object/total time). A mouse which does not remember the known object will consider it as equally interesting as the new object and spend an equal amount of time on exploring it, in other words, will show a recognition index of 50%. A mouse which remembers the known object will consider it as not interesting and therefore show a significantly higher recognition index. APP/L mice are known to be cognitively deficient at 4.5 months of age and exhibit a recognition index in the dimension of the random level, i.e. 50%.

Figure 3:
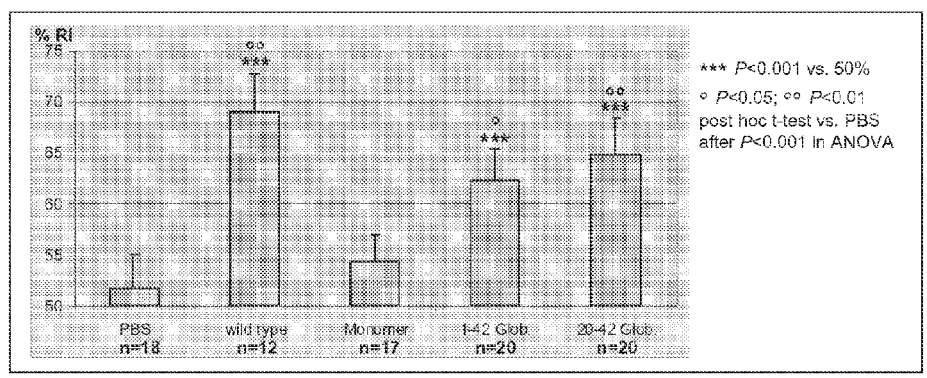

Results are shown in FIG. 3.

Object recognition test in mice. The test reports recognition of a known object in comparison to an unknown one, measured in terms of explorative behaviour during a 10 minute test phase. The recognition Index is defined as the percentage of time which the mouse spends on exploring the unknown object relative to the time spent on exploring both objects. The known object was explored by the mouse during a 10 minute acquisition phase three hours before the test phase. Five groups of mice (number n given below the columns) were compared. Normal C57Bl/6 mice (wild type) show a high RI significantly different from random level (50%, i.e. equal times of exploration spent on both the known and the unknown object) (**=p<0.001; Student's t-test). The other four groups of APP transgenic mice were subjected to active immunisation three months before. The immunogens used were Aβ(1-42) monomer, Aβ(1-42) globulomer and Aβ(20-42) globulomer. Phosphate-buffered saline (PBS) was used as control. Significant differences between PBS and the other groups are indicated with circles: °=p<0.05; °°=p<0.01 (post-hoc t-test after p<0.05 in ANOVA).

APP/L mice are known to show, in contrast to non-transgenic mice, a cognitive deficiency at 4.5 months of age, scoring results close to random level (i.e. 50% recognition index). In fact, the PBS-treated mice showed random behaviour, in contrast to non-transgenic mice (wild type). Immunization with native Aβ(1-42) globulomer as well as with Aβ(20-42) globulomer resulted in significantly Improved object recognition in APP/L mice.

As both globulomer preparations (native and truncated) resulted in memory improvement in APP transgenic animals and even superior recognition in animals treated with Aβ(20-42) globulomer it is reasonable to assume that induction of antibodies against truncated Aβ(20-42) globulomer will produce the best result, and that passive immunisation with antibodies reacting specifically with this species represents the optimal strategy of treatment.

Example 5

Dot-Blot Analysis of the Antibody Profile for Different Aβ-Forms after an Active Immunization of APP/L Tg mice with Aβ(20-42) Globulomer After immunization of mice (compare example 4) of APP/L mice (Moechars et al., 1999, J. Biol. Chem. 274, 6483-6492) with different forms of AP, plasma samples were assessed for anti-Aβ antibodies To this end, dilution series of the individual Aβ(1-42) forms ranging from 100 pmol/µl to 0.01 pmol/µl in PBS supplemented with 0.2 mg/ml BSA were made. 1 µl of each sample was blotted onto a nitrocellulose membrane. For detection the corresponding mouse plasma samples were used (diluted 1:400). Immunostaining was done using alkaline phosphatase conjugated anti-mouse-IgG and the staining reagent NBT/BCIP.

Aβ-standards for dot-blot:
1. Aβ(1-42) Globulomer

The preparation of the Aβ(1-42) globulomer is described in example 1a.
2. HFIP Pretreated Aβ(1-42) Monomer in Pluronic F68

3 mg of Aβ(1-42), (Bachem Inc; cat no. H-1368) were dissolved in 0.5 ml HFIP (6 mg/ml suspension) in an 1.7 ml Eppendorff tube and was shaken (Eppendorff Thermo mixer, 1400 rpm) for 1.5 h at 37° C. till a clear solution was obtained. The sample was dried in a SpeedVac concentrator (1.5 h) and resuspended in 13.2 µl DMSO, shaken for 10 sec., followed by sonification (20 sec), and shaking (e g. in Eppendorff Thermo mixer, 1400 rpm) for 10 min. 6 ml of 20 mM NaH$_2$PO$_4$; 140 mM NaCl; 0.1% Pluronic F68; pH 7.4 were added and stirred for 1 h at room temperature. The sample was centrifuged for 20 min at 3000 g. The supernatant was discarded and the precipitate solved in 0.6 ml 20 mM NaH$_2$PO$_4$; 140 mM NaCl; 1% Pluronic F68, pH 7.4. 3.4 ml of H$_2$O were added and stirred for 1 h at room temperature followed by 20 min centrifugation at 3000 g. Eight aliquots of each 0.5 ml of the supernatant were stored at −20° for further use.
3. Aβ(20-42) Globulomer The preparation of the Aβ(20-42) globulomer is described in example 1c.
4. Aβ(12-42) Globulomer The preparation of the Aβ(12-42) globulomer is described in example 1d.

5. HFIP Pretreated Aβ(1-40) Monomer, 5 mM in DMSO 1 mg Aβ(1-40), (Bachem Inc, cat. no. H-1194) were suspended in 0.25 ml HFIP (4 mg/ml suspension) in an Eppendorff tube. The tube was shaken (e.g. In Eppendorff Thermo mixer, 1400 rpm) for 1.5 h at 37° C. to get a clear solution and afterwards dried in a speed vac concentrator (1.5 h). The sample was redissolved in 46 µl DMSO (21.7 mg/ml solution=5 mM), shaken for 10 sec and subsequently sonicated for 20 sec. After 10 min shaking (e.g. in Eppendorff Thermo mixer, 1400 rpm) the sample is stored at −20° C. for further use.
6. Aβ(1-42) Monomer, 0.1% NH$_4$OH 1 mg Aβ(1-42) (Bachem Inc., cat no. H-1368) were dissolved in 0.5 ml 0.1% NH$_4$OH in H$_2$O (freshly prepared) (=2 mg/ml) and immediately shaken for 30 sec. at room temperature to get a clear solution. The sample was stored at −20° C. for further use.
7. Aβ(1-42) Fibrils 1 mg Aβ(1-42) (Bachem Inc. Catalog Nr.: H-1368) were dissolved in 500 µl aqueous 0.1% NH$_4$OH (Eppendorff tube) and the sample was stirred for 1 min at room temperature. 100 µl of this freshly prepared Aβ(1-42) solution were neutralized with 300 µl 20 mM NaH$_2$PO$_4$; 140 mM NaCl, pH 7.4. The pH was adjusted to pH 7.4 with 1% HCl. The sample was incubated for 24 h at 37° C. and centrifuged (10 min at 10000 g). The supernatant was discarded and the fibril pellet resuspended with 400 µl of 20 mM NaH$_2$PO$_4$; 140 mM NaCl, pH 7.4 by vortexing for 1 min.
8. sAPPα

Supplied from Sigma (cat.no. 89564; 25 µg in 20 mM NaH$_2$PO$_4$; 140 mM NaCl; pH 7.4). The sAPPα was diluted with 20 mM NaH$_2$PO$_4$, 140 mM NaCl, pH 7.4, 0.2 mg/ml BSA to 0.1 mg/ml (=1 pmol/µl).

Materials Dot Blot:
Aβ-Standards:
  Serial dilution of Aβ-antigens in 20 mM NaH$_2$PO$_4$, 140 mM NaCl, pH 7.4+0.2 mg/ml BSA
  1) 100 pmol/µl
  2) 10 pmol/µl
  3) 1 pmol/µl
  4) 0.1 pmol/µl
  5) 0.01 pmol/µl
Nitrocellulose:
  Trans-Blot Transfer medium, Pure Nitrocellulose Membrane (0.45 µm); BIO-RAD
Anti-Mouse-AP:
  AQ330A (Chemicon)
Detection Reagent:
  NBT/BCIP Tablets (Roche)
Bovine Serum Albumin, (BSA):
  A-7888 (SIGMA)
Blocking Reagent:
  5% low fat milk in TBS
Buffer Solutions:
  TBS
  25 mM Tris/HCl-buffer pH 7.5
  +150 mM NaCl
  TTBS
  25 mM Tris/HCl-buffer pH 7.5
  +150 mM NaCl
  +0.05% Tween 20
  PBS+0.2 mg/ml BSA
  20 mM NaH$_2$PO$_4$ buffer pH 7.4
  +140 mM NaCl
  +0.2 mg/ml BSA Antibody Solution I:
  Mouse plasma samples from an active immunization study with Aβ(20-42) globulomer (1:400 diluted in 20 ml 1% low fat milk in TBS)
Antibody Solution II:
  1:5000 dilution
  Anti-Mouse-AP in 1% low fat milk in TBS
Dot-Blot-Procedure:
  1) 1 µl each of the different A-standards (in their 5 serial dilutions) were dotted onto the nitrocellulose membrane in a distance of approximately 1 cm from each other.
  2) The Aβ-standards dots were allowed to dry on the nitrocellulose membrane on air for at least 10 min at room temperature (RT) (=dot blot)
  3) Blocking:
     The dot blot was incubated with 30 ml 5% low fat milk in TBS for 1.5 h at RT.
  4) Washing:
     The blocking solution was discarded and the dot blot was incubated under shaking with 20 ml TTBS for 10 min at RT.
  5) Antibody solution I:
     The washing buffer was discarded and the dot blot was incubated with antibody solution I overnight at RT.
  6) Washing:
     The antibody solution I was discarded and the dot blot was incubated under shaking with 20 ml TTBS for 10 min at RT. The washing solution was discarded and the dot blot was incubated under shaking with 20 ml TTBS for 10 min at RT. The washing solution was discarded and the dot blot was incubated under shaking with 20 ml TBS for 10 min at RT.
  7) Antibody solution II:
     The washing buffer was discarded and the dot blot was incubated with antibody solution II for 1 h at RT
  8) Washing:
     The antibody solution II was discarded and the dot blot was incubated under shaking with 20 ml TTBS for 10 min at RT. The washing solution was discarded and the dot blot was incubated under shaking with 20 ml TTBS for 10 min at RT. The washing solution was discarded and the dot blot was incubated under shaking with 20 ml TBS for 10 min at RT.
  9) Development:
     The washing solution was discarded. 1 tablet NBT/BCIP was dissolved in 20 ml $H_2O$ and the dot blot was incubated for 5 min with this solution. The development was stopped by intensive washing with $H_2O$.

Figure 4:
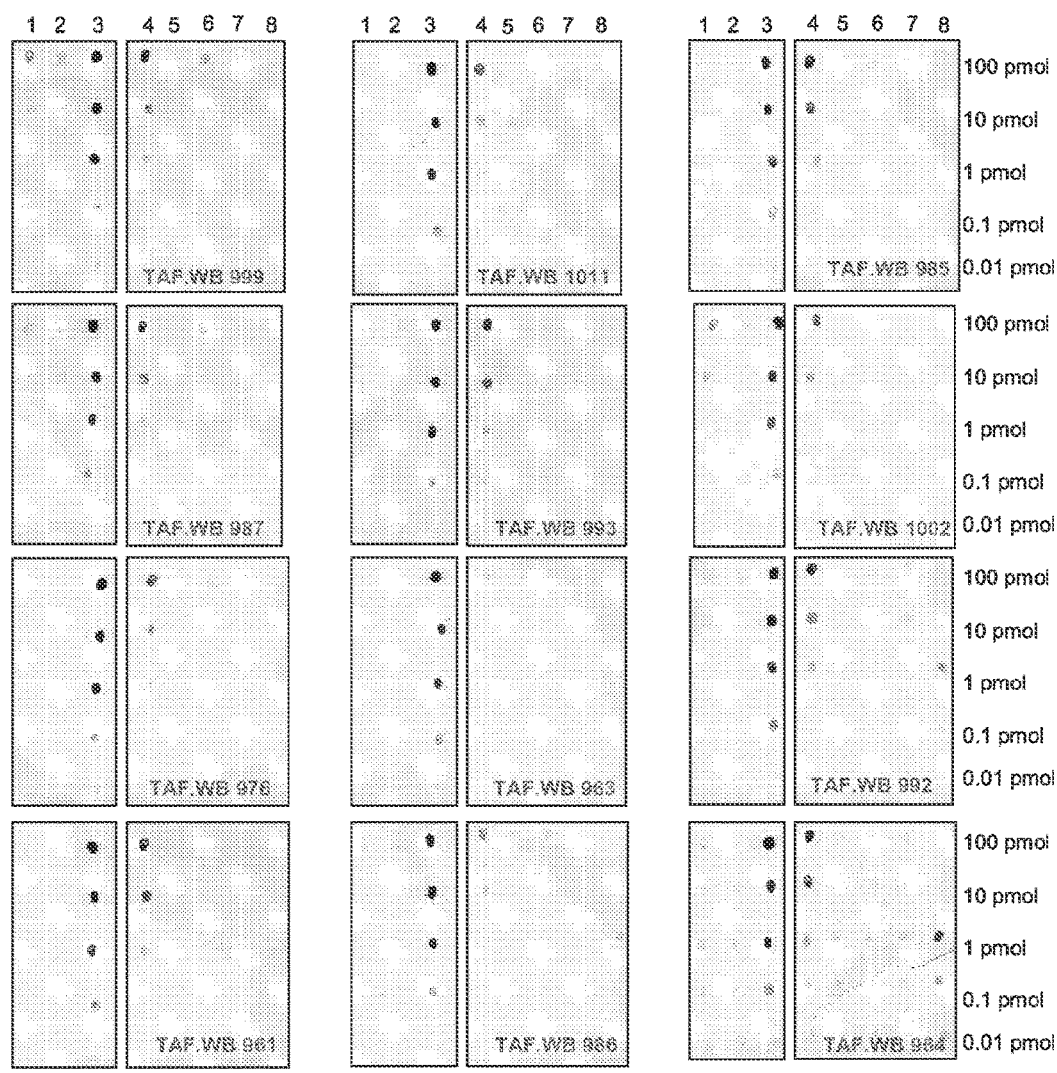

Results are shown in FIG. 4.

Dot blot analysis of anti-Aβ antibodies produced after active immunization of mice with Aβ(20-42) globulomer to assess their specificity towards different forms of AP. The individual forms of Aβ were blotted in serial dilutions and incubated with the corresponding mouse plasma containing anti AP-antibodies produced during immune reaction. The individual dot blots correspond to different individuals of Immunized mice.
  1. Aβ(1-42) globulomer
  2. Aβ(1-42) monomer, HFIP pretreated, in 0.1% Pluronic F68
  3. Aβ(20-42) globulomer
  4. Aβ(12-42) globulomer
  5. Aβ(1-40) monomer, HFIP pretreated, 5 mM in DMSO
  6. Aβ(1-40) monomer, 0.1% $NH_4OH$
  7. Aβ(1-42) fibril preparation
  8. sAPPα (Sigma); (first dot 1 pmol)

In the active immunization study of APP/L Tg-mice it was shown that immunization with Aβ(20-42) globulomer leads to the best result in alleviating a cognitive impairment in these mice compared to PBS treatment Plasma samples from APP/L Tg mice after being actively immunized with Aβ(20-42) globulomer exhibit an antibody profile (predominant recognition of Aβ(20-42) globulomer and Aβ(12-42) globulomer) which resembles that of the Aβ(20-42) globulomer mAbs claimed herein.

Example 6

Concentration of Soluble and Insoluble Aβ(1-42) and Aβ(1-40) Peptide in Brain ExTracts of Actively Immunized APP/PS1 Tg Mice with Either Aβ(1-42) Monomer, Aβ(1-42) Globulomer, Aβ(20-42) Globulomer or Vehicle as Control 40 female mice of a double transgenic mouse model of Alzheimer's Disease (APP/PS1 Tg mice) in FVBxC57Bl/6J background with an age of 4 months were used for this study. The APP/PS1 Tg mice contain the 695 amino acid form of human APP with the V7171 mutation (position referring to the longest APP-isoform) and in addition the human Presenilin 1 gene with the A264E mutation. Both genes are under control of the Thy1 promotor. The mice were generated and characterized in one of the founding laboratories of reMYND, the Experimental Genetics Group, Campus Gasthuisberg, Catholic University Leuven, by Prof. Fred Van Leuven et al.

All mice were genotyped by polymerase chain reaction (PCR) at the age of 3 weeks and received a unique identity number, once the PCR results were known.

Mice had free access to pre-filtered and sterile water (UV-lamp) and standard mouse chow. The food was stored under dry and cool conditions in a well-ventilated storage room. The amount of water and food was checked daily, supplied when necessary and by default refreshed twice a week.

Mice were housed under a reversed day-night rhythm: 14 hours light/10 hours darkness starting at 7 p.m., in standard metal cages type RVS T2 (area of 540 $cm^2$). The cages are equipped with solid floors and layer of bedding litter. The number of mice per cage was limited in accordance with legislation on animal welfare. Five days before the onset of the behaviour test, mice were re-caged in macrolon Type 2 cages and transported to the laboratory in order to adapt to the laboratory environment in preparation to the behaviour test.

The mice received either 100 µg of Aβ(1-42) monomer (0.1% $NH_4OH$), Aβ(1-42) globulomer or Aβ(20-42) globulomer in phosphate-buffered saline (PBS) mixed with an equal amount of complete Freund's adjuvant intraperitoneally, followed by booster injections with the same amount of antigene in incomplete Freund's adjuvant every third week for four months.

Biochemistry
The Aβ(1-40) and Aβ(1-42) in the soluble fraction of 1 hemisphere was determined by ELISA. In addition the Aβ(1-40) and Aβ(1-42) of the insoluble membrane fraction of 1 hemisphere was determined by ELISA The mice were anaesthetized with a 2:1:1 mixture of Ketalar (ketamin), Rompun (xylazin 2%) and atropin and flushed trans-cardially with physiological serum at 4° C. This was performed to remove blood from the brain vessels, a procedure which has no influence on organ integrity.

Cerebrospinal fluid (CSF) was collected via an incision in the neck muscles, between the skull and the first cervical vertebrae. A puncture into the cisterna magna was given with a 26 gauge needle and 10-20 µl of CSF was collected with a fine glass pipette.

Blood was collected via a heart puncture and a 1 ml syringe into heparin-coated Eppendorf tubes. The blood was centrifuged at 14, 000 rpm at 4° C. for 5 minutes. The serum was stored at −70° C.

The mice were flushed transcardially with physiological serum at 4° C.

The brain was removed from the cranium and hindbrain and forebrain were separated by a cut in the coronal/frontal plane. The cerebellum was discharged. The forebrain was divided evenly into left and right hemisphere by using a midline sagittal cut One hemisphere was immediately immersed in liquid nitrogen and stored at −70° C. until biochemical analysis.

Homogenization and Fractionation of One Brain Hemisphere

Brains were homogenized using a Potter, a glass tube (detergent free, 2 cm$^3$) and a mechanical homogenizer (650 rpm). A volume of 6.5×½ brain weight of freshly prepared 20 mM Tris/HCl buffer (pH 8.5) with Proteinase Inhibitors (1 tablet per 50 ml Tris/HCl buffer, Complete™, Roche, Mannheim, Germany) was used as homogenization buffer.

Samples were transferred from −70° C. into a sample holder with liquid nitrogen and each individual sample was pre-warmed by incubation on the bench for a few seconds prior to homogenization. The homogenates were collected in Beckman centrifuge tubes TLX and collected on ice prior to centrifugation. Between two samples, the Potter and the glass tube were rinsed carefully with distilled water (AD) without detergents and dried with absorption paper.

Samples were centrifuged in a pre-cooled ultracentrifuge (Beckman, Mannheim, Germany) for 1 hour and 20 minutes at 48000 rpm (135.000×g) at 4° C. Due to a limited number of centrifuge holders (N=8), samples were sorted by brain weight (to equilibrate the centrifuge) and randomized in order to divide the different treatment groups over the different centrifugation sessions.

The supernatant (soluble fraction containing secreted APP and amyloid peptides) was separated from the pellet (membrane fraction containing membrane-bound APP-fragments and plaque-associated amyloid peptides in case of aged mice). The supernatant was divided over two tubes of which one was stored at −20° C. as back-up and the other was processed further for column chromatography to concentrate the amyloid peptides.

Brain weights, volume Tris/HCl buffer used, centrifugation sessions (marked by colour) and volume soluble fraction used for column chromatography are given exemplary in the following table.

| Sample N° | Treatment | Mouse ID N° | Weight brain (W) (mg) | V Tris (=W × 6.5) (µl) | 50% V Tris (µl) |
|---|---|---|---|---|---|
| 19 | X | TAB.TPF 1305 | 157.8 | 1026 | 513 |
| 21 | X | TAB.TPF 1335 | 160.2 | 1041 | 521 |

Small reversed phase columns (C18-Sep-Pack Vac 3cc cartridges, Waters, Mass., MA) were mounted on a vacuum system and washed with 80% acetonitrile in 0.1% trifluoroacetic acid (A-TFA) followed with 0.1% TFA twice. Then the samples were applied and the columns were washed successively with 5% and 25% A-TFA. Amyloid peptides were eluted with 75% A-TFA and the eluates were collected in 2 ml tubes on ice. Eluates were freeze-dried in a SpeedVac concentrator (Savant, Farmingdale, N.Y.) overnight and resolved in 330 µl of the sample diluent furnished with the ELISA kits.

The pellets were further fractionated into different membrane fractions: membrane fraction A (MFA), membrane fraction B (MFB) containing full length APP and membrane fraction C (MFC) containing plaque associated amyloid. Therefore the pellets were dissolved in TBS buffer with proteinase inhibitors (1 tablet per 50 ml TBS buffer, Complete™, Roche, Mannheim, Germany) and the MFA was divided over two tubes of which one was stored at −20° C. as backup. 60% of MFA was further processed with addition of NP40 (2% of final volume) and Triton X-100 (2% of final volume) in TBS with proteinase inhibitors and centrifuged for one hour at 27.000 rpm (98,000×g) in a Beckman ultracentrifuge at 4° C. using a swing-out rotor (SW60). The supernatant (MFB) was separated from the pellet (MFC) and both were stored at −20° C.

Brain weights, 60% of the brain weight, the volumes TBS+PI+NP40+Triton X-100 buffer used and the centrifugation sessions (marked by colour) are given exemplary in the following table.

| Sample N° | Treatment | Mouse ID N° | Weight brain (W) (mg) | ⅗ × Weight brain (mg) | Volume buffer = ⅗ W × 15 (µl) |
|---|---|---|---|---|---|
| 19 | X | TAB.TPF 1305 | 157.8 | 95 | 1420 |
| 21 | X | TAB.TPF 1335 | 160.2 | 96 | 1442 |

ELISA of Human Aβ in the Soluble Fraction of One Hemisphere

To quantify the amount of human Aβ(1-40) and human Aβ(1-42) in the soluble fraction of the brain homogenates and/or in cerebrospinal fluid (CSF), commercially available Enzyme-Linked-Immunosorbent-Assay (ELISA) kits were used (h Amyloid β40 or β42 ELISA high sensitive, The Genetics Company, Zurich, Switzerland). The ELISA was performed according to the manufacturer's protocol. Briefly, standards (a dilution of synthetic Aβ(1-40) or Aβ(1-42)) and samples were prepared in a 96-well polypropylene plate without protein binding capacity (Greiner bio-one, Frickenhausen, Germany). The standard dilutions with final concentrations of 1000, 500, 250, 125, 62.5, 31.3 and 15.6 pg/ml and the samples were prepared in the sample diluent, furnished with the ELISA kit, to a final volume of 60 µl. Since amyloid levels increase with the age of the mouse and since the actual evaluation requires that the readings of the samples are within the linear part of the standard curve, the samples for Aβ(1-40) analysis were diluted 1:3, the samples for Aβ(1-42) analysis were diluted 1:6.

Samples, standards and blanks (50 µl) were added to the anti-Aβ-coated polystyrol plate (capture antibody selectively recognizes the C-terminal end of the antigen) in addition with a selective anti-An-antibody conjugate (biotinylated detection antibody) and incubated overnight at 4° C. in order to allow formation of the antibody-Amyloid-antibody-complex. The following day, a Streptavidine-Peroxidase-Conjugate was added, followed 30 minutes later by the addition of a TMB/peroxide mixture, resulting in the conversion of the substrate into a coloured product. This reaction was stopped by the addition of sulfuric acid (1 M) and the colour intensity was measured by means of photometry with an ELISA-reader with a 450 nm filter. Quantification of the Aβ content of the samples was obtained by comparing absorbance to the standard curve made with synthetic Aβ(1-40) or Aβ(1-42).

ELISA human Aβ in the insoluble fraction of one hemisphere

To quantify the amount of human Aβ(1-40) and human Aβ(1-42) in the insoluble membrane fraction of the brain homogenates, the MFC samples were further processed and dissolved in 8M Guanidine in 80 mM Tris/HCl. Subsequently samples were incubated for 3 hours in a thermomixer at 25° C. and pipetted up and down with a 100 µl pipette every hour to dissolve the MFC pellet into the guanidine buffer Finally samples were centrifuged for only 1 minute at 4000 rpm to remove debris.

Brain weight, the weight of the MFC pellet and the volume of 8M guanidine buffer are given exemplary in the following table.

| Sample N° | Treatment | Mouse ID N° | Weight brain (W) (mg) | Weight pellet of MFC (WMFC) (40% brain) | Volume 8M guanidine (WMFC × 1.6) (µl) |
|---|---|---|---|---|---|
| 19 | X | TAB.TPF 1305 | 157.8 | 63 | 101 |
| 2 | X | TAB.TPF 1335 | 160.2 | 64 | 103 |

To quantify the amount of human Aβ(1-40) and human Aβ(1-42) in the final samples, commercially available Enzyme-Linked-Immunosorbent-Assay (ELISA) kits were used (h Amyloid 40 or β42 ELISA high sensitive, The Genetics Company, Zurich, Switzerland). The ELISA was performed according to the manufacturer's protocol, except for the preparation of the standards (a dilution of synthetic Aβ(1-40) or Aβ(1-42)). The samples were prepared in the sample diluent, furnished with the ELISA kit, to a final volume of 60 µl. Since guanidine influences the OD-values of the standard curve, the standard dilutions with final concentrations of 1000, 500, 250, 125, 62.5, 31.3 and 15.6 pg/ml were prepared in sample diluent with the same concentration guanidine as for the samples. This was performed in a 96-well polypropylene plate without protein binding capacity (Greiner bio-one, Frickenhausen, Germany).

Since amyloid levels increase with the age of the mouse and since the actual evaluation requires that the readings of the samples are within the linear part of the standard curve, the samples for insoluble Aβ(1-40) and insoluble Aβ(1-42) analysis were diluted 1:500.

Samples, standards and blanks (50 µl) were added to the anti-Aβ-coated polystyrol plate (capture antibody selectively recognizes the C-terminal end of the antigen) in addition with a selective anti-Aβ-antibody conjugate (biotinylated detection antibody) and incubated overnight at 4° C. in order to allow formation of the antibody-Amyloid-antibody-complex. The following day, a streptavidin-peroxidase conjugate was added, followed 30 minutes later by the addition of a TMB/peroxide mixture, resulting in the conversion of the substrate into a coloured product. This reaction was stopped by the addition of sulfuric acid (1M) and the colour intensity was measured by means of photometry with an ELISA-reader with a 450 nm filter. Quantification of the Aβ content of the samples was obtained by comparing absorbance to the standard curve made with synthetic Aβ(1-40) or Aβ(1-42)

Figure 5:
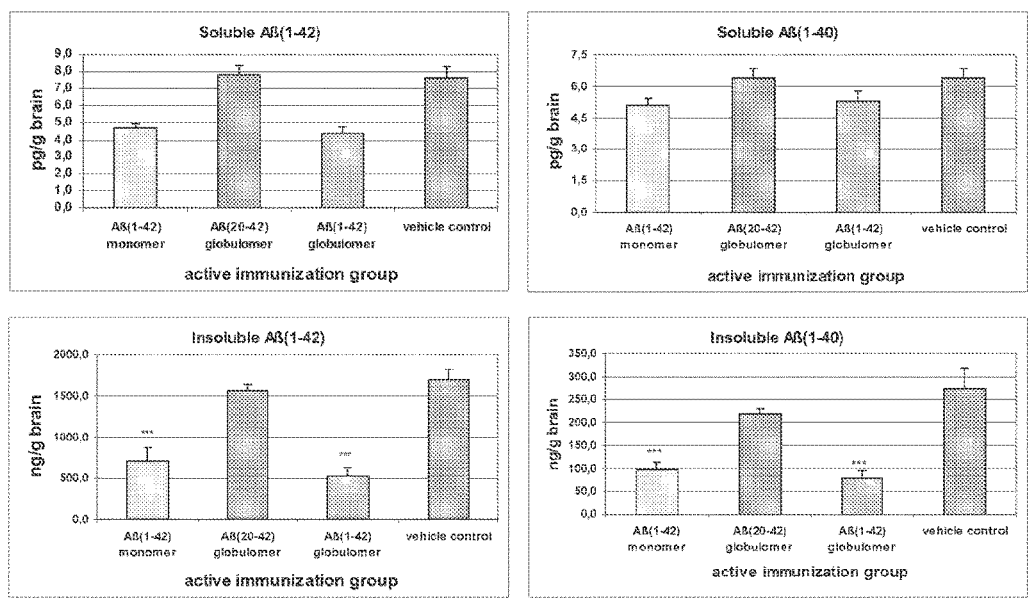
FIG. 5 is a bar diagram which shows the concentrations of soluble and Insoluble Aβ(1-42) and Aβ(1-40) peptide in brain extracts of actively immunized APP/PS1 Tg-mice with either Aβ(1-42) monomer (0.1% NH$_4$OH), Aβ(1-42) globulomer, Aβ(20-42) globulomer or vehicle as control.

Results are shown in FIG. 5

Concentration of soluble and insoluble Aβ(1-42) and Aβ(1-40) peptide in brain extracts of actively immunized APP/PS1 Tg-mice with either Aβ(1-42) monomer (0.1% NH$_4$OH), Aβ(1-42) globulomer, Aβ(20-42) globulomer or vehicle as control.

In the soluble and insoluble fraction of a brain extract of APP/PS1 Tg-mice actively Immunized with Aβ(20-42) globulomer the level of Aβ(1-40)- and Aβ(1-42)-peptide is not significantly different to the vehicle control. In contrast, immunization with Aβ(1-42) globulomer and Aβ(1-42) monomer leads to a reduction in brain Aβ(1-40)- and Aβ(1-42)-levels. This shows that an Aβ(20-42) globulomer directed immunization approach does not alter the total Aβ-brain levels significantly but nonetheless is effective in alleviating the Aβ-peptide related cognitive impairments (see example 4).

Example 7

Analysis of Cognitive Performance by Object Recognition Test in APP/L Transgenic Mice after Passive Immunization with Anti-Aβ(20-42) Globulomer Antibodies In these experiments mice overexpressing human APP with a point mutation were used. The point mutation refers to amino acid 717 (substitution of isoleucine for valine) and has been found in a London family where it leads to onset of AD before the beginning of the sixth decade of life (Mullan et al., Nature Genetics 2 (1992) 340-342). The transgenic mice, herein referred to as APP/L, were created by and first described in Leuven (Moechars et al., J. Biol. Chem. 274 (1999) 6483-6492). Female APP/L mice were subjected to passive immunization at 3 months of age. Mice received 250 µg of any of the monoclonal mouse antibodies 5F7, 10F11 or 7C6 in 100 µl of phosphate-buffered saline (PBS). Throughout the time course of the experiment the animals were kept under standard conditions in a reverted day/night cycle (14 hours of light beginning at 7 pm/10 hours of darkness). They tolerated passive immunization well, without any signs of adverse effects.

After the third injection (day 15 of experiment) cognitive ability of the mice was tested by an object recognition test as described in the art (Dewachter et al. Journal of Neuroscience 22 (2002) 3445-3453). To this end, mice were accustomed to an arena and then exposed for 10 minutes to an acquisition phase during which they were individually placed in the arena which now contained two identical elements (green cube or orange cylinder of similar size, ca. 4 cm). The duration and frequency with which the mouse explored the objects were recorded. During retention phase, 2.5 h later, mice were returned to the arena which now contained, in addition to the known object, the other object. Recognition of the new object was recorded as the time during which the mouse was exploring the old object relative to total time (exploration of old and new object). The "recognition index" expresses this relation (time for new object/total time). A mouse which does not remember the known object will consider it as equally interesting as the new object and spend an equal amount of time on exploring it, in other words, will show a recognition index of 50%. A mouse which remembers the known object will consider it as not interesting and therefore show a significantly higher recognition index. APP/L mice are known to be cognitively deficient at 4.5 months of age and exhibit a recognition index in the dimension of the random level, i.e. 50%.

Figure 6:
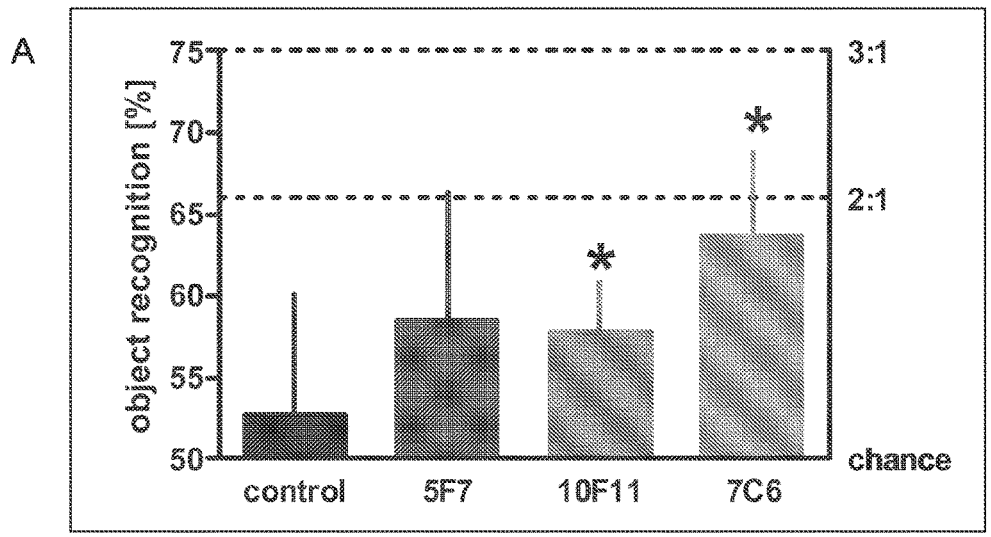
FIG. 6 is a bar diagram which shows the results of the object recognition test with APP/L transgenic mice after passive immunization with anti Aβ(20-42) globulomer antibodies 5F7, 10F11, and 7C6 as compared to control mice for A) each antibody separately and B) for all antibodies taken together.
Figure 6:
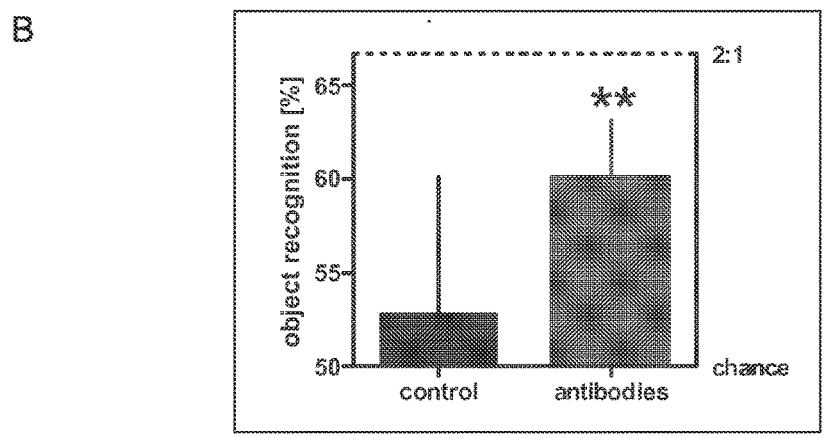

Results are shown in FIG. 6.

Object recognition test in mice. The test reports recognition of a known object in comparison to an unknown one, measured in terms of explorative behaviour during a 10 minute test phase. The recognition index is defined as the percentage of time which the mouse spends on exploring the unknown object relative to the time spent on exploring both objects. The known object was explored by the mouse during a 10 minute acquisition phase 2.5 hours before the test phase.

a) APP transgenic mice were immunized once a week for three weeks by intraperitoneal injection of 250 µg of the antibody 5F7 (n=9), the antibody 10F11 (n=11) or the antibody 7C6 (n=11); control animals received PBS (n=6). Significant differences from random level (50%, i.e. equal time of exploration spent on the known and the unknown object) are indicated with asterisks. *=p<0.05 (t-test)

b) Comparison of all mice treated with antibodies (5F7, 10F11 and 7C6; (n=31)) and mice treated with phosphate-buffered saline (PBS; n=6). The RI of the antibody-treated group different significantly from random level (**=P<0.01; t-Test).

APP/L mice are known to be cognitively deficient at 4.5 months of age and exhibit a recognition index in the dimension of the random level, i.e. 50%.

Indeed the PBS-treated mice showed random behaviour. Passive immunization with all three antibodies (5F7, 10F11 and 7C6) resulted in a markedly increased recognition index. When compared as a pooled group against the controls, the recognition index is significantly increased. This beneficial effect on memory performance of APP/L mice after administration of all three antibodies suggests that an antibody against truncated Aβ(20-42) globulomer is sufficient to achieve cognitive improvement.

Example 8

Dot-Blot Profile of the Selectivity of the Anti-Aβ(20-42) Globulomer Antibodies

In order to characterize the selectivity of the monoclonal anti Aβ(20-42) globulomer antibodies they were probed for recognition with different Aβ-forms. To this end, serial dilutions of the individual Aβ((1-42) forms ranging from 100 pmol/µl to 0.01 pmol/µl in PBS supplemented with 0.2 mg/ml BSA were made. 1 µl of each sample was blotted onto a nitrocellulose membrane. For detection the corresponding antibody was used (0.2 µg/ml). Immunostaining was done using peroxidase conjugated anti-mouse-IgG and the staining reagent BM Blue POD Substrate (Roche).

Aβ-Standards for Dot-Blot:
1. Aβ(1-42) Monomer, 0.1% NH$_4$OH
    1 mg Aβ(1-42) (Bachem Inc., cat. no. H-1368) were dissolved in 0.5 ml 0.1% NH$_4$OH In H$_2$O (freshly prepared) (=2 mg/ml) and immediately shaken for 30 sec at room temperature to get a clear solution. The sample was stored at −20° C. for further use.
2. Aβ(1-40) Monomer, 0.1% NH$_4$OH
    1 mg Aβ(1-40) (Bachem Inc., cat. no. H-1368) were dissolved in 0.5 ml 0.1% NH$_4$OH in H$_2$O (freshly prepared) (=2 mg/ml) and immediately shaken for 30 sec. at room temperature. The sample was stored at −20 C for further use.
3. Aβ(1-42) Monomer, 0.1% NaOH
    2.5 mg Aβ(1-42) (Bachem Inc., cat. no. H-1368) were dissolved in 0.5 ml 0.1% NaOH in H$_2$O (freshly prepared) (=5 mg/ml) and immediately shaken for 30 sec. at room temperature to obtain a clear solution. The sample was stored at −20° C. for further use.
4. Aβ(1-40) Monomer, 0.1% NaOH
    2.5 mg Aβ(1-40) (Bachem Inc, cat. no. H-1368) were dissolved in 0.5 ml 0.1% NaOH in H$_2$O (freshly prepared) (=5 mg/ml) and Immediately shaken for 30 sec. at room temperature to obtain a clear solution. The sample was stored at −20° C. for further use.
5. Aβ(1-42) Globulomer
    The preparation of the Aβ(1-42) globulomer is described in example 1a.
6. Aβ(12-42) Globulomer
    The preparation of the Aβ(12-42) globulomer is described in example 1d.
7. Aβ(20-42) Globulomer
    The preparation of the Aβ(20-42) globulomer is described in example 1c.
8. Aβ(1-42) Fibrils
    1 mg Aβ(1-42) (Bachem Inc. cat. no.: H-1368) were solved in 500 µl aqueous 0.1% NH$_4$OH (Eppendorff tube) and the sample was stirred for 1 min at room temperature. 100 µl of this freshly prepared Aβ(1-42) solution were neutralized with 300 µl 20 mM NaH$_2$PO$_4$; 140 mM NaCl, pH 7.4. The pH was adjusted to pH 7.4 with 1% HCl. The sample was incubated for 24 h at 37° C. and centrifuged (10 min at 10000 g) The supernatant was discarded and the fibril pellet resuspended with 400 µl 20 mM NaH$_2$PO$_4$; 140 mM NaCl, pH 7.4 by vortexing for 1 min.
9. sAPPα
    Supplied by Sigma (cat.no. S9564; 25 µg in 20 mM NaH$_2$PO$_4$; 140 mM NaCl; pH 7.4). The sAPPα was diluted to 0.1 mg/ml (=1 pmol/µl) with 20 mM NaH$_2$PO$_4$, 140 mM NaCl, pH 7.4, 0.2 mg/ml BSA.

Materials for Dot Blot:
Aβ-Standards:
    Serial dilution of Aβ antigens in 20 mM NaH$_2$PO$_4$, 140 mM NaCl, pH 7.4+0.2 mg/ml BSA
        1) 100 pmol/µl
        2) 10 pmol/µl
        3) 1 pmol/µl
        4) 0.1 pmol/µl
        5) 0.01 pmol/µl
Nitrocellulose:
    Trans-Blot Transfer medium, Pure Nitrocellulose Membrane (0.45 µm); BIO-RAD
Anti-Mouse-POD:
    Cat no: 715-035-150 (Jackson Immuno Research)
Detection Reagent:
    BM Blue POD Substrate, precipitating (Roche)
Bovine Serum Albumin, (BSA):
    Cat no: A-7888 (SIGMA)
Blocking Reagent:
    5% low fat milk in TBS
Buffer Solutions:
    TBS
    25 mM Tris/HCl buffer pH 7.5
    +150 mM NaCl
    TTBS
    25 mM Tris/HCl-buffer pH 7.5
    +150 mM NaCl
    +0.05% Tween 20
    PBS+0.2 mg/ml BSA
    20 mM NaH$_2$PO$_4$ buffer pH 7.4

+140 mM NaCl
+0.2 mg/ml BSA
Antibody Solution I:
  0.2 µg/ml antibody diluted in 20 ml 1% low fat milk in TBS
Antibody Solution II:
  1:5000 dilution
  Anti-Mouse-POD in 1% low fat milk in TBS
Dot Blot Procedure:
1) 1 µl each of the different Aβ-standards (in their 5 serial dilutions) were dotted onto the nitrocellulose membrane in a distance of approximately 1 cm from each other.
2) The Aβ-standards dots were allowed to dry on the nitrocellulose membrane on air for at least 10 min at room temperature (RT) (=dot blot)
3) Blocking:
  The dot blot was incubated with 30 ml 5% low fat milk in TBS for 1.5 h at RT.
4) Washing:
  The blocking solution was discarded and the dot blot was incubated under shaking with 20 ml TTBS for 10 min at RT.
5) Antibody solution I:
  The washing buffer was discarded and the dot blot was incubated with antibody solution I for 2 h at RT
6) Washing:
  The antibody solution I was discarded and the dot blot was incubated under shaking with 20 ml TTBS for 10 min at RT. The washing solution was discarded and the dot blot was incubated under shaking with 20 ml TTBS for 10 min at RT. The washing solution was discarded and the dot blot was incubated under shaking with 20 ml TBS for 10 min at RT.
7) Antibody solution II:
  The washing buffer was discarded and the dot blot was incubated with antibody solution II overnight at RT
8) Washing:
  The antibody solution II was discarded and the dot blot was incubated under shaking with 20 mil TTBS for 10 min at RT. The washing solution was discarded and the dot blot was incubated under shaking with 20 ml TTBS for 10 min at RT. The washing solution was discarded and the dot blot was incubated under shaking with 20 mil TBS for 10 min at RT.
9) Development:
  The washing solution was discarded. The dot blot was developed with 10 ml BM Blue POD Substrate for 10 min. The development was stopped by intense washing of the dot blot with $H_2O$. Quantitative evaluation was done using a densitometric analysis (GS800 densitometer (BioRad) and software package Quantity one, Version 4.5.0 (BioRad)) of the dot-intensity. Only dots were evaluated that had a relative density of greater than 20% of the relative density of the last optically unambiguously Identified dot of the Aβ(20-42) globulomer. This threshold value was determined for every dot-blot independently. The calculated value indicates the relation between recognition of Aβ(20-42) globulomer and the respective Aβ form for the antibody given
Results are shown in FIG. 7.
Dot blot analysis of the specificity of different anti-Aβ antibodies (6E10, 5F7, 487, 10F11, 6A2, 4D10, 2F2; 3B10, 7C6, 7E5, 10C1) towards different forms of Aβ. The monoclonal antibodies tested were obtained (except for 6E10) by active immunization of mice with Aβ(20-42) globulomer, followed by selection of the fused hybridoma cells. The individual Aβ forms were applied in serial delusions and incubated with the respective antibodies for immune reaction.
  1. Aβ(1-42) monomer, 0.1% $NH_4OH$
  2. Aβ(1-40) monomer, 0.1% $NH_4OH$
  3. Aβ(1-42) monomer, 0.1% NaOH
  4. Aβ(1-40) monomer, 0.1% NaOH
  5. Aβ(1-42) globulomer
  6. Aβ(12-42) globulomer
  7. Aβ(20-42) globulomer
  8. Aβ(1-42) fibril preparation
  9. sAPPα (Sigma); (first dot: 1 pmol)

The anti Aβ(20-42) globulomer selective mAbs can be divided in 3 classes with respect to the discrimination of Aβ(1-42) globulomer and Aβ(12-42) globulomer. The first class comprising the antibodies 6A2, 5F7 and 2F2 recognizes preferentially Aβ(20-42) globulomer and to some extent Aβ(1-42) globulomer (and also Aβ(12-42) globulomer). The second class comprising the antibodies 10F11, 4D10 and 3810 recognizes preferentially Aβ(20-42) globulomer and also recognizes Aβ(12-42) globulomer but to a lesser extent and do not significantly recognize Aβ(1-42) globulomer. The third class comprising the antibodies 7C6, 4B7, 7E5 And 10C1 recognizes Aβ(20-42) globulomer but shows no significant recognition of the others. All three classes do not significantly recognize monomeric Aβ(1-42), monomeric Aβ(1-40), A$(1-42) fibrils or sAPPα.

The selectivity profile of the anti-Aβ(20-42) globulomer antibodies shows that the significantly elevated recognition Index in the passive immunization (in FIG. 6) must mainly be due to a selective recognition of truncated Aβ(20-42) globulomer and Aβ(12-42) globulomer and to a much lesser extent of Aβ(1-42) globulomer and not monomeric Aβ(1-42), monomeric Aβ(1-40), Aβ(1-42) fibrils or sAPPα.

Example 9

In Situ Analysis of the Specific Reaction of Aβ(20-42) Selective Antibodies to Fibrillary Aβ Peptide in the Form of Aβ Plaques in Old TG2576 Mice and Aβ Amyloid in Meningeal Vessels For these experiments brain material of 19 month old TG2576 mice (Hslao et al., 1996, Science; 274(5284), 99-102) or 9 month old APP/LxPS1 mice (description as above; ReMYND, Leuven, Belgium) or autopsy material of two Alzheimer's disease patients (RZ16 and RZ55; obtained from BrainNet, Munich) was used. The mice overexpress human APP with the so-called Swedish mutation (K670N/M671L; Tg2576) or with the so-called London mutation (V7171) in addition with the human Presenillin 1 gene with the A264E mutation (APP/LxPS1) and formed β amyloid deposits in the brain parenchyma at about 7-11 months of age and P amyloid deposits in larger cerebral vessels at about 18 months of age (Tg2576). The animals were deeply anaesthetized and transcardially perfused with 0.1 M phosphate-buffered saline (PBS) to flush the blood. Then the brain was removed from the cranium and divided longitudinally. One hemisphere of the brain was shock-frozen, the other fixated by immersion into 4% paraformaldehyde. The immersion-fixated hemisphere was cryoprotected by soaking in 30% sucrose in PBS and mounted on a freezing microtome. The entire forebrain was cut into 40 µm section which were collected in PBS and used for the subsequent staining procedure. The human brain material was an about 1 $cm^3$ deep-frozen block of the neocortex. A small part of the block was immersion-fixated in 4% paraformaldehyde and further treated like the mouse brain material.

Individual sections were stained with Congo Red using the following protocol:

Material:
Amyloid dye Congo Red kit (Sigma-Aldrich; HT-60), consisting of alcoholic NaCl solution, NaOH solution and Congo Red solution
staining cuvettes
microscope slides SuperfrostPlus and coverslips
Ethanol, Xylol, embedding medium Reagents:
NaOH diluted 1:100 with NaCl solution yields alkaline saline
alkaline saline diluted 1:100 with Congo Red solution yields alkaline Congo Red solution (prepare no more than 15 min before use, filtrate)
mount sections on slide and allow them to dry
incubate slide in staining cuvette, first for 30-40 minutes in alkaline saline, then for 30-40 minutes in alkaline Congo Red solution
rinse three times with fresh ethanol and embed over xylol Staining was first photographed using a Zeiss Axioplan microscope and evaluated qualitatively. Red colour indicated amyloid deposits both in the form of plaques and in larger meningeal vessels. These Results are shown in FIG. 8A. Later on, evaluation of antibody staining focused on these structures.

Antibody staining was performed by incubating the sections with a solution containing 0.07-7.0 µg/ml of the respective antibody in accordance with the following protocol:

Materials:
TBST washing solution (Tris Buffered Saline with Tween 20; 10× concentrate; DakoCytomation; S3306 1:10 in Aqua bidest)
0.3% $H_2O_2$ in methanol
donkey serum (Serotec), 5% in TBST
monoclonal mouse-anti-globulomer antibody diluted in TBST
secondary antibody: biotinylated donkey-anti-mouse antibody (Jackson Immuno; 715-065-150; diluted 1:500 in TBST)
StreptABComplex (DakoCytomation; K 0377)
Peroxidase Substrate Kit diaminobenzdine (=DAB; Vector Laboratories; SK-4100)
SuperFrost Plus microscope slides and coverslips
xylol free embedding medium (Medite; X-tra Kitt)

Procedure:
transfer floating sections into ice-cold 0.3% $H_2O_2$ and incubate for 30 min
wash for 5 min in TBST buffer
incubate with donkey serum I TBST for 20 minutes
incubate with primary antibody for 24 hours at room temperature
wash in TBST buffer for 5 minutes
Incubate with blocking serum from the Vectastain Elite ABC peroxidase kit for 20 minutes
wash in TBST buffer for 5 minutes
incubate with secondary antibody for 60 minutes at ambient temperature
wash in TBST buffer for 5 minutes
incubate with StreptABComplex for 60 minutes at ambient temperature
wash in TBST buffer for 5 minutes
incubate with DAB from the Vectastain Elite ABC peroxidase kit for 20 minutes
mount the section on slides, air-dry them, dehydrate them with alcohol and embed them Besides visual inspection of the staining, plaque staining was additionally quantified by graphically excising 10 randomly selected plaques from the histological images using the ImagePro 5.0 Image analysis system and determining their average greyscale value. Optical density values were calculated from the greyscale values by subtracting the mean background density of the stained material from the density of amyloid plaques (0%—no plaque staining above surrounding background, 100%—no transmission/maximal staining), and the differences between control and antibodies and between 6G1 and the antibodies selective for Aβ(20-42), respectively, were tested for statistical significance with ANOVA.

Results of the staining in Tg2576 and APP/LxPS1 mice are shown in FIGS. 8 B-D and H.

Binding of different antibodies at a concentration of 0.7 µg/ml in transversal section of the neocortices of transgenic TG 2576 mice at 19 months of age:
  C) Parenchymal Aβ deposits (amyloid plaques) were stained only with 6G1 and 6E10 but not with the globulomer selective antibodies (i.e. 5F7, 2F2, 6A2, 4D10, 10F11, 3B10, 7C6, 7E5 and 10C1)
  D) All globulomer selective antibodies (i.e. 5F7, 2F2, 6A2, 4D10, 10F11, 3B10, 7C6, 7E5 and 10C1) showed significantly less parenchymal plaque staining compared to the commercially available antibodies 6E10 and 4G8.

Binding of different antibodies at a concentration of 0.07-7.0 µg/ml in transversal section of the neocortices of transgenic APP/LxPS1 mice at 11 months of age:
  E) Parenchymal Aβ deposits (amyloid plaques) were significantly more and at lower concentrations stained with 6G1, 6E10 and 4G8 than with the globulomer selective antibodies (i.e. 5F7, 2F2, 6A2, 4D10, 10F11, 3B10, 7C6, 7E5 and 10C1).

All amyloid deposits had been verified by congophilic staining before (Congo Red; see FIG. 8A). Bar=100 µm.

Evaluation of brown DAB deposits showed that the Ap-unselective 6G1 and 6E10 antibodies stained plaques and meningeal vessels, whereas the Aβ(20-42) globulomer selective antibodies 5F7, 2F2, 6A2, 4D10, 10F11, 3B10, 7C6, 7E5 and 10C1 did not. This finding demonstrates that there is no or markedly less binding of these antibodies to Aβ fibrils or other Aβ species present in the amyloid structures in vivo. This reduced binding is supposed to reduce the danger of side effects induced by too fast dissolution of plaques and subsequent increase in soluble Aβ or neuroinflammation due to the interaction of plaque-bound antibodies with microglia.

Results of the staining in human Alzheimer's disease brain are shown in FIG. 8 B, F-H.

Binding of different antibodies at a concentration of 0.7 µg/ml in transversal section of the neocortex of patient RZ55:
  B) Parenchymal Aβ deposits (amyloid plaques) were stained only with 6G1 and 6E10 but not with the globulomer selective antibodies (i.e. 5F7, 2F2, 6A2, 4D10, 10F11, 3B10, 7C6, 7E5 and 10C1).
  F) All globulomer selective antibodies (i.e. 5F7, 2F2, 6A2, 4D10, 10F11, 3B10, 7C6, 7E5 and 10C1) showed significantly less staining compared to the commercially available antibodies 6E10 and 4G8.

H) Vascular Aβ deposits (arrows) were stained only with 6G1 and 6E10 but not with globulomer selective antibodies (i.e. 5F7, 2F2, 6A2, 4D10, 10F11, 3B10, 7C6, 7E5 and 10C1).

Binding of different antibodies at a concentration of 0.07-7.0 μg/ml in transversal section of the neocortices of transgenic APP/LxPS1 mice at 11 months of age:
G) Parenchymal Aβ deposits (amyloid plaques) were significantly more and at lower concentrations stained with 6G1, 6E10 and 4G8 than with the globulomer selective antibodies (i.e. 5F7, 2F2, 6A2, 4D10, 10F11, 3B10, 7C6, 7E5 and 10C1).

All amyloid deposits had been verified by congophilic staining before (Congo Red; see FIG. 8A)

Evaluation of brown DAB deposits showed that the Aβ-unselective 6G1 and 6E10 antibodies stained plaques and meningeal vessels, whereas the Aβ(20-42) globulomer selective antibodies 5F7, 2F2, 6A2, 4010, 10F11, 3B10, 7C6, 7E5 and 10C1 did not. Commercially available antibodies 6E10 and 4G8 showed stronger staining compared to globulomer selective antibodies, but less staining than 6G1. This finding confirms the staining pattern in APP transgenic mice where there is no or markedly less binding of the globulomer selective antibodies to AP fibrils or other Aβ species present in the amyloid structures in vivo. This reduced binding to human amyloid is supposed to reduce the danger of side effects induced by too fast dissolution of plaques and subsequent increase in soluble Aβ or neuroinflammation due to the interaction of plaque-bound antibodies with microglia.

Example 10

Anti-AP-Antibody Titer and Dot-Blot Selectivity Profile in Plasma of TG2576 Mice Approximately One Year after Active Immunization Approximately one year after the last immunization (with Aβ(20-42) globulomer, Aβ(12-42) globulomer, Aβ(1-42) monomer and vehicle) of Tg 2576 mice (from example 9) plasma samples were assessed for anti-A, antibodies produced and still present. To this end, dilution series of the different forms of Aβ(1-42) in the concentration range from 100 pmol/μl to 0.01 pmol/μl in PBS+0.2 mg/ml BSA were made. Of each sample, 1 μl was applied to a nitrocellulose membrane. Detection was performed with suitable mouse plasma samples (diluted 1:400). Staining was done with anti-mouse-lgG conjugated alkaline phosphatase and addition of the staining reagent NBT/BCIP Aβ-Standards for Dot-Blot
1. Aβ(1-42) Globulomer
  The preparation of the Aβ(1-42) globulomer is described in example 1a.
2. HFIP Pretreated Aβ(1-42) Monomer in Pluronic F68
  3 mg Aβ(1-42), (Bachem Inc.; cat. no. H-1368) were dissolved in 0.5 ml HFIP (6 mg/ml suspension) in an 1.7 ml Eppendorff tube and was shaken (Eppendorff Thermo mixer, 1400 rpm) for 1.5 h at 37° C. till a clear solution was obtained. The sample was dried in a SpeedVac concentrator (1.5 h) and resuspended in 13.2 μl DMSO, shaken for 10 sec., followed by sonification (20 sec), and shaking (e.g. in Eppendorff Thermo mixer, 1400 rpm) for 10 min. 6 ml 20 mM $NaH_2PO_4$; 140 mM NaCl; 0.1% Pluronic F68; pH 7.4 was added and stirred for 1 h at room temperature. The sample was centrifuged for 20 min at 3000 g. The supernatant was discarded and the precipitate solved in 0.6 ml 20 mM $NaH_2PO_4$; 140 mM NaCl; 1% Pluronic F68, pH 7.4 3.4 ml $H_2O$ was added and stirred for 1 h at room temperature followed by 20 min centrifugation at 3000 g. Eight aliquots of each 0.5 ml of the supernatant were stored at −20° for further use.
3. Aβ(20-42) Globulomer
  The preparation of the Aβ(20-42) globulomer is described in example 1c.
4. Aβ(12-42) Globulomer
  The preparation of the Aβ(1-42) globulomer is described in example 1d.
5. Aβ(1-40) Monomer, HFIP Pretreated, 5 mM in DMSO
  1 mg Aβ(1-40), (Bachem Inc, cat. no. H-1194) were suspended in 0.25 ml HFIP (4 mg/ml suspension) in an Eppendorff tube. The tube was shaken (e.g. In Eppendorff Thermo mixer, 1400 rpm) for 1.5 h at 37° C. to get a clear solution and afterwards dried in a SpeedVac concentrator (for 1.5 h). The sample was redissolved in 46 μl DMSO (21.7 mg/ml solution=5 mM), shaken for 10 sec and subsequently sonicated for 20 sec. After shaking (e.g. In Eppendorff Thermo mixer, 1400 rpm) for 10 min the sample is stored at −20° C. for further use.
6. Aβ(1-42) monomer, 0.1% $NH_4OH$
  1 mg Aβ(1-42) (Bachem Inc., cat no. H-1368) were dissolved in 0.5 ml 0.1% $NH_4OH$ in $H_2O$ (freshly prepared) (=2 mg/ml) and immediately shaken for 30 sec. at room temperature to get a clear solution. The sample was stored at −20° C. for further use.
7. Aβ(1-42) Fibrils
  1 mg Aβ(1-42) (Bachem Inc. Catalog Nr.: H-1368) were solved in 500 μl aqueous 0.1% $NH_4OH$ (Eppendorff tube) and the sample was stirred for 1 min at room temperature. 100 μl of this freshly prepared Aβ(1-42) solution were neutralized with 300 μl 20 mM $NaH_2PO_4$; 140 mM NaCl, pH 7.4. The pH was adjusted to pH 7.4 with 1% HCl. The sample was incubated for 24 h at 37° C. and centrifuged (10 min at 10000 g). The supernatant was discarded and the fibril pellet resuspended with 400 μl 20 mM $NaH_2PO_4$; 140 mM NaCl, pH 7.4 by vortexing for 1 min.
8. sAPPα
  Supplied from Sigma (cat.no. S9564; 25 μg in 20 mM $NaH_2PO_4$; 140 mM NaCl; pH 7.4). The sAPPα was diluted with 20 mM $NaH_2PO_4$, 140 mM NaCl, pH 7.4, 0.2 mg/ml BSA to 0.1 mg/ml (=1 pmol/μl).

Materials for Dot Blot:
Aβ-Standards:
  Serial dilution of Aβ-antigens in 20 mM $NaH_2PO_4$, 140 mM NaCl, pH 7.4+0.2 mg/ml BSA
  1) 100 pmol/μl
  2) 10 pmol/μl
  3) 1 pmol/μl
  4) 0.1 pmol/μl
  5) 0.01 pmol/μl
Nitrocellulose:
  Trans-Blot Transfer medium, Pure Nitrocellulose Membrane (0.45 μm); BIO-RAD
Anti-Mouse-AP:
  AQ330A (Chemicon)
Detection Reagent:
  NBT/BCIP Tablets (Roche)
Bovine Serum Albumin, (BSA):
  A-7888 (Fa. SIGMA)
Blocking Reagent:
  5% low fat milk in TBS
Buffer Solutions:
  TBS
  25 mM Tris/HCl-buffer pH 7.5
  +150 mM NaCl TTBS
25 mM Tris/HCl-buffer pH 7.5
+150 mM NaCl
+0.05% Tween 20
PBS+0.2 mg/ml BSA
20 mM $NaH_2PO_4$ buffer pH 7.4
+140 mM NaCl
+0.2 mg/ml BSA Antibody Solution I:
   Plasma of the TG2576 mice actively immunized 1/400 diluted in 20 ml 1% low fat milk in TBS Antibody Solution II:
   1:5000 dilution
   Anti-Mouse-AP in 1% low fat milk in TBS Dot Blot Procedure:
   1) 1 µl each of the different Aβ standards (in their 5 serial dilutions) were dotted onto the nitrocellulose membrane in approximately 1 cm distance from each other.
   2) The Aβ standards dots are allowed to dry on the nitrocellulose membrane on air for at least 10 min at room temperature (RT) (=dot blot)
   3) Blocking:
      The dot blot is incubated with 30 ml 5% low fat milk in TBS for 1.5 h at RT.
   4) Washing:
      The blocking solution is discarded and the dot blot incubated under shaking with 20 ml TTBS for 10 min at RT.
   5) Antibody solution 1:
      The washing buffer is discarded and the dot blot incubated with antibody solution I overnight at RT
   6) Washing:
      The antibody solution I is discarded and the dot blot incubated under shaking with 20 ml TTBS for 10 min at RT. The washing solution is discarded and the dot blot incubated under shaking with 20 ml TTBS for 10 min at RT. The washing solution is discarded and the dot blot incubated under shaking with 20 ml TBS for 10 min at RT.
   7) Antibody solution II:
      The washing buffer is discarded and the dot blot incubated with antibody solution II for 1 h at RT.
   8) Washing:
      The antibody solution II is discarded and the dot blot incubated under shaking with 20 ml TTBS for 10 min at RT. The washing solution is discarded and the dot blot incubated under shaking with 20 ml TTBS for 10 min at RT. The washing solution is discarded and the dot blot incubated under shaking with 20 ml TBS for 10 min at RT.
   9) Development:
      The washing solution is discarded. 1 tablet NBT/BCIP is dissolved in 20 ml $H_2O$ and the dot blot is incubated for 5 min with this solution. The development is stopped by intensive washing with $H_2O$.

Results are shown in FIG. 9.

Sera of different immunization groups: a) Aβ(20-42) globulomers; b) Aβ(12-42) globulomers; c) Aβ(1-42) monomer, 0.1% $NH_4OH$; d) vehicle control were tested against different Aβ forms in a dot blot for differing antibody profiles.

1. Aβ(1-42) globulomer
2. Aβ(1-42) monomer, HFIP pretreated, in 0.1% Pluronic F68
3. Aβ(20-42) globulomer
4. Aβ(12-42) globulomer
5. Aβ(1-40) monomer, HFIP pretreated, 5 mM in DMSO
6. Aβ(1-42) monomer, dissolved in 0.1% $NH_4OH$
7. Aβ(1-42) fibril preparation
8. sAPPα (Sigma); (first dot: 1 pmol)

In contrast to the active immunizations with either vehicle as control or Aβ(1-42) monomer the immunization with Aβ(20-42) globulomer or Aβ(12-42) globulomer exhibits even after approximately one year of the last immunization a high titer of antibodies. These antibodies are selective for the Aβ(20-42) globulomer in the case of the Aβ(20-42) globulomer immunization or Aβ(20-42) globulomer and Aβ(12-42) globulomer selective in the case of the Aβ(12-42) globulomer immunization. This shows that the truncated Aβ(20-42) globulomer and Aβ(12-42) globulomer represent a very good antigen and that antibodies directed against them persist very long in vivo.

(Note that on some dot-blots an unspecific staining signal is observed which is most likely a cross reaction of murine antibodies to the BSA used in the serial dilutions of the Aβ peptides.)

Example 11

Brain-Levels of Aβ(20-42) Globulomer Epitopes in Alzheimer's Disease Patients

SDS-DTT-Brain Extract:
   AD brain samples: RZ 16; RZ 52 und RZ 55 (obtained from Brain Net, Munich) Control sample: RZ 92 (obtained from Brain Net, Munich)
   One tablet of Complete Protease Inhibitor (Roche, Cat. No. 1697 498) is dissolved in 1 ml $H_2O$ (=protease inhibitor solution). 100 mg of AD brain sample are homogenized in 2.5 ml $NaH_2PO_4$, 140 mM NaCl, 0.05% Tween 20, 0.5% BSA (supplemented with 25 µl protease inhibitor solution) with 20 strokes in a glass potter. The suspension is sonified for 30 sec on ice, then incubated at 37° C. for 16 h. The suspension is centrifuged at 100,000 g and 8° C. for one hour, then the supernatant is collected. The residue is dissolved in 5 mM $NaH_2PO_4$, 35 mM NaCl, pH 7.4 and homogenized with 10 strokes in a glass potter. 75 µl of 10% SDS and 125 µl of 0.16 mg/ml DTT are added and stirred for 20 minutes at ambient temperature. The sample was centrifuged for 10 minutes at 10,000 g, and the supernatant is stored overnight at −20° C. Before use the supernatant is thawed and centrifuged for another 10 min at 10,000 g. The supernatant (=SDS/DTT brain extract) is used for ELISA.

a) Sandwich-ELISA for Aβ(20-42) Globulomer Epitope
Reagent List:
   1. F96 Cert. Maxisorp NUNC-Immuno Plate (Cat.No.: 439454)
   2. Binding antibody: 5F7, 7C6, 10F11
   3. Coupling buffer:
      100 mM sodium hydrogen carbonate, pH9.6
   4. Blocking reagent for ELISA (Roche Diagnostics GmbH Cat.No.: 1112589)
   5. PBST buffer:
      20 mM $NaH_2PO_4$, 140 mM NaCl, 0.05% Tween 20, pH 7.4
   6. Aβ(20-42) calibration standard
   7. Primary antibody:
      anti-Aβ pRAb BA199; affinity purified (by Aβ(1-42) globulomer-Sepharose) IgG solution in PBS; Konz.: 0.22 mg/ml
   8. Secondary antibody:
      anti-rabbit-POD conjugate; (Jackson ImmunoResearch, Cat.No.: 111-036-045)

9. Development:
   TMB; (Roche Diagnostics GmbH Cat.No.: 92817060) 42 mM in DMSO
   3% $H_2O_2$ in $H_2O$
   100 mM sodium acetate, pH4.9
   Stop solution: 2M sulfuric acid Preparation of Reagents:
1. Binding Antibody:
   The individual binding antibodies 5F7, 7C6 and 10F11 are diluted to a final concentration of 0.7 µg/ml in coupling buffer.
2. Blocking reagent
   For preparation of the blocking stock solution the blocking reagent is dissolved in 100 ml $H_2O$ and stored at −20° C. in aliquots of 10 ml each.
   3 ml of the blocking stock solution are diluted with 27 ml $H_2O$ for blocking one ELISA plate.
3. Aβ(20-42) calibration standard (CS 1)
   The preparation of the Aβ(1-42) globulomer is described in example 1a.
   The Aβ(20-42) globulomer protein concentration was determined (6.81 mg/ml) after Bradford (BioRad). 14.68 µl Aβ(20-42) globulomer (6.81 mg/ml) are diluted in 10 ml 20 mM $NaH_2PO_4$, 140 mM NaCl, 0.05% Tween20, pH 7.4, 0.5% BSA (=10 µg/ml). 10 µl of the 10 µg/ml solution are further diluted in 10 ml 20 mM $NaH_2PO_4$, 140 mM NaCl, 0.05% Tween20, pH 7.4, 0.5% BSA (=10 ng/ml=CS1)

Calibration Standards for Aβ(20-42):

| Calibration standard | volume of calibration standard | PBST + 0.5% BSA | final concentration Aβ(20-42) (pg/ml) |
|---|---|---|---|
| CS1.1 | 1 ml of CS1 | 0 ml | 10000 |
| CS1.2 | 0.316 ml of CS1.1 | 0.684 ml | 3160 |
| CS1.3 | 0.316 ml of CS1.2 | 0.684 ml | 1000 |
| CS1.4 | 0.316 ml of CS1.3 | 0.684 ml | 316 |
| CS1.5 | 0.316 ml of CS1.4 | 0.684 ml | 100 |
| CS1.6 | 0.316 ml of CS1.5 | 0.684 ml | 31.6 |
| CS1.7 | 0.316 ml of CS1.6 | 0.684 ml | 10 |
| CS1.8 | 0.0 | 1.0 ml | 0.0 |

SDS/DTT-Brain Extracts:
   SDS/DTT-brain extracts=E#
   (#represents the 4 human brain samples (1) RZ 16; (2) RZ 52; (3) RZ 55; (4) RZ 92)

| extraction sample | volume of extraction sample | PBST + 0.5% BSA | dilution factor |
|---|---|---|---|
| E#. 1 | 1 ml of E# | 0.0 ml | direct |
| E#. 2 | 0.316 ml of E#. 1 | 0.684 ml | 1:3.16 |
| E#. 3 | 0.316 ml of E#. 1 | 0.684 ml | 1:10 |
| E#. 4 | 0.316 ml of E#. 1 | 0.684 ml | 1:31.6 |

4. Primary Antibody:
   The anti-Aβ pRAb stock solution is diluted to 0.05 µg/ml in PBST+0.5% BSA. The antibody solution is used immediately.

5. Secondary Antibody:
   Lyophilized anti-rabbit-POD conjugate is dissolved in 0.5 ml $H_2O$ and mixed with 500 µl glycerol. The antibody concentrate is then stored at −20° C. in aliquots of 100 µl. The concentrate is diluted 1:10,000 in PBST buffer. The antibody solution is used immediately.

6. TMB solution:
   20 ml of 100 mM sodium acetate, pH 4.9, are mixed with 200 µl TMB solution and 29.5 µl of 3% hydrogen peroxide. This solution is used immediately.

ELISA-Plate for Aβ(20-42):
   Calibration standards (CS1.1-CS1.8) and SDS/DTT-brain extracts of the 4 human brain samples (1) RZ 16; (2) RZ 52; (3) RZ 55; (4) RZ 92 (=E1-E4 in their 4 serial dilutions E#.1-E#.4) are determined in double:

|   | 1 | 2 | 3 | 4 | 5 | 6 | 7 | 8 | 9 | 10 | 11 | 12 |
|---|---|---|---|---|---|---|---|---|---|---|---|---|
| A | CS1.1 | CS1.1 | E1.1 | E1.1 | E3.1 | E3.1 | | | | | | |
| B | CS1.2 | CS1.2 | E1.2 | E1.2 | E3.2 | E3.2 | | | | | | |
| C | CS1.3 | CS1.3 | E1.3 | E1.3 | E3.3 | E3.3 | | | | | | |
| D | CS1.4 | CS1.4 | E1.4 | E1.4 | E3.4 | E3.4 | | | | | | |
| E | CS1.5 | CS1.5 | E2.1 | E2.1 | E4.1 | E4.1 | | | | | | |
| F | CS1.6 | CS1.6 | E2.2 | E2.2 | E4.2 | E4.2 | | | | | | |
| G | CS1.7 | CS1.7 | E2.3 | E2.3 | E4.3 | E4.3 | | | | | | |
| H | CS1.8 | CS1.8 | E2.4 | E2.4 | E4.4 | E4.4 | | | | | | |

ELISA is performed with each of the binding monoclonal antibodies 5F7, 7C6, 10F11.

Procedure
1. Add 100 µl mAb solution per well. Incubate the ELISA plate overnight at +6° C. (fridge).
2. Decant the antibody solution and wash wells three times with 250 µl PBST buffer each.
3. Add 250 µl/well of blocking solution. Incubate for 2 hours at ambient temperature.
4. Decant the blocking solution and wash wells three times with 250 µl PBST buffer each.
5. Add 100 µl/well each of calibration standards and SDS/DTT brain extracts. Incubate plate for 2 hours at ambient temperature, then overnight at 6° C.
6. Decant the calibration standards and SDS/DTT brain extracts solution and wash wells three times with 250 µl PBST buffer each.
7. Add 200 µl/well of primary antibody solution and incubate for 1 hour at ambient temperature.
8. Decant the primary antibody solution and wash wells three times with 250 µl PBST buffer each.
9. Add 200 µl/well of secondary antibody solution and incubate for 1 hour at ambient temperature.
10. Decant the secondary antibody solution and wash wells three times with 250 µl PBST buffer each.
11. Add 100 µl/well of TMB solution.
12. Monitor plate colour during development (5-15 min at ambient temperature) and terminate reaction by adding 50 µl/well of stop solution when an appropriate colour has developed.

13. Measure extinction at 450 nm.
14. Calculate results using calibration.
15. Evaluation: If the extinctions of the samples are beyond the linear calibration range, dilute them again and repeat.

Results are shown in FIG. 10.

Brain levels of Aβ(20-42) globulomer epitopes in brain extracts from AD patients and control subjects A sandwich ELISA was used to assess brain extracts for their truncated Aβ(20-42) globulomer epitope content. ELISAs with the respective antibodies against the Aβ(20-42) globulomer were used for calibration.

Extraction of Alzheimer's disease brain tissue shows that the Aβ(20-42) globulomer epitope content is significantly elevated compared to a control patient. This shows that Indeed the Aβ(20-42) globulomer epitope is a relevant Aβ-species in human Alzheimer's disease brain and not only relevant for Alzheimer's disease animal models. Antibodies directed against the Aβ(20-42) globulomer epitope therefore are highly desirable for the treatment of Alzheimer's disease.

Example 12

Development of Anti-Aβ(20-42) Globulomer Hybridoma Cell Lines

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references Incorporated herein by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

The particular protocol used to produce the antibodies described herein is as follows:

Immunization of mice: Balb/c and A/J mice (6-8 week old) were immunized subcutaneously with 50 ug of antigen in CFA. Animals were boosted every three weeks with 50 ug of antigen in Immuneasy™ (Qiagen) for a total of three boosts. Four days prior to fusion, mice were boosted with 10 ug of antigen Intravenously.

Cell fusion and hybridoma screening: Spleen cells from Immunized animals were fused with SP2/0-Ag14 myeloma cells at a ratio of 5:1 using standard techniques. Seven to ten days post fusion, when macroscopic colonies were observed, SN were tested by ELISA for antibody to Aβ(20-42) globulomer Cells from ELISA positive wells were scaled up and cloned by limiting dilution.

Antibody isotype determination: The isotype of the anti-Aβ(20-42) globulomer mAbs was determined using the Zymed EIA isotyping kit.

Scale up and purification of monoclonal antibodies: Hybridomas were expanded into media containing 5% Low IgG. Fetal bovine serum (Hyclone). Supernatant was harvested and concentrated. mAb was purified using Protein A chromatography and dialyzed into PBS.

Serum titers: Ten mice were immunized with the Aβ(20-42) globulomer. All mice seroconverted with ELISA titers (½ Max OD 450 nm) of 1:5000-10,000.

DESIGNATIONS OF HYBRIDOMAS PRODUCING MONOCLONAL ANTIBODIES

Internal designations of Abbott Laboratories used for the deposits.

Deposited Cell Lines:
1) ML 13-7C6.1D4.4A9.5G8 (also referred to herein as "7C6")
2) ML15-5F7.5B10 (also referred to herein as "5F7")
3) ML15-10F11.3D9 (also referred to herein as "10F11")
4) ML15-4B7.3A6 (also referred to herein as "4B7")
5) ML15-2F2.3E12 (also referred to herein as "2F2")
6) ML15-6A2.4B10 (also referred to herein as "6A2")
7) ML13-4D10.3F3 (also referred to herein as "4D10")
8) ML15-7E5.5E12 (also referred to herein as "7E5")
9) ML15-10C1.5C6.3H4 (also referred to herein as "10C1")
10) ML15-3B10.2D5.3F1 (also referred to herein as "3B10")

The invention claimed is:

1. An antibody selected from the group consisting of an isolated antibody, a monoclonal antibody and a recombinant antibody, wherein
   (a) said antibody has a binding affinity to an Aβ(20-42) globulomer that is greater than the binding affinity of the antibody to an Aβ(1-42) globulomer;
   (b) the binding affinity of the antibody to the Aβ(20-42) globulomer is at least 10 times greater than the binding affinity of the antibody to the Aβ(1-42) globulomer;
   (c) the antibody is humanized and binds to the same epitope as a monoclonal antibody 7C6 obtainable from a hybridoma designated by American Type Culture Collection deposit number PTA-7240;
   (d) the antibody comprises (i) a VH 7C6 CDR1 consisting of amino acid residues 31-35 of SEQ ID NO: 11, (ii) a VH 7C6 CDR2 consisting of amino acid residues 50-65 of SEQ ID NO: 11, (iii) a VH 7C6 CDR3 consisting of amino acid residues 98-107 of SEQ ID NO:11, (iv) a VL 7C6 CDR1 consisting of amino acid residues 24-39 of SEQ ID NO: 12, (v) a VL 7C6 CDR2 consisting of amino acid residues 55-61 of SEQ ID NO: 12, and (vi) a VL 7C6 CDR3 consisting of amino acid residues 94-102 of SEQ ID NO:12.

2. Antigen-binding moiety of an antibody of claim 1.

3. The antigen-binding moiety of claim 2, wherein the moiety is selected from the group consisting of a Fab fragment, a F(ab')₂ fragment and a single chain Fv fragment of the antibody.

4. A composition comprising said antibody of claim 1 or said antigen-binding moiety of claim 2.

5. The composition of claim 4, wherein said composition is a pharmaceutical composition and further comprises a pharmaceutical acceptable carrier.

6. An antibody selected from the group consisting of an isolated antibody, a monoclonal antibody and a recombinant antibody, wherein said antibody comprises two variable domains, wherein said two variable domains are SEQ ID NO:11 and SEQ ID NO:12.

7. The antibody of claim 6, wherein the antibody comprises a constant region.

8. The antibody of claim 7, wherein the antibody comprises a heavy chain constant region selected from the group consisting of IgG1, IgG2, IgG3, IgG4, IgM, IgA, IgD and IgE constant regions.

9. The antibody of claim 8, wherein the antibody comprises an IgG1 heavy chain constant region.

10. The antibody of claim 8, wherein the constant region is a human constant region.

11. The antibody of claim 7, wherein the constant region comprises the amino acid sequence of SEQ ID NO:39.

12. The antibody of claim 11, wherein the antibody possesses a human glycosylation pattern.

13. Monoclonal antibody (7C6) obtainable from a hybridoma designated by American Type Culture Collection deposit number PTA-7240.

14. Hybridoma designated by an American Type Culture Collection deposit number PTA-7240.

* * * * *